US009540394B2

(12) United States Patent
Basarab et al.

(10) Patent No.: US 9,540,394 B2
(45) Date of Patent: *Jan. 10, 2017

(54) COMPOUNDS AND METHODS FOR TREATING BACTERIAL INFECTIONS

(71) Applicant: Entasis Therapeutics Limited, London (GB)

(72) Inventors: Gregory Steven Basarab, Sudbury, MA (US); Madhusudhan Reddy Gowravaram, Acton, MA (US); Sheila Hauck, Lincoln, MA (US); Fei Zhou, Jamaica Plain, MA (US)

(73) Assignee: Entasis Therapeutics Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/881,595

(22) Filed: Oct. 13, 2015

(65) Prior Publication Data
US 2016/0130281 A1    May 12, 2016

Related U.S. Application Data

(63) Continuation of application No. 14/515,684, filed on Oct. 16, 2014, now Pat. No. 9,187,495, which is a continuation of application No. 14/159,773, filed on Jan. 21, 2014, now Pat. No. 8,889,671.

(60) Provisional application No. 61/859,910, filed on Jul. 30, 2013, provisional application No. 61/755,537, filed on Jan. 23, 2013.

(51) Int. Cl.
*C07D 498/22* (2006.01)
(52) U.S. Cl.
CPC .................. *C07D 498/22* (2013.01)
(58) Field of Classification Search
CPC .................................................. C07D 498/22
USPC .......................................... 544/70; 514/229.5
See application file for complete search history.

(56) References Cited

U.S. PATENT DOCUMENTS

| 7,371,757 B2 | 5/2008 | Morningstar et al. |
| 8,658,641 B2 | 2/2014 | Barvian et al. |
| 8,889,671 B2 * | 11/2014 | Basarab ............... C07D 498/22 514/229.5 |
| 9,040,528 B2 | 5/2015 | Barvian et al. |
| 9,187,495 B2 * | 11/2015 | Basarab ............... C07D 498/22 |
| 2014/0088093 A1 | 3/2014 | Curtis et al. |
| 2015/0368266 A1 | 12/2015 | Barvian et al. |

FOREIGN PATENT DOCUMENTS

| WO | WO-2004/031195 A1 | 4/2004 |
| WO | WO-2006/120563 A2 | 11/2006 |
| WO | WO-2007/072151 A1 | 6/2007 |
| WO | WO-2009/004382 A2 | 1/2009 |
| WO | WO-2010/043893 A1 | 4/2010 |

OTHER PUBLICATIONS

International Search Report for PCT/GB2009/051363; mailed Feb. 26, 2010.
International Search Report for PCT/GB2014/050164; mailed May 27, 2014.
Krasnov et al., "Diastereoselective Synthesis of 1-Alkyl-2,4,6-troxoperhydropyrimidine-5-spiro-3'-(1',2',3',4'-tetrahydroquinolines)", Tetrahedron (2010), 66(32):6054-6061.
Miller et al., "Discovery and Characterization of QPT-1, the Progenitor of a New Class of Bacterial Topoisomerase Inhibitors", Antimicrobial Agents & Chemotherapy (2008), 52(8):2806-2812.
Rabong et al., "Scope and Limitations of the T-Reaction Employing Some Functionalized C-H-Acids and Naturally Occurring Secondary Amines", *Heterocycles* (2008); 75; 5; 799-838.
Ruble et al., "Synthesis of (−)-PNU-286607 by Asymmetric Cyclization of Alkylidene Barbituates", JACS (2009), 131(11):3991-3997.

\* cited by examiner

*Primary Examiner* — Kahsay Habte
(74) *Attorney, Agent, or Firm* — McCarter & English, LLP; Steven G. Davis; Michael J. DeGrazia

(57) ABSTRACT

Compounds of formula (I), pharmaceutically acceptable salts thereof, and uses of the compounds of formula (I) for treating bacterial infections are disclosed.

4 Claims, 2 Drawing Sheets

SEQUENCE LISTING

<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttcttcttct tcttcttctt cttcttc                                              27

<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 ttcttcttc                                                                   9

COMPOUNDS AND METHODS FOR TREATING BACTERIAL INFECTIONS

RELATED APPLICATIONS

This application is a continuation of U.S. patent application Ser. No. 14/515,684, filed Oct. 16, 2014; which is a continuation of U.S. application Ser. No. 14/159,773, filed on Jan. 21, 2014, now U.S. Pat. No. 8,889,671, issued on Nov. 18, 2014; which claims the benefit under 35 U.S.C §119(e) of U.S. Provisional Patent Application No. 61/859,910, filed Jul. 30, 2013 and U.S. Provisional Patent Application No. 61/755,537 filed on Jan. 23, 2013. The contents of each of the foregoing applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 13, 2015, is named sequence_listing.txt and is 26,624 bytes in size.

BACKGROUND OF THE INVENTION

Antibiotic tolerance and resistance has become a grave threat to the successful treatment of many common bacterial infections. Indeed, according to the Infectious Disease Society of America, methicillin resistant *Staphylococcus aureus* (MRSA) kills more Americans every year than emphysema, HIV/AIDS, Parkinson's disease and homicide combined. Not only is multi-drug resistance in common infectious Gram-positive and -negative pathogens such as *Enterococcus faecium, Staphylococcus aureus, Klebsiella pneumoniae, Acinetobacter baumannii, Pseudomonas aeruginosa, Mycobacterium tuberculosis* and *Enterobacter* species on the rise, but evidence of resistance is being seen in *Salmonella* and *Clostridium difficile*, and increasingly *Neisseria gonorrheae* (Gerard D. Wright, "Antibiotics: A New Hope," 19 (2012) 3-10). Due to this increase in resistance, the development of new antibacterials is an important medical need.

SUMMARY

There remains a need for new therapies for treating bacterial infections. The present invention provides new compounds and methods for using the same for treating bacterial infections.

In one aspect, the invention provides a compound of formula (I), or a pharmaceutically acceptable salt thereof:

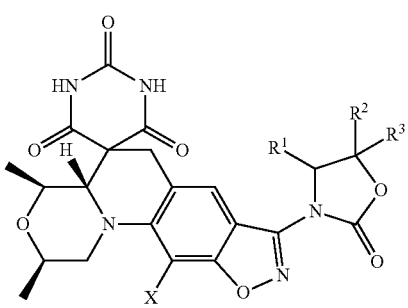

(I)

wherein
X is fluorine or chlorine;
$R^1$ is selected from the group consisting of hydrogen, phenyl, —C≡N, tetrahydropyranyl, N-methyl-1,2,4-triazolyl, pyrimidinyl, pyridinyl, pyrazinyl, cyclopropyl, —C≡CH, —CH═CH$_2$, and $C_1$-$C_3$ alkyl, which $C_1$-$C_3$ alkyl is optionally substituted with one or more of: —OR$^{10}$, halogen, —C≡N, —N$_3$, —SO$_2$CH$_3$, —SCH$_3$, —CH═CH$_2$, —CH═NOR$^{11}$ and phenyl;
$R^2$ is selected from the group consisting of hydrogen, —C≡N, pyridinyl, $C_1$-$C_3$ alkyl, which $C_1$-$C_3$ alkyl is optionally substituted with one or more of: halogen, —OR$^{20}$ and O—CH═NOR$^{21}$;
$R^3$ is hydrogen or $C_1$-$C_3$ alkyl;
$R^{10}$ is for each occurrence independently selected from the group consisting of hydrogen, $C_1$-$C_4$ alkyl and —(CH$_2$)$_2$OCH$_3$; and
$R^{11}$, $R^{20}$ and $R^{21}$ are for each occurrence independently hydrogen or $C_1$-$C_4$ alkyl.

In one aspect, the invention provides a pharmaceutical composition comprising a compound of formula (I), or a pharmaceutically acceptable salt thereof, and a pharmaceutically acceptable excipient or diluent.

In one aspect, the invention provides a method for treating a bacterial infection in a subject in need thereof comprising administering an effective amount of a compound of formula (I), or a pharmaceutically acceptable salt thereof, to the subject.

In one aspect, the invention provides the use of a compound of formula (I), or a pharmaceutically acceptable salt thereof, for treating a bacterial infection.

In one aspect, the invention provides the use of a compound of formula (I), or a pharmaceutically acceptable salt thereof, in the manufacture of a medicament for treating a bacterial infection.

In one aspect, the invention provides a pharmaceutical composition comprising a compound of formula (I), or a pharmaceutically acceptable salt thereof, for treating a bacterial infection.

In one aspect, the invention provides a method for inhibiting bacterial DNA gyrase in a subject in need thereof, comprising administering an effective amount of a compound of formula (I), or a pharmaceutically acceptable salt thereof.

In one aspect, the invention provides the use of a compound of formula (I), or a pharmaceutically acceptable salt thereof, for inhibiting bacterial DNA gyrase.

In one aspect, the invention provides the use of a compound of formula (I), or a pharmaceutically acceptable salt thereof, in the manufacture of a medicament for inhibiting bacterial DNA gyrase.

In one aspect, the invention provides a pharmaceutical composition comprising a compound of formula (I), or a pharmaceutically acceptable salt thereof, for inhibiting bacterial DNA gyrase.

DETAILED DESCRIPTION OF THE INVENTION

Compounds

Figure 1:
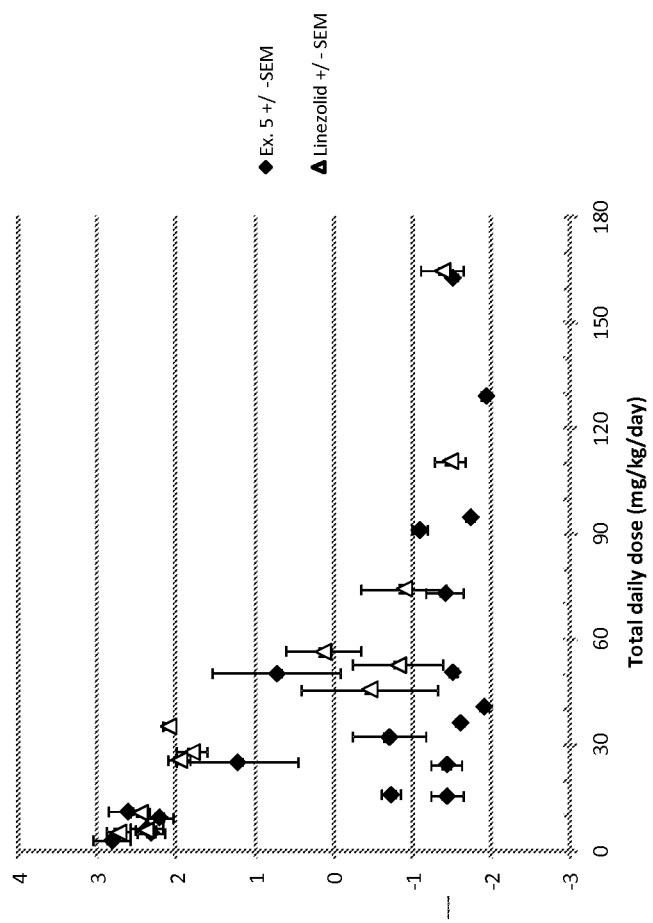
FIG. 1 is a graph illustrating the efficacy of Example 5 in a thigh lesion model induced by *S. aureus* USA100 in neutropenic CD1 mice.

The present invention provides, at least in part, to compounds, and pharmaceutically acceptable salts thereof, of formula (I):

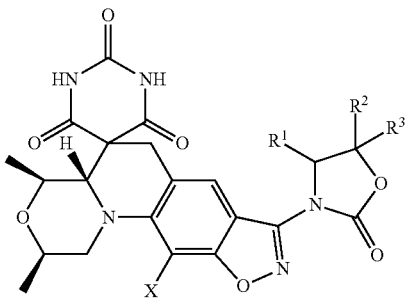

wherein

X is fluorine or chlorine;

$R^1$ is selected from the group consisting of hydrogen, phenyl, —C≡N, tetrahydropyranyl, N-methyl-1,2,4-triazolyl, pyrimidinyl, pyridinyl, pyrazinyl, cyclopropyl, —C≡CH, —CH═CH$_2$, and C$_1$-C$_3$ alkyl, which C$_1$-C$_3$ alkyl is optionally substituted with one or more of: —OR$^{10}$, halogen, —C≡N, —N$_3$, —SO$_2$CH$_3$, —SCH$_3$, —CH═CH$_2$, —CH═NOR$^{11}$ and phenyl;

$R^2$ is selected from the group consisting of hydrogen, —C≡N, pyridinyl, C$_1$-C$_3$ alkyl, which C$_1$-C$_3$ alkyl is optionally substituted with one or more of: halogen, —OR$^{20}$ and —CH═NOR$^{21}$;

$R^3$ is hydrogen or C$_1$-C$_3$ alkyl;

$R^{10}$ is for each occurrence independently selected from the group consisting of hydrogen, C$_1$-C$_4$ alkyl and —(CH$_2$)$_2$OCH$_3$; and $R^{11}$, $R^{20}$ and $R^{21}$ are for each occurrence independently hydrogen or C$_1$-C$_4$ alkyl.

In one aspect, $R^1$ is hydrogen, methyl, ethyl, phenyl, —CH$_2$-phenyl, —CH$_2$F, —CH$_2$OCH$_3$, —CH$_2$CH═CH$_2$, tetrahydropyranyl, —(CH$_2$)$_3$OH, —(CH$_2$)$_3$F, —(CH$_2$)$_3$OH, —(CH$_2$)$_3$F, —CH═CH$_2$, —C≡N, —CH═NOCH$_3$, —CH$_2$SCH$_3$, —CH$_2$SO$_2$CH$_3$, —CH$_2$N$_3$, —CH$_2$OCH$_2$CH$_3$, —CH$_2$O(CH$_2$)$_2$OCH$_3$, cyclopropyl, pyridinyl, —CH(CH$_3$)OCH$_3$, pyrimidinyl, pyrazinyl, —C≡CH, N-methyl-1,2,4-triazolyl, —CH(OH)CH$_3$, —CH═NOH or —CH$_2$OH.

In one aspect, $R^2$ is hydrogen, methyl, ethyl, —CH$_2$F, —CH$_2$OCH$_3$, —CH$_2$OH, —CH═NOH, —CH$_2$N$_3$, pyridinyl, —C≡N or —CH═NHOCH$_3$.

In one aspect, $R^3$ is hydrogen or methyl.

In one aspect, $R^{10}$ is hydrogen, methyl, ethyl or —(CH$_2$)$_2$OCH$_3$.

In one aspect, $R^{11}$ is hydrogen or methyl.

In one aspect, $R^{20}$ is hydrogen, methyl or ethyl.

In one aspect $R^{21}$ is hydrogen or methyl.

In one aspect, in the compound of formula (I), X is fluorine and $R^1$, $R^2$ and $R^3$ are each hydrogen.

In one aspect, in the compound of formula (I), X is fluorine, $R^1$ is methyl and $R^2$ and $R^3$ are each hydrogen.

In one aspect, in the compound of formula (I), X is fluorine, $R^1$ and $R^3$ are each hydrogen and $R^2$ is methyl.

In one aspect, in the compound of formula (I), X is fluorine, $R^1$ is ethyl and $R^2$ and $R^3$ are each hydrogen.

In one aspect, in the compound of formula (I), X is fluorine, $R^1$ is phenyl and $R^2$ and $R^3$ are each hydrogen.

In one aspect, in the compound of formula (I), X is fluorine, $R^1$ is —CH$_2$-phenyl and $R^2$ and $R^3$ are each hydrogen.

In one aspect, in the compound of formula (I), X is fluorine, $R^1$ is hydrogen and $R^2$ and $R^3$ are each methyl.

In one aspect, in the compound of formula (I), X is fluorine, $R^1$ and $R^3$ are each hydrogen and $R^2$ is ethyl.

In one aspect, in the compound of formula (I), X is fluorine, $R^1$ is —CH$_2$F and $R^2$ and $R^3$ are each hydrogen.

In one aspect, in the compound of formula (I), X is fluorine, $R^1$ is —CH$_2$OCH$_3$ and $R^2$ and $R^3$ are each hydrogen.

In one aspect, in the compound of formula (I), X is fluorine, $R^1$ and $R^3$ are each hydrogen and $R^2$ is —CH$_2$F.

In one aspect, in the compound of formula (I), X is chlorine, $R^1$ and $R^3$ are each hydrogen and $R^2$ is —CH$_2$OCH$_3$.

In one aspect, in the compound of formula (I), X is chlorine, $R^1$ and $R^3$ are each hydrogen and $R^2$ is methyl.

In one aspect, in the compound of formula (I), X is fluorine, $R^1$ and $R^2$ are each methyl and $R^3$ is hydrogen.

In one aspect, in the compound of formula (I), X is fluorine, $R^1$ is —CH$_2$CH═CH$_2$ and $R^2$ and $R^3$ are each hydrogen.

In one aspect, in the compound of formula (I), X is fluorine, $R^1$ and $R^3$ are each hydrogen and $R^2$ is —CH$_2$OH.

In one aspect, in the compound of formula (I), X is fluorine, $R^1$ is tetrahydropyranyl and $R^2$ and $R^3$ are each hydrogen.

In one aspect, in the compound of formula (I), X is fluorine, $R^1$ is —(CH$_2$)$_3$OH and $R^2$ and $R^3$ are each hydrogen.

In one aspect, in the compound of formula (I), X is fluorine, $R^1$ is —(CH$_2$)$_3$F and $R^2$ and $R^3$ are each hydrogen.

In one aspect, in the compound of formula (I), X is chlorine, $R^1$ and $R^3$ are each hydrogen and $R^2$ is —CH$_2$F.

In one aspect, in the compound of formula (I), X is chlorine, $R^1$ is —(CH$_2$)$_3$OH and $R^2$ and $R^3$ are each hydrogen.

In one aspect, in the compound of formula (I), X is chlorine, $R^1$ is —(CH$_2$)$_3$F and $R^2$ and $R^3$ are each hydrogen.

In one aspect, in the compound of formula (I), X is fluorine, $R^1$ and $R^3$ are each hydrogen and $R^2$ is —CH$_2$OCH$_3$.

In one aspect, in the compound of formula (I), X is fluorine, $R^1$ is —CH═CH$_2$ and $R^2$ and $R^3$ are each hydrogen.

In one aspect, in the compound of formula (I), X is fluorine, $R^1$ and $R^3$ are each hydrogen and $R^2$ is —CH═NOH.

In one aspect, in the compound of formula (I), X is fluorine, $R^1$ is —C≡N and $R^2$ and $R^3$ are each hydrogen.

In one aspect, in the compound of formula (I), X is fluorine, $R^1$ is —CH═NOCH$_3$ and $R^2$ and $R^3$ are each hydrogen.

In one aspect, in the compound of formula (I), X is fluorine, $R^1$ and $R^3$ are each hydrogen and $R^2$ is —CH═NHOCH$_3$.

In one aspect, in the compound of formula (I), X is fluorine, $R^1$ and $R^3$ are each hydrogen and $R^2$ is —CH$_2$N$_3$.

In one aspect, in the compound of formula (I), X is fluorine, $R^1$ is —CH$_2$SCH$_3$ and $R^2$ and $R^3$ are each hydrogen.

In one aspect, in the compound of formula (I), X is fluorine, $R^1$ is —$CH_2SO_2CH_3$ and $R^2$ and $R^3$ are each hydrogen.

In one aspect, in the compound of formula (I), X is fluorine, $R^1$ is —$CH_2N_3$ and $R^2$ and $R^3$ are each hydrogen.

In one aspect, in the compound of formula (I), X is fluorine, $R^1$ is —$CH_2OCH_2CH_3$ and $R^2$ and $R^3$ are each hydrogen.

In one aspect, in the compound of formula (I), X is fluorine, $R^1$ is —$CH_2O(CH_2)_2OCH_3$ and $R^2$ and $R^3$ are each hydrogen.

In one aspect, in the compound of formula (I), X is fluorine, $R^1$ is —$CHF_2$ and $R^2$ and $R^3$ are each hydrogen.

In one aspect, in the compound of formula (I), X is fluorine, $R^1$ is cyclopropyl and $R^2$ and $R^3$ are each hydrogen.

In one aspect, in the compound of formula (I), X is fluorine, $R^1$ and $R^3$ are each hydrogen and $R^2$ is pyridinyl.

In one aspect, in the compound of formula (I), X is fluorine, $R^1$ is pyridinyl and $R^2$ and $R^3$ are each hydrogen.

In one aspect, in the compound of formula (I), X is fluorine, $R^1$ is —$CH(CH_3)OCH_3$ and $R^2$ and $R^3$ are each hydrogen.

In one aspect, in the compound of formula (I), X is fluorine, $R^1$ is pyrimidinyl and $R^2$ and $R^3$ are each hydrogen.

In one aspect, in the compound of formula (I), X is fluorine, $R^1$ is pyrazinyl and $R^2$ and $R^3$ are each hydrogen.

In one aspect, in the compound of formula (I), X is fluorine, $R^1$ is —C≡CH and $R^2$ and $R^3$ are each hydrogen.

In one aspect, in the compound of formula (I), X is chlorine, $R^1$ is methyl and $R^2$ and $R^3$ are each hydrogen.

In one aspect, in the compound of formula (I), X is fluorine, $R^1$ is N-methyl-1,2,4-triazolyl and $R^2$ and $R^3$ are each hydrogen.

In one aspect, in the compound of formula (I), X is fluorine, $R^1$ is —$CH(OH)CH_3$ and $R^2$ and $R^3$ are each hydrogen.

In one aspect, in the compound of formula (I), X is fluorine, $R^1$ is —$CH(OH)CH_2OH$ and $R^2$ and $R^3$ are each hydrogen.

In one aspect, in the compound of formula (I), X is fluorine, $R^1$ is —CH=NOH and $R^2$ and $R^3$ are each hydrogen.

In one aspect, in the compound of formula (I), X is fluorine, $R^1$ and $R^3$ are each hydrogen and $R^2$ is —C≡N.

In one aspect, in the compound of formula (I), X is fluorine, $R^1$ is —$CH_2OCH_3$, $R^2$ is methyl and $R^3$ is hydrogen.

In one aspect, in the compound of formula (I), X is fluorine, $R^1$ is —$CH_2F$, $R^2$ is methyl and $R^3$ is hydrogen.

In one aspect, in the compound of formula (I), X is fluorine, $R^1$ is —$CH_2OH$ and $R^2$ and $R^3$ are each hydrogen.

In some embodiments, the compound of formula (I) has the structure of formula (Ia), or a pharmaceutically acceptable salt thereof:

(Ia)

wherein
$R^{1a}$ is hydrogen or $C_1$-$C_3$ alkyl, which $C_1$-$C_3$ alkyl is optionally substituted with halogen or $OR^{11a}$;
$R^{2a}$ is hydrogen or $C_1$-$C_3$ alkyl, which $C_1$-$C_3$ alkyl is optionally substituted with halogen or $OR^{21a}$; and
$R^{11a}$ and $R^{21a}$ are for each occurrence independently hydrogen or $C_1$-$C_4$ alkyl.

In one aspect, $R^{1a}$ is hydrogen, —$(CH_2)_3OH$, —$(CH_2)_3F$ or methyl.

In one aspect, $R^{2a}$ is —$CH_2OCH_3$, methyl, —$CH_2F$ or hydrogen.

In one aspect, $R^{11a}$ is hydrogen or methyl.

In one aspect, $R^{21a}$ is hydrogen or methyl

In one aspect, in the compound of formula (Ia), $R^{1a}$ is hydrogen and $R^{2a}$ is —$CH_2OCH_3$.

In one aspect, in the compound of formula (Ia), $R^{1a}$ is hydrogen and $R^{2a}$ is methyl.

In one aspect, in the compound of formula (Ia), $R^{1a}$ is hydrogen and $R^{2a}$ is —$CH_2F$.

In one aspect, in the compound of formula (Ia), $R^{1a}$ is —$(CH_2)_3OH$ and $R^{2a}$ is hydrogen.

In one aspect, in the compound of formula (Ia), $R^{1a}$ is —$(CH_2)_3F$ and $R^{2a}$ and is hydrogen.

In one aspect, in the compound of formula (Ia), $R^{1a}$ is methyl and $R^{2a}$ is hydrogen.

In some embodiments, the compound of formula (I) has the structure of formula (Ib):

(Ib)

wherein
$R^{1b}$ is selected from the group consisting of hydrogen, phenyl, —C≡N, tetrahydropyranyl, 1,2,4-triazolyl, pyrimidinyl, pyridinyl, pyrazinyl, cyclopropyl, —C≡CH, —CH=$CH_2$ and $C_1$-$C_3$ alkyl, which $C_1$-$C_3$ alkyl is optionally substituted with one or more of: $OR^{1ob}$, halogen, —C≡N, —$N_3$, —$SO_2CH_3$, —$SCH_3$, —CH=$CH_2$, —CH=$NOR^{11b}$ and phenyl;
$R^{2b}$ is selected from the group consisting of hydrogen, —C≡N, $C_1$-$C_3$ alkyl, which $C_1$-$C_3$ alkyl is optionally substituted with one or more of: halogen, $OR^{20b}$ and CH=$NOR^{21b}$;

$R^{3b}$ is hydrogen or $C_1$-$C_4$ alkyl;

$R^{10b}$ is for each occurrence independently selected from the group consisting of hydrogen, $C_1$-$C_4$ alkyl and —$(CH_2)_2OCH_3$; and $R^{11b}$, $R^{20b}$ and $R^{21b}$ are for each occurrence independently hydrogen or $C_1$-$C_4$ alkyl.

In one aspect, $R^{1b}$ is hydrogen, methyl, ethyl, phenyl, —$CH_2$-phenyl, —$CH_2F$, —$CH_2OCH_3$, —$CH_2CH$=$CH_2$, tetrahydropyranyl, —$(CH_2)_3OH$, —$(CH_2)_3F$, —$(CH_2)_3OH$, —$(CH_2)_3F$, —$CH$=$CH_2$, —$C$≡$N$, —$CH$=$NOCH_3$, —$CH_2SCH_3$, —$CH_2SO_2CH_3$, —$CH_2N_3$, —$CH_2OCH_2CH_3$, —$CH_2O(CH_2)_2OCH_3$, cyclopropyl, pyridinyl, —$CH(CH_3)OCH_3$, pyrimidinyl, pyrazinyl, —$C$≡$CH$, N-methyl-1,2,4-triazolyl, —$CH(OH)CH_3$, —$CH$=$NOH$ or —$CH_2OH$.

In one aspect, $R^{2b}$ is hydrogen, methyl, ethyl, —$CH_2F$, —$CH_2OH$, —$CH$=$NOH$, —$CH_2N_3$, pyridinyl, —$C$≡$N$ or —$CH$=$NHOCH_3$.

In one aspect, $R^{3b}$ is hydrogen or methyl.

In one aspect, $R^{10b}$ is hydrogen, methyl, ethyl or —$(CH_2)_2OCH_3$.

In one aspect, $R^{11b}$ is hydrogen or methyl.

In one aspect, $R^{20b}$ is hydrogen, methyl or ethyl.

In one aspect $R^{21b}$ is hydrogen or methyl.

In one aspect, in the compound of formula (Ib), $R^{1b}$ is methyl and $R^{2b}$ and $R^{3b}$ are each hydrogen.

In one aspect, in the compound of formula (Ib), $R^{1b}$ and $R^{3b}$ are each hydrogen and $R^{2b}$ is methyl.

In one aspect, in the compound of formula (Ib), $R^{1b}$ is ethyl and $R^{2b}$ and $R^{3b}$ are each hydrogen.

In one aspect, in the compound of formula (Ib), $R^{1b}$ is phenyl and $R^{2b}$ and $R^{3b}$ are each hydrogen.

In one aspect, in the compound of formula (Ib), $R^{1b}$ is —$CH_2$-phenyl and $R^{2b}$ and $R^{3b}$ are each hydrogen.

In one aspect, in the compound of formula (Ib), $R^{1b}$ is hydrogen and $R^{2b}$ and $R^{3b}$ are each methyl.

In one aspect, in the compound of formula (Ib), $R^{1b}$ and $R^{3b}$ are each hydrogen and $R^{2b}$ is ethyl.

In one aspect, in the compound of formula (Ib), $R^{1b}$ is —$CH_2F$ and $R^{2b}$ and $R^{3b}$ are each hydrogen.

In one aspect, in the compound of formula (Ib), $R^{1b}$ is —$CH_2OCH_3$ and $R^{2b}$ and $R^{3b}$ are each hydrogen.

In one aspect, in the compound of formula (Ib), $R^{1b}$ and $R^{3b}$ are each hydrogen and $R^{2b}$ is —$CH_2F$.

In one aspect, in the compound of formula (Ib), $R^{1b}$ and $R^{2b}$ are each methyl and $R^{3b}$ is hydrogen.

In one aspect, in the compound of formula (Ib), $R^{1b}$ is —$CH_2CH$=$CH_2$ and $R^{2b}$ and $R^{3b}$ are each hydrogen.

In one aspect, in the compound of formula (Ib), $R^{1b}$ and $R^{3b}$ are each hydrogen and $R^{2b}$ is —$CH_2OH$.

In one aspect, in the compound of formula (Ib), $R^{1b}$ is tetrahydropyranyl and $R^{2b}$ and $R^{3b}$ are each hydrogen.

In one aspect, in the compound of formula (Ib), $R^{1b}$ is —$(CH_2)_3OH$ and $R^{2b}$ and $R^{3b}$ are each hydrogen.

In one aspect, in the compound of formula (Ib), $R^{1b}$ is —$(CH_2)_3F$ and $R^{2b}$ and $R^{3b}$ are each hydrogen.

In one aspect, in the compound of formula (Ib), $R^{1b}$ and $R^{3b}$ are each hydrogen and $R^{2b}$ is —$CH_2OCH_3$.

In one aspect, in the compound of formula (Ib), $R^{1b}$ is —$CH$=$CH_2$ and $R^{2b}$ and $R^{3b}$ are each hydrogen.

In one aspect, in the compound of formula (Ib), $R^{1b}$ and $R^{3b}$ are each hydrogen and $R^{2b}$ is —$CH$=$NOH$.

In one aspect, in the compound of formula (Ib), $R^{1b}$ is —$C$≡$N$ and $R^{2b}$ and $R^{3b}$ are each hydrogen.

In one aspect, in the compound of formula (Ib), $R^{1b}$ is —$CH$=$NOCH_3$ and $R^{2b}$ and $R^{3b}$ are each hydrogen.

In one aspect, in the compound of formula (Ib), $R^{1b}$ and $R^{3b}$ are each hydrogen and $R^{2b}$ is —$CH$=$NHOCH_3$.

In one aspect, in the compound of formula (Ib), $R^{1b}$ and $R^{3b}$ are each hydrogen and $R^{2b}$ is —$CH_2N_3$.

In one aspect, in the compound of formula (Ib), $R^{1b}$ is —$CH_2SCH_3$ and $R^{2b}$ and $R^{3b}$ are each hydrogen.

In one aspect, in the compound of formula (Ib), $R^{1b}$ is —$CH_2SO_2CH_3$ and $R^{2b}$ and $R^{3b}$ are each hydrogen.

In one aspect, in the compound of formula (Ib), $R^{1b}$ is —$CH_2N_3$ and $R^{2b}$ and $R^{3b}$ are each hydrogen.

In one aspect, in the compound of formula (Ib), $R^{1b}$ is —$CH_2OCH_2CH_3$ and $R^{2b}$ and $R^{3b}$ are each hydrogen.

In one aspect, in the compound of formula (Ib), $R^{1b}$ is —$CH_2O(CH_2)_2OCH_3$ and $R^{2b}$ and $R^{3b}$ are each hydrogen.

In one aspect, in the compound of formula (Ib), $R^{1b}$ is —$CHF_2$ and $R^{2b}$ and $R^{3b}$ are each hydrogen.

In one aspect, in the compound of formula (Ib), $R^{1b}$ is cyclopropyl and $R^{2b}$ and $R^{3b}$ are each hydrogen.

In one aspect, in the compound of formula (I), $R^{1b}$ and $R^{3b}$ are each hydrogen and $R^{2b}$ is pyridinyl.

In one aspect, in the compound of formula (I), $R^{1b}$ is pyridinyl and $R^{2b}$ and $R^{3b}$ are each hydrogen.

In one aspect, in the compound of formula (Ib), $R^{1b}$ is —$CH(CH_3)OCH_3$ and $R^{2b}$ and $R^{3b}$ are each hydrogen.

In one aspect, in the compound of formula (Ib), $R^{1b}$ is pyrimidinyl and $R^{2b}$ and $R^{3b}$ are each hydrogen.

In one aspect, in the compound of formula (Ib), $R^{1b}$ is pyrazinyl and $R^{2b}$ and $R^{3b}$ are each hydrogen.

In one aspect, in the compound of formula (Ib), $R^{1b}$ is —$C$≡$CH$ and $R^{2b}$ and $R^{3b}$ are each hydrogen.

In one aspect, in the compound of formula (Ib), $R^{1b}$ is N-methyl-1,2,4-triazolyl and $R^{2b}$ and $R^{3b}$ are each hydrogen.

In one aspect, in the compound of formula (Ib), $R^{1b}$ is —$CH(OH)CH_3$ and $R^{2b}$ and $R^{3b}$ are each hydrogen.

In one aspect, in the compound of formula (Ib), $R^{1b}$ is —$CH(OH)CH_2OH$ and $R^{2b}$ and $R^{3b}$ are each hydrogen.

In one aspect, in the compound of formula (Ib), $R^{1b}$ is —$CH$=$NOH$ and $R^{2b}$ and $R^{3b}$ are each hydrogen.

In one aspect, in the compound of formula (Ib), $R^{1b}$ and $R^{3b}$ are each hydrogen and $R^{3b}$ is —$C$≡$N$.

In one aspect, in the compound of formula (Ib), $R^{1b}$ is —$CH_2OCH_3$, $R^{2b}$ is methyl and $R^{3b}$ is hydrogen.

In one aspect, in the compound of formula (Ib), $R^{1b}$ is —$CH_2F$, $R^{2b}$ is methyl and $R^{3b}$ is hydrogen.

In one aspect, in the compound of formula (Ib), $R^{1b}$ is —$CH_2OH$ and $R^{2b}$ and $R^{3b}$ are each hydrogen.

In some embodiments, the compound of formula (I) has the structure of formula (Ic), or a pharmaceutically acceptable salt thereof:

(Ic)

wherein $R^{1c}$ is phenyl, N-methyl-1,2,4-triazolyl, tetrahydropyranyl, pyrimidinyl, pyridinyl, pyrazinyl or $C_1$-$C_3$ alkyl, $C_1$-$C_3$ alkyl is which optionally substituted with one or more of: phenyl, halogen, —N$_3$ or OR$^{10c}$; and R$^{10c}$ is for each occurrence hydrogen or C$_1$-C$_4$ alkyl.

In one aspect, R$^{1c}$ is methyl, ethyl, phenyl, —CH$_2$-phenyl, —CH$_2$F, —CH$_2$OCH$_3$, tetrahydropyranyl, —CH$_2$N$_3$, pyridinyl, pyrimidinyl, pyrazinyl, —CH(CH$_3$)OCH$_3$, N-methyl-1,2,4-triazolyl or —CH$_2$OH.

In one aspect, R$^{10c}$ is hydrogen or methyl.

In one aspect, in the compound of formula (Ic), R$^{1c}$ is methyl.

In one aspect, in the compound of formula (Ic), R$^{1c}$ is ethyl.

In one aspect, in the compound of formula (Ic), R$^{1c}$ is phenyl.

In one aspect, in the compound of formula (Ic), R$^{1c}$ is —CH$_2$-phenyl.

In one aspect, in the compound of formula (Ic), R$^{1c}$ is —CH$_2$F.

In one aspect, in the compound of formula (Ic), R$^{1c}$ is —CH$_2$OCH$_3$.

In one aspect, in the compound of formula (Ic), R$^{1c}$ is tetrahydropyranyl.

In one aspect, in the compound of formula (Ic), R$^{1c}$ is —CH$_2$N$_3$.

In one aspect, in the compound of formula (Ic), R$^{1c}$ is pyridinyl.

In one aspect, in the compound of formula (Ic), R$^{1c}$ is pyrimidinyl.

In one aspect, in the compound of formula (Ic), R$^{1c}$ is pyrazinyl.

In one aspect, in the compound of formula (Ic), R$^{1c}$ is —CH(CH$_3$)OCH$_3$.

In one aspect, in the compound of formula (Ic), R$^{1c}$ is N-methyl-1,2,4-triazolyl.

In one aspect, in the compound of formula (Ic), R$^{1c}$ is —CH$_2$OH.

In some embodiments, the compound of formula (I) has the structure of formula (Id), or a pharmaceutically acceptable salt thereof:

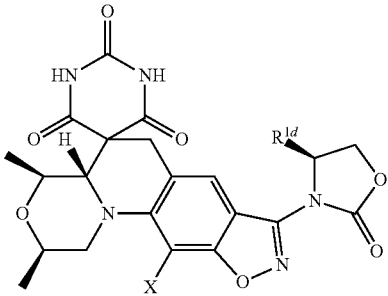

(Id)

wherein

X is chlorine or fluorine;

R$^{1d}$ is selected from the group consisting of hydrogen, phenyl, —C≡N, tetrahydropyranyl, N-methyl-1,2,4-triazolyl, pyrimidinyl, pyridinyl, pyrazinyl, cyclopropyl, —C≡CH, —CH═CH$_2$, and C$_1$-C$_3$ alkyl, which C$_1$-C$_3$ alkyl is optionally substituted with one or more of: —OR$^{10d}$, halogen, —C≡N, —N$_3$, —SO$_2$CH$_3$, —SCH$_3$, —CH═CH$_2$, —CH═NOR$^{11d}$ and phenyl;

R$^{10d}$ is for each occurrence independently selected from the group consisting of hydrogen, C$_1$-C$_4$ alkyl and —(CH$_2$)$_2$OCH$_3$; and R$^{11d}$ is for each occurrence independently hydrogen or C$_1$-C$_4$ alkyl.

In one aspect, R$^{1d}$ is methyl, ethyl, phenyl, —CH$_2$-phenyl, —CH$_2$F, —CH$_2$OCH$_3$, —CH$_2$CH═CH$_2$, tetrahydropyranyl, —(CH$_2$)$_3$OH, —(CH$_2$)$_3$F, —CH═CH$_2$, —C≡N, —CH═NOCH$_3$, —CH$_2$SCH$_3$, —CH$_2$SO$_2$CH$_3$, —CH$_2$N$_3$, —CH$_2$OCH$_2$CH$_3$, —CH$_2$O(CH$_2$)$_2$OCH$_3$, pyridinyl, —CH(CH$_3$)OCH$_3$, pyrimidinyl, pyrazinyl, —C≡CH, N-methyl-1,2,4-triazolyl, —CH(OH)CH$_3$, —CH(OH)CH$_2$OH or —CH═NOH.

In one aspect, R$^{10d}$ is hydrogen, methyl or ethyl.

In one aspect, R$^{10d}$ is hydrogen or methyl.

In one aspect, in the compound of formula (Id), X is fluorine and R$^{1d}$ is methyl.

In one aspect, in the compound of formula (Id), X is fluorine and R$^{1d}$ is ethyl.

In one aspect, in the compound of formula (Id), X is fluorine and R$^{1d}$ is phenyl.

In one aspect, in the compound of formula (Id), X is fluorine and R$^{1d}$ is —CH$_2$-phenyl.

In one aspect, in the compound of formula (Id), X is fluorine and R$^{1d}$ is —CH$_2$F.

In one aspect, in the compound of formula (Id), X is fluorine and R$^{1d}$ is —CH$_2$OCH$_3$.

In one aspect, in the compound of formula (Id), X is fluorine and R$^{1d}$ is —CH$_2$CH═CH$_2$.

In one aspect, in the compound of formula (Id), X is fluorine and R$^{1d}$ is tetrahydropyranyl.

In one aspect, in the compound of formula (Id), X is fluorine and R$^{1d}$ is —(CH$_2$)$_2$OH.

In one aspect, in the compound of formula (Id), X is fluorine and R$^{1d}$ is —(CH$_2$)$_2$F.

In one aspect, in the compound of formula (Id), X is chlorine and R$^{1d}$ is —(CH$_2$)$_3$OH.

In one aspect, in the compound of formula (Id), X is chlorine and R$^{1d}$ is —(CH$_2$)$_3$F.

In one aspect, in the compound of formula (Id), X is fluorine and R$^{1d}$ is —(CH$_2$)$_3$OH.

In one aspect, in the compound of formula (Id), X is fluorine and R$^{1d}$ is —CH═CH$_2$.

In one aspect, in the compound of formula (Id), X is fluorine and R$^{1d}$ is —(CH$_2$)$_3$OH.

In one aspect, in the compound of formula (Id), X is fluorine and R$^{1d}$ is —C≡N.

In one aspect, in the compound of formula (Id), X is fluorine and R$^{1d}$ is —CH═NOCH$_3$.

In one aspect, in the compound of formula (Id), X is fluorine and R$^{1d}$ is —CH$_2$SCH$_3$.

In one aspect, in the compound of formula (Id), X is fluorine and R$^{1d}$ is —CH$_2$SO$_2$CH$_3$.

In one aspect, in the compound of formula (Id), X is fluorine and R$^{1d}$ is —CH$_2$N$_3$.

In one aspect, in the compound of formula (Id), X is fluorine and R$^{1d}$ is —CH$_2$OCH$_2$CH$_3$.

In one aspect, in the compound of formula (Id), X is fluorine and R$^{1d}$ is —CH$_2$O(CH$_2$)$_2$OCH$_3$.

In one aspect, in the compound of formula (Id), X is fluorine and R$^{1d}$ is —CHF$_2$.

In one aspect, in the compound of formula (Id), X is fluorine and R$^{1d}$ is pyridinyl.

In one aspect, in the compound of formula (Id), X is fluorine and R$^{1d}$ is —CH(CH$_3$)OCH$_3$.

In one aspect, in the compound of formula (Id), X is fluorine and R$^{1d}$ is pyrimidinyl.

In one aspect, in the compound of formula (Id), X is fluorine and R$^{1d}$ is pyrazinyl.

In one aspect, in the compound of formula (Id), X is fluorine and $R^{1d}$ is —C≡CH.

In one aspect, in the compound of formula (Id), X is chlorine and $R^{1d}$ is methyl.

In one aspect, in the compound of formula (Id), X is fluorine and $R^{1d}$ is N-methyl-1,2,4-triazolyl.

In one aspect, in the compound of formula (Id), X is fluorine and $R^{1d}$ is —CH(OH)CH$_3$.

In one aspect, in the compound of formula (Id), X is fluorine and $R^{1d}$ is —CH(OH)CH$_2$OH.

In one aspect, in the compound of formula (Id), X is fluorine and $R^{1d}$ is —CH=NOH.

In some embodiment, the compound of formula (I) has the structure of formula (Ie) or a pharmaceutically acceptable salt thereof:

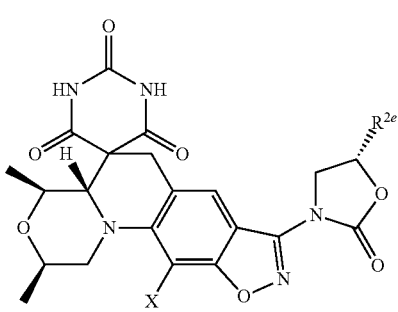

(Ie)

wherein
X is chlorine or fluorine;
$R^{2e}$ is selected from the group consisting of pyridinyl, —C≡N or $C_1$-$C_3$ alkyl, which $C_1$-$C_3$ alkyl is optionally substituted with one or more of: $OR^{20e}$, halogen, azido and CH=NOR$^{21e}$; and
$R^{20e}$ and $R^{21e}$ are for each occurrence independently hydrogen or $C_1$-$C_4$ alkyl.

In one aspect, $R^{2e}$ is methyl, ethyl, —CH$_2$OCH$_3$, —CH$_2$OH, —CH$_2$F, —CH$_2$N$_3$, pyridinyl, —CH=NOH or —CH=NOCH$_3$.

In one aspect $R^{20e}$ is hydrogen or methyl.

In one aspect, $R^{21e}$ is hydrogen or methyl.

In one aspect, in the compound of formula (Ie), X is fluorine and $R^{2e}$ is methyl.

In one aspect, in the compound of formula (Ie), X is fluorine and $R^{2e}$ is ethyl.

In one aspect, in the compound of formula (Ie), X is chlorine and $R^{2e}$ is —CH$_2$OCH$_3$.

In one aspect, in the compound of formula (Ie), X is chlorine and $R^{2e}$ is methyl.

In one aspect, in the compound of formula (Ie), X is fluorine and $R^{2e}$ is —CH$_2$OCH$_3$.

In one aspect, in the compound of formula (Ie), X is fluorine and $R^{2e}$ is —CH$_2$OH.

In one aspect, in the compound of formula (Ie), X is fluorine and $R^{2e}$ is —CH$_2$F.

In one aspect, in the compound of formula (Ie), X is fluorine and $R^{2e}$ is —CH$_2$N$_3$.

In one aspect, in the compound of formula (Ie), X is fluorine and $R^{2e}$ is pyridinyl.

In one aspect, in the compound of formula (Ie), X is fluorine and $R^{2e}$ is —CH=NOH In one aspect, in the compound of formula (Ie), X is fluorine and $R^{2e}$ is —CH=NOCH$_3$.

In some embodiments, the compound of formula (I) has the structure of formula (If) or a pharmaceutically acceptable salt thereof:

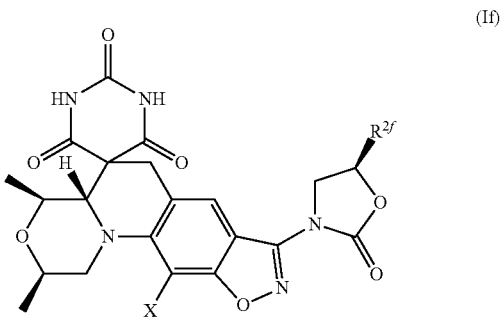

(If)

wherein
X is chlorine or fluorine;
$R^{2f}$ is pyridinyl or $C_1$-$C_3$ alkyl, which $C_1$-$C_3$ alkyl is optionally substituted with one or more halogen or —OR$^{20f}$; and
$R^{20f}$ is for each occurrence independently hydrogen or $C_1$-$C_4$ alkyl.

In one aspect, $R^{2f}$ is methyl, ethyl, —CH$_2$F, —CH$_2$OCH$_3$ or —CH$_2$OH.

In one aspect, $R^{20f}$ is hydrogen or methyl.

In one aspect, in the compound of formula (If), X is fluorine and $R^{2f}$ is methyl.

In one aspect, in the compound of formula (If), X is fluorine and $R^{2f}$ is ethyl.

In one aspect, in the compound of formula (If), X is fluorine and $R^{2f}$ is —CH$_2$F.

In one aspect, in the compound of formula (If), X is chlorine and $R^{2f}$ is —CH$_2$OCH$_3$.

In one aspect, in the compound of formula (If), X is chlorine and $R^{2f}$ is methyl.

In one aspect, in the compound of formula (If), X is fluorine and $R^{2f}$ is —CH$_2$OH.

In one aspect, in the compound of formula (If), X is chlorine and $R^{2f}$ is —CH$_2$F.

In one aspect, in the compound of formula (If), X is fluorine and $R^{2f}$ is —CH$_2$OCH$_3$.

In some embodiments, the compound of formula (I) has the structure of formula (Ig) or a pharmaceutically acceptable salt thereof:

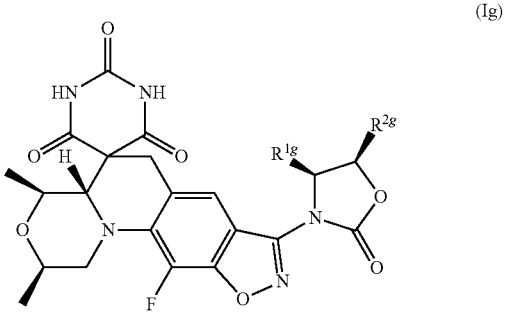

(Ig)

wherein
$R^{1g}$ is $C_1$-$C_3$ alkyl optionally substituted by one or more of halogen and OR$^{10g}$;
$R^{2g}$ is $C_1$-$C_3$ alkyl; and $R^{10g}$ is for each occurrence independently hydrogen or $C_1$-$C_4$ alkyl.

In one aspect, $R^{1g}$ is methyl, —CH$_2$OCH$_3$ or —CH$_2$F.

In one aspect, $R^{2g}$ is methyl.

In one aspect, $R^{10g}$ is hydrogen or methyl.

In one aspect, in the compound of formula (Ig), X is fluorine, $R^{1g}$ and $R^{2d}$ are each methyl.

In one aspect, in the compound of formula (Ig), X is fluorine, $R^{1g}$ is —CH$_2$OCH$_3$ and $R^{2d}$ is methyl.

In one aspect, in the compound of formula (Ig), X is fluorine, $R^{1g}$ is —CH$_2$F and $R^{2d}$ is methyl.

In one aspect, the present invention provides, at least in part, to the following compounds, or a pharmaceutically acceptable salt, thereof:

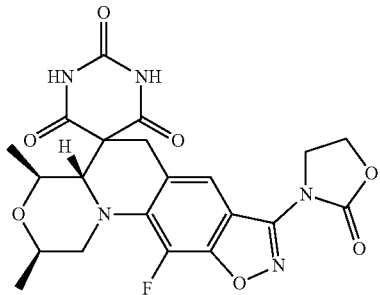

(2R,4S,4aS)-11-Fluoro-2,4-dimethyl-8-(2-oxo-1,3-oxazolidin-3-yl)-1,2,4,4a-tetrahydro-2′H,6H-spiro[1,4-oxazino[4,3-a][1,2]oxazolo[4,5-g]quinoline-5,5′-pyrimidine]-2′,4′,6′(1′H,3′H)-trione

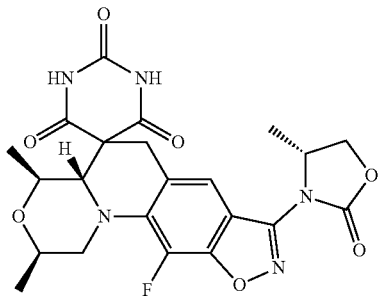

(2R,4S,4aS)-11-Fluoro-2,4-dimethyl-8-[(4R)-4-methyl-2-oxo-1,3-oxazolidin-3-yl]-1,2,4,4a-tetrahydro-2′H,6H-spiro[1,4-oxazino[4,3-a][1,2]oxazolo[4,5-g]quinoline-5,5′-pyrimidine]-2′,4′,6′(1′H,3′H)-trione

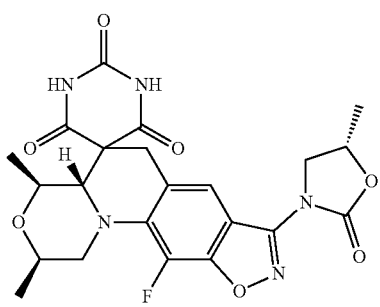

(2R,4S,4aS)-11-Fluoro-2,4-dimethyl-8-[(5S)-5-methyl-2-oxo-1,3-oxazolidin-3-yl]-1,2,4,4a-tetrahydro-2′H,6H-spiro[1,4-oxazino[4,3-a][1,2]oxazolo[4,5-g]quinoline-5,5′-pyrimidine]-2′,4′,6′(1′H,3′H)-trione -continued

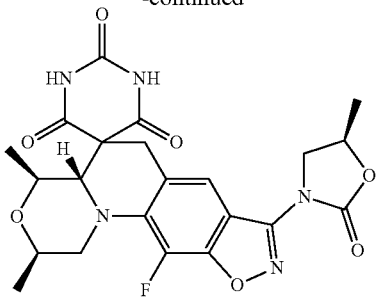

(2R,4S,4aS)-11-Fluoro-2,4-dimethyl-8-[(5R)-5-methyl-2-oxo-1,3-oxazolidin-3-yl]-1,2,4,4a-tetrahydro-2′H,6H-spiro[1,4-oxazino[4,3-a][1,2]oxazolo[4,5-g]quinoline-5,5′-pyrimidine]-2′,4′,6′(1′H,3′H)-trione

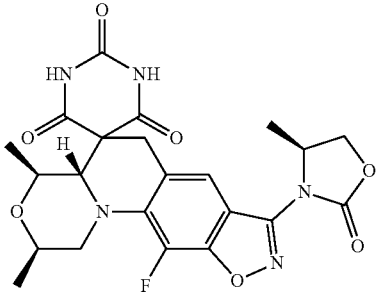

(2R,4S,4aS)-11-Fluoro-2,4-dimethyl-8-[(4S)-4-methyl-2-oxo-1,3-oxazolidin-3-yl]-1,2,4,4a-tetrahydro-2′H,6H-spiro[1,4-oxazino[4,3-a][1,2]oxazolo[4,5-g]quinoline-5,5′-pyrimidine]-2′,4′,6′(1′H,3′H)-trione

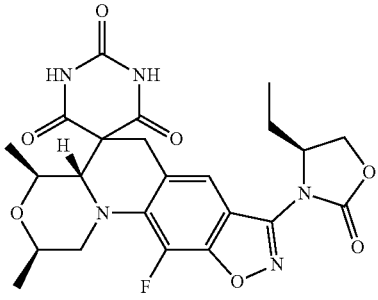

(2R,4S,4aS)-8-[(4S)-4-Ethyl-2-oxo-1,3-oxazolidin-3-yl]-11-fluoro-2,4-dimethyl-1,2,4,4a-tetrahydro-2′H,6H-spiro[1,4-oxazino[4,3-a][1,2]oxazolo[4,5-g]quinoline-5,5′-pyrimidine]-2′,4′,6′(1′H,3′H)-trione

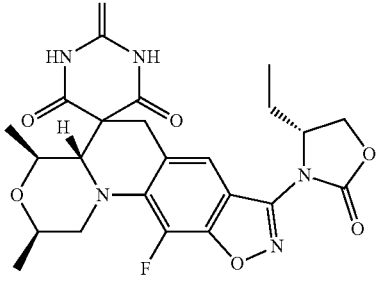

(2R,4S,4aS)-8-[(4R)-4-Ethyl-2-oxo-1,3-oxazolidin-3-yl]-11-fluoro-2,4-dimethyl-1,2,4,4a-tetrahydro-2′H,6H-spiro[1,4-oxazino[4,3-a][1,2]oxazolo[4,5-g]quinoline-5,5′-pyrimidine]-2′,4′,6′(1′H,3′H)-trione -continued

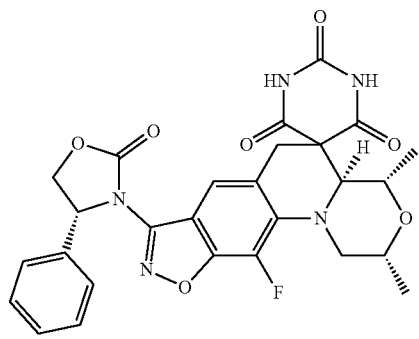

(2R,4S,4aS)-11-Fluoro-2,4-dimethyl-8-[(4R)-2-oxo-4-phenyl-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

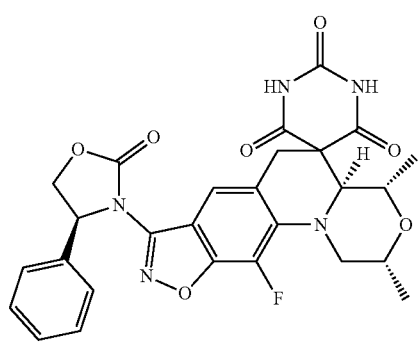

(2R,4S,4aS)-11-Fluoro-2,4-dimethyl-8-[(4S)-2-oxo-4-phenyl-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

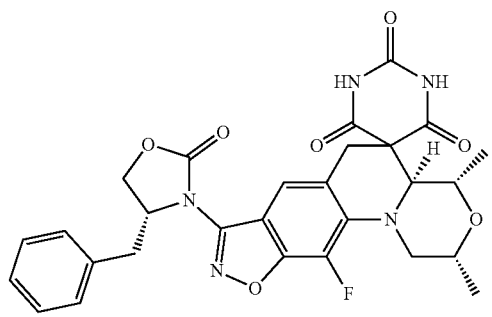

(2R,4S,4aS)-8-[(4R)-4-Benzyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

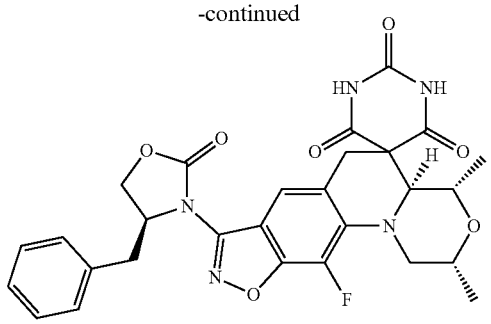

(2R,4S,4aS)-8-[(4S)-4-Benzyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

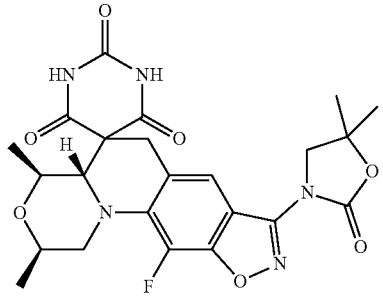

(2R,4S,4aS)-8-(5,5-Dimethyl-2-oxo-1,3-oxazolidin-3-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

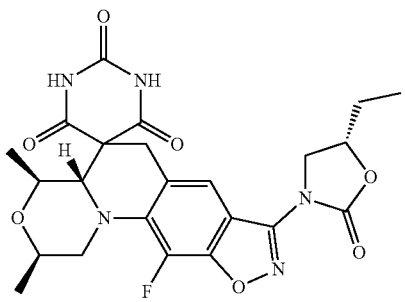

(2R,4S,4aS)-8-[(5S)-5-Ethyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

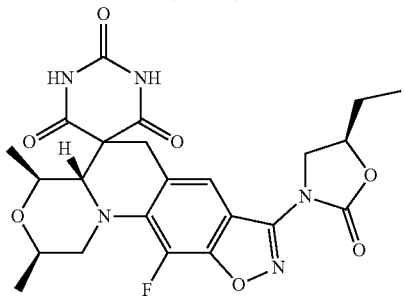

(2R,4S,4aS)-8-[(5R)-5-Ethyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

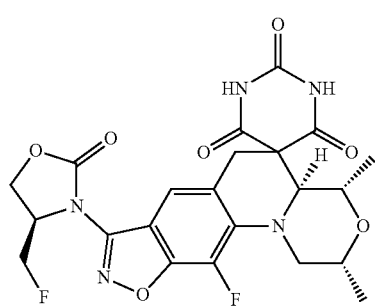

(2R,4S,4aS)-11-Fluoro-8-[(4R)-4-(fluoromethyl)-
2-oxo-1,3-oxazolidin-3-yl]-2,4-dimethyl-1,2,4,4a-
tetrahydro-2′H,6H-spiro[1,4-oxazino[4,3-
a][1,2]oxazolo[4,5-g]quinoline-5,5′-pyrimidine]-
2′,4′,6′(1′H,3′H)-trione

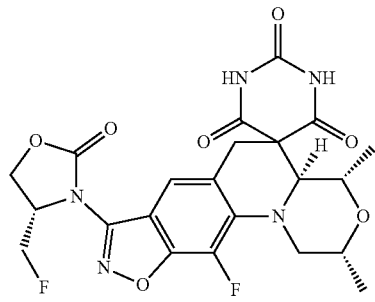

(2R,4S,4aS)-11-Fluoro-8-[(4S)-4-(fluoromethyl)-
2-oxo-1,3-oxazolidin-3-yl]-2,4-dimethyl-1,2,4,4a-
tetrahydro-2′H,6H-spiro[1,4-oxazino[4,3-
a][1,2]oxazolo[4,5-g]quinoline-5,5′-pyrimidine]-
2′,4′,6′(1′H,3′H)-trione

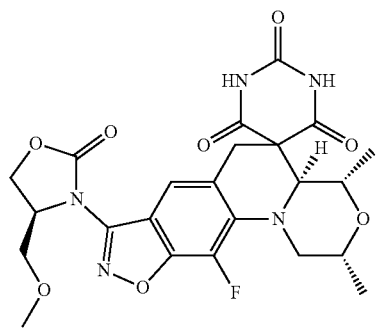

(2R,4S,4aS)-11-Fluoro-8-[(4S)-4-
(methoxymethyl)-2-oxo-1,3-
oxazolidin-3-yl]-2,4-dimethyl-1,2,4,4a-
tetrahydro-2′H,6H-spiro[1,4-oxazino[4,3-
a][1,2]oxazolo[4,5-g]quinoline-5,5′-pyrimidine]-
2′,4′,6′(1′H,3′H)-trione

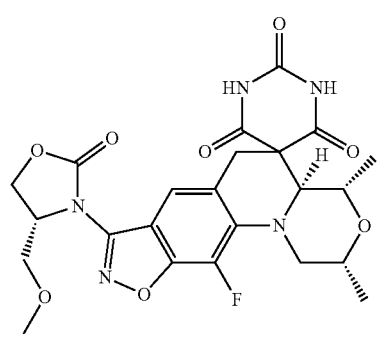

(2R,4S,4aS)-11-Fluoro-8-[(4R)-4-
(methoxymethyl)-2-oxo-1,3-
oxazolidin-3-yl]-2,4-dimethyl-1,2,4,4a-
tetrahydro-2′H,6H-spiro[1,4-oxazino[4,3-
a][1,2]oxazolo[4,5-g]quinoline-5,5′-pyrimidine]-
2′,4′,6′(1′H,3′H)-trione

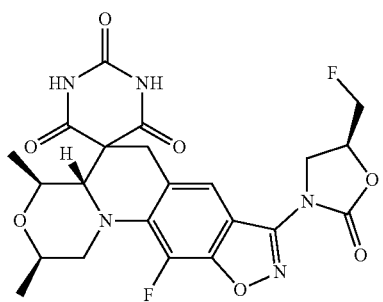

(2R,4S,4aS)-11-Fluoro-8-((S)-5-(fluoromethyl)-
2-oxooxazolidin-3-yl)-2,4-dimethyl-2,4,4a,6-
tetrahydro-1H,1′H-spiro[isoxazolo[4,5-
g][1,4]oxazino[4,3-a]quinoline-
5,5′-pyrimidine]-2′,4′,6′(3′H)-trione

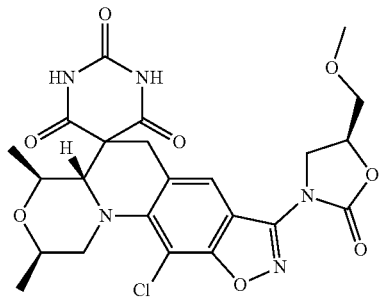

(2R,4S,4aS)-11-Chloro-8-[(5S)-4-
(methoxymethyl)-2-oxo-1,3-
oxazolidin-3-yl]-2,4-dimethyl-
1,2,4,4a-tetrahydro-2′H,6H-
spiro[1,4-oxazino[4,3-a][1,2]oxazolo[4,5-
g]quinoline-5,5′-pyrimidine]-
2′,4′,6′(1′H,3′H)-trione

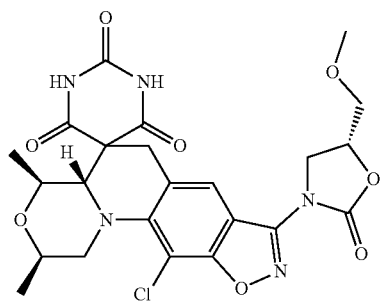

(2R,4S,4aS)-11-Chloro-8-[(5R)-4-
(methoxymethyl)-2-oxo-1,3-
oxazolidin-3-yl]-2,4-dimethyl-
1,2,4,4a-tetrahydro-2'H,6H-
spiro[1,4-oxazino[4,3-a][1,2]oxazolo[4,5-
g]quinoline-5,5'-pyrimidine]-
2',4',6'(1'H,3'H)-trione

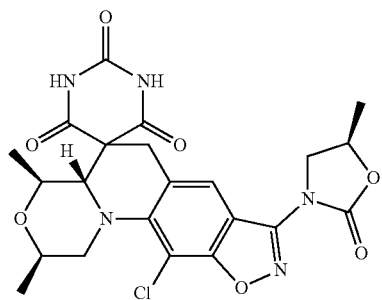

((2R,4S,4aS)-11-Chloro-2,4-dimethyl-8-((R)-5-
methyl-2-oxooxazolidin-3-yl)-2,4,4a,6-
tetrahydro-1H,1'H-spiro[isoxazolo[4,5-
g][1,4]oxazino[4,3-a]quinoline-5,5'-
pyrimidine]-2',4',6'(3'H)-trione

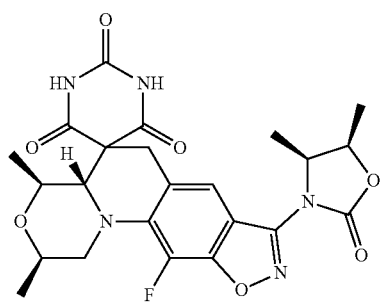

(2R,4S,4aS)-8-((4S,5R)-4,5-Dimethyl-2-
oxooxazolidin-3-yl)-11-fluoro-2,4-dimethyl-
2,4,4a,6-tetrahydro-1H,1'H-
spiro[isoxazolo[4,5-g][1,4]oxazino[4,3-
a]quinoline-5,5'-pyrimidine]-2',4',6'(3'H)-
trione

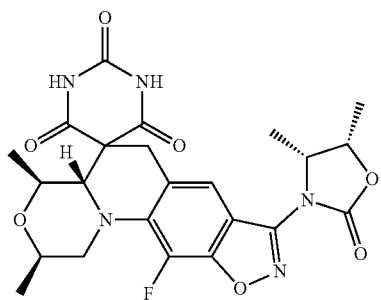

(2R,4S,4aS)-8-((4S,5R)-4,5-Dimethyl-2-
oxooxazolidin-3-yl)-11-fluoro-2,4-dimethyl-
2,4,4a,6-tetrahydro-1H,1'H-
spiro[isoxazolo[4,5-g][1,4]oxazino[4,3-
a]quinoline-5,5'-pyrimidine]-2',4',6'(3'H)-
trione

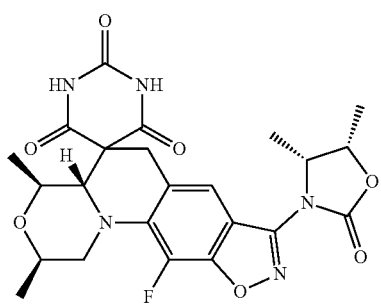

(2R,4S,4aS)-8-((S)-4-Allyl-2-
oxooxazolidin-3-yl)-11-fluoro-2,4-dimethyl-
2,4,4a,6-tetrahydro-1H,1'H-
spiro[isoxazolo[4,5-g][1,4]oxazino[4,3-
a]quinoline-5,5'-pyrimidine]-2',4',6'(3'H)-
trione

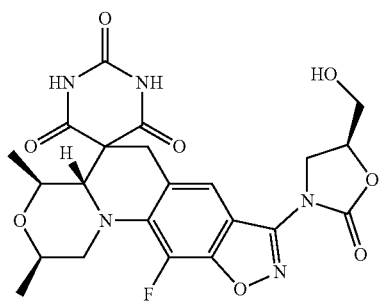

(2R,4S,4aS)-11-Fluoro-8-((S)-5-
(hydroxymethyl)-2-oxooxazolidin-3-yl)-
2,4-dimethyl-2,4,4a,6-tetrahydro-
1H,1'H-spiro[isoxazolo[4,5-
g][1,4]oxazino[4,3-a]quinoline-5,5'-
pyrimidine]-2',4',6'(3'H)-trione -continued

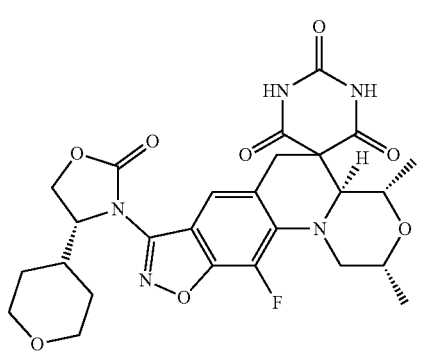

((2R,4S,4aS)-11-Fluoro-2,4-dimethyl-8-[(4R-(tetrahydro-2H-pyran-4-yl)-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

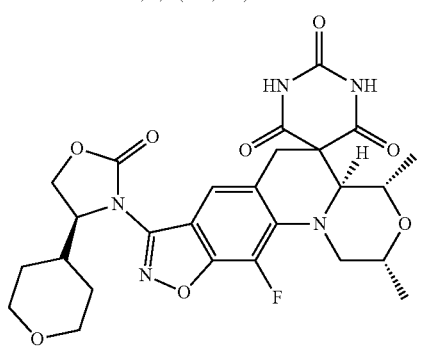

(2R,4S,4aS)-11-Fluoro-2,4-dimethyl-8-[(4S-(tetrahydro-2H-pyran-4-yl)-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

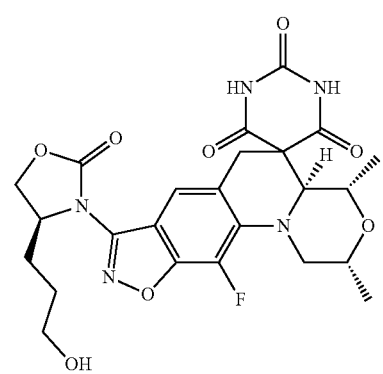

(2R,4S,4aS)-11-Fluoro-8-((S)-4-(3-hydroxypropyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione -continued

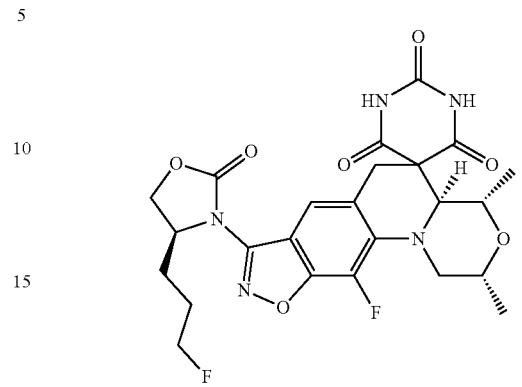

(2R,4S,4aS)-11-Fluoro-8-((S)-4-(3-fluoropropyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

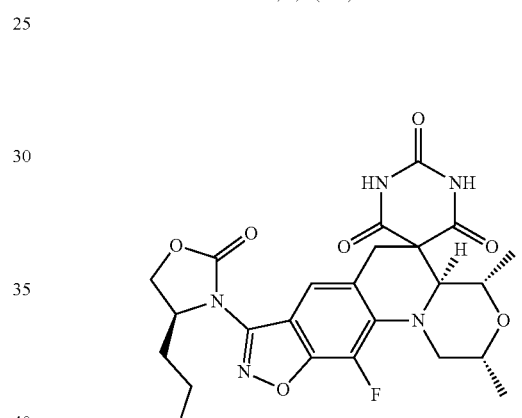

(2R,4S,4aS)-11-Fluoro-8-((S)-4-(2-hydroethyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

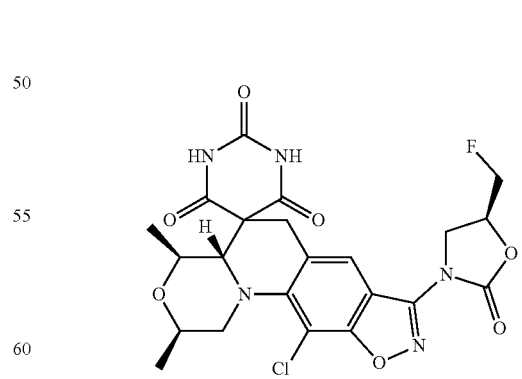

(2R,4S,4aS)-11-Chloro-8-((S)-5-(fluoromethyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione -continued

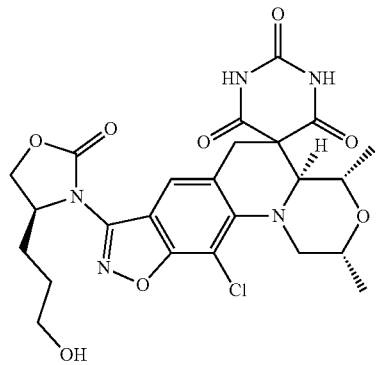

(2R,4S,4aS)-11-Choro-8-((S)-4-(3-hydroxpropyl)-
2-oxooxazolidin-3-yl)-2,4-dimethyl-2,4,4a,6-
tetrahydro-1H,1'H-spiro[isoxazolo[4,5-
g][1,4]oxazino[4,3-a]quinoline-5,5'-pyrimidine]-
2',4',6'(3'H)-trione

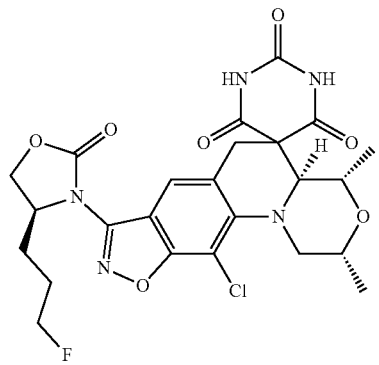

(2R,4S,4aS)-11-Choro-8-((S)-4-(3-fluoropropyl)-
2-oxooxazolidin-3-yl)-2,4-dimethyl-2,4,4a,6-
tetrahydro-1H,1'H-spiro[isoxazolo[4,5-
g][1,4]oxazino[4,3-a]quinoline-5,5'-pyrimidine]-
2',4',6'(3'H)-trione

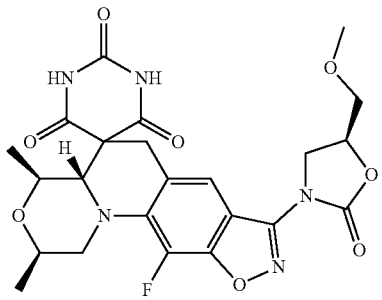

(2R,4S,4aS)-11-Fluoro-8-[(5S)-4-(methoxymethyl)-
2-oxo-1,3-oxazolidin-3-yl]-2,4-dimethyl-1,2,4,4a-
tetrahydro-2'H,6H-spiro[1,4-oxazino[4,3-
a][1,2]oxazolo[4,5-g]quinoline-5,5'-
pyrimidine]-2',4',6'(1'H,3'H)-trione -continued

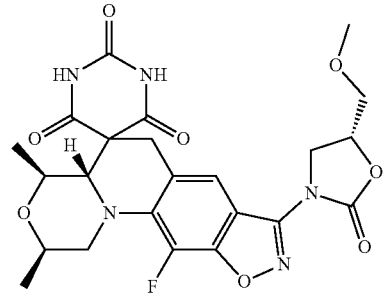

(2R,4S,4aS)-11-Fluoro-8-[(5R)-4-(methoxymethyl)-
2-oxo-1,3-oxazolidin-3-yl]-2,4-dimethyl-1,2,4,4a-
tetrahydro-2'H,6H-spiro[1,4-oxazino[4,3-
a][1,2]oxazolo[4,5-g]quinoline-5,5'-
pyrimidine]-2',4',6'(1'H,3'H)-trione

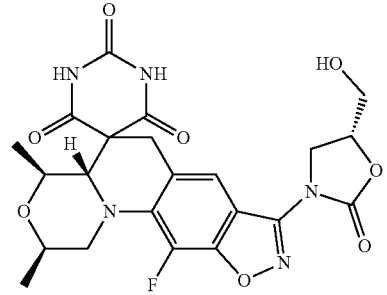

(2R,4S,4aS)-11-Fluoro-8-[(5R)-5-(hydroxymethyl)-
2-oxo-1,3-oxazolidin-3-yl]-2,4-dimethyl-1,2,4,4a-
tetrahydro-2'H,6H-spiro[1,4-oxazino[4,3-
a][1,2]oxazolo[4,5-g]quinoline-5,5'-
pyrimidine]-2',4',6'(1'H,3'H)-trione

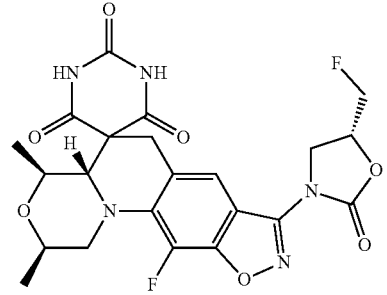

(2R,4S,4aS)-11-Fluoro-8-[(5R)-5-(fluoromethyl)-
2-oxo-1,3-oxazolidin-3-yl]-2,4-dimethyl-1,2,4,4a-
tetrahydro-2'H,6H-spiro[1,4-oxazino[4,3-
a][1,2]oxazolo[4,5-g]quinoline-5,5'-
pyrimidine]-2',4',6'(1'H,3'H)-trione -continued

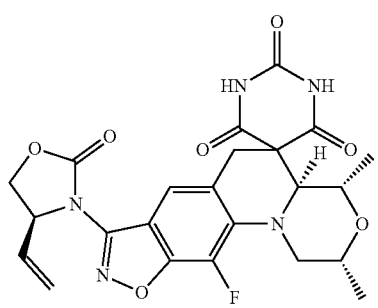

(2R,4S,4aS)-11-Fluoro-2,4-dimethyl-8-((S)-2-
oxo-4-vinyloxazolidin-3-yl)-2,4,4a,6-
tetrahydro-1H,1′H-spiro[isoxazolo[4,5-
g][1,4]oxazino[4,3-a]quinoline-5,5′-
pyrimidine]-2′,4′,6′(3′H)-trione

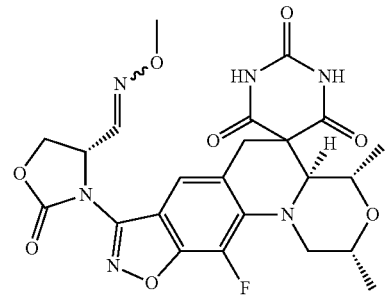

(2R,4S,4aS)-11-Fluoro-8-{(4S)-4-
[(methoxyimino)methyl]-2-oxo-1,3-oxazolidin-
3-yl}-2,4-dimethyl-1,2,4,4a-tetrahydro-
2′H,6H-spiro[1,4-oxazino[4,3-a][1,2]oxazolo[4,5-
g]quinoline-5,5′-pyrimidine]-2′,4′,6′(1′H,3′H)-
trione

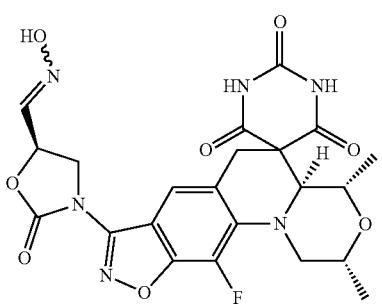

(2R,4S,4aS)-11-Fluoro-8-{(5R)-5-
[(hydroxyimino)methyl]-2-oxo-1,3-oxazolidin-
3-yl}-2,4-dimethyl-1,2,4,4a-tetrahydro-
2′H,6H-spiro[1,4-oxazino[4,3a][1,2]oxazolo[4,5-
g]quinoline-5,5′-pyrimidine]-2′,4′,6′(1′H,3′H)-
trione

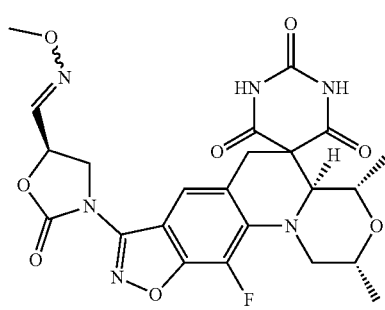

(2R,4S,4aS)-11-Fluoro-8-{(5R)-5-
[(methoxyimino)methyl]-2-oxo-1,3-oxazolidin-
3-yl}-2,4-dimethyl-1,2,4,4a-tetrahydro-
2′H,6H-spiro[1,4-oxazino[4,3-a][1,2]oxazolo[4,5-
g]quinoline-5,5′-pyrimidine]-2′,4′,6′(1′H,3′H)-
trione

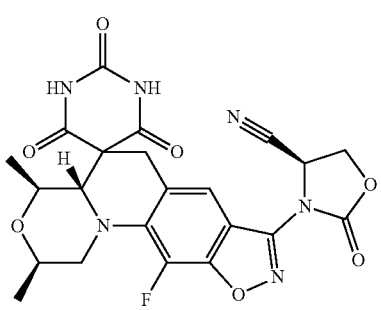

(4S)-3-[(2R,4S,4aS)-11-Fluoro-2,4-dimethyl-
2′,4′,6′-trioxo-1,1′,2,3′,4,4′,4a,6′-octahydro-
2′H,6H-spiro[1,4-oxazino[4,3-a][1,2]oxazolo[4,5-
g]quinoline-5,5′-pyrimidin]-8-yl]-2-oxo-
1,3-oxazolidine-4-carbonitrile

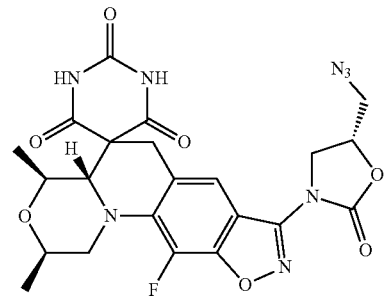

(2R,4S,4aS)-8-[(5R)-5-(Azidomethyl)-
2-oxo-1,3-oxazolidin-3-yl]-11-fluoro-2,4-
dimethyl-1,2,4,4a-tetrahydro-2′H,6H-
spiro[1,4-oxazino[4,3-a][1,2]oxazolo[4,5-
g]quinoline-5,5′-pyrimidine]-2′,4′,6′(1′H,3′H)-
trione

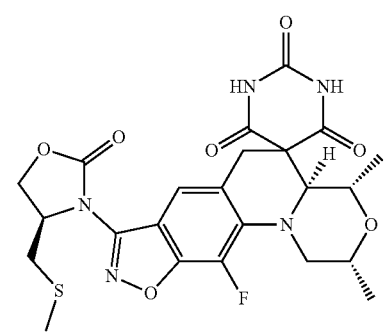

(2R,4S,4aS)-11-Fluoro-2,4-dimethyl-8-((R)-4-((methylthio)methyl)-2-oxooxazolidin-3-yl)-2,4,4a,6-tetrahydro-1H,1'H-spiro[isoxasolo[4,5-g][1,4]oxazino[4,3-a]quinoline-5,5'-pyrimidine]-2',4',6'(3'H)-trione

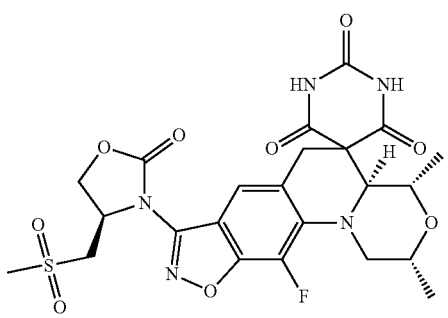

(2R,4S,4aS)-11-Fluoro-2,4-dimethyl-8-((R)-4-((methylsulfony)methyl)-2-oxooxazolidin-3-yl)-2,4,4a,6-tetrahydro-1H,1'H-spiro[isoxasolo[4,5-g][1,4]oxazino[4,3-a]quinoline-5,5'-pyrimidine]-2',4',6'(3'H)-trione

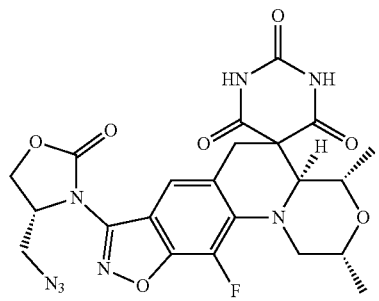

(2R,4S,4aS)-8-((R)-4-(Azidomethyl)-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

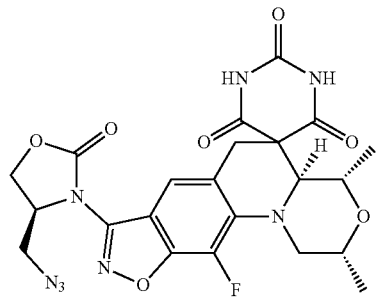

(2R,4S,4aS)-8-((S)-4-(azidomethyl)-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

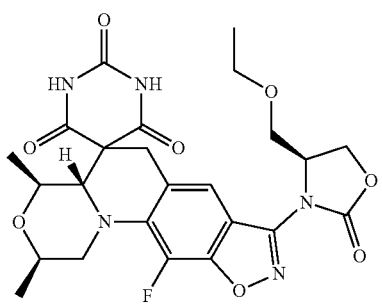

(2R,4S,4aS)-8-[(4S)-5-(Ethoxymethyl)-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

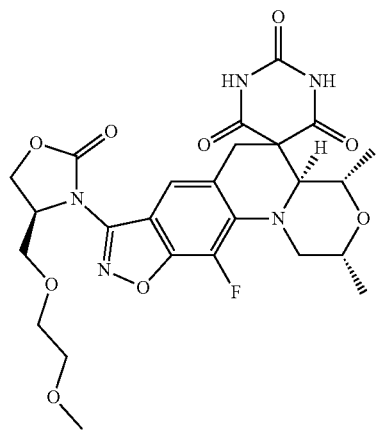

(2R,4S,4aS)-11-Fluoro-8-{(4S)-4-[(2-methoxyethoxy)methyl]-2-oxo-1,3-oxazolidin-3-yl}-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

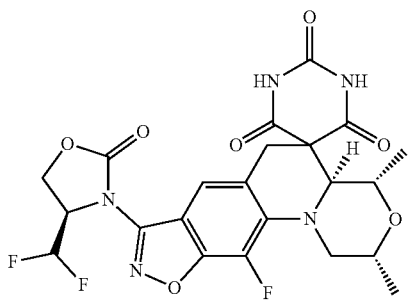

(2R,4S,4aS)-8-((R)-4-(Difluoromethyl)-2-oxooxazolidin-3-yl)-11-fluoro-2,4-dimethyl-2,4,4a,6-tetrahydro-1H,1'H-spiro[isoxazalo[4,5-g][1,4]quinoline-5,5'-pyrimidine]-2',4',6'(3'H)-trione

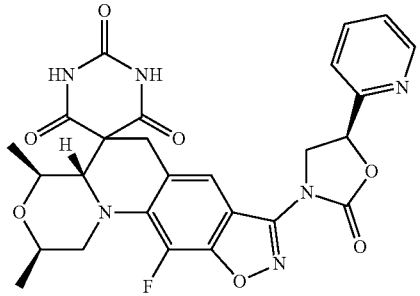

(2R,4S,4aS)-11-fluoro-2,4-dimethyl-8-((S)-2-oxo-5-(pyridin-2-yl)oxazolidin-3-yl)-2,4,4a,6-tetrahydro-1H,1'H-spiro[isoxazalo[4,5-g][1,4]oxazino[4,3-a]quinoline-5,5'-pyrimidine]-2',4',6'(3'H)-trione

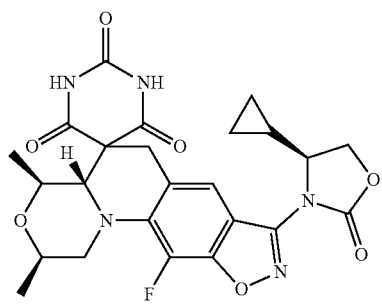

(2R,4S,4aS)-8-((S)-4-Cyclopropyl-2-oxooxazolidin-3-yl)-11-fluoro-2,4-dimethyl-2,4,4a,6-tetrahydro-1H,1'H-spiro[isoxazalo[4,5-g][1,4]oxazino[4,3-a]quinoline-5,5'-pyrimidine]-2',4',6'(3'H)-trione

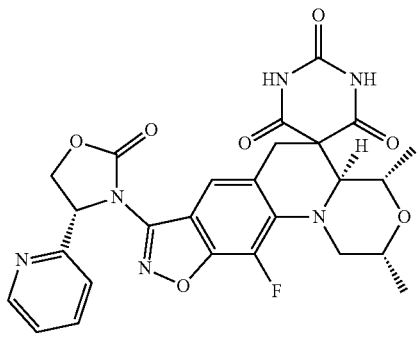

(2R,4S,4aS)-11-Fluoro-2,4-dimethyl-8-((R)-2-oxo-4-(pyridin-2-yl)oxazolidin-3-yl)-2,4,4a,6-tetrahydro-1H,1'H-spiro[isoxazalo[4,5-g][1,4]oxazino[4,3-a]quinoline-5,5'-pyrimidine]-2',4',6'(3'H)-trione

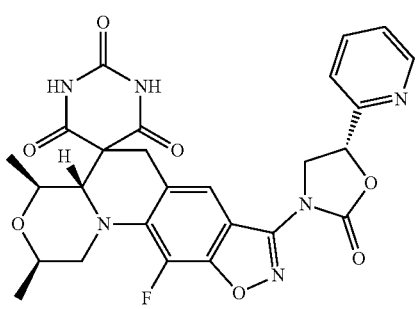

(2R,4S,4aS)-11-Fluoro-2,4-dimethyl-8-((R)-2-oxo-5-(pyridin-2-yl)oxazolidin-3-yl)-2,4,4a,6-tetrahydro-1H,1'H-spiro[isoxazalo[4,5-g][1,4]oxazino[4,3-a]quinoline-5,5'-pyrimidine]-2',4',6'(3'H)-trione

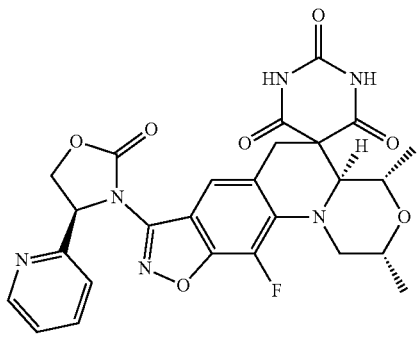

(2R,4S,4aS)-11-fluoro-2,4-dimethyl-8-((S)-2-oxo-4-(pyridin-2-yl)oxazolidin-3-yl)-2,4,4a,6-tetrahydro-1H,1'H-spiro[isoxazalo[4,5-g][1,4]oxazino[4,3-a]quinoline-5,5'-pyrimidine]-2',4',6'(3'H)-trione

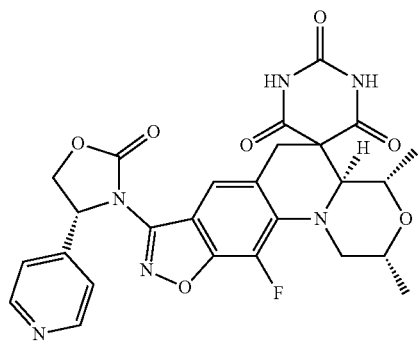

(2R,4S,4aS)-11-Fluoro-2,4-dimethyl-8-((R)-2-oxo-4-(pyridin-4-yl)oxazolidin-3-yl)-2,4,4a,6-tetrahydro-1H,1'H-spiro[isoxazalo[4,5-g][1,4]oxazino[4,3-a]quinoline-5,5'-pyrimidine]-2',4',6'(3'H)-trione

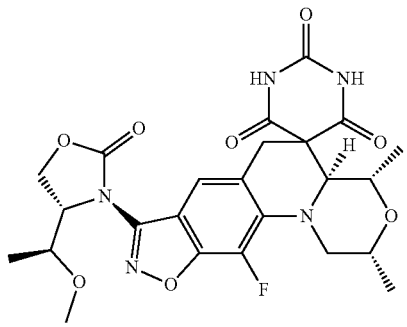

(2R,4S,4aS)-11-Fluoro-8-((R)-4-((S)-1-methoxyethyl)-2-oxooxazolidin-3-yl)-2,4-dimethyl-2,4,4a,6-tetrahydro-1H,1'H-spiro[isoxazalo[4,5-g][1,4]oxazino[4,3-a]quinoline-5,5'-pyrimidine]-2',4',6'(3'H)-trione

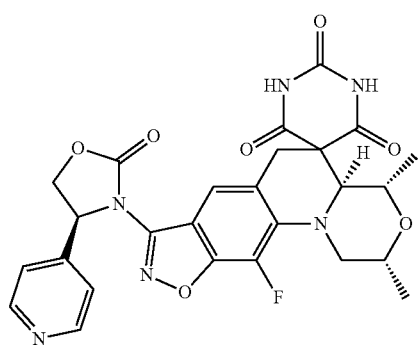

(2R,4S,4aS)-11-fluoro-2,4-dimethyl-8-((S)-2-oxo-4-(pyridin-4-yl)oxazolidin-3-yl)-2,4,4a,6-tetrahydro-1H,1'H-spiro[isoxazalo[4,5-g][1,4]oxazino[4,3-a]quinoline-5,5'-pyrimidine]-2',4',6'(3'H)-trione

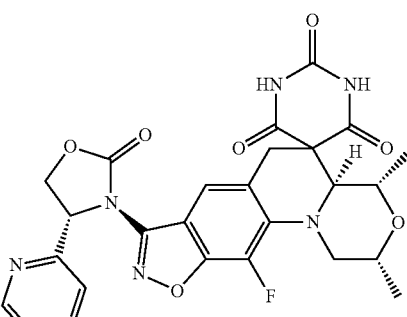

(2R,4S,4aS)-11-Fluoro-2,4-dimethyl-8-((R)-2-oxo-4-(pyrazin-2-yl)oxazolidin-3-yl)-2,4,4a,6-tetrahydro-1H,1'H-spiro[isoxazalo[4,5-g][1,4]oxazino[4,3-a]quinoline-5,5'-pyrimidine]-2',4',6'(3'H)-trione

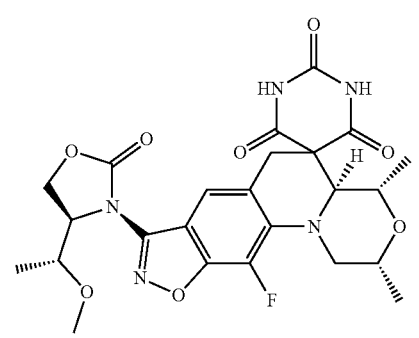

(2R,4S,4aS)-11-Fluoro-8-((R)-4-((R)-1-methoxyethyl)-2-oxooxazolidin-3-yl)-2,4-dimethyl-2,4,4a,6-tetrahydro-1H,1'H-spiro[isoxazalo[4,5-g][1,4]oxazino[4,3-a]quinoline-5,5'-pyrimidine]-2',4',6'(3'H)-trione

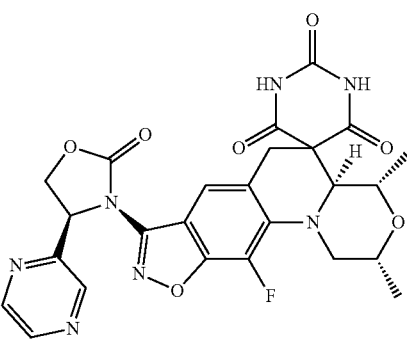

(2R,4S,4aS)-11-fluoro-2,4-dimethyl-8-((S)-2-oxo-4-(pyrazin-2-yl)oxazolidin-3-yl)-2,4,4a,6-tetrahydro-1H,1'H-spiro[isoxazalo[4,5-g][1,4]oxazino[4,3-a]quinoline-5,5'-pyrimidine]-2',4',6'(3'H)-trione -continued

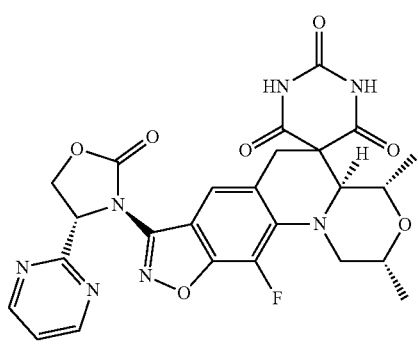

(2R,4S,4aS)-11-Fluoro-2,4-dimethyl-8-((R)-2-oxo-4-(pyrimidin-2-yl)oxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

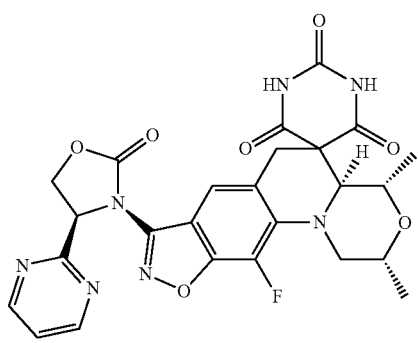

(2R,4S,4aS)-11-fluoro-2,4-dimethyl-8-((S)-2-oxo-4-(pyrimidin-2-yl)oxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

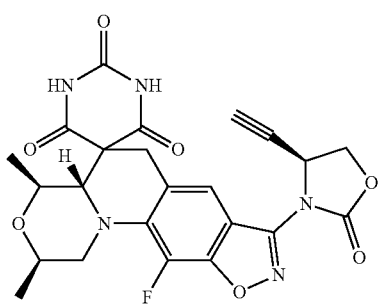

(2R,4S,4aS)-8-((S)-4-Ethynyl-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione -continued

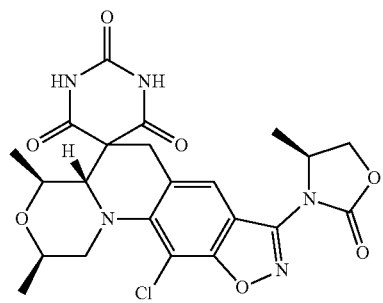

(2R,4S,4aS)-11-Chloro-2,4-dimethyl-8-((S)-4-methyl-2-oxooxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

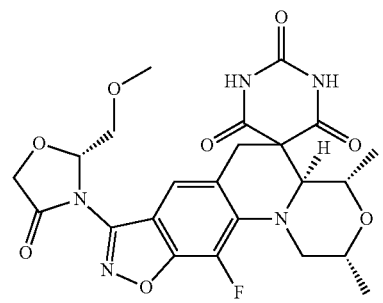

(2R,4S,4aS)-11-Fluoro-8[(4S)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

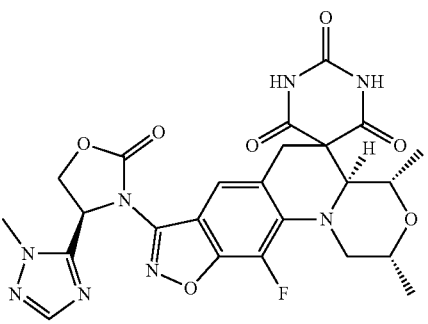

(2R,4S,4aS)-11-Fluoro-2,4-dimethyl-8-((S)-4-(1-methyl-1H-1,2,4-triazol-5-yl)-2-oxooxazolidin-3-yl)-2,4,4a,6-tetrahydro-1H,1'H-spiro[isoxazolo[4,5-g][1,2]oxazino[4,5-a]quinoline-5,5'-pyrimidine]-2',4',6'(3'H)-trione

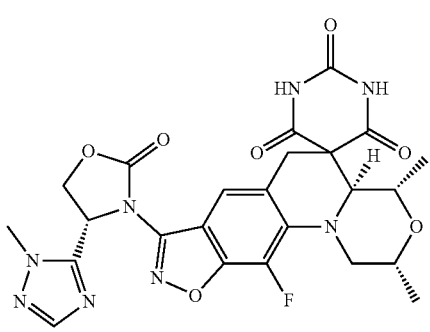

(2R,4S,4aS)-11-Fluoro-2,4-dimethyl-8-((R)-4-(1-methyl-1H-1,2,4-triazol-5-yl)-2-oxooxazolidin-3-yl)-2,4,4a,6-tetrahydro-1H,1'H-spiro[isoxazolo[4,5-g][1,2]oxazino[4,5-a]quinoline-5,5'-pyrimidine]-2',4',6'(3'H)-trione

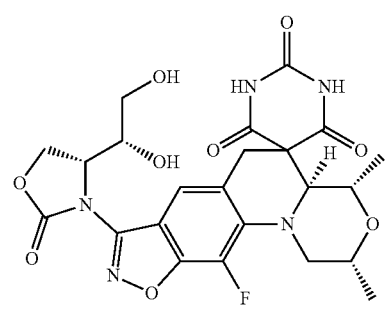

(2R,4S,4aS)-8-((R)-4-((R)-1,2-Dihydroxyethyl)-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

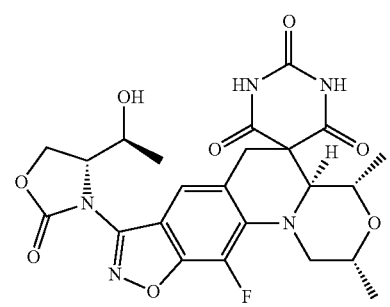

(2R,4S,4aS)-11-Fluoro-8-((R)-4-((S)-1-hydroxyethyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

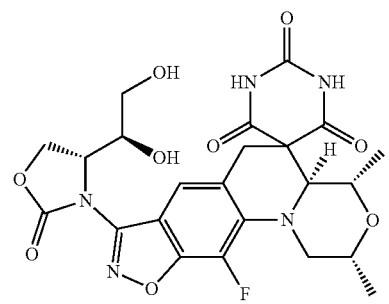

(2R,4S,4aS)-8-((R)-4-((S)-1,2-Dihydroxyethyl)-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

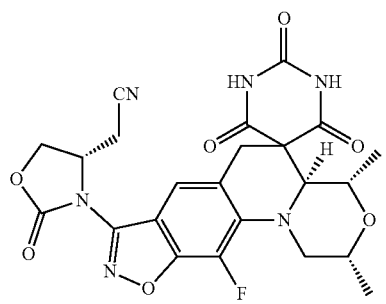

{(4S)-3-[(2R,4S,4aS)-11-Fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-2-oxo-1,3-oxazolidin-4-yl}acetonitrile

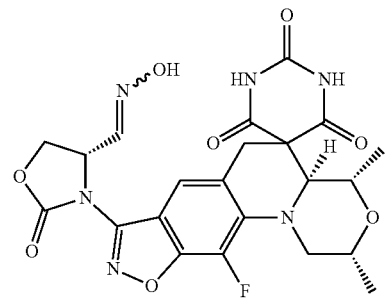

(2R,4S,4aS)-11-fluoro-8-{(4S)-4-[(hydroxyimino)methyl]-2-oxo-1,3-oxazolidin-3-yl}-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

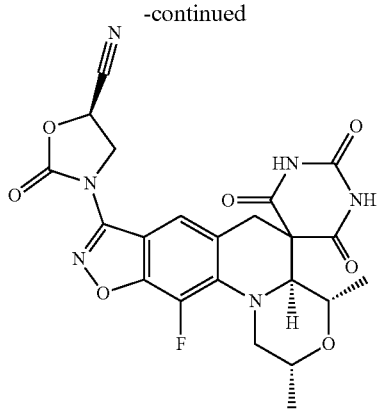

(5R)-3-[(2R,4S,4aS)-11-Fluoro-2,4-dimethyl-
2',4',6'-trioxo-1,1',2,3',4,4',4a,6'-octahydro-
2'H,6H-spiro[1,4-oxazino[4,3-
a][1,2]oxazolo[4,5-g]quinoline-5,5'-
pyrimidin]-8-yl]-2-oxo-1,3-oxazolidine-5-
carbonitrile

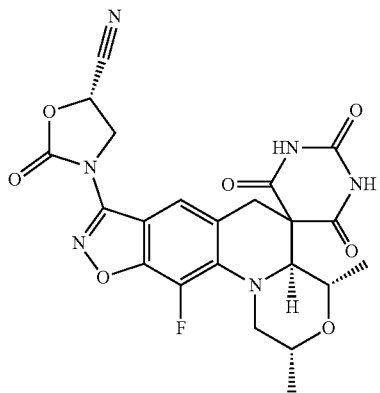

(5S)-3-[(2R,4S,4aS)-11-fluoro-2,4-dimethyl-
2',4',6'-trioxo-1,1',2,3',4,4',4a,6'-octahydro-
2'H,6H-spiro[1,4-oxazino[4,3-
a][1,2]oxazolo[4,5-g]quinoline-5,5'-
pyrimidin]-8-yl]-2-oxo-1,3-oxazolidine-5-
carbonitrile In one aspect, the invention pertains to a product obtainable by any process described in the Exemplification of the Invention.

The term "alkyl" includes straight and branched chain saturated hydrocarbon radicals having the specified number of carbon atoms. For example, "$C_1$-$C_3$ alkyl" includes alkyl groups with 1-3 carbon atoms, for example, methyl, ethyl, n-propyl and isopropyl groups. Likewise, the language "$C_1$-$C_4$ alkyl" includes alkyl groups with 1-4 carbon atoms, for example methyl, ethyl, n-propyl, isopropyl, n-butyl, isobutyl and tert-butyl groups.

The term "halogen" includes chlorine, fluorine, bromine and iodine.

The term "tetrahydropyranyl" includes

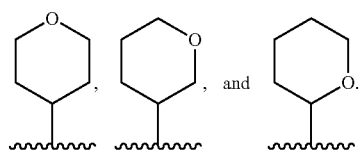

The term "N-methyl-1,2,4-triazolyl" includes

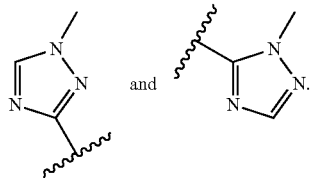

The term "pyridinyl" includes

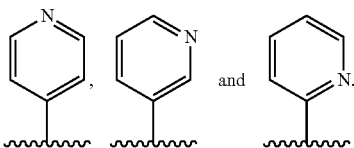

The term "pyrimidinyl" includes

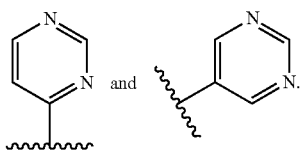 [SMILES: *c1ccncn1 ; *c1cncnc1]

The term "pyrazinyl" includes

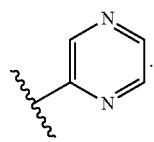

The language "pharmaceutically acceptable salt" includes acid addition or base salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, subsalicylate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as $Na^+$, $Ca^{2+}$, $Mg^{2+}$, or $K^+$ hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms for the compound of formula (I). Isotopically labeled compounds have structures depicted by the formulas given herein except that one or more atoms are replaced by an atom having a selected atomic mass or mass number. Examples of isotopes that can be incorporated into the compound of formula (I) include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{16}F$, $^{31}P$, $^{32}P$, $^{35}S$, $^{36}Cl$ and $^{125}I$. The invention includes various isotopically labeled compounds of formula (I) into which radioactive isotopes, such as $^2H$, $^3H$, $^{13}C$ and $^{14}C$, are present. Isotopically labeled compounds of formula (I) can generally be prepared by convention techniques known to those skilled in the art or by processes analogous to those described in the accompanying Examples using appropriate isotopically labeled reagents in place of the non-labeled reagents previously employed.

The compounds of formula (I) may have different isomeric forms. The language "optical isomer" or "stereoisomer" refers to any of the various stereoisomeric configurations which may exist for a given compound of the present invention. It is understood that a substituent may be attached at a chiral center of a carbon atom and, therefore, the invention includes enantiomers, diastereomers and racemates of the compound. The term "enantiomer" includes pairs of stereoisomers that are non-superimposable mirror images of each other. A 1:1 mixture of a pair of enantiomers is a racemic mixture. The term is used to designate a racemic mixture where appropriate. The terms "diastereomers" or "diastereoisomers" include stereoisomers that have at least two asymmetric atoms, but which are not mirror images of each other. The absolute stereochemistry is specified according to the Cahn-Ingold-Prelog R-S system. When a compound is a pure enantiomer, the stereochemistry at each chiral center may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers or other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques well known in the art, such as chiral HPLC.

Pharmaceutical Compositions

In some embodiments, the invention provides a pharmaceutical composition comprising a compound of formula (I) and a pharmaceutically acceptable excipient or diluent.

The language "pharmaceutically acceptable excipient or diluent" includes compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder), for parenteral administration (for example, as a sterile aqueous or oily solution for intravenous, subcutaneous, intramuscular or intramuscular dosing or as a suppository for rectal dosing) or for intraocular administration. The compositions of the invention may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient. For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

In some embodiments, the total amount of a compound of formula (I) administered to a subject may be between 400 mg to 10 g, between 400 mg-4 g, between 400-4000 mg, between 400-2000 mg, between 500-1900 mg, between 600-1800 mg, between 700-1700 mg or between 800-1600 mg, for example, 800 mg, 825 mg, 875 mg, 900 mg, 925 mg, 950 mg, 975 mg, 1000 mg, 1025 mg, 1050 mg, 1075 mg, 1100 mg, 1125 mg, 1150 mg, 1175 mg, 1200 mg, 1225 mg, 1250 mg, 1275 mg, 1300 mg, 1325 mg, 1350 mg, 1375 mg, 1400 mg, 1425 mg, 1450 mg, 1475 mg, 1500 mg, 1525 mg, 1550 mg, 1575 mg or 1600 mg. In some embodiments, the total amount of a compound of formula (I) administered to a subject may be between 400-500 mg, 500-600 mg, 600-700 mg, 700-800 mg, 800-900 mg, 900-1000 mg, 1000-1100 mg, 1100-1200 mg, 1200-1300 mg, 1300-1400 mg, 1400-1500 mg, 1500-1600 mg, 1600-1700 mg, 1700-1800 mg, 1800-1900 mg or 1900-2000 mg.

The compound of formula (I) may be administered once, twice, three times a day or as many times in a 24 hour period as medically necessary. One of skill in the art would readily be able to determine the amount of each individual dose based on the subject. In some embodiments, the compound of formula (I) is administered in one dosage form. In some embodiments, the compound of formula (I) is administered in multiple dosage forms.

Methods of Use

In one aspect, the invention provides a method for treating a bacterial infection in a subject in need thereof comprising administering an effective amount of a compound of formula (I), or a pharmaceutically acceptable salt thereof.

In one aspect, the invention provides the use of a compound of formula (I), or a pharmaceutically acceptable salt thereof, for treating a bacterial infection.

In one aspect, the invention provides the use of a compound of formula (I), or a pharmaceutically acceptable salt thereof, in the manufacture of a medicament for treating a bacterial infection.

In one aspect, the invention provides a pharmaceutical composition comprising a compound of formula (I), or a pharmaceutically acceptable salt thereof, for treating a bacterial infection.

The language "bacterial infection" includes infections caused by one or more species of Gram-negative, Gram-positive, or atypical bacteria.

In some embodiments, the bacterial infection is caused by Gram-positive bacteria, such as *Staphylococcus aureus, Streptococcus pyogenes, Streptococcus pneumoniae, Streptococcus agalactiae, Bacillus anthracis, Bacillus cereus* and *Bacillus subtilis.*

In some embodiments, the infection is caused by Gram-negative bacteria, such as *Haemophilus influenzae, Acinetobacter baumannii, Citrobacter freundii, Escherichia coli, Enterobacter cloacae, Pseudomonas aeruginosa, Klebsiella pneumoniae,* and *Neisseria gonorrhoeae.*

In some embodiments, the infection is caused by Mycobacteriaceae, such as *Mycobacterium tuberculosis, Mycobacterium avium-intracellulare, Mycobacterium marinum, Mycobacterium ulcerans* and *Mycobacterium kansasii.*

In some embodiments, the infection is caused by atypical bacteria, such as *Mycoplasma pneumoniae, Chlamydophila pneumoniae,* and *Legionella pneumophila.*

In some embodiments, the bacteria are resistant to one or more antibacterials other than the compounds of formula (I) described herein. The language "resistance" and "antibacterial resistance" refers to bacteria that are able to survive exposure to one or more antibacterials. In some embodiments, the antibacterial-resistant bacteria include *Streptococcus pyogenes, Streptococcus agalactiae, Streptococcus pneumoniae* (including penicillin-resistant *Streptococcus pneumoniae*), *Staphylococcus aureus* (including vancomycin-resistant *Staphylococcus aureus* (VRSA)), methicillin-resistant *Staphylococcus aureus* (MRSA) (including hospital-acquired MRSA, community acquired MRSA and coagulase negative staphylocci) and *Neisseria gonorrhoeae* (including penicillin-resistant *Neisseria gonorrhoeae,* for example, chromosomally-mediated penicillin resistant *Neisseria gonorrhoeae* (CMRNG) and penicillinase-mediated resistant *Neisseria gonorrhoeae* (PPNG), cephalosporin-resistant *Neisseria gonorrhoeae,* for example ceftriaxone-resistant *Neisseria gonorrhoeae* and cefixime-resistant *Neisseria gonorrhoeae,* quinolone-resistant *Neisseria gonorrhoeae* (QRNG), for example ciprofloxacin-resistant *Neisseria gonorrhoeae,* tetracycline-resistant *Neisseria gonorrhoeae,* for example, chromosomally-mediated tetracycline resistant *Neisseria gonorrhoeae* and plasmid-mediated penicillin resistant *Neisseria gonorrhoeae,* co-trimoxazole resistant *Neisseria gonorrhoeae* and aminoglycoside resistant *Neisseria gonorrhoeae,* for example, kanamycin resistant *Neisseria gonorrhoeae* and gentamicin resistant *Neisseria gonorrhoeae,* sulfonamide-resistant *Neisseria gonorrhoeae* and macrolide resistant *Neisseria gonorrhoeae,* for example, azithromycin resistant *Neisseria gonorrhoeae*).

In some embodiments, the *Neisseria gonorrhoeae* is multiple drug resistant *Neisseria gonorrhoeae* (MDRNG). The language "multiple drug resistant *Neisseria gonorrhoeae*" includes *Neisseria gonorrhoeae* that is resistant to two or more of antibiotics typically used for the treatment of *Neisseria gonffhoeae* infections, for example, tetracycline, penicillin, cephalosporins (e.g., ceftriazone or cefixime), quinolones (e.g., norfloxacin, ciprofloxacin or ofloxacin), co-trimoxazole, sulfonamides, aminoglycosides (e.g., kanamycin or gentamicin) and macrolides (e.g., azithromycin).

In one aspect, the invention provides a method for treating a Gram-positive bacterial infection in a subject in need thereof comprising administering an effective amount of a compound of formula (I), or a pharmaceutically acceptable salt thereof.

In one aspect, the invention provides the use of a compound of formula (I), or a pharmaceutically acceptable salt thereof, for treating a Gram-positive bacterial infection.

In one aspect, the invention provides the use of a compound of formula (I), or a pharmaceutically acceptable salt thereof, in the manufacture of a medicament for treating a Gram-positive bacterial infection.

In one aspect, the invention provides a pharmaceutical composition comprising a compound of formula (I), or a pharmaceutically acceptable salt thereof, for treating a Gram-positive bacterial infection.

In one aspect, the invention provides a method for treating complicated skin and skin structure infections in a subject in need thereof comprising administering an effective amount of a compound of formula (I), or a pharmaceutically acceptable salt thereof.

In one aspect, the invention provides the use of a compound of formula (I), or a pharmaceutically acceptable salt thereof, for treating a complicated skin and skin structure infections.

In one aspect, the invention provides the use of a compound of formula (I), or a pharmaceutically acceptable salt thereof, in the manufacture of a medicament for treating complicated skin and skin structure infections.

In one aspect, the invention provides a pharmaceutical composition comprising a compound of formula (I), or a pharmaceutically acceptable salt thereof, for treating complicated skin and skin structure infections.

The language "complicated skin and skin structure infections" includes infections of the skin and the surrounding soft tissues that may require significant surgical intervention, including, for example, infected ulcers, burns or major abscesses. In some embodiments, the complicated skin and skin structure infections are caused by *Streptococcus pyogenes, Streptococcus agalactiae,* or *Staphylococcus aureus,* including MRSA and/or VRSA.

In one aspect, the invention provides a method for treating pneumonia in a subject in need thereof comprising administering an effective amount of a compound of formula (I), or a pharmaceutically acceptable salt thereof.

In one aspect, the invention provides the use of a compound of formula (I), or a pharmaceutically acceptable salt thereof, for treating pneumonia.

In one aspect, the invention provides the use of a compound of formula (I), or a pharmaceutically acceptable salt thereof, in the manufacture of a medicament for treating pneumonia.

In one aspect, the invention provides a pharmaceutical composition comprising a compound of formula (I), or a pharmaceutically acceptable salt thereof, for treating pneumonia.

The term "pneumonia" refers to an inflammatory condition of the lungs caused by a bacterial infection. In some embodiments, the pneumonia is caused by a *Streptococcus pneumoniae* or *Staphylococcus aureus* infection. In some embodiments, the pneumonia is nocosomial pneumonia (e.g., hospital-acquired pneumonia) or community-acquired pneumonia. In some embodiments, the pneumonia is caused by penicillin-resistant *Streptococcus pneumoniae.*

In one aspect, the invention provides a method for treating a Gram-negative bacterial infection in a subject in need thereof comprising administering an effective amount of a compound of formula (I), or a pharmaceutically acceptable salt thereof.

In one aspect, the invention provides the use of a compound of formula (I), or a pharmaceutically acceptable salt thereof, for treating a Gram-negative bacterial infection.

In one aspect, the invention provides the use of a compound of formula (I), or a pharmaceutically acceptable salt thereof, in the manufacture of a medicament for treating a Gram-negative bacterial infection.

In one aspect, the invention provides a pharmaceutical composition comprising a compound of formula (I), or a pharmaceutically acceptable salt thereof, for treating a Gram-negative bacterial infection.

In one aspect, the invention provides a method for treating an atypical bacterial infection in a subject in need thereof comprising administering an effective amount of a compound of formula (I), or a pharmaceutically acceptable salt thereof.

In one aspect, the invention provides the use of a compound of formula (I), or a pharmaceutically acceptable salt thereof, for treating an atypical bacterial infection.

In one aspect, the invention provides the use of a compound of formula (I), or a pharmaceutically acceptable salt thereof, in the manufacture of a medicament for treating a atypical bacterial infection.

In one aspect, the invention provides a pharmaceutical composition comprising a compound of formula (I), or a pharmaceutically acceptable salt thereof, for treating an atypical bacterial infection.

In one aspect, the invention provides a method for inhibiting bacterial DNA gyrase in a subject in need thereof, comprising administering an effective amount of a compound of formula (I), or a pharmaceutically acceptable salt thereof.

In one aspect, the invention provides the use of a compound of formula (I), or a pharmaceutically acceptable salt thereof, for inhibiting bacterial DNA gyrase.

In one aspect, the invention provides the use of a compound of formula (I), or a pharmaceutically acceptable salt thereof, in the manufacture of a medicament for inhibiting bacterial DNA gyrase.

In one aspect, the invention provides a pharmaceutical composition comprising a compound of formula (I), or a pharmaceutically acceptable salt thereof, for inhibiting bacterial DNA gyrase.

The language "bacterial DNA gyrase" refers to a bacterial type II topoisomerase that introduces negative supercoils into DNA.

The language "effective amount" includes an amount of the compound of formula (I) that will elicit a biological or medical response of a subject, for example, the reduction or inhibition of enzyme or protein activity related to a bacterial DNA gyrase or a bacterial infection, amelioration of symptoms of a bacterial infection, or the slowing or delaying of progression of a bacterial infection. In some embodiments, the language "effective amount" includes the amount of a compound of formula (I), that when administered to a subject, is effective to at least partially alleviate, inhibit, and/or ameliorate a bacterial infection or inhibit bacterial DNA gyrase, and/or reduce or inhibit the bacterial growth, replication or bacterial load of a bacteria in a subject.

In one aspect, the invention provides a method for treating a *Neisseria gonorrhoeae* infection in a subject in need thereof comprising administering an effective amount of a compound of formula (I), or a pharmaceutically acceptable salt thereof.

In one aspect, the invention provides the use of a compound of formula (I), or a pharmaceutically acceptable salt thereof, for treating a *Neisseria gonorrhoeae* infection.

In one aspect, the invention provides the use of a compound of formula (I), or a pharmaceutically acceptable salt thereof, in the manufacture of a medicament for treating a *Neisseria gonorrhoeae* infection.

In one aspect, the invention provides a pharmaceutical composition comprising a compound of formula (I), or a pharmaceutically acceptable salt thereof, for treating a *Neisseria gonorrhoeae* infection.

The term "subject" includes warm blooded mammals, for example, primates, cows, pigs, sheep, dogs, cats, rabbits, rats, and mice. In some embodiments, the subject is a primate, for example, a human. In some embodiments, the subject is suffering from a Gram-positive bacterial infection. In some embodiments, the subject is in need of treatment (e.g., the subject would benefit biologically or medically from treatment). In some embodiments, the subject is suffering from a significant underlying disease state that complicates the response to treatment of a bacterial infection, for example diabetes mellitus.

The language "inhibit," "inhibition" or "inhibiting" includes a decrease in the baseline activity of a biological activity or process.

The language "treat," "treating" and "treatment" includes the reduction or inhibition of enzyme or protein activity related to a bacterial infection or bacterial DNA gyrase in a subject, amelioration of one or more symptoms of a bacterial infection in a subject, or the slowing or delaying of progression of a bacterial infection in a subject. The language "treat," "treating" and "treatment" also includes the reduction or inhibition of the bacterial growth, replication or a reduction or inhibition of the bacterial load of bacteria in a subject.

EXEMPLIFICATION OF THE INVENTION

The invention is now illustrated by, but not limited to, the following Examples:
Synthetic Methods
Unless otherwise stated:
(i) evaporations were carried out by rotary evaporation in vacuo and work-up procedures were carried out after removal of residual solids by filtration;
(ii) temperatures are quoted as ° C.; operations were carried out at room temperature, that is typically in the range 18-26° C. and without the exclusion of air unless otherwise stated, or unless the skilled person would otherwise work under an inert atmosphere;
(iii) column chromatography (by the flash procedure) was used to purify compounds and was performed on Merck Kieselgel silica (Art. 9385) unless otherwise stated;
(iv) in general, the course of reactions was followed by TLC, HPLC, or LC/MS and reaction times are given for illustration only; yields are given for illustration only and are not necessarily the maximum attainable;
(v) the structure of the end-products of the invention was generally confirmed by NMR and mass spectral techniques. Proton magnetic resonance spectra ($^1$H NMR) were generally determined using a Bruker DRX-300 spectrometer or a Bruker DRX-400 spectrometer, operating at a field strength of 300 MHz, or 400 MHz, respectively. In cases where the NMR spectrum is complex, only diagnostic signals are reported. Chemical shifts are reported in parts per million downfield from tetramethylsilane as an external standard (δ scale) and peak multiplicities are shown thus: s, singlet; d, doublet; dd, doublet of doublets; dt, doublet of triplets; dm, doublet of multiplets; t, triplet, m, multiplet; br, broad. Chemical shifts are reported with errors of ±0.1 ppm. Fast-atom bombardment (FAB) mass spectral data were generally obtained using a Platform spectrometer (supplied by Micromass) run in electrospray and, where appropriate, either positive ion data or negative ion data were collected or using Agilent 1100 series LC/MS equipped with Sedex 75ELSD, and where appropriate, either positive ion data or negative ion data were collected. The lowest mass major ion is reported for molecules where isotope splitting results in multiple mass spectral peaks (for example when chlorine is present). Reversed Phase HPLC was carried out using YMC Pack ODS-AQ (100×20 mmID, S-5µ particle size, 12 nm pore size) on Agilent instruments; and (vi) each intermediate was purified to the standard required for the subsequent stage and was characterized in sufficient detail to confirm that the assigned structure was correct; purity was assessed by HPLC (high-pressure liquid chromatography), TLC, or NMR and identity was determined by infra-red spectroscopy (IR), mass spectroscopy (MS) or NMR spectroscopy as appropriate.

(vii) compounds were named using ACD/Name (Release 12.00, Product Version 12.01).

Intermediate 1

3-Chloro-6-[(2R,6S)-2,6-dimethylmorpholin-4-yl]-7-fluoro-1,2-benzoxazole-5-carbaldehyde

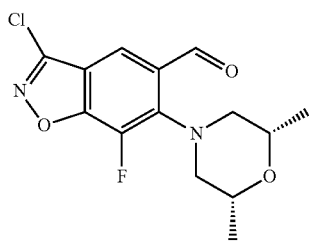 [SMILES: C[C@@H]1CN(c2c(C=O)cc3c(Cl)noc3c2F)C[C@H](C)O1]

To an ice cooled solution of 3-chloro-6,7-difluoro-1,2-benzoxazole-5-carbaldehyde (prepared according to the procedure described in International Application Publication No. WO 2010/043893, 5.0 g, 23.0 mmol) in anhydrous acetonitrile (50 ml) was added diisopropylethylamine (5.9 g, 45.9 mmol) followed by cis-2,6-dimethylmorpholine (2.6 g, 23.0 mmol) and the mixture was heated at 85° C. for 12 hours in a sealed tube. The solution was cooled to room temperature and the volatiles were removed under vacuum. The residue was dissolved in Ethyl acetate, washed with water followed by brine and then dried over anhydrous $Na_2SO_4$. Removal of solvent under vacuum afforded the crude product, which was purified over silica gel column using a gradient of ethyl acetate in pet. ether to give title compound as solid. Yield: 6.0 g (84%). $^1$H NMR (400 MHz, DMSO-$d_6$) δ: 1.0 (d, 6H), 2.9 (t, 2H), 3.1 (d, 2H), 3.8 (m, 2H), 7.7 (s, 1H), 10.2 (s, 1H). MS (ES) MH$^+$: 313 for $C_{14}H_{14}ClFN_2O_3$.

Intermediate 2

3-Chloro-5-(dimethoxymethyl)-6-[(2R,6S)-2,6-dimethlmorpholin-4-yl]-7-fluoro-1,2-benzoxazole

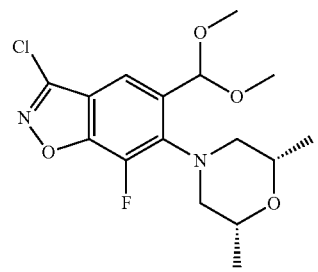 [SMILES: COC(OC)c1cc2c(Cl)noc2c(F)c1N1C[C@@H](C)O[C@@H](C)C1]

A solution of Intermediate 1 (3.0 g, 9.6 mmol) and a pinch of p-toluenesulfonic acid in 2,2'-dimethoxy propane (15 mL) was heated at 60° C. for 3 hours. Water (10 mL) was added to the reaction mixture at room temperature. Extraction with ethyl acetate (3×10 mL), drying ($Na_2SO_4$) of the combined organic layers and removal of solvents under vacuum followed by trituration with cold diethyl ether (15 mL) afforded crude product as a yellow solid. Yield: 2.7 g (80%). $^1$H NMR (400 MHz, DMSO-$d_6$) δ: 1.1 (d, 6H), 2.8 (t, 2H), 3.0 (d, 2H), 3.3 (s, 6H), 3.8 (m, 2H), 5.7 (s, 1H), 7.6 (s, 1H).

Intermediate 3

3-{5-(Dimethoxymethyl)-6-[(2R,6S)-2,6-dimethyl-morpholin-4-yl]-7-fluoro-1,2-benzoxazol-3-yl}-1,3-oxazolidin-2-one

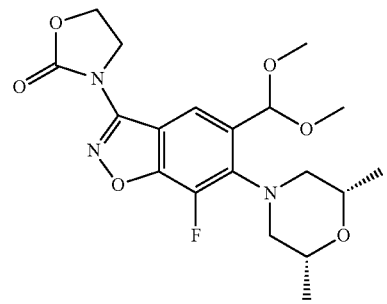 [SMILES: COC(OC)c1cc2c(N3CCOC3=O)noc2c(F)c1N1C[C@@H](C)O[C@@H](C)C1]

A solution of 2-oxazolidinone (0.18 g, 2.1 mmol) in dimethylformamide (1 mL) was added slowly to a stirred suspension of NaH (0.06 g, 2.5 mmol) in dimethylformamide (1 mL) at 0° C. The mixture was stirred at the room temperature for 30 minutes, and a solution of Intermediate 2 (0.25 g, 0.7 mmol) in dimethylformamide (3 mL) was added at the same temperature. This mixture was heated at 60° C. for 16 hours, poured into ice-cooled water, and extracted with ethyl acetate (2×20 mL). The organic layers were dried over anhydrous $Na_2SO_4$ and the solvents were removed under vacuum. The crude product was purified by silica gel column chromatography using a gradient of ethyl acetate in pet. ether to afford the title compound. Yield: 37 mg (13%). MS (ES) MH$^+$: 410.4 for $C_{19}H_{24}FN_3O_6$.

Intermediate 4

3-Chloro-6-[(2R,6R)-2,6-dimethylmorpholin-4-yl]-7-fluoro-1,2-benzoxazole-5-carbaldehyde

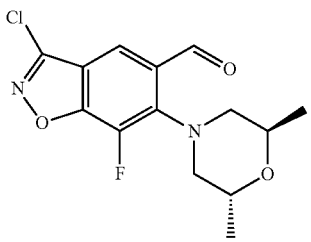 [SMILES: C[C@@H]1CN(c2c(C=O)cc3c(Cl)noc3c2F)C[C@@H](C)O1]

To an ice cooled solution of 3-chloro-6,7-difluoro-1,2-benzoxazole-5-carbaldehyde (prepared according to the procedure described in International Application Publication No. WO 2010/043893, 10.0 g, 46.0 mmol) in anhydrous acetonitrile (50 mL) was added diisopropylethylamine (11.9 g, 91.9 mmol) followed by (2R,6R)-2,6-dimethylmorpholine (5.2 g, 46.0 mmol) and the mixture was heated at 85° C. for 12 hours in a sealed tube. After cooling to room temperature, the volatiles were removed under vacuum. The residue was dissolved in ethyl acetate (50 mL), washed with water (2×15 mL) followed by brine and then dried over anhydrous $Na_2SO_4$. Removal of solvent under vacuum afforded the crude product that was purified over silica gel column using a gradient of ethyl acetate in pet. ether to give title compound as solid. Yield: 11.0 g (76%). $^1$H NMR (400 MHz, DMSO-$d_6$) δ: 1.2 (d, 6H), 3.0 (m, 2H), 3.4 (m, 2H), 4.1 (m, 2H), 8.0 (s, 1H), 10.3 (s, 1H). ES MH$^+$: 313.3 for $C_{14}H_{14}ClFN_2O_3$.

Intermediate 5

3-Chloro-5-(dimethoxymethyl)-6-((2R,6R)-2,6-dimethylmorpholino)-7-fluorobenzo[d]isoxazole

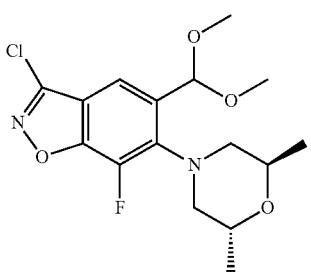 [SMILES: COC(OC)c1cc2c(Cl)noc2c(F)c1N1C[C@@H](C)O[C@H](C)C1]

A mixture of Intermediate 4 (14.42 g, 46.10 mmol), 2,2-dimethoxypropane (57.4 ml, 461.00 mmol) and p-toluenesulfonic acid (0.088 g, 0.46 mmol) was stirred at room temperature for 16 hours. The reaction was quenched with the addition of saturated aqueous $NaHCO_3$ solution and extracted with ethyl acetate. The organic layer was washed with water, brine, and dried over $Na_2SO_4$. The filtrate was concentrated under vacuum to give the title compound (15.35 g, 90%). MS (ES) MH$^+$: 359 for $C_{16}H_{20}ClFN_2O_4$.

Intermediate 6

3-(5-(Dimethoxymethyl)-6-((2R,6R)-2,6-dimethylmorpholino)-7-fluorobenzo[d]isoxazol-3-yl)oxazolidin-2-one

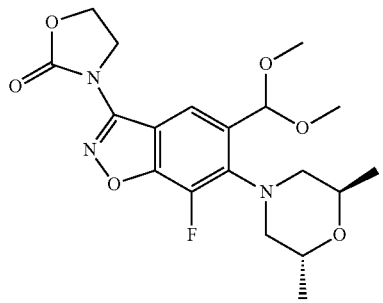 [SMILES: COC(OC)c1cc2c(N3CCOC3=O)noc2c(F)c1N1C[C@@H](C)O[C@H](C)C1]

Oxazolidin-2-one (purchased from Sigma-Aldrich, 728 mg, 8.36 mmol) in 1 dimethylformamide (1 mL) was added to a suspension of NaH (290 mg, 7.25 mmol, 60% in mineral oil) in dimethylformamide (1 mL), and the mixture was stirred at room temperature for 10 minutes. Intermediate 5 (2.0 g, 5.57 mmol) in dimethylformamide (2 mL) was added slowly. The resulting mixture was heated at 80° C. for 5 hours before being cooled and poured into ice cold aqueous $NH_4Cl$, and extracted with ethyl acetate. The organic layer washed with water, brine, and dried ($Na_2SO_4$). After concentration, the residue was purified on a silica gel column (elution 20-50% ethyl acetate in $CHCl_3$) to give the title compound (800 mg, 35%). $^1$H NMR (300 MHz, DMSO-D6) δ: 1.2 (br s, 6H) 2.7-2.9 (m, 2H) 3.06-3.35 (m, 8H) 3.9-4.25 (m, 4H) 4.45-4.7 (m, 2H) 5.7 (s, 1H) 8.35 (s, 1H). MS (ES) MH$^+$: 410 for $C_{19}H_{24}FN_3O_6$.

Intermediate 7

3-Chloro-6-[(2R,6S)-2,6-dimethylmorpholin-4-yl]-5-(1,3-dioxolan-2-yl)-7-fluoro-1,2-benzoxazole

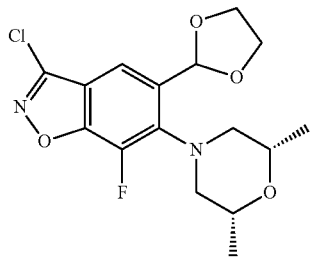 [SMILES: C[C@@H]1CN(c2c(C3OCCO3)cc3c(Cl)noc3c2F)C[C@H](C)O1]

A solution of Intermediate 1 (16.3 g, 52.2 mmol), ethylene glycol (8.1 g, 130.6 mmol) and pyridinium p-toluenesulfonate (1.31 g, 5.2 mmol) in toluene (300 mL) was heated at reflux in a Dean-Stark apparatus for 16 hours. The solvents were removed under vacuum and the residue was dissolved in diethyl ether (75 mL), washed with water (3×25 mL) and aqueous brine (25 mL). The organic layers were dried over anhydrous $Na_2SO_4$ and filtered. Removal of solvents under vacuum afforded the title compound, which was further purified by trituration with hot hexane. Yield:

18.0 g (80%). $^1$H NMR (400 MHz, DMSO-d$_6$) δ: 1.1 (d, 6H), 2.8 (t, 2H), 3.0 (d, 2H), 3.3 (m, 4H), 3.8 (m, 2H), 5.7 (s, 1H), 7.6 (s, 1H).

Intermediate 8

(4R)-3-{6-[(2R,6S)-2,6-Dimethylmorpholin-4-yl]-5-(1,3-dioxolan-2-yl)-7-fluoro-1,2-benzoxazol-3-yl}-4-methyl-1,3-oxazolidin-2-one

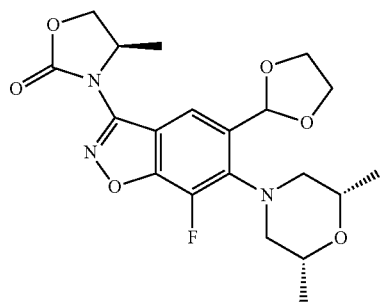 [SMILES: C[C@@H]1CN(c2c(C3OCCO3)cc3c(N4C(=O)OC[C@H]4C)noc3c2F)C[C@H](C)O1]

To a stirred solution of NaH (0.24 g, 9.9 mmol) in dimethylformamide (10 mL), a solution of (4R)-4-methyl-1,3-oxazolidin-2-one (synthesized according to the procedure described in Nishiyama, T.; Matsui, Shigeki; Yamada, F. J. Het. Chem. (1986), 23(5), 1427-9) (1.0 g, 9.9 mmol) in dimethylformamide (10 mL) was added slowly at 0° C. over a period of 10 minutes. The mixture was stirred at the room temperature for 30 minutes and a solution of Intermediate 7 (1.1 g, 3.1 mmol) in dimethylformamide (5 mL) was added at the same temperature. This mixture was heated at 80° C. for 12 hours and poured into ice-cooled water and extracted with ethyl acetate (2×20 mL). The organic layers were dried over anhydrous Na$_2$SO$_4$ and the solvents were removed under vacuum. The crude product was purified by silica gel column chromatography using a gradient of ethyl acetate in pet. ether. Yield: 0.15 g (12%). MS (ES) MH$^+$: 422.4 for C$_{20}$H$_{24}$FN$_3$O$_6$.

Intermediates 9 and 10 were prepared from Intermediate 7 and the indicated oxazolidinone starting material using a method similar to the one described for the synthesis of Intermediate 8.

Intermediate 9

(5S)-3-{6-[(2R,6S)-2,6-Dimethylmorpholin-4-yl]-5-(1,3-dioxolan-2-yl)-7-fluoro-1,2-benzoxazol-3-yl}-5-methyl-1,3-oxazolidin-2-one

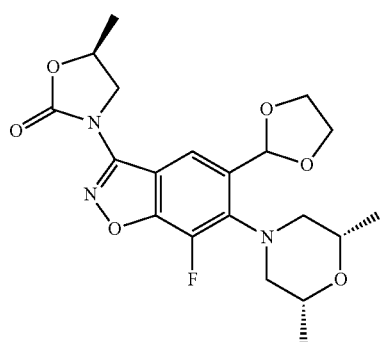

Starting material: (5S)-5-methyl-1,3-oxazolidin-2-one (synthesized according to the procedure described in Rein, K.; Goicoechea-Pappas, M.; Anklekar, T. V.; Hart, G. C.; Smith, G. A.; Gawley, R. E. JACS (1989), 111(6), 2211-17). MS (ES) MH$^+$: 422.4 for C$_{20}$H$_{24}$FN$_3$O$_6$.

Intermediate 10

(5R)-3-{6-[(2R,6S)-2,6-Dimethylmorpholin-4-yl]-5-(1,3-dioxolan-2-yl)-7-fluoro-1,2-benzoxazol-3-yl}-5-methyl-1,3-oxazolidin-2-one

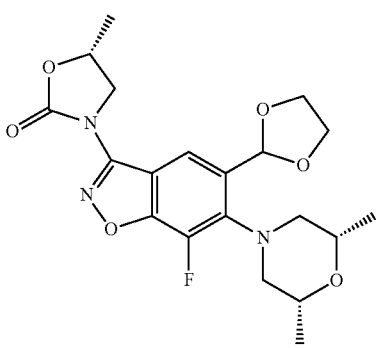 [SMILES: C[C@@H]1CN(c2noc3c(F)c(N4C[C@@H](C)O[C@@H](C)C4)c(C4OCCO4)cc23)C(=O)O1]

Starting material: (5R)-5-methyl-1,3-oxazolidin-2-one (synthesized according to the procedure described in Chouhan, G.; Alper, H. J. Org. Chem. (2009), 74(16), 6181-6189). MS (ES) MH$^+$: 422.4 for C$_{20}$H$_{24}$FN$_3$O$_6$.

Intermediate 11

3-Chloro-6-[(2R,6R)-2,6-dimethylmorpholin-4-yl]-5-(1,3-dioxolan-2-yl)-7-fluoro-1,2-benzoxazole

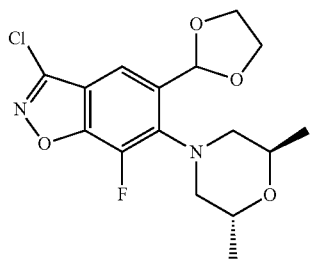 [SMILES: C[C@@H]1CN(c2c(C3OCCO3)cc3c(Cl)noc3c2F)C[C@@H](C)O1]

A solution of Intermediate 4 (11.0 g, 35.3 mmol), ethylene glycol (5.7 g, 91.9 mmol) and pyridinium p-toluenesulfonic acid (0.92 g, 3.7 mmol) in toluene was heated at reflux in a Dean-Stark apparatus for 16 hours. The solvents were removed under vacuum and the residue was dissolved in diethyl ether (75 mL), washed with water (3×25 mL) followed by brine solution (25 mL). The organic layers were dried over anhydrous Na$_2$SO$_4$ and filtered. Removal of solvents under vacuum afforded the title compound, which was further purified by trituration with hot hexane. Yield: 9.0 g (72%). $^1$H NMR (400 MHz, DMSO-d$_6$) δ: 1.2 (d, 6H), 2.9 (m, 2H), 3.2 (d, 2H), 4.05 (m, 4H), 4.15 (m, 2H), 6.2 (s, 1H), 7.7 (s, 1H). MS (ES) MH$^+$: 357.3 for C$_{16}$H$_{18}$ClFN$_2$O$_4$.

Intermediate 12

(R)-3-(6-((2R,6R)-2,6-Dimethylmorpholino)-5-(1,3-dioxolan-2-yl)-7-fluorobenzo[d]isoxazol-3-yl)-5-methyloxazolidin-2-one

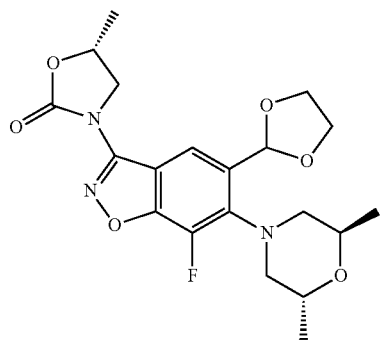 [SMILES: C[C@@H]1CN(c2noc3c(F)c(N4C[C@@H](C)O[C@H](C)C4)c(C4OCCO4)cc23)C(=O)O1]

(R)-5-Methyloxazolidin-2-one (1.134 g, 11.21 mmol, synthesized according to the procedure described in Chouhan, G.; Alper, H. *J. Org. Chem.* (2009), 74(16), 6181-6189) in dimethylformamide (10 mL) was added to a suspension of NaH (0.448 g, 11.21 mmol, 60% in mineral oil) in dimethylformamide (10 mL). The mixture was stirred at room temperature for 30 minutes. Intermediate 11 (4 g, 11.2 mmol) in dimethylformamide (10 mL) was added slowly, and the resulting mixture was heated at 80° C. for 2 hours. The reaction was cooled, poured into ice cold aqueous NH$_4$Cl and extracted with ethyl acetate. The organic layer washed with water, brine, and dried. The crude product after concentration was purified on a silica gel column (elution 40-50% ethyl acetate in hexanes) to give the title compound. $^1$H NMR (300 MHz, DMSO-d$_6$) ϵ: 1.2 (d, 6H), 1.5 (d, 3H), 2.8-3.3 (m, 4H), 3.7-4.3 (m, 8H), 4.9-5.1 (m, 1H), 6.2 (s, 1H), 8.4 (s, 1H). MS (ES) MH$^+$: 422 for C$_{20}$H$_{24}$FN$_3$O$_6$.

Intermediate 13

2-(2,3,4-Trifluorophenyl)-1,3-dioxolane

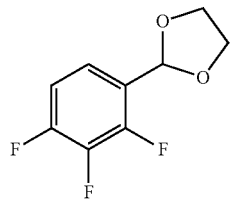 [SMILES: Fc1ccc(C2OCCO2)c(F)c1F]

Ethylene glycol (348.7 g, 5.62 mol) was added in one portion to a stirred mixture of 2,3,4-trifluorobenzaldehyde (300.0 g, 1.87 mol) and p-toluenesulfonic acid monohydrate (35.6 g, 0.18 mol) in toluene (4.5 L) at ambient temperature. The resulting mixture was heated at reflux with azeotropic removal of water using a Dean-Stark apparatus. The water was removed from time to time (3 hour intervals). After 24 hours, the toluene was removed and the residue was diluted with ethyl acetate (1.5 L) and washed with saturated aqueous NaHCO$_3$ (2×750 mL), water (2×500 mL) and brine solution (500 mL). The organic layers were dried over sodium sulphate and the solvent was removed under vacuum. The crude product was subjected to distillation at 60-70° C. in high vacuum (0.1 mm of Hg) to remove the starting material and impurities. The fraction obtained at 75-85° C. (0.1 mm of Hg) is consistent the title compound. Yield: 300.0 g (78%). $^1$H NMR (400 MHz, DMSO-d$_6$) δ: 3.9-4.1 (m, 4H), 6.0 (s, 1H), 7.3-7.4 (m, 2H).

Intermediate 14

5-(1,3-Dioxolan-2-yl)-2,3,4-trifluorobenzaldehyde

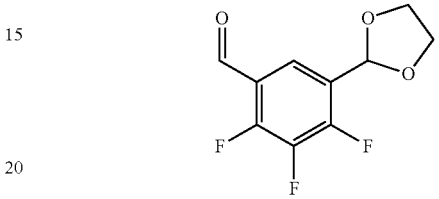

n-Butyllithium (2.5 M solution in hexane, 300 mL, 0.75 mol) was added drop wise to a solution of Intermediate 13 (118.0 g, 0.57 mol) in tetrahydrofuran (2.3 L) at −70° C. over 45 minutes, and the mixture was stirred at that temperature for a an hour. Dimethylformamide (236 mL, 3.27 mol) was added drop wise over a period of 30 minutes stirring at −70° C. and stirring was continued at the same temperature for 1 hour before quenching with saturated aqueous NH$_4$Cl solution at 0° C. The mixture was extracted with ethyl acetate (2×500 mL) and the organic layers were washed with water (2×500 mL), brine (500 mL) and dried over Na$_2$SO$_4$. The crude product was purified by silica gel (60-120 mesh) flash column chromatography using gradient of 10% ethyl acetate in pet. ether. Yield: 125.0 g (93%). $^1$H NMR (400 MHz, DMSO-d$_6$) δ: 4.0-4.1 (m, 4H), 6.05 (s, 1H), 7.8 (m, 1H), 10.1 (s, 1H).

Intermediate 15

1-[5-(1,3-Dioxolan-2-yl)-2,3,4-trifluorophenyl]-N-hydroxymethanimine

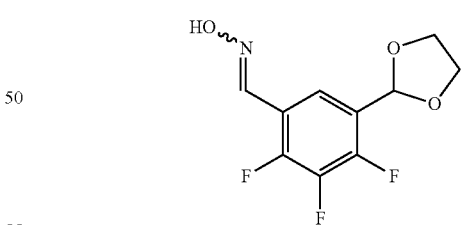

Pyridine (95.3 g, 1.2 mol) and hydroxylamine hydrochloride (62.8 g, 0.90 mol) were added sequentially to a stirred solution of Intermediate 14 (140.0 g, 0.60 mol) in ethanol (1500 mL) at 0° C. The mixture was stirred at the room temperature for 18 hours. The volatiles were removed under vacuum and the residue was diluted with ethyl acetate (2.0 L) and washed with water (2×500 mL), brine (2×500 mL) and dried over sodium sulphate. Solvents were removed to obtain the crude product that was purified by washing with a mixture of diethyl ether and heptane (1:9). Yield: 100.0 g (1$^{st}$ crop). 20 g of the product was also obtained by silica gel column purification of the mother liquor obtained from the 1st crop using gradient of ethyl acetate in pet ether. Total yield: 120.0 g (80%). $^1$H NMR (400 MHz, DMSO-d$_6$) δ: 3.95-4.1 (m, 4H), 6.0 (s, 1H), 7.6 (m, 1H), 8.2 (s, 1H), 11.8 (s, 1H).

Intermediate 16

5-(1,3-Dioxolan-2-yl)-2,3,4-trifluoro-N-hydroxybenzimidoyl chloride

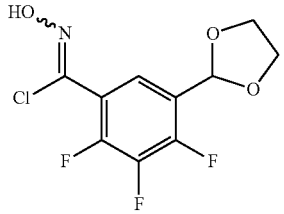 [SMILES: ON=C(Cl)c1cc(C2OCCO2)c(F)c(F)c1F]

N-Chlorosuccinimide (49.0 g, 0.36 mol) was added in portions to a stirred solution of Intermediate 15 (70.0 g, 0.28 mol) in dimethylformamide (360 mL) at ambient temperature under an atmosphere of N$_2$. After stirring for 4 hours, N$_2$ was bubbled through the reaction mixture for 30 minutes before and pouring the mixture into ice water (2 L). The resultant mixture was stirred for 1 hour and the solids were filtered and washed with water (2×250 mL). The solids were stirred in toluene (300 mL) for 30 min and filtered to obtain 53.0 g as a 1st crop. The toluene filtrate was treated with heptane (400 ml) precipitating additional solids that were filtered and washed with additional heptane (50 mL) affording 7 g as 2nd crop. Total yield: 60.0 g (76%). $^1$H NMR (400 MHz, DMSO-d$_6$) δ: 3.95-4.1 (m, 4H), 6.0 (s, 1H), 7.6 (m, 1H), 12.8 (s, 1H).

Intermediate 17

(2R)-1-[[5-(1,3-Dioxolan-2-yl)-6,7-difluoro-1,2-benzoxazol-3-yl]amino]propan-2-ol

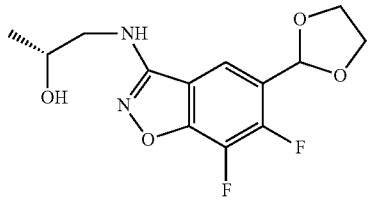 [SMILES: C[C@@H](O)CNc1noc2c(F)c(F)c(C3OCCO3)cc12]

(R)-1-aminopropan-2-ol (1.3 ml, 16.6 mmol) was added to a solution of Intermediate 16 (2.22 g, 7.88 mmol) in dimethylformamide (30 mL) at ambient temperature. There was a slow exotherm for the reaction. After stirring for 10 minutes, LC-MS showed consumption of starting material with a new intermediate material (MH$^+$=321). After stirring for 30 minutes more, potassium tert-butoxide (1.77 g, 15.8 mmol) was added all at once. A slow exotherm ensued. After stirring for 1 hour, LC-MS showed conversion to material consistent with the title compound (MH$^+$=301) with some intermediate material consistent (MH$^+$=321) remaining. Additional potassium tert-butoxide was added (400 mg, 3.6 mmol), and the mixture was stirred at room temperature for 1 hour. LC-MS showed complete conversion to material with MH$^+$=321. The mixture was quenched with aqueous NH$_4$Cl, and solvent was removed in vacuo. The solid residue was taken up in water (50 mL) while breaking up the solid mass, and the mixture was stirred at ambient temperature overnight. The solids were filtered and rinsed through with water before being dried in vacuo to give material consistent with the title compound. Yield 2.24 g (95%). $^1$H NMR (400 MHz, DMSO-d$_6$) δ: 1.1 (d, 3H) 3.2 (t, 2H) 3.8-4.0 (m, 1H) 4.0-4.1 (m, 4H) 4.8 (d, 1H) 6.1 (s, 1H) 7.3 (t, 1H) 8.0 (dd, 1H). ES MH$^+$: 301 for $C_{13}H_{14}F_2N_2O_4$.

Intermediate 18

(R)-3-(5-(1,3-Dioxolan-2-yl)-6,7-difluorobenzo[d]isoxazol-3-yl)-5-methyloxazolidin-2-one

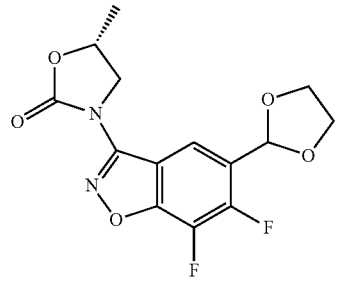 [SMILES: C[C@@H]1CN(c2noc3c(F)c(F)c(C4OCCO4)cc23)C(=O)O1]

A mixture of Intermediate 17 (500 mg, 1.67 mmol), di(1H-imidazol-1-yl)methanone (405 mg, 2.50 mmol), and dimethylaminopyridine (102 mg, 0.83 mmol) in tetrahydrofuran (10 mL) was heated at reflux overnight (21 hours). The solvent was removed to afford an oily residue. The residue was taken up in 1N HCl, and the mixture was stirred at ambient temperature for 90 minutes affording solids. The solids were filtered and rinsed well with water breaking them up with a spatula before drying in vacuo. The material is consistent with the title compound with about 5% impurity due to hydrolysis to corresponding aldehyde. Yield 407 mg (75%). $^1$H NMR (300 MHz, DMSO-d$_6$) δ: 1.5 (d, 3H) 3.8 (dd, 1H) 4.0-4.1 (m, 4H) 4.3 (t, 1H) 5.0 (m, 1H) 6.1 (s, 1H) 8.45 (d, 1H). ES MH$^+$: 327 for $C_{14}H_{12}F_2N_2O_5$;

Intermediate 19

(R)-6,7-Difluoro-3-(5-methyl-2-oxooxazolidin-3-yl)benzo[d]isoxazole-5-carbaldehyde

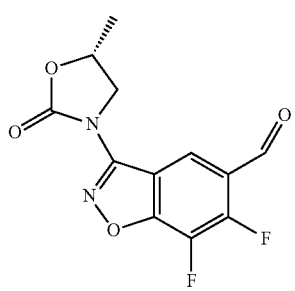 [SMILES: C[C@@H]1CN(c2noc3c(F)c(F)c(C=O)cc23)C(=O)O1]

A solution of Intermediate 18 (404 mg, 1.24 mmol) in HCl (1.0 M in water) (10 mL, 10.00 mmol) and tetrahydrofuran (10 mL) was stirred at room temperature for 3 days. The reaction mixture was diluted with water and extracted 2 times with ethyl acetate and each extract was washed with brine. The organic layers were combined and dried over MgSO$_4$, filtered and evaporated to afford material as an off-white solid consistent with the title compound. Yield 350 mg (100%). $^1$H NMR (300 MHz, CDCl$_3$) δ: 1.6 (d, 3H) 3.8 (dd, 1H) 4.3 (dd, 1H) 4.9 (m, 1H) 8.9 (dd, 1H) 10.2 (s, 1H). ES MH$^+$: 283 for C$_{12}$H$_8$F$_2$N$_2$O$_4$.

Intermediate 20

6-((2R,6R)-2,6-Dimethylmorpholino)-7-fluoro-3-((R)-5-methyl-2-oxooxazolidin-3-yl)benzo[d]isoxazole-5-carbaldehyde

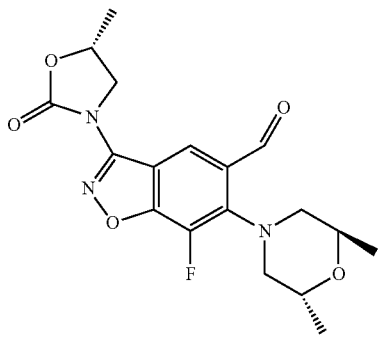 [SMILES: C[C@@H]1CN(c2noc3c(F)c(N4C[C@@H](C)O[C@H](C)C4)c(C=O)cc23)C(=O)O1]

A mixture of Intermediate 19 (92 mg, 0.33 mmol), (2R,6R)-2,6-dimethylmorpholine (45.1 mg, 0.39 mmol) and K$_2$CO$_3$ in butyronitrile (3 mL) and water (0.5 mL) was heated at 100° C. in a microwave reactor vessel. The solvent was removed and the residue diluted with water and extracted 2 times with ethyl acetate with each extract being washed with brine. The organic layers were combined and dried over MgSO$_4$, filtered and evaporated to afford material that was chromatographed on silica gel (50% hexanes in CH$_2$CH$_2$ followed by gradient elution to 100% CH$_2$CH$_2$) to afford a yellow solid consistent with the title compound. Yield 100 mg (81%). $^1$H NMR (300 MHz, CDCl$_3$) δ 1.2 (d, 6H) 1.5 (d, 3H) 2.9-3.0 (m, 2H) 3.4 (dt, 2H) 3.7 (dd, 1H) 4.1-4.3 (m, 3H) 4.8-5.0 (m, 1H) 8.7 (d, 1H) 10.3 (s, 1H). MS (ES) MH$^+$: 378 for C$_{18}$H$_{20}$FN$_3$O$_5$.

Intermediate 21

(4S)-3-{6-[(2R,6S)-2,6-Dimethylmorpholin-4-yl]-5-(1,3-dioxolan-2-yl)-7-fluoro-1,2-benzoxazol-3-yl}-4-methyl-1,3-oxazolidin-2-one

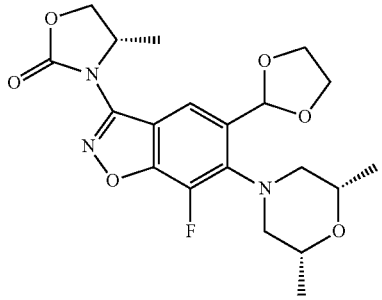 [SMILES: C[C@@H]1CN(c2c(C3OCCO3)cc3c(N4C(=O)OC[C@@H]4C)noc3c2F)C[C@H](C)O1]

Intermediate 21 was prepared from Intermediate 7 using (4S)-4-methyl-1,3-oxazolidin-2-one (synthesized according to the procedure described in Nishiyama, T.; Matsui, Shigeki; Yamada, F. *J. Het. Chem.* (1986), 23(5), 1427-9) in a method similar to the one described for the synthesis of Intermediate 8. MS (ES) MH$^+$: 422.4 for C$_{20}$H$_{24}$FN$_3$O$_6$.

Intermediate 22

(S)-3-(6-((2R,6R)-2,6-Dimethylmorpholino)-5-(1,3-dioxolan-2-yl)-7-fluorobenzo[d]isoxazol-3-yl)-4-methyloxazolidin-2-one

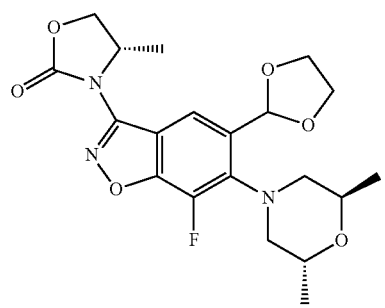 [SMILES: C[C@@H]1CN(c2c(C3OCCO3)cc3c(N4C(=O)OC[C@@H]4C)noc3c2F)C[C@@H](C)O1]

Intermediate 22 was prepared from Intermediate 11 and (4S)-4-methyl-1,3-oxazolidin-2-one (synthesized according to the procedure described in Nishiyama, T.; Matsui, Shigeki; Yamada, F. *J. Het. Chem.* (1986), 23(5), 1427-9) using a method similar to the one described for the synthesis of Intermediate 12. $^1$H NMR (300 MHz, DMSO-d$_6$) δ: 1.2 (d, 6H), 1.35-1.5 (m, 3H), 2.8-3.3 (m, 4H), 3.9-4.3 (m, 7H), 4.6-4.8 (m, 2H), 6.0-6.3 (m, 1H), 6.2 (s, 1H), 8.2 (s, 1H). MS (ES) MH$^+$: 422. for C$_{20}$H$_{24}$FN$_3$O$_6$.

Intermediates 23-29 were prepared from Intermediate 7 and the indicated oxazolidinone starting material using a method similar to the one described for the synthesis of Intermediate 8.

Intermediate 23

(4S)-3-{6-[(2R,6S)-2,6-Dimethylmorpholin-4-yl]-5-(1,3-dioxolan-2-yl)-7-fluoro-1,2-benzoxazol-3-yl}-4-ethyl-1,3-oxazolidin-2-one

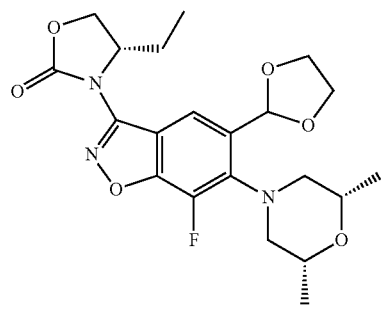 [SMILES: CC[C@H]1COC(=O)N1c1noc2c(F)c(N3C[C@@H](C)O[C@@H](C)C3)c(C3OCCO3)cc12]

Starting material: (4S)-4-ethyl-1,3-oxazolidin-2-one (synthesized according to the procedure described in Begis, G.; Cladingboel, D. E.; Jerome, L.; Motherwell, W. B.; Sheppard, T. D. *Eur. J. Org. Chem.* (2009), (10), 1532-1548). MS (ES) MH$^+$: 436.4 for $C_{21}H_{26}FN_3O_6$.

Intermediate 24

(4R)-3-{6-[(2R,6S)-2,6-Dimethylmorpholin-4-yl]-5-(1,3-dioxolan-2-yl)-7-fluoro-1,2-benzoxazol-3-yl}-4-ethyl-1,3-oxazolidin-2-one

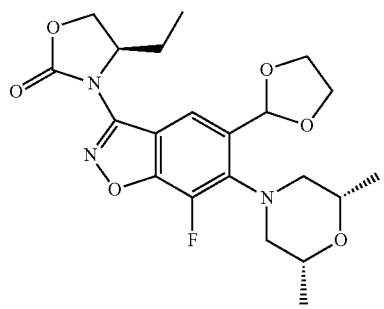 [SMILES: CC[C@@H]1COC(=O)N1c1noc2c(F)c(N3C[C@@H](C)O[C@@H](C)C3)c(C3OCCO3)cc12]

Starting material: (4R)-4-ethyl-1,3-oxazolidin-2-one-(5R)-5-methyl-1,3-oxazolidin-2-one (synthesized according to the procedure described in Chouhan, G.; Alper, H. *J. Org. Chem.* (2009), 74(16), 6181-6189). MS (ES) MH$^+$: 436.4 for $C_{21}H_{26}FN_3O_6$.

Intermediate 25

(4R)-3-{6-[(2R,6S)-2,6-Dimethylmorpholin-4-yl]-5-(1,3-dioxolan-2-yl)-7-fluoro-1,2-benzoxazol-3-yl}-4-phenyl-1,3-oxazolidin-2-one

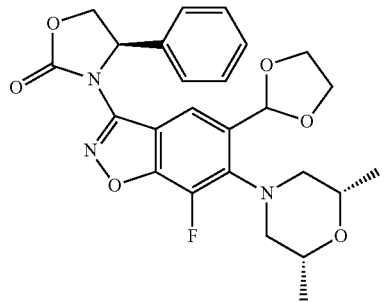 [SMILES: C[C@@H]1CN(c2c(C3OCCO3)cc3c(N4C(=O)OC[C@H]4c4ccccc4)noc3c2F)C[C@H](C)O1]

Starting material: (4R)-4-phenyl-1,3-oxazolidin-2-one (synthesized according to the procedure described in Begis, G.; Cladingboel, D. E.; Jerome, L.; Motherwell, W. B.; Sheppard, T. D. *Eur. J. Org. Chem.* (2009), (10), 1532-1548). MS (ES) MH$^+$: 484.5 for $C_{25}H_{26}FN_3O_6$.

Intermediate 26

(4S)-3-{6-[(2R,6S)-2,6-Dimethylmorpholin-4-yl]-5-(1,3-dioxolan-2-yl)-7-fluoro-1,2-benzoxazol-3-yl}-4-phenyl-1,3-oxazolidin-2-one

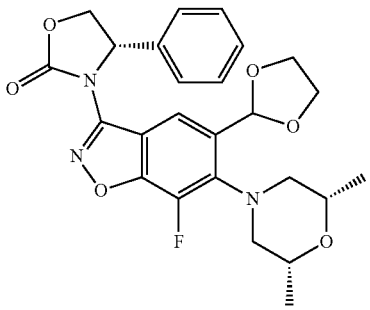 [SMILES: C[C@@H]1CN(c2c(C3OCCO3)cc3c(N4C(=O)OC[C@@H]4c4ccccc4)noc3c2F)C[C@H](C)O1]

Starting material: (4S)-4-phenyl-1,3-oxazolidin-2-one (synthesized according to the procedure described in MacNevin, C. J.; Moore, R. L.; Liotta, D. C. *J. Org. Chem.* (2008), 73(4), 1264-1269). MS (ES) MH$^+$: 484.5 for $C_{25}H_{26}FN_3O_6$.

Intermediate 27

(4R)-4-Benzyl-3-{6-[(2R,6S)-2,6-dimethylmorpholin-4-yl]-5-(1,3-dioxolan-2-yl)-7-fluoro-1,2-benzoxazol-3-yl}-1,3-oxazolidin-2-one

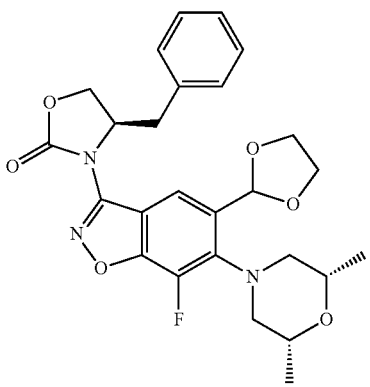 [SMILES: C[C@@H]1CN(c2c(C3OCCO3)cc3c(N4C(=O)OC[C@H]4Cc4ccccc4)noc3c2F)C[C@H](C)O1]

Starting material: (4R)-4-benzyl-1,3-oxazolidin-2-one (synthesized according to the procedure described in Paz, J.; Perez-Balado, C.; Iglesias, B.; Munoz, L. *J. Org. Chem.* (2010), 75(9), 3037-3046). MS (ES) MH$^+$: 498.5 for $C_{26}H_{28}FN_3O_6$.

Intermediate 28

(4S)-4-Benzyl-3-{6-[(2R,6S)-2,6-dimethylmorpholin-4-yl]-5-(1,3-dioxolan-2-yl)-7-fluoro-1,2-benzoxazol-3-yl}-1,3-oxazolidin-2-one

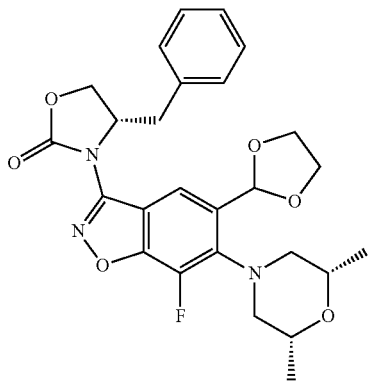 [SMILES: C[C@@H]1CN(c2c(C3OCCO3)cc3c(N4C(=O)OC[C@@H]4Cc4ccccc4)noc3c2F)C[C@H](C)O1]

Starting material: (4S)-4-benzyl-1,3-oxazolidin-2-one (synthesized according to the procedure described in Begis, G.; Cladingboel, D. E.; Jerome, L.; Motherwell, W. B.; Sheppard, T. D. *Eur. J. Org. Chem.* (2009), (10), 1532-1548). MS (ES) MH$^+$: 498.5 for $C_{26}H_{28}FN_3O_6$.

Intermediate 29

3-{6-[(2R,6S)-2,6-Dimethylmorpholin-4-yl]-5-(1,3-dioxolan-2-yl)-7-fluoro-1,2-benzoxazol-3-yl}-5,5-dimethyl-1,3-oxazolidin-2-one

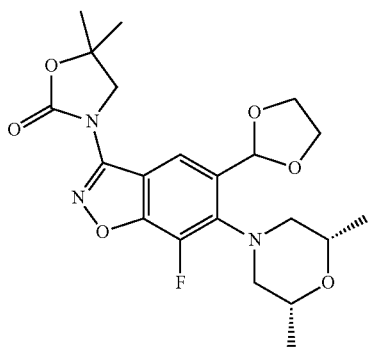 [SMILES: C[C@@H]1CN(c2c(C3OCCO3)cc3c(N4CC(C)(C)OC4=O)noc3c2F)C[C@H](C)O1]

Starting material: 5,5-dimethyl-1,3-oxazolidin-2-one (synthesized according to the procedure described in Jones, S.; Smanmoo, C. *Tet. Lett.* (2004), 45(8), 1585-1588). $^1$H NMR (400 MHz, DMSO-d$_6$) δ: 1.1 (d, 6H), 1.5 (s, 6H), 2.8 (t, 2H), 3.1 (d, 2H), 3.8 (m, 2H), 4.0 (m, 4H), 4.1 (m, 2H), 6.1 (s, 1H), 8.4 (s, 1H). MS (ES) MH$^+$: 436.4 for $C_{21}H_{26}FN_3O_6$.

Mixture of Intermediates 30 and 31

(5R)-3-{6-[(2R,6S)-2,6-Dimethylmorpholin-4-yl]-5-(1,3-dioxolan-2-yl)-7-fluoro-1,2-benzoxazol-3-yl}-5-ethyl-1,3-oxazolidin-2-one and (5S)-3-{6-[(2R,6S)-2,6-dimethylmorpholin-4-yl]-5-(1,3-dioxolan-2-yl)-7-fluoro-1,2-benzoxazol-3-yl}-5-ethyl-1,3-oxazolidin-2-one

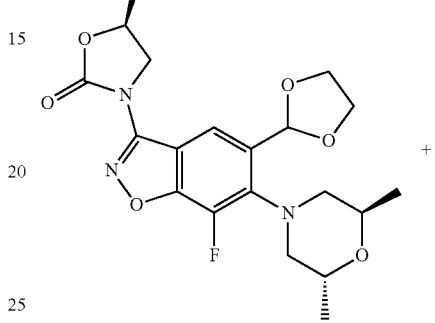

+

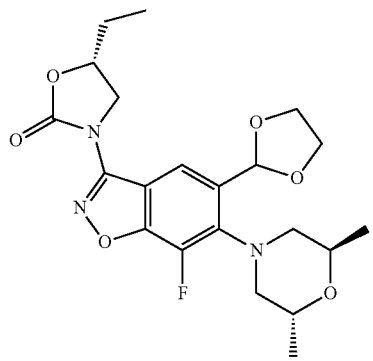

Intermediates 30 and 31 were prepared from Intermediate 11 and 5-ethyl-1,3-oxazolidin-2-one (synthesized according to the procedure described in European Patent Application Publication No. EP 244810) using a method similar to the one described for the synthesis of Intermediate 12. The diastereomers were separated via HPLC using Chiralpak IC (250×4.6) mm (hexane:ethanol, 80:20, 1.0 ml/min).

Intermediate 30 ((5R)-3-{6-[(2R,6S)-2,6-dimethylmorpholin-4-yl]-5-(1,3-dioxolan-2-yl)-7-fluoro-1,2-benzoxazol-3-yl}-5-ethyl-1,3-oxazolidin-2-one) was the first eluting diastereomer. R$_T$=16.2 min; $^1$H NMR (400 MHz, DMSO-d$_6$) δ: 1.0 (t, 3H), 0.95-1.0 (m, 6H), 1.8 (m, 2H), 2.9 (m, 2H), 3.2 (m, 2H), 3.8 (dd, 1H), 4.0 (m, 2H), 4.0-4.05 (m, 4H), 4.2 (t, 1H), 6.2 (s, 1H), 8.4 (s, 1H). MS (ES) MH$^+$: 436.4 for $C_{21}H_{26}FN_3O_6$.

Intermediate 31 ((5S)-3-{6-[(2R,6S)-2,6-dimethylmorpholin-4-yl]-5-(1,3-dioxolan-2-yl)-7-fluoro-1,2-benzoxazol-3-yl}-5-ethyl-1,3-oxazolidin-2-one) was second eluting diastereomer. R$_T$=18.9 min; $^1$H NMR (400 MHz, DMSO-d$_6$) δ: 1.0 (t, 3H), 0.95-1.0 (m, 6H), 1.8 (m, 2H), 2.9 (m, 2H), 3.2 (m, 2H), 3.8 (dd, 1H), 4.0 (m, 2H), 4.0-4.05 (m, 4H), 4.2 (t, 1H), 6.2 (s, 1H), 8.4 (s, 1H). MS (ES) MH$^+$: 436.4 for $C_{21}H_{26}FN_3O_6$.

Intermediate 32

(4R)-4-({[tert-Butyl(dimethyl)silyl]oxy}methyl)-3-{6-[(2R,6S)-2,6-dimethylmorpholin-4-yl]-5-(1,3-dioxolan-2-yl)-7-fluoro-1,2-benzoxazol-3-yl}-1,3-oxazolidin-2-one

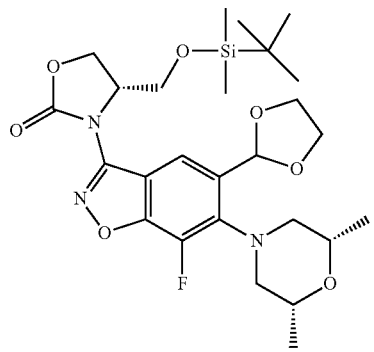 [SMILES: C[C@@H]1CN(c2c(C3OCCO3)cc3c(N4C(=O)OC[C@@H]4CO[Si](C)(C)C(C)(C)C)noc3c2F)C[C@H](C)O1]

A solution of (4R)-4-({[tert-butyl(diphenyl)silyl]oxy}methyl)-1,3-oxazolidin-2-one (synthesized according to the procedure described in Berkowitz, D. B.; Sloss, D. G. *J. Org. Chem.* (1995), 60(21), 7047-50) in dimethylformamide (15 mL) was added to a stirred solution of NaH (0.83 g, 34.6 mmol) in dimethylformamide (10 mL) at 0° C. over a period of 10 minutes. The mixture was stirred at the room temperature for 30 minutes and a solution of Intermediate 7 (6.17 g, 17.3 mmol) in dimethylformamide (25 mL) was added at the same temperature. This mixture was heated at 60° C. for 2 hours and poured into ice-cooled water, extracted with ethyl acetate (2×20 mL). The organic layers were dried over anhydrous $Na_2SO_4$ and the solvents were removed under vacuum. The crude product was purified by silica gel column chromatography using a gradient of ethyl acetate in pet. ether. Yield: 1.2 g (13%). $^1$H NMR (400 MHz, DMSO-$d_6$) δ: −0.2 (s, 3H), −0.1 (s, 3H), 0.75 (s, 9H), 1.1 (d, 6H), 2.8 (t, 2H), 3.1 (d, 2H), 3.7 (m, 3H), 4.0 (m, 2H), 4.0-4.1 (m, 2H), 4.1 (d, 1H), 4.4 (d, 1H), 4.7 (d, 2H), 6.1 (s, 1H), 8.3 (s, 1H). MS (ES) MH$^+$: 552.6 for $C_{26}H_{38}FN_3O_7Si$.

Mixture of Intermediates 33 and 34

(4S)-3-{6-[(2R,6S)-2,6-Dimethylmorpholin-4-yl]-5-(1,3-dioxolan-2-yl)-7-fluoro-1,2-benzoxazol-3-yl}-4-(hydroxymethyl)-1,3-oxazolidin-2-one and (4R)-3-{6-[(2R,6S)-2,6-dimethylmorpholin-4-yl]-5-(1,3-dioxolan-2-yl)-7-fluoro-1,2-benzoxazol-3-yl}-4-(hydroxymethyl)-1,3-oxazolidin-2-one

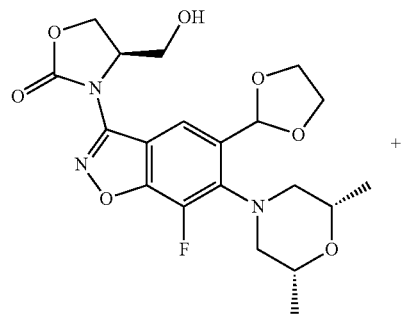

+

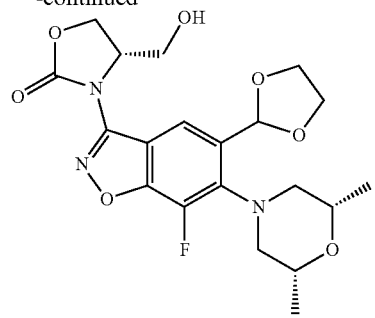

To a stirred solution of Intermediate 32 (1.5 g, 2.7 mmol) in tetrahydrofuran (50 mL), 1M solution of tetrabutylammonium fluoride in tetrahydrofuran (1.4 g, 5.4 mmol) was added at 0° C., and the mixture was stirred at the room temperature for 10 minutes. Water (3 mL) was added to the reaction mixture and the organic layer was separated and dried over anhydrous $Na_2SO_4$. Evaporation of the solvent under vacuum afforded a solid that was a 68%+27% mixture of enantiomers by chiral HPLC analysis. Yield: 1.1 g (92%). $^1$H NMR (400 MHz, DMSO-$d_6$) δ: 1.1 (d, 6H), 2.8 (t, 2H), 3.1 (d, 2H), 3.5-3.6 (m, 1H), 3.7-3.8 (m, 2H), 3.9-4.0 (m, 3H), 4.05-4.1 (m, 2H), 4.5 (dd, 1H), 4.6-4.65 (m, 2H), 5.2 (t, 1H), 6.1 (s, 1H), 8.3 (s, 1H). MS (ES) MH$^+$: 438.4 for $C_{20}H_{24}FN_3O_7$.

The R and S enantiomers of Mixture of Intermediates 33 and 34 were separated by chiral HPLC using Chiralpak IC (250×4.6 mm) column (hexane:ethanol (80:20); 1.0 mL/min) to afford 2 components, Intermediate 33 as the major component and Intermediate 34 as the minor component.

Intermediate 33 ((4S)-3-{6-[(2R,6S)-2,6-dimethylmorpholin-4-yl]-5-(1,3-dioxolan-2-yl)-7-fluoro-1,2-benzoxazol-3-yl}-4-(hydroxymethyl)-1,3-oxazolidin-2-one) was the first eluting enantiomer. $R_T$=10.86 min; yield: 550 mg. MS (ES) MH$^+$: 438.4 for $C_{20}H_{24}FN_3O_7$.

Intermediate 34 ((4R)-3-{6-[(2R,6S)-2,6-dimethylmorpholin-4-yl]-5-(1,3-dioxolan-2-yl)-7-fluoro-1,2-benzoxazol-3-yl}-4-(hydroxymethyl)-1,3-oxazolidin-2-one) was the second eluting enantiomer. $R_T$=14.99 min; yield: 420 mg. MS (ES) MH$^+$: 438.4 for $C_{20}H_{24}FN_3O_7$.

Intermediate 35

(4R)-3-{6-[(2R,6S)-2,6-Dimethylmorpholin-4-yl]-5-(1,3-dioxolan-2-yl)-7-fluoro-1,2-benzoxazol-3-yl}-4-(fluoromethyl)-1,3-oxazolidin-2-one

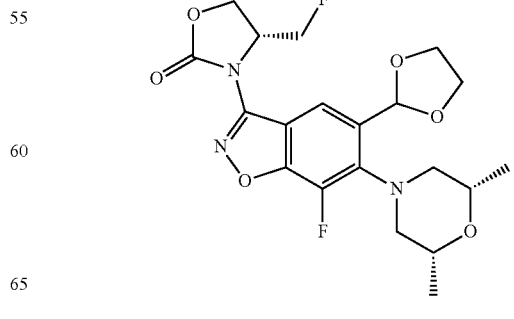

Diethylaminosulfur trifluoride (1.0 g, 6.3 mmol) was added to a stirred solution of Intermediate 33 (0.55 g, 1.25 mmol) in tetrahydrofuran (25 mL) at −78° C., and the mixture was stirred for 1 hour before warming to room temperature for 1 hour. Methanol (1 mL) was added, and the volatiles were removed under vacuum. The residue was dissolved in ethyl acetate (15 mL) and washed with saturated NaHCO$_3$ (5 mL), water (10 mL) and aqueous brine. The organic layer was dried over Na$_2$SO$_4$, and the solvent was removed under vacuum to afford the title compound as a solid. Yield: 0.44 g (80%). MS (ES) MH$^+$: 440.4 for C$_{20}$H$_{23}$F$_2$N$_3$O$_6$.

Intermediate 36

(4S)-3-{6-[(2R,6S)-2,6-Dimethylmorpholin-4-yl]-5-(1,3-dioxolan-2-yl)-7-fluoro-1,2-benzoxazol-3-yl}-4-(fluoromethyl)-1,3-oxazolidin-2-one

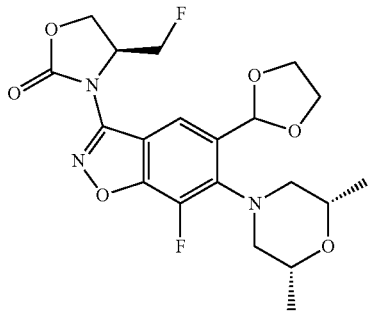 [SMILES: C[C@@H]1CN(c2c(C3OCCO3)cc3c(N4C(=O)OC[C@H]4CF)noc3c2F)C[C@H](C)O1]

Intermediate 36 was prepared from Intermediate 34 using a method similar to the one described for the synthesis of Intermediate 35. MS (ES) MH$^+$: 440.4 for C$_{20}$H$_{23}$F$_2$N$_3$O$_6$.

Mixture of Intermediates 37 and 38

(4R)-3-{6-[(2R,6S)-2,6-Dimethylmorpholin-4-yl]-5-(1,3-dioxolan-2-yl)-7-fluoro-1,2-benzoxazol-3-yl}-4-(methoxymethyl)-1,3-oxazolidin-2-one and (4S)-3-{6-[(2R,6S)-2,6-dimethylmorpholin-4-yl]-5-(1,3-dioxolan-2-yl)-7-fluoro-1,2-benzoxazol-3-yl}-4-(methoxymethyl)-1,3-oxazolidin-2-one

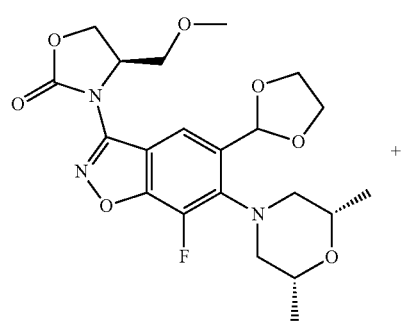

+

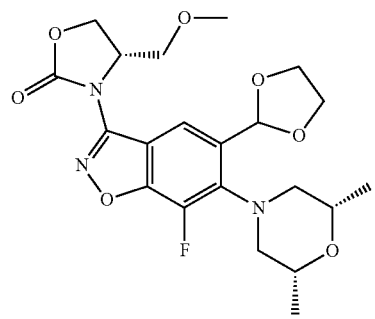

A mixture of Intermediates 33 and 34, 0.55 g, 1.3 mmol) and methyl iodide (0.54 g, 3.8 mmol) were added to a stirred mixture of NaH (0.06 g, 2.5 mmol) in dimethylformamide (5 mL) at 0° C., and the resultant mixture was stirred at the room temperature for an hour. The reaction mixture was quenched with saturated aqueous NH$_4$Cl (5 ml) and extracted with ethyl acetate (3×10 ml). The combined organic layers were washed with water and dried over Na$_2$SO$_4$. Evaporation of the solvent under vacuum afforded the crude title compound which was purified by flash column silica gel chromatography using a gradient of ethyl acetate in pet.ether. Yield: 0.4 g (70%). $^1$H NMR (400 MHz, DMSO-d$_6$) δ: 1.1 (d, 6H), 2.8 (t, 2H), 3.1 (d, 2H), 3.2 (s, 3H), 3.5 (dd, 1H), 3.7-3.75 (m, 2H), 3.9 (d, 1H), 3.9-34.0 (m, 2H), 4.0-4.1 (m, 2H), 4.4 (dd, 1H), 4.6-4.7 (m, 2H), 6.1 (s, 1H), 8.3 (s, 1H). MS (ES) MH$^+$: 452.4 for C$_{21}$H$_{26}$FN$_3$O$_7$.

Intermediate 39

(4S)-4-(Methoxymethyl)-1,3-oxazolidin-2-one

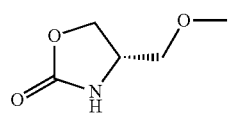

To a stirred solution of tert-butyl [(2R)-1-hydroxy-3-methoxypropan-2-yl]carbamate (synthesized according to the procedure described in Sowinski, J. A.; Toogood, P. L. *J. Org. Chem.* (1996), 61(22), 7671-7676) (8.3 g, 40.4 mmol) tetrahydrofuran (100 mL), 1M solution of potassium t-butoxide in tetrahydrofuran (80.9 mL, 80.9 mmol) was added dropwise at 0° C. and the mixture was stirred at the room temperature for 2 hours. Water (20 ml) was added to the reaction mixture and extracted with ethyl acetate (3×50 ml). The combined organic layers were washed with brine and dried over Na$_2$SO$_4$. Yield: 5.0 g (94%). $^1$H NMR (300 MHz, DMSO-d$_6$) δ: 3.3 (s, 3H), 3.3 (m, 2H), 3.9 (m, 1H), 4.0 (dd, 1H), 4.3 (t, 1H), 7.7 (d, 1H). [α]$_D^{25}$=−5.876.

Intermediate 40

(4S)-3-{6-[(2R,6S)-2,6-Dimethylmorpholin-4-yl]-5-(1,3-dioxolan-2-yl)-7-fluoro-1,2-benzoxazol-3-yl}-4-(methoxymethyl)-1,3-oxazolidin-2-one

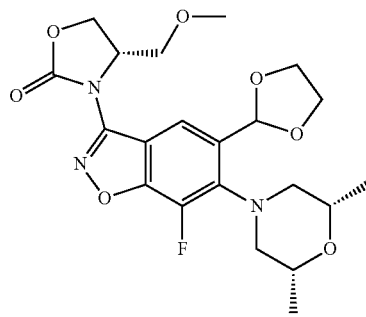

Intermediate 40 was prepared from Intermediate 39 and Intermediate 7 using a method similar to the one described for the synthesis of Intermediate 32. $^1$H NMR (400 MHz, DMSO-$d_6$) δ: 1.1 (d, 6H), 2.8 (t, 2H), 3.1 (d, 2H), 3.2 (s, 3H), 3.5 (dd, 1H), 3.7-3.75 (m, 2H), 3.9 (d, 1H), 3.95-4.0 (m, 2H), 4.0-4.1 (m, 2H), 4.4 (dd, 1H), 4.45-4.7 (m, 2H), 6.1 (s, 1H), 8.3 (s, 1H). MS (ES) MH$^+$: 452.4 for $C_{21}H_{26}FN_3O_7$.

Intermediate 41

(S)-5-((tert-Butyldiphenylsilyloxy)methyl)oxazolidin-2-one

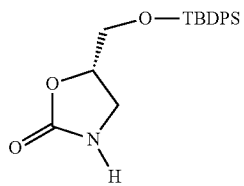

(S)-5-(hydroxymethyl)oxazolidin-2-one (570 mg, 4.87 mmol, as described by Danielmeier, K.; Steckhan, E. *Tet. Asymmetry*, 6(5), 1995, 1181) and imidazole (331 mg, 4.87 mmol) were dissolved in dimethylformamide (5 mL) and cooled to 0° C. tert-Butylchlorodiphenylsilane (1.34 g, 4.87 mmol) was added dropwise at 0° C. The reaction mixture was allowed to warm to room temperature and stirred for 5 hours. The mixture was was poured into 0.5 N HCl (50 ml), and the resultant mixture was extracted with ethyl acetate. The layers were separated, and the organic phase was washed with saturated sodium bicarbonate, water and brine. The organic phase was dried over sodium sulfate and the solvent removed to afford crude material that was purified on a silica gel column (50% ethyl acetate in hexanes) to give the title compound (1.28 g, 74.0%). $^1$H NMR (300 MHz, DMSO-$d_6$) δ: 1.0 (s, 9H) 3.3-3.6 (m, 2H) 3.6-3.9 (m, 2H) 4.6-4.8 (m, 1H) 7.3-7.8 (m, 11H). MS (ES) (M+23)$^+$: 278 for the Na$^+$ adduct of $C_{20}H_{25}NO_3Si$.

Intermediate 42

(S)-5-((tert-Butyldiphenylsilyloxy)methyl)-3-(6-((2R,6R)-2,6-dimethylmorpholino)-5-(1,3-dioxolan-2-yl)-7-fluorobenzo[d]isoxazol-3-yl)oxazolidin-2-one

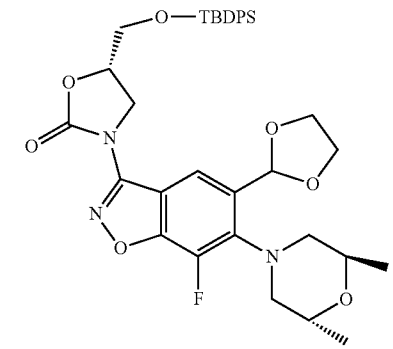

Intermediate 42 was prepared from Intermediate 41 and Intermediate 11 using a method similar to the one described for the synthesis of Intermediate 32. $^1$H NMR (300 MHz, DMSO-$d_6$) δ: 0.9 (s, 9H) 1.2 (d, 6H) 2.9 (dd, 2H) 3.2-3.3 (m, 2H) 3.8-4.1 (m, 9H) 4.3 (t, 1H) 4.95-5.1 (m, 1H) 6.2 (s, 1H) 7.3-7.7 (m, 10H) 8.5 (s, 1H). MS (ES) MH$^+$: 676 for $C_{36}H_{42}FN_3O_7Si$.

Intermediate 43

(S)-3-(6-((2R,6R)-2,6-Dimethylmorpholino)-5-(1,3-dioxolan-2-yl)-7-fluorobenzo[d]isoxazol-3-yl)-5-(hydroxymethyl)oxazolidin-2-one

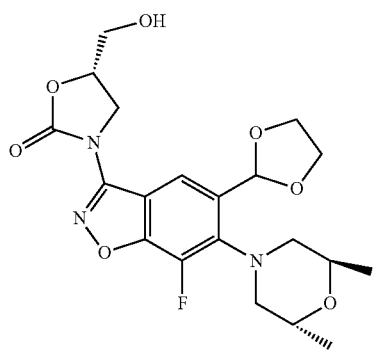 [SMILES: C[C@@H]1CN(c2c(C3OCCO3)cc3c(N4C[C@@H](CO)OC4=O)noc3c2F)C[C@@H](C)O1]

Acetic acid (0.89 mL, 15.5 mmol) and a solution of 1M tetrabutylammonium fluoride (3.1 mL, 3.1 mmol) in tetrahydrofuran were added sequentially to a solution of Intermediate 42 (2.1 g, 3.11 mmol) dissolved in 15 mL of tetrahydrofuran. The mixture was stirred at room temperature for 18 hours. The reaction mixture was diluted with water and extracted with ethyl acetate, which was concentrated to afford crude material that was purified on a silica gel column (50-70% ethyl acetate gradient in hexanes) to give the title compound (1.33 g, 98% yield). $^1$H NMR (300 MHz, DMSO-$d_6$) δ: 1.2 (d, 6H) 2.8-3.3 (m, 4H) 3.5-3.8 (m, 2H) 3.9-4.3 (m, 8H) 4.7-5.05 (m, 1H) 6.2 (s, 1H) 8.4 (s, 1H). MS (ES) MH$^+$: 438 for $C_{20}H_{24}FN_3O_7$.

Intermediate 44

(S)-3-(6-((2R,6R)-2,6-Dimethylmorpholino)-5-(1,3-dioxolan-2-yl)-7-fluorobenzo[d]isoxazol-3-yl)-5-(fluoromethyl)oxazolidin-2-one

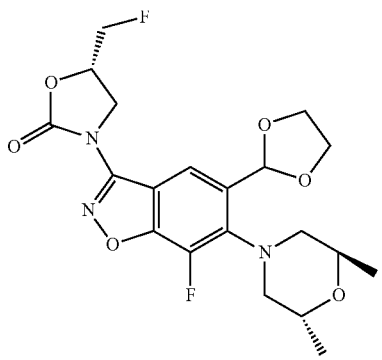 [SMILES: C[C@@H]1CN(c2c(C3OCCO3)cc3c(N4C[C@@H](CF)OC4=O)noc3c2F)C[C@@H](C)O1]

Intermediate 44 was prepared from Intermediate 43 using a method similar to the one described for the synthesis of Intermediate 35. $^1$H NMR (300 MHz, CDCl$_3$) δ: 1.3 (d, 6H) 3.0 (dd, 2H) 4.0-4.2 (m, 8H) 4.3 (t, 1H) 4.55-4.9 (m, 3H) 5.0-5.25 (m, 1H) 6.3 (s, 1H) 8.5 (s, 1H). MS (ES) MH$^+$: 440 for C$_{20}$H$_{23}$F$_2$N$_3$O$_6$.

Intermediate 45

3-Chloro-4-fluoro-2-hydroxybenzoic acid

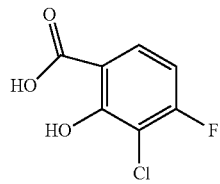 [SMILES: O=C(O)c1ccc(F)c(Cl)c1O]

Sodium hydroxide (208 g, 5.21 mol) was added in portions to a stirred solution of 3-chloro-2,4-difluorobenzoic acid (200 g, 1.04 mol) in 1,3-dimethyl imidazolidin-2-one (1 L), and the mixture was heated to 140° C. for 2 hours. The reaction mixture was cooled to room temperature and neutralized with ice-cooled 2N HCl (350 mL) precipitating a white solid that was collected by filtration. The filtered solid was dissolved in methyl t-butyl ether (500 mL), washed with saturated brine solution (150 mL) and dried over Na$_2$SO$_4$. Removal of solvent under vacuum afforded the title compound as off white solid. Yield: 180 g (91%). $^1$H NMR (300 MHz, MeOH-d$_4$) δ: 6.8 (t, 1H), 7.90 (dd, 1H), 11.3 (s, 1H). MS (ES) MH$^-$: 189 for C$_7$H$_4$ClFO$_3$.

Intermediate 46

Methyl 3-chloro-4-fluoro-2-hydroxybenzoate

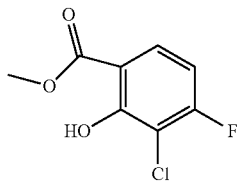

Oxalyl chloride (75.9 g, 0.60 mol) and dimethylformamide (1 mL) were added sequentially to an ice cooled and stirred solution of Intermediate 45 (57.0 g, 0.29 mol) in dry dichloromethane (570 mL), and the mixture was stirred at the room temperature for 16 hours. Volatiles were removed under vacuum affording a yellow solid to which methanol (350 mL) was added at 0° C., and the resultant mixture was stirred at the same temperature for 1 hour. The reaction mixture was poured slowly into an ice-cooled solution of 2N HCl (1.0 L) precipitating a solid that was collected by filtration. This wet solid was dissolved in diethyl ether (1.5 L), which was separated and dried over Na$_2$SO$_4$. Removal of the solvent under vacuum afforded the title compound as white solid. Yield: 58.0 g (95%). $^1$H NMR (400 MHz, DMSO-d$_6$) δ: 3.9 (s, 3H), 7.0 (t, 1H), 7.8 (dd, 1H), 11.3 (s, 1H).

Intermediate 47

3-Chloro-4-fluoro-N,2-dihydroxybenzamide

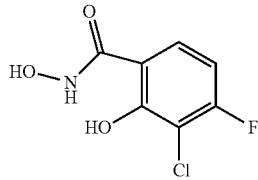 [SMILES: O=C(NO)c1ccc(F)c(Cl)c1O]

Hydroxylamine hydrochloride (43.3 g, 0.62 mol) and KOH pellets (73.2 g, 1.30 mol) were added sequentially to a solution of Intermediate 46 (58.0 g, 0.28 mol) in methanol (580 mL) at 0° C., and the mixture was refluxed for 16 hours. The reaction mixture was cooled to 10° C. and the pH of the solution was adjusted to 2 by addition of an ice-bath cooled solution of 1.5N HCl (3.0 L) precipitating white solids. The solids were filtered and dried well under vacuum. The solids were then dissolved in ethyl acetate (500 mL), which was washed with 1.5N hydrochloric acid (200 mL), brine solution (200 mL) and dried over Na$_2$SO$_4$. Removal of solvent afforded the title product as white solid. Yield: 55.0 g (94%). $^1$H NMR (300 MHz, DMSO-d$_6$) δ: 7.0 (t, 1H), 7.7 (dt, 1H), 9.6 (br s, 1H), 11.9 (s, 1H), 13.9 (s, 1H). MS (ES) MH$^+$: 206 for C$_7$H$_5$ClFNO$_3$.

Intermediate 48

7-Chloro-6-fluorobenzo[d]isoxazol-3(2H)-one

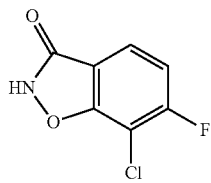 [SMILES: O=c1[nH]oc2c(Cl)c(F)ccc12]

Carbonyl diimidazole (86.75 g, 0.54 mol) in dry tetrahydrofuran (100 mL) was added drop wise to a stirred solution of Intermediate 47 (55.0 g, 0.27 mol) in dry tetrahydrofuran (550 mL) at 70° C. over an hour, and the reaction mixture was stirred at the same temperature for an additional hour. Solvents were removed under vacuum, and the semi-solid obtained was stirred vigorously with ice-cooled 2N hydrochloric acid (500 mL) for 10 minutes. The white solid obtained was filtered dissolved in ethyl acetate (500 mL), which was washed with brine solution (150 mL) and dried over $Na_2SO_4$. Removal of solvent afforded the title compound as white solid. Yield: 47.0 g (94%). $^1$H NMR (300 MHz, DMSO-$d_6$) δ: 8.0 (t, 1H), 8.4 (dd, 1H), 13.5 (br s, 1H). MS (ES) MH$^-$: 186 for $C_7H_3ClFNO_2$.

Intermediate 49

3,7-Dichloro-6-fluorobenzo[d]isoxazole

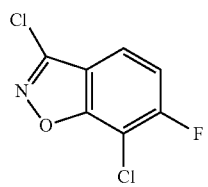 [SMILES: Fc1ccc2c(Cl)noc2c1Cl]

To an ice cooled mixture of Intermediate 48 (47.0 g, 0.25 mol), phosphorous oxychloride (114.3 g, 0.75 mol) and triethylamine (25.36 g, 0.25 mol) were added and the mixture was heated at 140° C. in a sealed tube for 6 hours. The reaction mass was cooled to room temperature and then ice cooled water was added slowly with vigorous stirring. The solid obtained was filtered and washed with saturated sodium bicarbonate solution (200 mL) and ice-cooled water. The wet solid was then dissolved in diethyl ether (2.0 L), which was dried over $Na_2SO_4$. Removal of solvent at 35° C. afforded the title compound as pale brown solid. Yield: 32.0 g (62%). $^1$H NMR (300 MHz, DMSO-$d_6$) δ: 7.6 (t, 1H), 7.9 (dd, 1H). MS (ES) MH$^-$: 206.0 for $C_7H_2Cl_2FNO$.

Intermediate 50

3,7-Dichloro-6-fluorobenzo[d]isoxazole-5-carbaldehyde

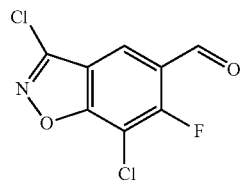 [SMILES: O=Cc1cc2c(Cl)noc2c(Cl)c1F]

A solution of 1.6 M solution of n-butyllithium (194.17 mL, 0.31 mol) in hexanes was added drop wise to a solution of tetramethylpiperidine (48.26 g, 0.34 mol) in tetrahydrofuran (160 mL) at −10° C., and the solution stirred for 40 minutes. The reaction mixture was cooled to −78° C. and into this was added Intermediate 49 (32.0 g, 0.16 mol) in tetrahydrofuran (160 mL). After stirring −78° C. for 2 hours, dimethylformamide (22.69 g, 0.31 mol) was added and stirring was continued at −78° C. for 1 hour. The reaction was quenched by the addition of acetic acid (46.6 g, 0.78 mol) and warmed to room temperature. The mixture was diluted with water and extracted with ethyl acetate (2×250 mL). The combined organic layers were washed with water and brine and then dried over anhydrous $Na_2SO_4$. Removal of the solvent under vacuum afforded the crude product, which was purified over a silica gel column (230-400 mesh) using a gradient of 2% ethyl acetate in pet. ether. Yield: 27.5 g (76%). $^1$H NMR (400 MHz, DMSO-$d_6$) δ: 8.4 (d, 1H), 10.2 (s, 1H). MS (ES) MH$^+$: 233 for $C_8H_2Cl_2FNO_2$.

Intermediate 51

3,7-Dichloro-6-((2R,6R)-2,6-dimethylmorpholino)benzo[d]isoxazole-5-carbaldehyde

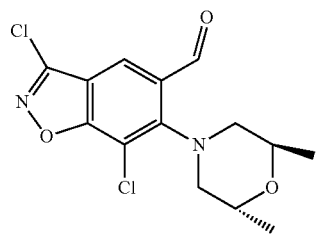 [SMILES: C[C@@H]1CN(c2c(C=O)cc3c(Cl)noc3c2Cl)C[C@@H](C)O1]

A mixture of Intermediate 50 (15 g, 64.10 mmol), (2R, 6R)-2,6-dimethylmorpholine (7.38 g, 64.10 mmol), and $K_2CO_3$ (13.29 g, 96.15 mmol) in butyronitrile (80 mL) and water (8 mL) was heated at reflux for 6 hours. The solvent was removed. The mixture was diluted with ethyl acetate and washed with water and brine. The combined aqueous layers were extracted with ethyl acetate, which was washed with water and brine. The combined ethyl acetate extracts were dried ($Na_2SO_4$) and concentrated to give a pale yellow solid that is consistent with the title compound (21.2 g, 100%). $^1$H NMR (300 MHz, DMSO-$d_6$) δ: 1.2 (d, 6H) 3.0 (dd, 2H) 3.55 (dd, 2H) 4.1-4.2 (m, 2H) 8.1 (s, 1H) 10.3 (s, 1H). MS (ES) MH$^+$: 329 for $C_{14}H_{14}Cl_2N_2O_3$.

Intermediate 52

3,7-Dichloro-6-((2R,6R)-2,6-dimethylmorpholino)-5-(1,3-dioxolan-2-yl)benzo[d]isoxazole

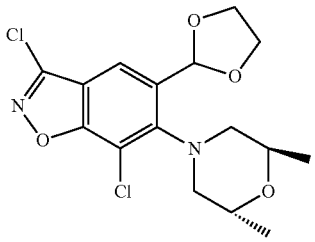 [SMILES: C[C@@H]1CN(c2c(C3OCCO3)cc3c(Cl)noc3c2Cl)C[C@@H](C)O1]

To a solution of Intermediate 51 (21 g, 63.8 mmol) dissolved in 200 mL of toluene was added ethane-1,2-diol (15.8 g, 255 mmol) and 4-methylbenzenesulfonic acid (0.55 g, 3.19 mmol). The mixture was heated at reflux with azeotropic removal of water for 4 hours. The reaction was cooled and diluted with ether, which was washed with water, aqueous NaHCO$_3$, and water. Drying (MgSO$_4$) and removal of solvent gave a residue that was purified on silica gel (25% ethyl acetate in hexanes) to give the title compound (21.35 g, 90%). $^1$H NMR (300 MHz, DMSO-d$_6$) δ: 1.2 (br. s., 3H) 1.3 (br. s., 3H) 2.7-3.2 (m, 3H) 3.5-3.75 (m, 1H) 3.9-4.25 (m, 6H) 6.2 (s, 1H) 7.9 (s, 1H). MS (ES) MH$^+$: 373 for C$_{16}$H$_{18}$Cl$_2$N$_2$O$_4$.

The following 3 Intermediates were prepared from the indicated starting materials using a method similar to the one described for the synthesis of Intermediate 42.

Intermediate 53

(S)-3-(6-((2R,6R)-2,6-Dimethylmorpholino)-5-(1,3-dioxolan-2-yl)-7-chlorobenzo[d]isoxazol-3-yl)-5-(methoxymethyl)oxazolidin-2-one

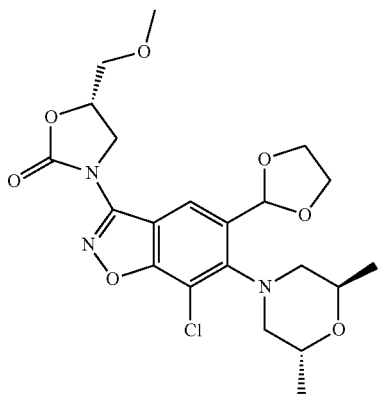 [SMILES: COC[C@@H]1CN(c2noc3c(Cl)c(N4C[C@@H](C)O[C@H](C)C4)c(C4OCCO4)cc23)C(=O)O1]

Starting materials: (S)-5-(methoxymethyl)oxazolidin-2-one (purchased from Sanyo Co., LTD) and Intermediate 52. $^1$H NMR (300 MHz, CDCl$_3$) δ: 1.0-1.3 (m, 3H), 1.3-1.6 (m, 3H), 2.8 (d, 1H), 2.9 (s, 1H), 3.0 (s, 1H), 3.05 (d, 1H), 3.2 (d, 1H) 3.4-3.5 (m, 3H), 3.7 (qd, 2H), 3.8-4.0 (m, 1H), 4.1-4.35 (m, 6H), 4.9 (ddd, 1H), 6.35 (s, 1H), 8.7 (s, 1H). MS (ES) MH$^+$: 468 for C$_{21}$H$_{26}$ClN$_3$O$_7$.

Intermediate 54

(R)-3-(6-((2R,6R)-2,6-Dimethylmorpholino)-5-(1,3-dioxolan-2-yl)-7-fluorobenzo[d]isoxazol-3-yl)-5-(methoxymethyl)oxazolidin-2-one

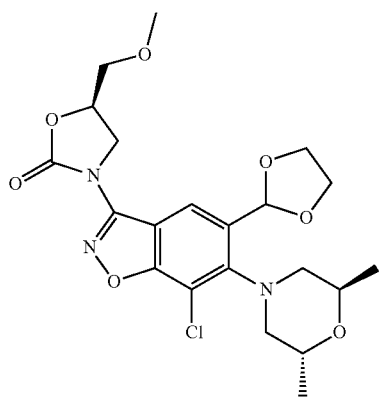 [SMILES: COC[C@H]1CN(c2noc3c(Cl)c(N4C[C@@H](C)O[C@H](C)C4)c(C4OCCO4)cc23)C(=O)O1]

Starting material: (R)-5-(methoxymethyl)oxazolidin-2-one (purchased from SanyoCo., LTD) and Intermediate 52. $^1$H NMR (300 MHz, CDCl$_3$) δ: 1.2 (m, 3H), 1.45 (m, 3H) 2.8 (d, 1H), 3.1 (d, 1H), 3.2-3.4 (m, 2H), 3.4-3.5 (m, 3H), 3.7 (qd, 2H), 3.85 (d, 2H), 3.9-4.3 (m, 6H), 4.8-5.0 (m, 1H) 6.35 (s, 1H) 8.7 (s, 1H). MS (ES) MH$^+$: 468 for C$_{21}$H$_{26}$FN$_3$O$_7$.

Intermediate 55

(R)-3-(7-Chloro-6-((2R,6R)-2,6-dimethylmorpholino)-5-(1,3-dioxolan-2-yl)benzo[d]isoxazol-3-yl)-5-methyloxazolidin-2-one

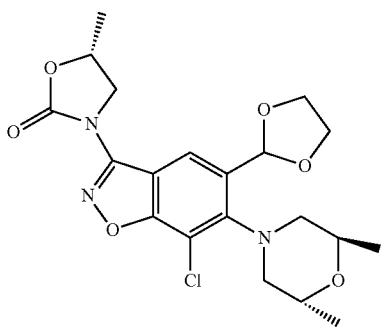 [SMILES: C[C@@H]1CN(c2noc3c(Cl)c(N4C[C@@H](C)O[C@H](C)C4)c(C4OCCO4)cc23)C(=O)O1]

Starting material: (R)-5-methyloxazolidin-2-one (synthesized according to the procedure described in Chouhan, G.; Alper, H. *J. Org. Chem.* (2009), 74(16), 6181-6189) and Intermediate 52. $^1$H NMR (300 MHz, DMSO-d$_6$) δ: 1.1 (s, 3H) 1.3 (s, 3H) 1.5 (d, 3H) 2.7-3.2 (m, 3H) 3.5-4.3 (m, 9H) 4.9-5.2 (m, 1H) 6.2 (s, 1H) 8.6 (s, 1H). MS (ES) MH$^+$: 438 for C$_{20}$H$_{24}$ClN$_3$O$_6$.

Intermediate 56 and 57

(4S,5R)-3-[6-[(2R,6R)-2,6-Dimethylmorpholin-4-yl]-5-(1,3-dioxolan-2-yl)-7-fluoro-1,2-benzoxazol-3-yl]-4,5-dimethyl-oxazolidin-2-one and (4R,5S)-3-[6-[(2R,6R)-2,6-dimethylmorpholin-4-yl]-5-(1,3-dioxolan-2-yl)-7-fluoro-1,2-benzoxazol-3-yl]-4,5-dimethyl-oxazolidin-2-one

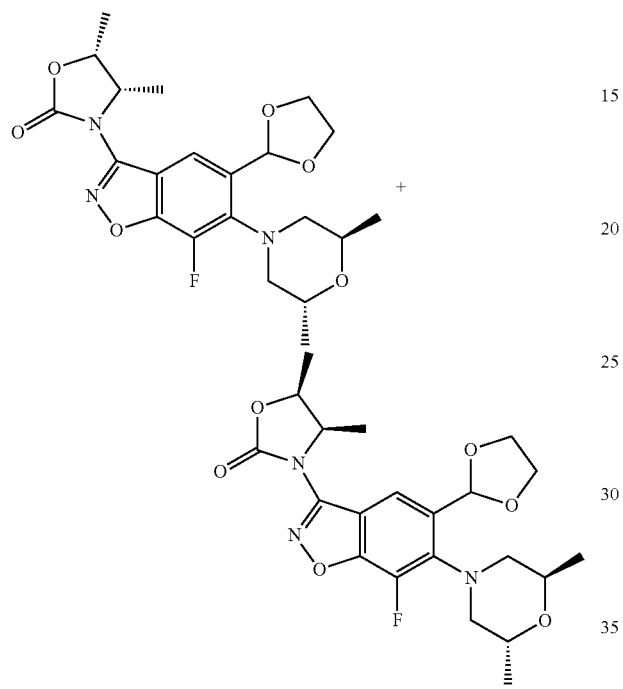

A suspension of NaH in 10 mL dimethylformamide was added slowly to a solution of 4,5-dimethyloxazolidin-2-one (2.7 g, 18.8 mmol, synthesized according to the procedure described in Chouchan, Gagan; C. *J.O.C.*, 2009, 74, pg 6181) in 50 mL of dimethylformamide at room temperature. After 10 minutes stirring, Intermediate 11 (6.7 g, 18.8 mmol) was added and the mixture was heated in the microwave at 100° C. for one hour. The resulting mixture was cooled and poured into ice cold aqueous $NH_4Cl$, and extracted with ethyl acetate. The organic layer was washed with water, brine, and dried ($Na_2SO_4$). After concentration, the residue was purified on a silica gel column (elution with 0-5% methanol in $CHCl_3$) to give a solid as a mixture of diastereomers. The diastereomers were separated by chiral HPLC using Chiralpak IC (250×4.6 mm) column (hexane:methanol:ethanol (70:15:15) 1.0 ml/min) to afford 2 components, Intermediate 56 as the first eluting isomer and Intermediate 57 as the second eluting isomer.

Intermediate 56 was the first eluting isomer. Yield: 840 mg (10%). $^1$H NMR (300 MHz, DMSO-$d_6$) δ: 1.2 (d, 6H), 1.3 (d, 3H), 1.4 (d, 3H), 2.9 (s, 2H), 3.2 (d, 2H), 3.9-4.2 (m, 6H), 4.7 (s, 1H), 5.1 (s, 1H), 6.2 (s, 1H), 8.3 (s, 1H). MS (ES) MH$^+$: 436 for $C_{21}H_{26}ClN_3O_6$.

Intermediate 57 was the second eluting isomer. Yield: 920 mg (11%). $^1$H NMR (300 MHz, DMSO-$d_6$) δ: 1.2 (d, 6H), 1.3 (d, 3H), 1.4 (d, 3H), 2.9 (dd, 2H), 3.2 (d, 2H), 3.9-4.2 (m, 6H), 4.5-4.9 (m, 1H), 4.9-5.2 (m, 1H), 6.2 (s, 1H), 8.3 (s, 1H). MS (ES) MH$^+$: 436 for $C_{21}H_{26}ClN_3O_6$.

Intermediate 58

(S)-2-(5-(1,3-Dioxolan-2-yl)-6,7-difluorobenzo[d]isoxazol-3-ylamino)pent-4-en-1-ol

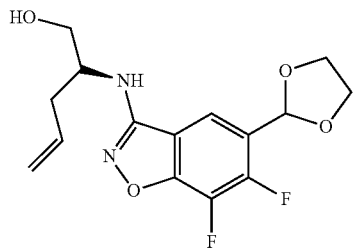

Intermediate 58 was prepared from Intermediate 16 and (S)-2-aminopent-4-en-1-ol using the method described for the synthesis of Intermediate 17. $^1$H NMR (300 MHz, CDCl$_3$) δ: 1.6 (br. s, 1H), 2.5 (t, 2H), 3.7-4.0 (m, 3H), 4.0-4.35 (m, 4H), 4.5 (d, 1H), 5.0-5.3 (m, 2H), 5.7-6.0 (m, 1H), 6.1 (s, 1H), 7.5 (dd, 1H). MS (ES) MH$^+$: 327 for $Cl_5H_{16}F_2N_2O_4$.

Intermediate 59

(S)-3-(5-(1,3-Dioxolan-2-yl)-6,7-difluorobenzo[d]isoxazol-3-yl)-4-allyloxazolidin-2-one

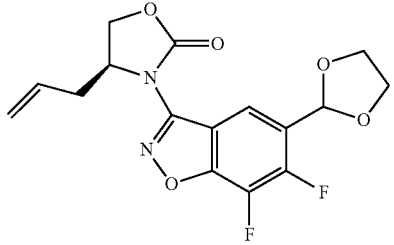 [SMILES: C=CC[C@H]1COC(=O)N1c1noc2c(F)c(F)c(C3OCCO3)cc12]

Intermediate 59 was prepared from Intermediate 58 using the method described for the synthesis of Intermediate 18. $^1$H NMR (300 MHz, CDCl$_3$) δ: 2.5-2.7 (m, 1H), 2.7-2.9 (m, 1H), 4.0-4.3 (m, 4H), 4.4 (dd, 1H), 4.6 (t, 1H), 4.7-4.9 (m, 1H), 5.1-5.3 (m, 2H), 5.6-5.9 (m, 1H), 6.1 (s, 1H), 8.4 (dd, 1H). MS (ES) MH$^+$: 353 for $C_{16}H_{14}F_2N_2O_5$.

Intermediate 60

(S)-3-(4-Allyl-2-oxooxazolidin-3-yl)-6,7-difluorobenzo[d]isoxazole-5-carbaldehyde

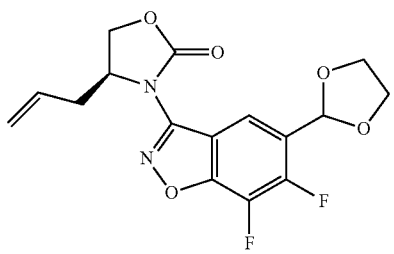 [SMILES: C=CC[C@H]1COC(=O)N1c1noc2c(F)c(F)c(C3OCCO3)cc12]

Intermediate 60 was prepared from Intermediate 59 using the method described for the synthesis of Intermediate 19. MS (ES) MH+: 309 for $C_{14}H_{10}F_2N_2O_4$.

Intermediate 61

3-((S)-4-Allyl-2-oxooxazolidin-3-yl)-6-((2R,6R)-2,6-dimethylmorpholino)-7-fluorobenzo[d]isoxazole-5-carbaldehyde

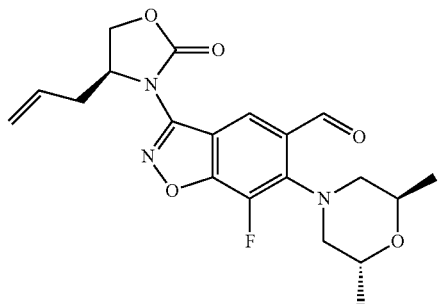

Intermediate 61 was prepared from Intermediate 60 using the method described for the synthesis of Intermediate 20. $^1$H NMR (300 MHz, CDCl$_3$) δ: 1.2-1.4 (m, 6H), 2.5-2.7 (m, 1H), 2.7-2.9 (m, 1H), 2.9-3.1 (m, 2H), 3.4 (dt, 2H), 3.9-4.3 (m, 2H), 4.3-4.5 (m, 1H), 4.5-4.8 (m, 2H), 5.0-5.4 (m, 2H), 5.5-5.9 (m, 1H), 8.7 (s, 1H), 10.4 (s, 1H). MS (ES) MH+: 404 for $C_{20}H_{22}FN_3O_5$.

Intermediate 62

2-(5-(1,3-Dioxolan-2-yl)-6,7-difluorobenzo[d]isoxazol-3-ylamino)-2-(tetrahydro-2H-pyran-4-yl)ethanol

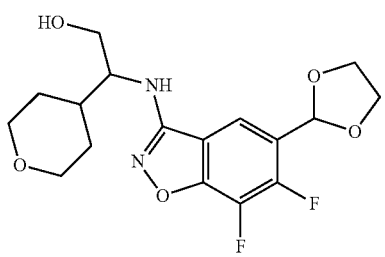 [SMILES: OCC(Nc1noc2c(F)c(F)c(C3OCCO3)cc12)C1CCOCC1]

Intermediate 62 was prepared from Intermediate 16 and 4-(tetrahydro-2H-pyran-4-yl)oxazolidin-2-one (purchased from Pharmacore, Inc.) using the method described for the synthesis of Intermediate 17. MS (ES) MH+: 371 for $C_{17}H_{20}F_2N_2O_3$.

Intermediate 63

3-(5-(1,3-Dioxolan-2-yl)-6,7-difluorobenzo[d]isoxazol-3-yl)-4-(tetrahydro-2H-pyran-4-yl)oxazolidin-2-one

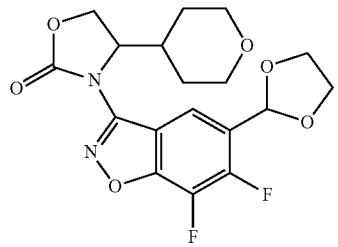 [SMILES: O=C1OCC(C2CCOCC2)N1c1noc2c(F)c(F)c(C3OCCO3)cc12]

Intermediate 63 was prepared from Intermediate 62 using the method described for the synthesis of Intermediate 18. $^1$H NMR (300 MHz, CDCl$_3$) δ: 0.7-1.0 (m, 2H), 1.4-1.6 (m, 5H), 2.6 (d, 1H), 3.15-3.5 (m, 2H), 3.9-4.2 (m, 6H), 4.35-4.7 (m, 3H), 5.1-5.5 (m, 2H), 6.1 (s, 1H), 8.4 (dd, 1H). MS (ES) MH+: 397 for $C_{18}H_{18}F_2N_2O_6$.

Intermediate 64

6,7-Difluoro-3-(2-oxo-4-(tetrahydro-2H-pyran-4-yl)oxazolidin-3-yl)benzo[d]isoxazole-5-carbaldehyde

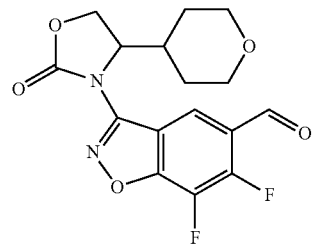 [SMILES: O=Cc1cc2c(N3C(=O)OCC3C3CCOCC3)noc2c(F)c1F]

Intermediate 64 was prepared from Intermediate 63 using the method described for the synthesis of Intermediate 19. MS (ES) MH+: 353 for $C_{16}H_{14}F_2N_2O_5$.

Intermediate 65

6-((2R,6R)-2,6-Dimethylmorpholino)-7-fluoro-3-((2-oxo-4-(tetrahydro-2H-pyran-4-yl)-2-oxazolidin-3-yl)benzo[d]isoxazole-5-carbaldehyde

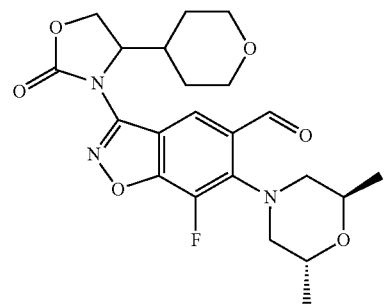 [SMILES: C[C@@H]1CN(c2c(C=O)cc3c(N4C(=O)OCC4C4CCOCC4)noc3c2F)C[C@@H](C)O1]

Intermediate 65 was prepared from Intermediate 64 using the method described for the synthesis of Intermediate 20. MS (ES) MH$^+$: 448 for $C_{22}H_{26}FN_3O_6$.

Intermediate 66

(S)-4-(3-Hydroxypropyl)oxazolidin-2-one

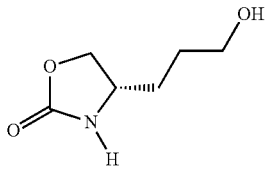

NaH (0.365 g, 9.12 mmol, 60% dispersion) was added in portions to an ice-bath cooled mixture of (S)-tert-butyl 1,5-dihydroxypentan-2-ylcarbamate (1 g, 4.56 mmol) dissolved in 10 mL of tetrahydrofuran. The mixture was warmed to 60° C. for 2.5 hours. After cooling to room temperature, the solution was acidified with 10% HCl and concentrated. The residue was diluted with methanol and any insoluble material was filtered off. The filtrate was concentrated to give crude oxazolidinone and used in the next step without any further purification. $^1$H NMR (300 MHz, DMSO-d$_6$) δ: 1.1-1.2 (m, 3H) 3.4 (d, 2H) 3.5 (q, 2H) 3.8-4.0 (m, 1H) 4.0-4.1 (m, 1H) 4.2-4.4 (m, 1H) 4.6-4.7 (m, 2H) 7.7 (br. s, 1H).

Intermediate 67

(S)-4-(3-(tert-Butyldiphenylsilyloxy)propyl)oxazolidin-2-one

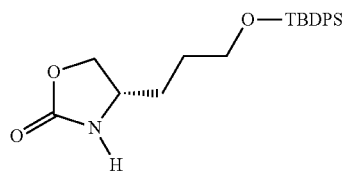

Intermediate 67 was prepared from Intermediate 66 using the method similar to synthesis of Intermediate 41. $^1$H NMR (300 MHz, DMSO-d$_6$) δ: 1.0 (s, 9H) 1.45-1.7 (m, 4H) 3.6-3.8 (m, 3H) 3.9 (dd, 1H) 4.3 (t, 1H) 7.4-7.5 (m, 6H) 7.6-7.7 (m, 4H) 7.7 (s, 1H).

Intermediate 68

(S)-4-(3-(tert-Butyldiphenylsilyloxy)propyl)-3-(6-((2R,6R)-2,6-Dimethylmorpholino)-5-(1,3-dioxolan-2-yl)-7-fluorobenzo[d]isoxazol-3-yl)oxazolidin-2-one

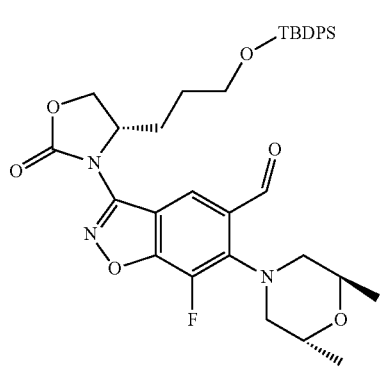

Intermediate 68 was prepared from Intermediate 67 and Intermediate 11 using the method similar to the one described for the synthesis of Intermediate 42. MS (ES) MH$^+$: 704 for $C_{38}H_{46}FN_3O_7Si$.

Intermediate 69

(S)-3-(6-((2R,6R)-2,6-Dimethylmorpholino)-5-(1,3-dioxolan-2-yl)-7-fluorobenzo[d]isoxazol-3-yl)-4-(3-hydroxypropyl)oxazolidin-2-one

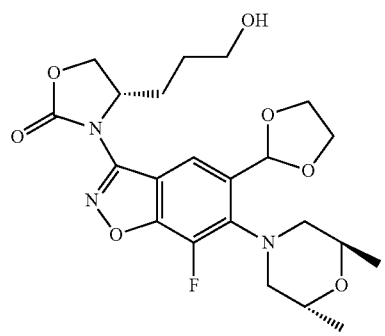

Intermediate 69 was prepared from Intermediate 68 using the method described for the synthesis of Intermediate 43. $^1$H NMR (300 MHz, DMSO-d$_6$) δ: 1.2 (d, 5H) 1.3-1.5 (m, 2H) 1.7-2.0 (m, 2H) 2.9 (dd, 2H) 3.2-3.4 (m. 4H) 3.95-4.1 (m, 6H) 4.3-4.5 (m, 2H) 4.6-4.8 (m, 2H) 6.2 (s, 1H) 8.25 (s, 1H). MS (ES) MH$^+$: 466 for $C_{22}H_{28}FN_3O_7$.

Intermediate 70

(S)-3-(6-((2R,6R)-2,6-Dimethylmorpholino)-5-(1,3-dioxolan-2-yl)-7-fluorobenzo[d]isoxazol-3-yl)-4-(3-fluoropropyl)oxazolidin-2-one

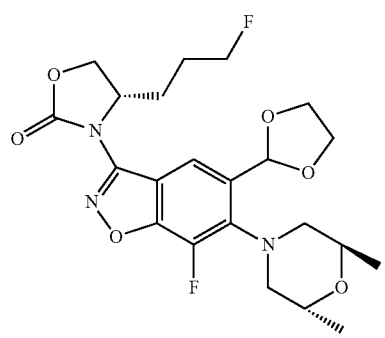 [SMILES: C[C@@H]1CN(c2c(C3OCCO3)cc3c(N4C(=O)OC[C@@H]4CCCF)noc3c2F)C[C@@H](C)O1]

A solution of bis(2-methoxyethyl)amino-sulfur trifluoride (0.149 ml, 50% in tetrahydrofuran, 0.40 mmol) was added to a ice-bath cooled solution of Intermediate 69 (125 mg, 0.27 mmol) in 10 mL CH$_2$Cl$_2$. The solution was warmed to room temperature with stirring for 18 hours. After quenching with aqueous NaHCO$_3$, the mixture was extracted with CH$_2$Cl$_2$. Solvent was removed from the organic extract, and the residue was chromatographed on silica gel (50% ethyl acetate in hexanes) to afford 83 mg (66% yield) of the title compound. $^1$H NMR (300 MHz, DMSO-d$_6$) δ: 1.2 (d, 6H) 1.5-2.1 (m, 4H) 2.9 (dd, 2H) 3.2-3.3 (m, 2H) 3.9-4.1 (m, 6H)

4.3-4.6 (m, 3H) 4.6-4.8 (m, 2H) 6.2 (s, 1H) 8.25 (s, 1H). MS (ES) MH⁺: 468 for $C_{22}H_{27}F_2N_3O_6$.

Intermediate 71

N-(1,4-Dihydroxybutan-2-yl)-5-(1,3-dioxolan-2-yl)-2,3,4-trifluoro-N'-hydroxybenzimidamide

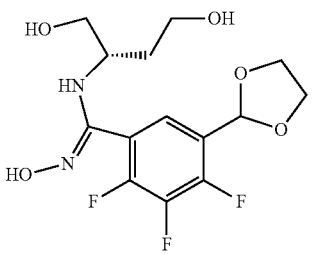 [SMILES: OCC[C@@H](CO)N/C(=N\O)c1cc(C2OCCO2)c(F)c(F)c1F]

Intermediate 16 (2.07 g, 7.34 mmol) and (S)-2-aminobutane-1,4-diol (1.3 g, 9.18 mmol) were stirred in 50 mL dimethylformamide while cooling with an ice water bath. Triethylamine (7.68 mL, 55.09 mmol) was slowly added over 10 minutes, and the reaction was allowed to warm to room temperature with stirring for 18 hours. The solvent was removed, and the residue was dissolved in 4 mL of water and 5 mL of ethyl acetate. The thick solution was filtered through a silica gel tube (10 mL capacity) with elution with ethyl acetate. The eluent was concentrated to afford 3.45 g (100% yield). ¹H NMR (300 MHz, DMSO-d₆) δ: 1.4-1.7 (m, 2H) 3.3 (t, 2H) 3.3-3.5 (m, 3H) 3.9-4.1 (m, 6H) 4.3 (t, 1H) 4.6 (t, 1H) 5.7 (d, 1H) 5.9-6.1 (m, 1H) 7.3 (td, 1H) 9.9 (s, 1H). MS (ES) MH⁺: 351 for $C_{14}H_{17}F_3N_2O_5$.

Intermediate 72

(S)-2-(5-(1,3-Dioxolan-2-yl)-6,7-difluorobenzo[d]isoxazol-3-ylamino)butane-1,4-diol

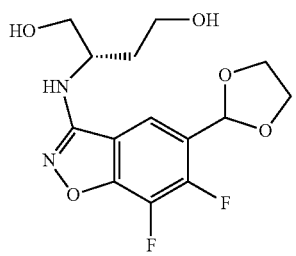 [SMILES: OCC[C@@H](CO)Nc1noc2c(F)c(F)c(C3OCCO3)cc12]

A mixture of Intermediate 71 (3.2 g, 9.14 mmol) and CsCO₃ (5.95 g, 18.27 mmol) was dissolved in dimethylformamide (50 mL) was stirred at room temperature over night. The solution was decanted away from the solid salts and filtered. The solids were washed 3× with ether and filtered. The combined filtrates were concentrated and the residue was partitioned between water and ethyl acetate. The ethyl acetate was separated and the aqueous layer was extracted 3 times with ethyl acetate. The organic layers were washed 3 times with saturated aqueous NaCl, dried over MgSO₄ and concentrated to give an oil. The oil was purified on silica gel column using a gradient of CH₂Cl₂ to 10% CH₂Cl₂ in ethyl acetate to afford the title compound. Yield 1.0 g, 33%. ¹H NMR (300 MHz, DMSO-d₆) δ: 1.6-1.9 (m, 2H) 3.4-3.6 (m, 4H) 3.7 (td, 1H) 3.9-4.2 (m, 4H) 4.4 (t, 1H) 4.6-4.8 (m, 1H) 5.7-5.8 (m, 1H) 6.1 (s, 1H) 7.05 (d, 1H) 8.0 (dd, 1H). MS (ES) MH⁺: 331 for $C_{14}H_{16}F_2N_2O_5$.

Intermediate 73

(S)-6,7-Difluoro-3-(4-(2-hydroxyethyl)-2-oxooxazolidin-3-yl)benzo[d]isoxazole-5-carbaldehyde

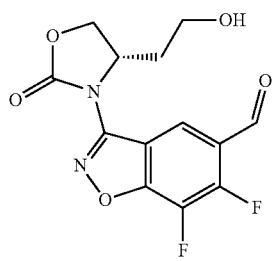 [SMILES: O=Cc1cc2c(N3C(=O)OC[C@@H]3CCO)noc2c(F)c1F]

Intermediate 72 (220 mg, 0.67 mmol) and carbonyl diimidazole (412 mg, 2.54 mmol) were dissolved in dimethylformamide (20 mL). Dimethylaminopyridine (31 mg, 0.25 mmol) was added and the reaction was stirred at 60° C. for 2 hours. After cooling to room temperature, the 5 mL of aqueous 1N HCl was added and the reaction mixture heated to 60° C. for 4 hours. Then, 2 mL of 6N HCl was added, and the reaction mixture was stirred at 60° C. for 2 hours. The reaction mixture was concentrated and the residue was extracted 3 times with ethyl acetate. The organic layers were washed with brine, dried over MgSO₄ and concentrated to give an oil. The residue was purified on a silica gel column using a gradient of hexanes to ethyl acetate to give the 100 mg (48% yield) of the title compound. ¹H NMR (300 MHz, DMSO-d₆) δ: 1.9 (m, 1H), 2.2 (m, 1H) 3.5 (q, 2H), 4.5-4.6 (m, 1H), 4.6-4.7 (m, 2H), 4.7-4.8 (m, 2H), 8.7 (dd, 1H), 10.2 (s, 1H). MS (ES) MH⁺: 313 for $C_{13}H_{10}F_2N_2O_6$.

Intermediate 74

6-((2R,6R)-2,6-Dimethylmorpholino)-7-fluoro-3-((S)-4-(2-hydroxyethyl)-2-oxooxazolidin-3-yl)benzo[d]isoxazole-5-carbaldehyde

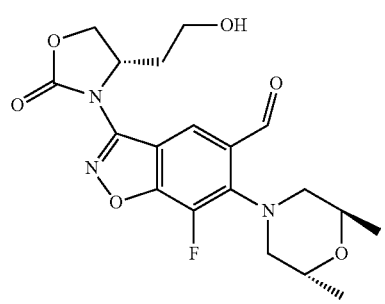 [SMILES: C[C@@H]1CN(c2c(C=O)cc3c(N4C(=O)OC[C@@H]4CCO)noc3c2F)C[C@@H](C)O1]

A solution of Intermediate 73 (100 mg, 0.32 mmol), diisopropylethylamine (225 μL, 1.29 mmol) and (2R,6R)-2,6-dimethylmorpholine (44 μl, 0.35 mmol) in 5 mL of acetonitrile was heated at 80° C. for 18 hours. The reaction mixture was diluted with water and extracted 3 times with ethyl acetate. The organic layers were washed twice with brine, dried over MgSO₄ and concentrated to give an oil. The residue was purified on a silica gel column using a gradient of hexanes to ethyl acetate to afford the title compound (60 mg, 0.147 mmol, 46.0% yield). ¹H NMR (300 MHz, CDCl₃) δ: 1.3-1.4 (m, 6H), 1.9-2.1 (m, 1H), 2.3-2.5 (m, 1H), 3.0 (ddd, 2H), 3.4 (dt, 2H), 3.7-3.9 (m, 2H), 4.2-4.3 (m, 2H), 4.5-4.5 (m, 1H), 4.7-4.9 (m, 2H), 8.7 (d, 1H), 10.4 (s, 1H). MS (ES) MH⁺: 408 for $C_{19}H_{22}FN_3O_6$.

Intermediate 75

(S)-5-((tert-Butyldiphenylsilyloxy)methyl)-3-(7-chloro-6-((2R,6R)-2,6-dimethylmorpholino)-5-(1,3-dioxolan-2-yl)benzo[d]isoxazol-3-yl)oxazolidin-2-one

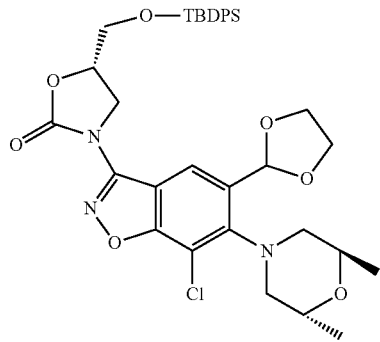

Intermediate 75 was prepared from Intermediates 41 and 52 using the method described for the synthesis of Intermediate 32. MS (ES) MH⁺: 693 for $C_{36}H_{42}ClN_3O_7Si$.

Intermediate 76

(S)-3-(7-Chloro-6-((2R,6R)-2,6-dimethylmorpholino)-5-(1,3-dioxolan-2-yl)benzo[d]isoxazol-3-yl)-5-(hydroxymethyl)oxazolidin-2-one

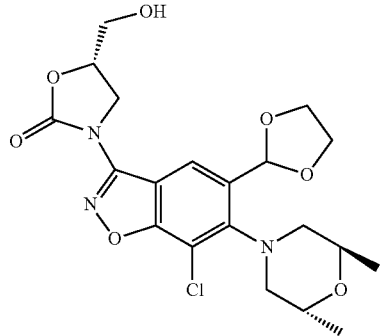 [SMILES: C[C@@H]1CN(c2c(C3OCCO3)cc3c(N4C[C@@H](CO)OC4=O)noc3c2Cl)C[C@@H](C)O1]

Intermediate 76 was prepared from Intermediate 75 using the method described for the synthesis of Intermediate 43. ¹H NMR (300 MHz, DMSO-d₆) δ: 1.1 (br. s, 3H) 1.3 (br. s, 3H) 2.7-2.9 (m, 1H) 3.0-3.2 (m, 2H) 3.6-3.8 (m, 3H) 3.9-4.2 (m, 8H) 4.8-5.0 (m, 1H) 5.3 (t, 1H) 6.2 (s, 1H) 8.6 (s, 1H). MS (ES) MH⁺: 454 for $C_{20}H_{24}ClN_3O_7$.

Intermediate 77

(S)-3-(7-Chloro-6-((2R,6R)-2,6-dimethylmorpholino)-5-(1,3-dioxolan-2-yl)benzo[d]isoxazol-3-yl)-5-(fluoromethyl)oxazolidin-2-one

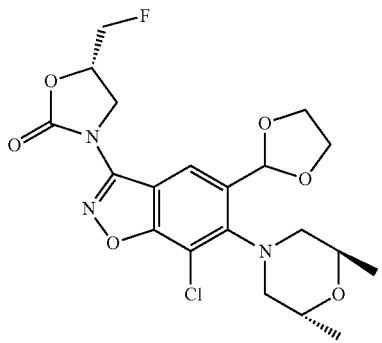 [SMILES: C[C@@H]1CN(c2c(C3OCCO3)cc3c(N4C[C@@H](CF)OC4=O)noc3c2Cl)C[C@@H](C)O1]

Intermediate 77 was prepared from Intermediate 76 using a method similar to the one described for the synthesis of Intermediate 70. ¹H NMR (300 MHz, DMSO-d₆) δ: 1.1 (br s, 3H) 1.3 (br s, 3H) 2.65-2.9 (m, 1H) 2.9-3.2 (m, 2H) 3.5-3.7 (m, 1H) 3.8-4.2 (m, 7H) 4.2-4.35 (m, 1H) 4.6-4.9 (m, 2H) 5.05-5.3 (m, 1H) 6.2 (s, 1H) 8.6 (s, 1H). MS (ES) MH⁺: 456 for $C_{20}H_{23}ClFN_3O_6$.

Intermediate 78

(S)-4-(3-(ter-Butyldiphenylsilyloxy)propy)-3-(7-chloro-6-((2R,6R)-2,6-dimethylmorpholino)-5-(1,3-dioxolan-2-yl)benzo[d]isoxazol-3-yl)oxazolidin-2-one

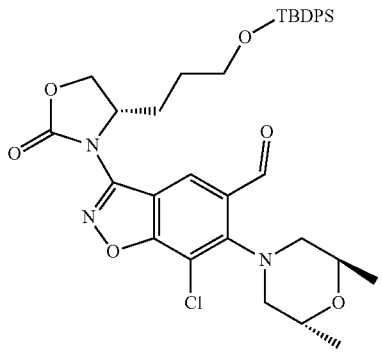

Intermediate 78 was prepared from Intermediate 67 and Intermediate 52 using a method similar to the one described for the synthesis of Intermediate 42. ¹H NMR (300 MHz, DMSO-d₆) δ: 0.9 (s, 9H) 1.1 (br. s., 3H) 1.3 (br. s., 3H) 1.4-1.65 (m, 2H) 1.85-2.0 (m, 2H) 2.7-3.1 (m, 3H) 3.5-3.7 (m, 3H) 3.95-4.2 (m, 6H) 4.3-4.4 (m, 1H) 4.6-4.8 (m, 2H) 6.2 (s, 1H) 7.3-7.5 (m, 6H) 7.5-7.6 (m, 4H) 8.4 (s, 1H). MS (ES) MH⁺: 720 for $C_{38}H_{46}1N_3O_7Si$.

Intermediate 79

(S)-3-(7-Chloro-6-((2R,6R)-2,6-dimethylmorpholino)-5-(1,3-dioxolan-2-yl)benzo[d]isoxazol-3-yl)-4-(3-hydroxypropyl)oxazolidin-2-one

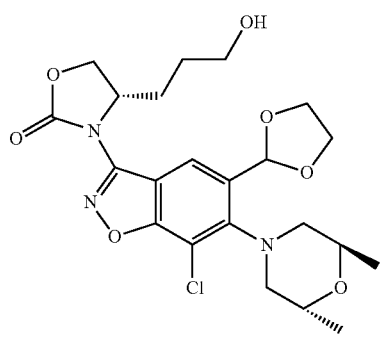

Intermediate 79 was prepared from Intermediate 78 using the method described for the synthesis of Intermediate 43. $^1$H NMR (300 MHz, DMSO-$d_6$) δ: 1.1 (br. s, 3H) 1.25-1.5 (m, 5H) 1.7-2.0 (m, 2H) 2.7-2.9 (m, 1H) 3.0-3.2 (m, 2H) 3.3-3.45 (m, 2H) 3.5-3.7 (m, 1H) 3.9-4.15 (m, 6H) 4.3-4.5 (m, 2H) 4.6-4.8 (m, 2H) 6.2 (s, 1H) 8.4 (s, 1H). MS (ES) MH$^+$: 482 for $C_{22}H_{28}ClN_3O_7$.

Intermediate 80

(S)-3-(7-Chloro-6-((2R,6R)-2,6-dimethylmorpholino)-5-(1,3-dioxolan-2-yl)benzo[d]isoxazol-3-yl)-4-(3-fluoropropyl)oxazolidin-2-one

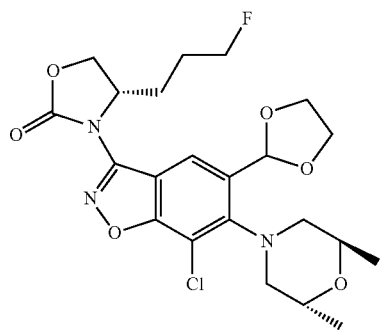

Intermediate 80 was prepared from Intermediate 79 using the method described for the synthesis of Intermediate 70. $^1$H NMR (300 MHz, DMSO-$d_6$) δ: 1.1 (br. s, 3H) 1.3 (br. s, 3H) 1.5-2.0 (m, 4H) 2.7-2.9 (m, 1H) 3.0-3.1 (m, 2H) 3.5-3.7 (m, 1H) 3.9-4.15 (m, 6H) 4.3-4.6 (m, 3H) 4.65-4.8 (m, 2H) 6.2 (s, 1H) 8.4 (s, 1H). MS (ES) MH$^+$: 484 for $C_{22}H_{27}ClFN_3O_6$.

Intermediate 81

(S)-3-(6-((2R,6R)-2,6-Dimethylmorpholino)-5-(1,3-dioxolan-2-yl)-7-fluorobenzo[d]isoxazol-3-yl)-5-(methoxymethyl)oxazolidin-2-one

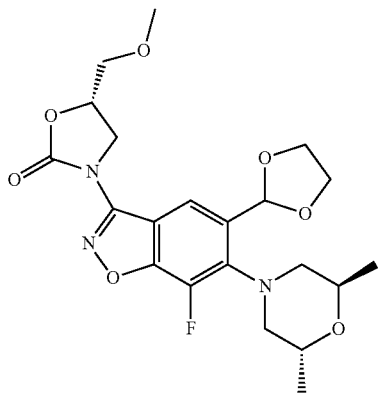 [SMILES: COC[C@@H]1CN(c2noc3c(F)c(N4C[C@@H](C)O[C@H](C)C4)c(C4OCCO4)cc23)C(=O)O1]

Intermediate 81 was prepared from Intermediate 11 and (S)-5-(methoxymethyl)oxazolidin-2-one (purchased from Daisco Co., LTD) using the method described for Intermediate 12. $^1$H NMR (300 MHz, DMSO-$d_6$) δ: 1.2 (d, 6H), 2.9 (dd, 2H), 3.2-3.3 (m, 2H), 3.3 (s, 3H), 3.6-4.3 (m, 9H), 4.9-5.2 (m, 1H), 6.2 (s, 1H), 8.4 (s, 1H). MS (ES) MH$^+$: 452 for $C_{21}H_{26}FN_3O_7$.

Intermediate 82

(R)-3-(6-((2R,6R)-2,6-Dimethylmorpholino)-5-(1,3-dioxolan-2-yl)-7-fluorobenzo[d]isoxazol-3-yl)-5-(methoxymethyl)oxazolidin-2-one

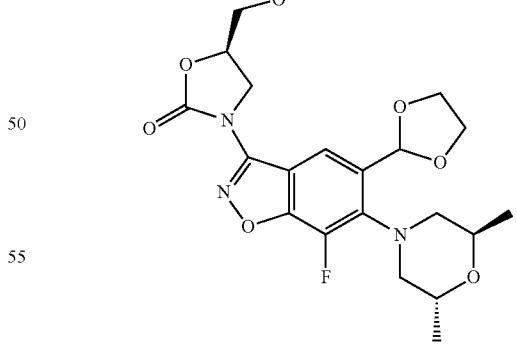

Intermediate 82 was prepared from (R)-5-(methoxymethyl)oxazolidin-2-one (purchased from Daisco Co., LTD) and Intermediate 11 using the method described for the synthesis of Intermediate 12. $^1$H NMR (300 MHz, DMSO-$d_6$) δ: 1.2 (d, 6H) 2.9 (dd, 4.8 Hz, 2H) 3.1-3.3 (m, 2H) 3.3 (s, 3H) 3.6-4.3 (m, 9H) 4.9-5.1 (m, 1H) 6.2 (s, 1H) 8.4 (s, 1H). MS (ES) MH$^+$: 452 for $C_{21}H_{26}FN_3O_7$.

Intermediate 83

(5R)-5-(Hydroxymethyl)-1,3-oxazolidin-2-one

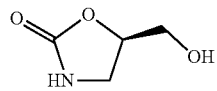

To a stirred solution of 3-amino-1,2-propanediol (5.07 g, 55.7 mmol) in water (60 mL), sodium bicarbonate (20.70 g, 195.3 mmol) followed by triphosgene (4.70 g, 15.8 mmol) portion wise and the mixture was stirred at the room temperature for 16 hours. The reaction mixture was neutralized with 1.5N hydrochloric acid carefully and the water was removed under vacuum to and the residue was dissolved in ethanol (250 mL) and filtered through celite. The residue was washed with ethanol (250 mL) and the solvents of the filtrates were removed under vacuum. The solid thus obtained was purified by silica gel column chromatography using a gradient of methanol in ethyl acetate. Yield: 3.30 (51%) $^1$H NMR (300 MHz, DMSO-$d_6$) δ: 3.18-3.30 (m, 1H), 3.45-3.56 (m, 3H), 4.47-4.55 (m, 1H), 4.05 (t, 1H), 7.39 (s, 1H).

Intermediate 84

(5R)-5-[(Tetrahydro-2H-pyran-2-yloxy)methyl]-1,3-oxazolidin-2-one

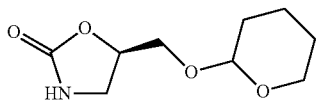 [SMILES: O=C1NC[C@H](COC2CCCCO2)O1]

To a stirred solution of Intermediate 83 (5.0 g, 42.7 mmol) in dichloromethane (50 mL), pyridinium p-toluenesulfonate (1.07 g, 4.27 mmol) and 3,4-dihydropyran (5.84 mL, 64.1 mmol) were added and the mixture was stirred at the room temperature for 16 hours. The reaction mixture was quenched with brine solution (25 mL) and extracted with dichloromethane (3×25 mL). The combined organic layers were dried over sodium sulfate and the solvents were removed under vacuum. The crude product obtained was purified by silica gel flash column chromatography using 50% ethyl acetate in hexane. Yield: 5.0 g (58%)$^1$H NMR (300 MHz, DMSO-$d_6$): δ 1.45-1.49 (m, 4H), 1.57-1.73 (m, 2H), 3.12-3.28 (m, 1H), 3.45-3.55 (m, 3H), 3.67-3.75 (m, 2H), 4.62-4.63 (m, 1H), 4.70-4.72 (m, 1H), 7.50 (s, 1H). MS (ELSD) MH$^+$: 202.2 for $C_9H_{15}FNO_4$.

Intermediate 85

(5R)-3-{6-[(2R,6R)-2,6-Dimethylmorpholin-4-yl]-5-(1,3-dioxolan-2-yl)-7-fluoro-1,2-benzoxazol-3-yl}-5-[(tetrahydro-2H-pyran-2-yloxy)methyl]-1,3-oxazolidin-2-one

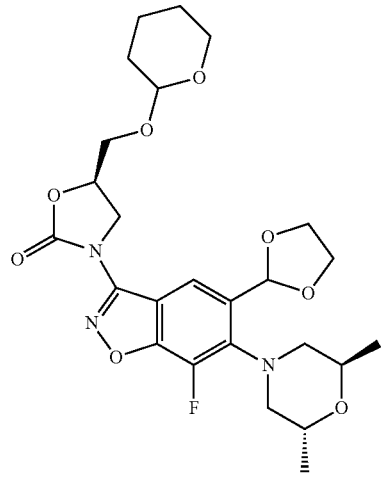 [SMILES: C[C@@H]1CN(c2c(C3OCCO3)cc3c(N4C[C@H](COC5CCCCO5)OC4=O)noc3c2F)C[C@@H](C)O1]

To a stirred solution of sodium hydride (0.61 g, 25.5 mmol) in dimethyl formamide (10 mL), a solution of Intermediate 84 (2.57 g, 12.7 mmol) in dimethyl formamide (20 mL) was added slowly at 0° C. over a period of 10 minutes. The mixture was stirred at the room temperature for 30 minutes and a solution of Intermediate 11 (4.55 g, 12.7 mmol) in dimethyl formamide (20 mL) was added at the same temperature and the mixture was heated at 60° C. for 2 hours. The reaction was quenched with saturated ammonium chloride solution (10 mL), extracted with ethyl acetate (3×50 mL). The combined organic layers were dried over anhydrous sodium sulfate and the solvents were removed under vacuum. The crude product was purified by silica gel column chromatography using a gradient of ethyl acetate in hexane. Yield: 2.0 g (30%). $^1$H NMR (400 MHz, DMSO-$d_6$) δ: 1.16 (d, 6H), 1.39-1.48 (m, 5H), 2.85-2.90 (m, 2H), 3.18-3.21 (m, 4H), 3.58-3.83 (m, 2H), 3.93-3.99 (m, 2H), 4.04-4.07 (m, 5H), 4.46-4.58 (m, 2H), 4.67-4.76 (m, 2H), 6.15 (s, 1H), 8.25 (d, 1H). MS (ES) MH$^+$: 522.2 for $C_{25}H_{32}FN_3O_8$.

Intermediate 86

(5R)-3-{6-[(2R,6R)-2,6-Dimethylmorpholin-4-yl]-5-(1,3-dioxolan-2-yl)-7-fluoro-1,2-benzoxazol-3-yl}-5-(hydroxymethyl)-1,3-oxazolidin-2-one

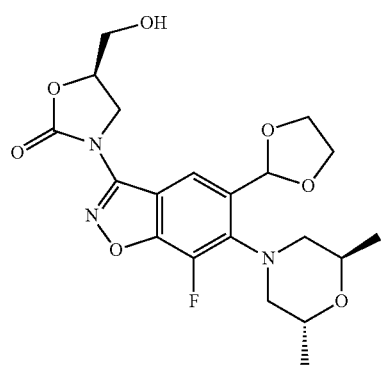 [SMILES: C[C@@H]1CN(c2c(C3OCCO3)cc3c(N4C[C@H](CO)OC4=O)noc3c2F)C[C@@H](C)O1]

To a stirred solution of Intermediate 85 (2.6 g, 4.99 mmol) in toluene (20 mL), ethylene glycol (2.0 mL) followed by pyridinium p-toluene sulfonate (0.23 g, 0.99 mmol) and the mixture was heated at 110° C. for 1.5 hours. The reaction mixture was quenched with saturated sodium bicarbonate solution (10 mL) and extracted with ethyl acetate (3×25 mL). The organic layers were washed with brine, dried over sodium sulfate and the solvents were removed under vacuum. The crude product was purified by flash column silica gel chromatography using 30% ethyl acetate in hexane. Yield: 1.40 g (66%). $^1$H NMR (400 MHz, DMSO-$d_6$) δ: 1.20 (d, 6H), 2.88-2.92 (m, 2H), 3.21-3.23 (m, 2H), 3.61-3.65 (m, 1H), 3.72-3.77 (m, 1H), 3.93-4.01 (m, 3H), 4.04-4.10 (m, 4H), 4.19 (t, 1H), 4.88-4.92 (m, 1H), 5.30 (t, 1H), 6.18 (s, 1H), 8.45 (s, 1H). MS (ES) MH$^+$: 438.4 for $C_{20}H_{24}FN_3O_7$.

Intermediate 87

(5R)-3-{6-[(2R,6R)-2,6-Dimethylmorpholin-4-yl]-5-(1,3-dioxolan-2-yl)-7-fluoro-1,2-benzoxazol-3-yl}-5-(fluoromethyl)-1,3-oxazolidin-2-one

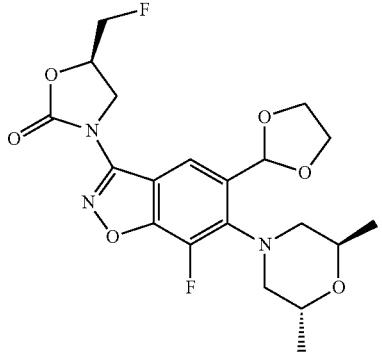 [SMILES: C[C@@H]1CN(c2c(C3OCCO3)cc3c(N4C[C@H](CF)OC4=O)noc3c2F)C[C@@H](C)O1]

To a stirred solution of Intermediate 86 (0.10 g, 0.21 mmol) in tetrahydrofuran (3 mL), diethylaminosulfur trifluoride (0.17 g, 1.06 mmol) was added at −78° C. and the mixture was stirred at the same temperature for another hour and then it was stirred at the room temperature for 2 hours. Methanol (1 mL) was added to the reaction mixture and the volatiles were removed under vacuum. The residue was dissolved in ethyl acetate (15 mL) and washed with saturated sodium bicarbonate (5 mL), water (10 mL) and finally with brine solution. The organic layer was dried over sodium sulfate and the solvent was removed under vacuum. The solid obtained was pure enough and it was taken to the next step without further purification. Yield: 0.05 g (55%). MS (ES) MH$^+$: 440.4 for $C_{20}H_{23}F_2N_3O_6$.

Intermediate 88

(4S)-3-{6-[(2R,6R)-2,6-Dimethylmorpholin-4-yl]-5-(1,3-dioxolan-2-yl)-7-fluoro-1,2-benzoxazol-3-yl}-4-ethenyl-1,3-oxazolidin-2-one

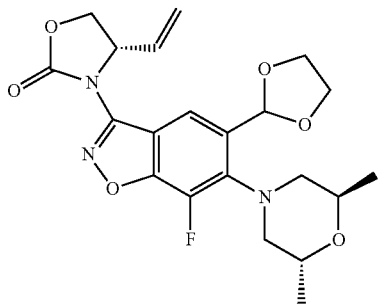 [SMILES: C=C[C@H]1COC(=O)N1c1noc2c(F)c(N3C[C@@H](C)O[C@H](C)C3)c(C3OCCO3)cc12]

To a stirred suspension of sodium hydride (0.71 g, 17.6 mmol) in dimethyl formamide (10 mL), a solution of (4S)-4-ethenyl-1,3-oxazolidin-2-one (prepared according to the literature procedure Chem. Eur. J. 2006, 12, 6607-6620, 2.0 g, and 17.6 mmol) in dimethylformamide (10 mL) was added slowly at 0° C. over a period of 10 minutes. The mixture was stirred at the room temperature for 30 minutes and a solution of Intermediate 11 (3.1 g, 8.84 mmol) in dimethylformamide (10 mL) was added at the same temperature. This mixture was heated at 80° C. for 12 hours and poured into ice-cooled water and extracted with ethyl acetate (3×25 mL). The organic layers were dried over anhydrous sodium sulfate and the solvents were removed under vacuum. The crude product was purified by silica gel column chromatography using a gradient of ethyl acetate in pet. ether. Yield: 0.70 g (19%). MS (ES) MH$^+$: 434.3 for $C_{21}H_{24}FN_3O_6$.

Intermediate 89

(5R)-3-{6-[(2R,6R)-2,6-Dimethylmorpholin-4-yl]-5-(1,3-dioxolan-2-yl)-7-fluoro-1,2-benzoxazol-3-yl}-5-[(E)-(hydroxyimino)methyl]-1,3-oxazolidin-2-one

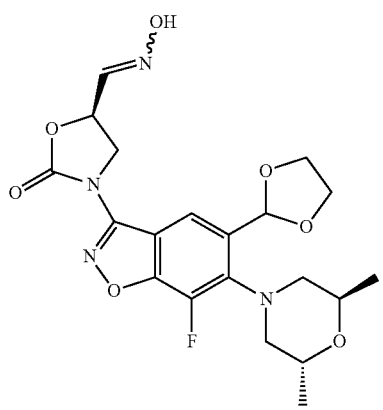 [SMILES: C[C@@H]1CN(c2c(C3OCCO3)cc3c(N4C[C@H](C=NO)OC4=O)noc3c2F)C[C@@H](C)O1]

To a solution of dimethyl sulfoxide (0.22 g, 2.74 mmol), in dichloromethane (3 mL), oxalyl chloride (0.18 g, 1.37 mmol) was added at −80° C. under nitrogen atmosphere and the mixture was stirred at that temperature for 30 minutes. To this, a solution of Intermediate 86 (0.4 g, 0.92 mmol) in dichloromethane (3 mL) was added drop wise at the same temperature and the reaction mixture was stirred at this temperature for 3 hours before adding triethylamine (0.46 g, 4.50 mmol) at the same temperature. Then it was brought to the 0° C. where it was stirred for 1.5 hours and water was added to it (5 mL) and diluted with dichloromethane (5 mL). The organic layers were extracted and dried over sodium sulfate and the solvent was removed under vacuum at the room temperature. The crude material (0.36 g) was dissolved in absolute ethanol (10 mL) and hydroxylamine hydrochloride (0.9 g, 1.20 mmol) was added followed by sodium acetate (0.08 g, 1.20 mmol) and the mixture was refluxed for 3 hours. Volatiles were removed and the residue was poured into water and filtered and the precipitates were washed with water (25 mL) and dried. The crude product was purified by silica gel flash column chromatography using a gradient of ethyl acetate in pet. ether. The compound was obtained as an undefined mixture of E & Z isomers (1:2 ratio by $^1$H NMR). Yield: 0.13 g (35%) $^1$HNMR (400 MHz, DMSO-$d_6$) δ: 1.24 (br s, 6H), 2.89-2.93 (m, 2H), 3.21-3.24 (m, 2H), 3.95-4.00 (m, 2H), 4.02-4.11 (m, 4H), 4.20 (t, 1H), 4.34 & 4.44 (t, 1H), 5.43 & 5.82 (quin, 1H), 6.18 (s, 1H), 7.21 & 7.65 (d, 1H), 8.41-8.42 (m, 1H), 11.58 & 11.78 (s, 1H). MS (ES) MH$^+$: 451.4 for $C_{20}H_{23}FN_4O_7$.

Intermediate 90

(4R)-3-{6-[(2R,6R)-2,6-Dimethylmorpholin-4-yl]-5-(1,3-dioxolan-2-yl)-7-fluoro-1,2-benzoxazol-3-yl}-2-oxo-1,3-oxazolidine-4-carbaldehyde

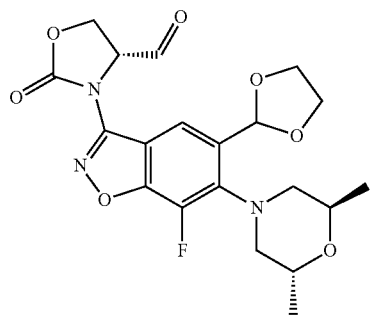 [SMILES: C[C@@H]1CN(c2c(C3OCCO3)cc3c(N4C(=O)OC[C@@H]4C=O)noc3c2F)C[C@@H](C)O1]

To a solution of Intermediate 88 (0.4 g, 0.92 mmol) in tetrahydrofuran (4 mL) and water (4 mL), N-methyl morpholine-N-oxide (0.22 g, 1.84 mmol) and 2 wt % in solution osmium tetroxide in t-butanol (0.02 g, 0.05 mmol) were added and the mixture was stirred at the room temperature for 3 hours. To this solution, benzene iodosodiacetate (0.75 g, 2.3 mmol) was added and it was stirred for 16 hours. The reaction mass was extracted with ethyl acetate (3×20 mL), the combined organic layers were washed with water (15 mL), dried over sodium sulfate and the solvents were removed under vacuum. The solid was taken to the next step without further purification. Yield: 0.40 g (crude). $^1$HNMR (400 MHz, DMSO-$d_6$) δ: 1.24 (d, 6H), 2.89-2.96 (m, 2H), 3.31-3.50 (m, 2H), 4.02-4.17 (m, 8H), 4.56-4.74 (m, 1H), 6.32 (s, 1H), 8.52 (s, 1H), 9.90 (s, 1H). MS (ES) MH$^+$: 451.4 for $C_{20}H_{22}FN_3O_7$.

Intermediate 91

(4S)-3-{6-[(2R,6R)-2,6-Dimethylmorpholin-4-yl]-5-(1,3-dioxolan-2-yl)-7-fluoro-1,2-benzoxazol-3-yl}-4-[(E)-(hydroxyimino)methyl]-1,3-oxazolidin-2-one

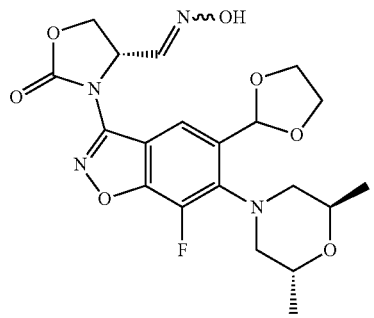 [SMILES: C[C@@H]1CN(c2c(C3OCCO3)cc3c(N4C(=O)OC[C@@H]4C=NO)noc3c2F)C[C@@H](C)O1]

To a solution of Intermediate 90 (0.4 g, 0.92 mmol) in pyridine (5 mL) and methanol (5 mL), hydroxylamine hydrochloride (0.08 g, 1.1 mmol) was added and the mixture was heated at 95° C. for 30 minutes. The volatiles were removed under vacuum and the crude product was dissolved in ethyl acetate (30 mL), washed with water (2×15 mL) and brine (15 mL), dried over sodium sulfate. Removal of solvent under vacuum afforded the title compound as 40:60 mixture of E/Z isomer which was further purified by washing with hexane (25 mL). Yield: 0.37 g (90%)$^1$HNMR (400 MHz, DMSO-$d_6$) δ: 1.24 (d, 6H), 2.89-2.91 (m, 2H), 3.19-3.22 (m, 2H), 3.96-4.07 (m, 6H), 4.31 & 4.52 (dd, 1H), 4.75 & 4.87 (t, 1H), 5.25-5.29 & 5.51-5.61 (m, 1H), 6.16 & 6.17 (s, 1H), 7.12 & 7.53 (d, 1H), 8.27 & 8.37 (s, 1H), 11.24 & 11.55 (s, 1H). MS (ES) MH$^+$: 451.4 for $C_{20}H_{23}FN_4O_7$.

Intermediate 92

(4S)-3-{6-[(2R,6R)-2,6-Dimethylmorpholin-4-yl]-5-(1,3-dioxolan-2-yl)-7-fluoro-1,2-benzoxazol-3-yl}-2-oxo-1,3-oxazolidine-4-carbonitrile

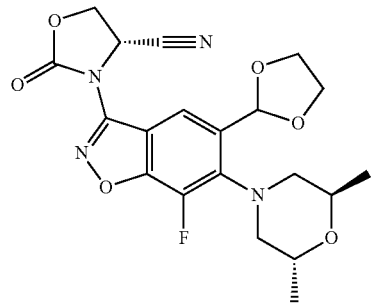 [SMILES: C[C@@H]1CN(c2c(C3OCCO3)cc3c(N4C(=O)OC[C@@H]4C#N)noc3c2F)C[C@@H](C)O1]

A solution of Intermediate 91 (0.18 g, 0.4 mmol) in trichloroacetonitrile (10 mL) was heated at 95° C. for an hour. The volatiles were evaporated and the crude product was recrystallised using ethyl acetate and hexane. Yield: 0.09 g (53%). $^1$HNMR (400 MHz, DMSO-$d_6$) δ: 1.21 (d, 6H), 2.87-2.93 (m, 2H), 3.23 (d, 2H), 3.94-4.04 (m, 6H), 4.85 (d, 2H), 5.64 (dd, 1H), 6.17 (s, 1H), 8.32 (s, 1H). MS (ES) MH$^+$: 436.4 for $C_{20}H_{23}FN_4O_7$.

Intermediate 93

(4S)-3-{6-[(2R,6R)-2,6-Dimethylmorpholin-4-yl]-5-(1,3-dioxolan-2-yl)-7-fluoro-1,2-benzoxazol-3-yl}-4-[(E)-(methoxyimino)methyl]-1,3-oxazolidin-2-one

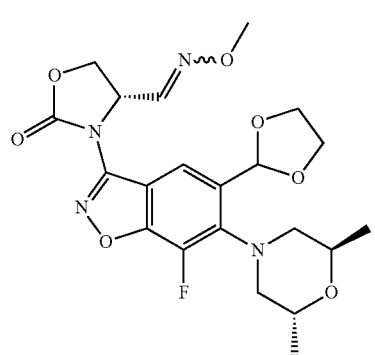

Intermediate 93 was prepared from Intermediate 90 and O-methyl hydroxylamine hydrochloride using the method described for the synthesis of Intermediate 91. $^1$HNMR (400 MHz, DMSO-d$_6$) δ: 1.24 (d, 6H), 2.89-2.91 (m, 2H), 3.19-3.22 (m, 2H), 3.32 & 3.72 (s, 3H), 3.96-4.09 (m, 6H), 4.31 & 4.52 (dd, 1H), 4.75 & 4.87 (t, 1H), 5.25-5.29 & 5.51-5.61 (m, 1H), 6.17 (s, 1H), 7.25 & 7.66 (d, 1H), 8.27 & 8.36 (s, 1H). MS (ES) MH$^+$: 465.4 for C$_{21}$H$_{25}$FN$_4$O$_7$.

Intermediate 94

(5R)-3-{6-[(2R,6R)-2,6-Dimethylmorpholin-4-yl]-5-(1,3-dioxolan-2-yl)-7-fluoro-1,2-benzoxazol-3-yl}-5-[(E)methoxyimino)methyl]-1,3-oxazolidin-2-one

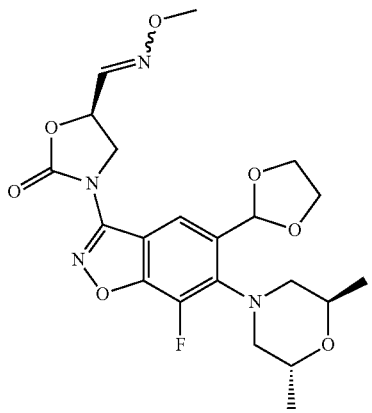 [SMILES: CON=C[C@H]1CN(c2noc3c(F)c(N4C[C@@H](C)O[C@H](C)C4)c(C4OCCO4)cc23)C(=O)O1]

Intermediate 94 was prepared from Intermediate 85 and O-methyl hydroxylamine hydrochloride using the method described for the synthesis of Intermediate 86. The compound was obtained as an undefined mixture of E & Z isomers (1:2.3). Yield: 0.13 (30%). $^1$HNMR (400 MHz, DMSO-d$_6$) δ: 1.24 (d, 6H), 2.86-2.91 (m, 2H), 3.19-3.25 (m, 2H), 3.76 & 3.83 (s, 3H), 3.91-3.99 (m, 2H), 4.00-4.07 (m, 4H), 4.14-4.19 (m, 1H), 4.32-4.44 (m, 1H), 5.25-5.39-5.46 & 5.75-5.76 (m, 1H), 6.16 (s, 1H), 7.31 & 7.75 (d, 1H), 8.40 (s, 1H). MS (ES) MH$^+$: 465.3 for C$_{21}$H$_{25}$FN$_4$O$_7$.

Intermediate 95

[(5R)-3-{6-[(2R,6R)-2,6-Dimethylmorpholin-4-yl]-5-(1,3-dioxolan-2-yl)-7-fluoro-1,2-benzoxazol-3-yl}-2-oxo-1,3-oxazolidin-5-yl]methyl 4-methylbenzenesulfonate

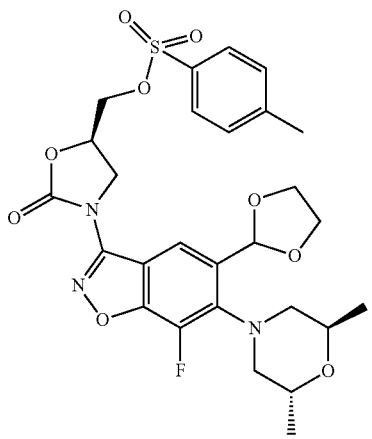 [SMILES: Cc1ccc(S(=O)(=O)OC[C@H]2CN(c3noc4c(F)c(N5C[C@@H](C)O[C@H](C)C5)c(C5OCCO5)cc34)C(=O)O2)cc1]

To a stirred solution of Intermediate 86 (2.7 g, 6.10 mmol) in dichloromethane (50 mL), 4-dimethylaminopyridine (1.50 g, 12.3 mmol) was added at 0° C. followed by p-toluene sulfonyl chloride (1.76 g, 9.20 mmol). The resulting solution was brought to the room temperature after stirred at the same temperature for an hour where it was stirred for a further period of an hour. The reaction mixture was washed with citric acid solution (25 mL), water (25 mL), saturated sodium bicarbonate solution (25 mL) and again with water (2×25 mL). The organic layer was dried over sodium sulfate and the solvents were removed under vacuum to obtained crude product which was purified by silica gel flash column chromatography using a gradient of ethyl acetate in hexane. Yield: 3.2 g (88%)$^1$H NMR (400 MHz, DMSO-d$_6$) δ: 1.20 (d, 6H), 2.39 (s, 3H), 2.88-2.92 (m, 2H), 3.19-3.22 (m, 2H), 3.78 (dd, 1H), 3.94-3.99 (m, 2H), 4.04-4.10 (m, 4H), 4.19 (t, 1H), 4.41 (d, 2H), 5.05-5.07 (m, 1H), 6.16 (s, 1H), 7.45 (d, 2H), 7.77 (d, 2H), 8.38 (s, 1H). MS (ES) MH$^+$: 592.4 for C$_{27}$H$_{30}$FN$_3$O$_9$S.

Intermediate 96

(5R)-5-(Azidomethyl)-3-{6-[(2R,6R)-2,6-dimethylmorpholin-4-yl]-5-(1,3-dioxolan-2-yl)-7-fluoro-1,2-benzoxazol-3-yl}-1,3-oxazolidin-2-one

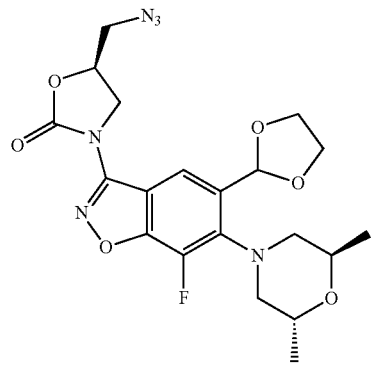 [SMILES: C[C@@H]1CN(c2c(C3OCCO3)cc3c(N4C[C@H](CN=[N+]=[N-])OC4=O)noc3c2F)C[C@@H](C)O1]

To a stirred solution of Intermediate 95 (3.20 g, 5.40 mmol) in dimethylformamide (30 mL) in a sealed tube, sodium azide (1.0 g, 16.20 mmol) was added and the mixture was heated at 90° C. for 3 hours. The reaction was quenched with water (15 mL) after being brought to room temperature and extracted with ethyl acetate (2×15 mL). The combined organic layers were washed with water (2×10 mL) and brine solution (10 mL), dried over sodium sulfate and the solvent was removed under vacuum afforded the crude title compound, which was further purified by flash column chromatography using a gradient of ethyl acetate in pet. ether to obtain the pure product as colorless viscous liquid. Yield: 2.1 g (51%). $^1$H NMR (400 MHz, DMSO-d$_6$) δ: 1.24 (d, 6H), 2.90 (dd, 2H), 3.22 (d, 2H), 3.82 (d, 2H), 3.88 (dd, 1H), 3.95-4.00 (m, 2H), 4.02-4.10 (m, 4H), 4.25 (t, 1H), 5.08-5.11 (m, 1H), 6.18 (s, 1H), 8.44 (s, 1H). MS (ES) MH$^+$: 463.4 for C$_{20}$H$_{23}$FN$_6$O$_6$.

Intermediate 97

Methyl (4R)-2-oxo-1,3-oxazolidine-4-carboxylate

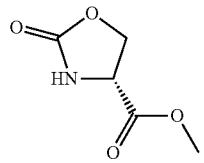

To a suspension of D-serine methyl ester hydrochloride (25.0 g, 160.7 mmol) in tetrahydrofuran (150 mL), a solution of triphosgene (47.68 g, 160.7 mmol) in tetrahydrofuran (100 mL) was added at 0° C. and the mixture was stirred at 80° C. for 2 hours. The volatiles were evaporated under vacuum and the residue was subjected to flash column silica gel chromatography using 5% methanol in chloroform. Yield: 17.5 g (75%). $^1$H NMR (400 MHz, DMSO-$d_6$) δ: 3.69 (s, 3H), 4.32-4.33 (m, 1H), 4.32-4.33 (m, 2H), 8.22 (s, 1H).

Intermediate 98

(4S)-4-(Hydroxymethyl)-1,3-oxazolidin-2-one

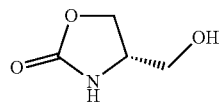

To a stirred solution of Intermediate 97 (15.0 g, 103.4 mmol) in ethanol (100 mL), sodium borohydride (1.96 g, 51.7 mmol) was added portionwise at 0° C. and the mixture was stirred at room temperature for 30 minutes. To this mixture, 1.5 N hydrochloric acid was added and the volatiles were removed under vacuum. Methanol (50 mL) was added to the residue, filtered through celite and the solvents were removed under vacuum. The title compound was obtained as colorless oil, which was used in the further step without purification. Chiral HPLC data showed a mixture of 91.3:8.7 enantiomers [Column: Chiralpak AD-H (250×4.6) mm 5 μm; Mobile Phase: Hexane:Ethanol (85:15)]. $^1$H NMR (400 MHz, DMSO-$d_6$) δ: 3.34-3.35 (m, 2H), 3.70-3.72 (m, 1H), 4.04 (dd, 1H), 2.96 (t, 1H), 4.96 (t, 1H), 7.59 (s, 1H).

Intermediate 99

[(4R)-2-Oxo-1,3-oxazolidin-4-yl]methyl 4-methylbenzenesulfonate

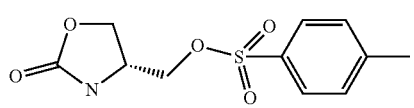 [SMILES: Cc1ccc(S(=O)(=O)OC[C@H]2COC(=O)N2)cc1]

To a stirred solution of Intermediate 98 (11.0 g, 94.0 mmol) in dichloromethane (250 mL), 4-dimethylamino pyridine (22.94 g, 188.0 mmol) and p-toluene sulfonylchloride (26.88 g, 141.0 mmol) were added at 0° C. and it was stirred for an hour before bringing to the room temperature, and the reaction was stirred for an hour. The reaction mixture was washed with 1.5N hydrochloric acid (50 mL), water (50 mL), saturated sodium bicarbonate (50 mL) and finally with brine. The organic layer was dried over sodium sulfate and the solvent was removed under vacuum. The crude product was then purified by flash column chromatography in silica gel using a gradient of ethyl acetate in pet. ether. $^1$H NMR (300 MHz, DMSO-$d_6$) δ: 2.49 (s, 3H), 3.91-3.95 (m, 2H), 3.99-4.02 (m, 2H), 4.30 (t, 1H), 7.49 (d, 2H), 7.80 (d, 2H), 7.88 (s, 1H). Yield: 12.0 g (47%).

Intermediate 100

(R)-4-((Methylthio)methyl)oxazolidin-2-one

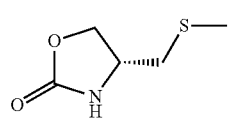

To a stirred solution Intermediate 99 (4.00 g, 14.76 mmol) in methanol (30 mL) in a sealed tube, sodium thiomethoxide (3.12 g, 44.28 mmol) was added and the mixture was stirred at room temperature for 2 hours. The volatiles were removed under vacuum and the residue was dissolved in dichloromethane (50 mL) and the organic layer was washed with water (2×25 mL), brine (25 mL) and dried over sodium sulfate. Removal of the solvent afforded the title compound. Yield: 0.82 g (38%). $^1$H NMR (300 MHz, DMSO-$d_6$) δ: 2.08 (s, 3H), 2.59 (d, 2H), 3.93-4.03 (m, 2H), 4.37 (t, 1H), 7.78 (s, 1H).

Intermediate 101

(R)-3-(6-((2R,6R)-2,6-Dimethylmorpholino)-5-(1,3-dioxolan-2-yl)-7-fluorobenzo[d]isoxazol-3-yl)-4-((methylthio)methyl)oxazolidin-2-one

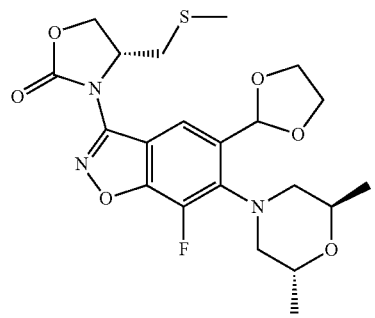 [SMILES: CSC[C@H]1COC(=O)N1c1noc2c(F)c(N3C[C@@H](C)O[C@H](C)C3)c(C3OCCO3)cc12]

To a stirred suspension of sodium hydride (0.22 g, 5.5 mmol) in dimethyl formamide (5 mL), a solution of Intermediate 100 (0.82 g, and 5.5 mmol) in dimethylformamide (10 mL) was added slowly at 0° C. over a period of 10 minutes. The mixture was stirred at the room temperature for 10 minutes and a solution of (Intermediate 11 (1.96 g, 5.50 mmol) in dimethylformamide (10 mL) was added at the same temperature. This mixture was heated at 80° C. for 2 hours and poured into ice-cooled saturated ammonium chloride solution (20 mL) and extracted with ethyl acetate (3×20 mL). The organic layers were dried over anhydrous sodium sulfate and the solvents were removed under vacuum. The crude product was purified by silica gel column chromatography using a gradient of ethyl acetate in pet.ether. Yield: 0.70 g (27%). $^1$H NMR (300 MHz, DMSO-$d_6$) δ: 1.22 (br s, 6H), 2.04 (s, 3H), 2.86-2.91 (m, 2H), 3.02-3.04 (m, 2H), 3.19-3.22 (m, 2H), 3.96-4.07 (m, 6H), 4.42 (dd, 1H), 4.73 (t, 1H), 4.84-4.86 (m, 1H), 6.16 (s, 1H), 8.28 (s, 1H). MS (ES) MH$^+$: 468.2 for $C_{21}H_{26}FN_3O_6S$.

Intermediate 102

(R)-3-(6-((2R,6R)-2,6-Dimethylmorpholino)-5-(1,3-dioxolan-2-yl)-7-fluorobenzo[d]isoxazol-3-yl)-4-((methylsulfonyl)methyl)oxazolidin-2-one

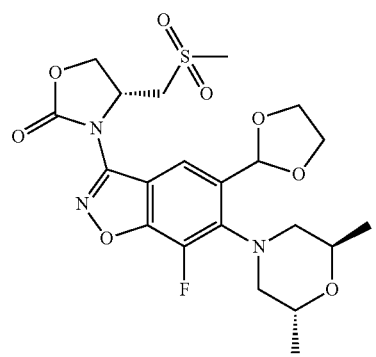 [SMILES: C[C@@H]1CN(c2c(C3OCCO3)cc3c(N4C(=O)OC[C@@H]4CS(C)(=O)=O)noc3c2F)C[C@@H](C)O1]

To a stirred solution of Intermediate 101 (0.20 g, 0.42 mmol) in tetrahydrofuran (5 mL) m-chloroperbenzoic acid (0.37 g, 2.14 mmol) was added and the mixture was stirred at the room temperature for 2 hours. Water (2 mL) was added to the reaction mixture and extracted with ethyl acetate (3×5 mL). The combined organic layers were washed with water (2×5 mL), brine (5 mL) and dried over sodium sulfate. Removal of the solvent under vacuum afforded the title compound as pale yellow solid. Yield: 0.20 g (94%). $^1$H NMR (300 MHz, DMSO-$d_6$) δ: 1.22 (br s, 6H), 2.88-2.92 (m, 2H), 3.10 (s, 3H), 3.20-3.23 (m, 2H), 3.77-3.83 (m, 1H), 3.88-3.93 (m, 1H), 3.96-4.00 (m, 2H), 4.02-4.10 (m, 4H), 4.68 (dd, 1H), 4.81 (t, 1H), 5.10-5.14 (m, 1H), 6.17 (s, 1H), 8.27 (s, 1H). MS (ES) MH$^+$: 500.3 for $C_{21}H_{26}FN_3O_8S$.

Intermediate 103

Methyl N-(tert-butoxycarbonyl)-O-(tetrahydro-2H-pyran-2-yl)-L-serinate

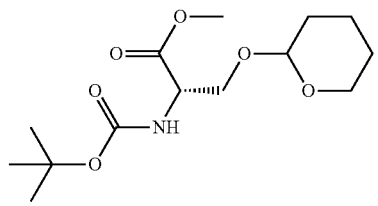 [SMILES: COC(=O)[C@H](COC1CCCCO1)NC(=O)OC(C)(C)C]

To a stirred solution of methyl N-(tert-butoxycarbonyl)-L-serinate (prepared according to the reported procedure: *Bioorg. Med. Chem.* 2007, 15, 2860-2867, 10.0 g, 64.27 mmol) in dichloromethane (100 mL), p-toluenesulfonic acid (0.24 g, 1.28 mmol) and 3,4-dihydro-1H-pyran (8.8 mL, 96.67 mmol) were added and the mixture was stirred at the room temperature for 16 hours. The reaction mixture was quenched with saturated sodium bicarbonate solution (50 mL) and extracted with dichloromethane (3×50 mL). The combined organic layers were washed with water (2×50 mL), brine solution (50 mL) and dried over sodium sulfate. Removal of solvent under vacuum and also high vacuum to remove excess 3,4-dihydro-1H-pyran. The residue was dissolved in ethyl acetate (10 mL) and pet. ether (100 mL) was added over it was stirred for 10 minutes. The solid obtained was filtered and washed with pet. ether (50 mL). Yield: 12.0 g (78%). $^1$H NMR (400 MHz, DMSO-$d_6$) δ: 1.33-1.34 (m, 1H), 1.39 (s, 9H), 1.41-1.68 (m, 6H), 3.41-3.45 (m, 1H), 3.55-3.59 (m, 1H), 3.61 (s, 3H), 3.81-3.84 (m, 1H), 4.23-4.28 (m, 1H), 4.58 (br s, 1H), 7.15 (d, 1H).

Intermediate 104 tert-Butyl [(2R)-1-hydroxy-3-(tetrahydro-2H-pyran-2-yloxy)propan-2-yl]carbamate

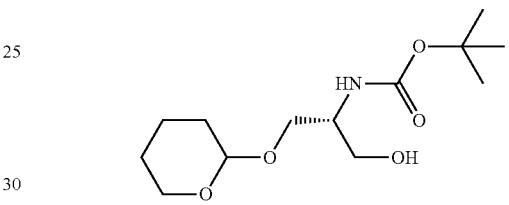

To a stirred solution of Intermediate 103 (41.0 g, 135.0 mmol) in tetrahydrofuran (250 mL) and methanol (125 mL), sodium borohydride (15.32 g, 405.0 mmol) was added portion wise at 0° C. and the mixture was stirred at the room temperature for 30 minutes. The volatiles were removed in vacuo and the residue was taken in ethyl acetate (250 mL) and washed with water (2×50 mL) and brine solution (50 mL). The organic layers were dried over sodium sulfate and the solvents were removed under vacuum. The crude product was purified by flash column chromatography using silica gel (40% ethyl acetate in pet. ether). Yield: 35.5 g (96%). $^1$H NMR (300 MHz, DMSO-$d_6$) δ: 1.41 (s, 9H), 1.44-1.70 (m, 7H), 3.34-3.41 (m, 3H), 3.47-3.69 (m, 2H), 3.70-3.75 (m, 1H), 4.53-4.61 (m, 2H), 6.46 (d, 1H).

Intermediate 105

(4S)-4-[(Tetrahydro-2H-pyran-2-yloxy)methyl]-1,3-oxazolidin-2-one

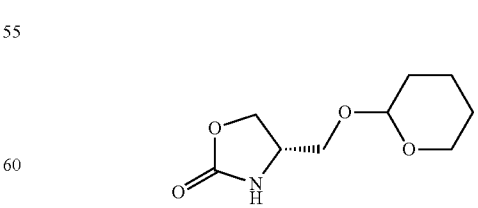

To a stirred solution of Intermediate 104 (35.5 g, 129.0 mmol) in tetrahydrofuran (250 mL), 1M solution of potassium t-butoxide in tetrahydrofuran (258.0 mL, 258.0 mmol) was added at 0° C. and the mixture was stirred at the room temperature for 30 minutes. The reaction mixture was quenched with water (50 mL) at 0° C. and extracted with ethyl acetate (3×50 mL). The combined organic layers were washed with water (50 mL), brine solution (50 mL) and dried over sodium sulfate and the solvents were removed under vacuum. The crude product obtained was purified by silica gel flash column chromatography using a gradient of ethyl acetate in hexane. Yield: 22.0 g (85%). $^1$H NMR (400 MHz, DMSO-$d_6$): δ 1.38-1.51 (m, 4H), 1.59-1.62 (m, 1H), 1.73-1.75 (m, 1H), 3.35-3.37 (m, 1H), 3.45-3.47 (m, 1H), 3.56-3.59 (m, 1H), 3.72-3.77 (m, 1H), 3.93 (h, 1H), 4.05-4.08 (m, 1H), 4.35 (t, 1H), 4.60 (t, 1H), 7.75 (t, 1H). MS (ELSD) MH$^+$: 202.2 for $C_9H_{15}FNO_4$.

Intermediate 106

(4S)-3-{6-[(2R,6R)-2,6-Dimethylmorpholin-4-yl]-5-(1,3-dioxolan-2-yl)-7-fluoro-1,2-benzoxazol-3-yl}-4-[(tetrahydro-2H-pyran-2-yloxy)methyl]-1,3-oxazolidin-2-one

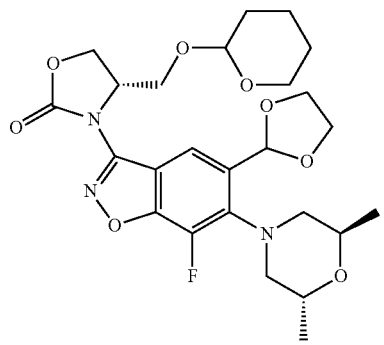 [SMILES: C[C@@H]1CN(c2c(C3OCCO3)cc3c(N4C(=O)OC[C@@H]4COC4CCCCO4)noc3c2F)C[C@@H](C)O1]

To a stirred solution of sodium hydride (1.41 g, 35.3 mmol) in dimethyl formamide (10 mL), a solution of Intermediate 105 (7.1 g, 35.3 mmol) in dimethyl formamide (50 mL) was added slowly at 0° C. over a period of 10 minutes and the mixture was stirred at the room temperature for 30 minutes. A solution of Intermediate 11 (12.59 g, 35.3 mmol) in dimethyl formamide (50 mL) was added at the same temperature and the mixture was heated at 60° C. for 2 hours. The reaction was quenched with saturated ammonium chloride solution (10 mL), extracted with ethyl acetate (3×50 mL). The combined organic layers were dried over anhydrous sodium sulfate and the solvents were removed under vacuum. The crude product was purified by silica gel column chromatography using a 3% methanol in chloroform. Yield: 4.3 g (23%). $^1$H NMR (400 MHz, DMSO-$d_6$) δ: 1.18 (d, 6H), 1.30-1.58 (m, 5H), 2.85-2.90 (m, 2H), 3.18-3.21 (m, 4H), 3.58-3.83 (m, 2H), 3.93-3.99 (m, 2H), 4.04-4.07 (m, 5H), 4.46-4.58 (m, 2H), 4.67-4.76 (m, 2H), 6.15 (s, 1H), 8.25 (d, 1H). MS (ES) MH$^+$: 522.2 for $C_{25}H_{32}FN_3O_8$.

Intermediate 107

(4S)-3-{6-[(2R,6R)-2,6-Dimethylmorpholin-4-yl]-5-(1,3-dioxolan-2-yl)-7-fluoro-1,2-benzoxazol-3-yl}-4-(hydroxymethyl)-1,3-oxazolidin-2-one

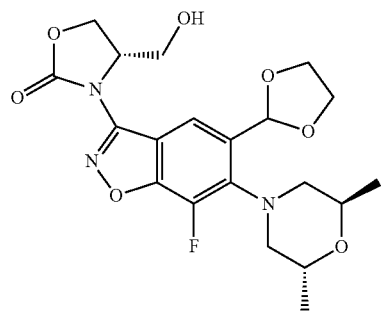 [SMILES: C[C@@H]1CN(c2c(C3OCCO3)cc3c(N4C(=O)OC[C@@H]4CO)noc3c2F)C[C@@H](C)O1]

To a stirred solution of Intermediate 106 (3.2 g, 6.21 mmol) in toluene (30 mL), ethylene glycol (2.0 mL) followed by pyridinium p-toluene sulfonate (0.59 g, 23.6 mmol) and the mixture was heated at 110° C. for 1.5 hours. The reaction mixture was quenched with saturated sodium bicarbonate solution (10 mL) and extracted with ethyl acetate (3×25 mL). The organic layers were washed with brine, dried over sodium sulfate and the solvents were removed under vacuum. The crude product thus obtained was purified by flash column silica gel chromatography using 30% ethyl acetate in hexane. Chiral HPLC data shows that it was 97% de [Column: Chiralpak IC (250×4.6 mm); Mobile Phase: hexane:ethanol (80:20)]. Yield: 1.63 g (60%). $^1$H NMR (400 MHz, DMSO-$d_6$) δ: 1.09 (d, 6H), 2.83 (t, 2H), 3.08 (d, 2H), 3.53-3.57 (m, 1H), 3.73-3.76 (m, 2H), 3.91-3.99 (m, 3H), 4.06-4.09 (m, 2H), 4.48 (dd, 1H), 4.63-4.65 (m, 2H), 5.19 (t, 1H), 6.11 (s, 1H), 8.32 (s, 1H). MS (ES) MH$^+$: 438.4 for $C_{20}H_{24}FN_3O_7$.

Intermediate 108

((R)-3-(6-((2R,6R)-2,6-Dimethylmorpholino)-5-(1,3-dioxolan-2-yl)-7-fluorobenzo[d]isoxazol-3-yl)-2-oxooxazolidin-4-yl)methyl 4-methylbenzenesulfonate

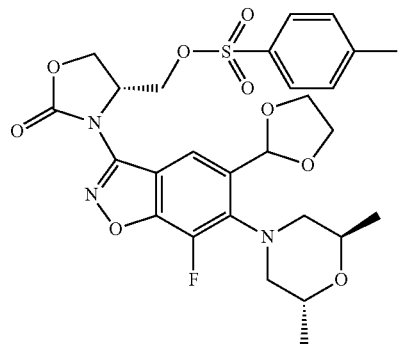 [SMILES: Cc1ccc(S(=O)(=O)OC[C@H]2COC(=O)N2c2noc3c(F)c(N4C[C@@H](C)O[C@H](C)C4)c(C4OCCO4)cc23)cc1]

To a stirred solution of Intermediate 107 (4.5 g, 10.29 mmol) in dichloromethane (100 mL), N,N-dimethylaminopyridine (2.51 g, 20.59 mmol) and p-toluene sulfonyl chloride (2.94 g, 15.43 mmol) were added and the solution was stirred at 0° C. for an hour before it was brought to the room temperature where it was stirred for an additional hour. The reaction mixture was washed with 1.5 N hydrochloric acid (50 mL), water (2×50 mL) and saturated sodium bicarbonate solution (50 mL), dried over sodium sulfate. Removal of solvent under vacuum afforded off white solid which was further purified by silica gel flash column chromatography using a gradient of ethyl acetate in hexane. Yield: 5.0 g (82%). $^1$H NMR (300 MHz, DMSO-d$_6$) δ: 1.21 (d, 6H), 2.16 (s, 3H), 2.86-2.92 (m, 2H), 3.08 (d, 2H), 3.95-4.10 (m, 6H), 4.35 (d, 1H), 4.44-4.47 (m, 1H), 4.55 (d, 1H), 4.67 (t, 1H), 4.78-4.83 (m, 1H), 6.19 (s, 1H), 7.1 (d, 2H), 7.54 (d, 2H), 8.29 (s, 1H). MS (ES) MH$^+$: 592.6 for C$_{27}$H$_{30}$FN$_3$O$_9$S.

Intermediate 109

(S)-4-(Azidomethyl)-3-(6-((2R,6R)-2,6-dimethyl-morpholino)-5-(1,3-dioxolan-2-yl)-7-fluorobenzo[d]isoxazol-3-yl)oxazolidin-2-one

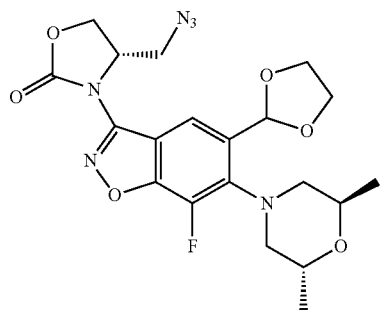 [SMILES: C[C@@H]1CN(c2c(C3OCCO3)cc3c(N4C(=O)OC[C@@H]4CN=[N+]=[N-])noc3c2F)C[C@@H](C)O1]

To a stirred solution of Intermediate 108 (1.5 g, 2.53 mmol) in dimethylformamide (15 mL) in a sealed tube, sodium azide (0.99 g, 15.22 mmol) was added and the mixture was heated at 90° C. for 2 hours. The reaction was quenched with water (15 mL) after being brought to room temperature and extracted with ethyl acetate (2×30 mL). The combined organic layers were washed with water (2×10 mL) and brine solution (10 mL), dried over sodium sulfate and the solvent was removed under vacuum afforded the crude title compound which was further purified by flash column chromatography using a gradient of ethyl acetate in pet. ether to obtain the pure product as colorless viscous liquid. Yield: 0.85 g (73%). $^1$H NMR (400 MHz, DMSO-d$_6$) δ: 1.20 (br s, 6H), 2.91-2.93 (m, 2H), 3.21-3.23 (m, 2H), 3.70 (d, 2H), 3.98-4.15 (m, 7H), 4.71 (t, 1H), 4.80-4.82 (m, 1H), 6.18 (s, 1H), 8.29 (s, 1H). MS (ES) MH$^+$: 463.4 for C$_{20}$H$_{23}$FN$_6$O$_6$.

Intermediate 110

Methyl N-[(benzyloxy)carbonyl]-O-ethyl-L-serinate

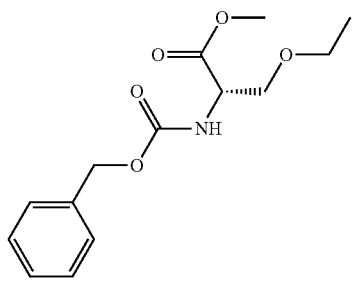 [SMILES: CCOC[C@H](NC(=O)OCc1ccccc1)C(=O)OC]

To a stirred solution of (S)-1-benzyl 2-methyl aziridine-1,2-dicarboxylate (prepared according to the literature procedure: *Org. Biomol. Chem.*, 2005, 3, 3357, 2.7 g, 11.4 mmol) in dichloromethane (30 mL), boron trifluoride etherate (0.01 mL, 0.11 mmol) was added at 0° C. followed by absolute ethanol (1.05 g, 22.9 mmol). The reaction mixture was stirred at room temperature for an hour, after which the solution was quenched with saturated bicarbonate solution (2 mL), extracted with dichloromethane (3×25 mL), organic layers were washed with water (25 mL), brine solution (25 mL) and dried over sodium sulfate. The removal of solvents afforded crude product, which was purified by silica gel column chromatography using a gradient of ethyl acetate in pet. ether. Yield: 2.0 g (63%). $^1$H NMR (400 MHz, DMSO-d$_6$) δ: 1.08 (t, 3H), 3.38-3.46 (m, 2H), 3.57-3.63 (m, 2H), 3.70 (s, 3H), 4.26-4.31 (m, 1H), 5.04 (s, 2H), 7.30-7.39 (m, 5H), 7.73 (d, 1H).

Intermediate 111

Benzyl [(2R)-1-ethoxy-3-hydroxypropan-2-yl]carbamate

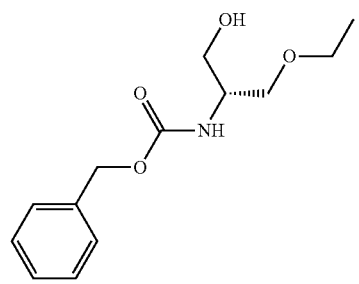 [SMILES: CCOC[C@@H](CO)NC(=O)OCc1ccccc1]

To a stirred solution of Intermediate 110 (2.0 g, 7.10 mmol) in a 9:1 mixture of tetrahydrofuran and methanol (20 mL), sodium borohydride (0.54 g, 14.21 mmol) was added in portion at 0° C. and the mixture was stirred at the room temperature for 2 hours. The reaction was quenched with water (5 mL), poured into ice-cooled water (25 mL) and extracted with ethyl acetate (3×20 mL). The organic layers were washed with water (20 mL), brine solution (20 mL) and dried over sodium sulfate. Removal of solvent afforded crude product which was purified over silica gel column chromatography using a gradient of ethyl acetate in pet. ether. Yield: 0.7 g (35%). $^1$H NMR (400 MHz, DMSO-d$_6$) δ: 1.07 (t, 3H), 3.35-3.46 (m, 6H), 3.55-3.60 (m, 1H), 4.65 (t, 1H), 5.00 (s, 2H), 7.02 (d, 1H), 7.27-7.35 (m, 5H).

Intermediate 112

(4S)-4-(Ethoxymethyl)-1,3-oxazolidin-2-one

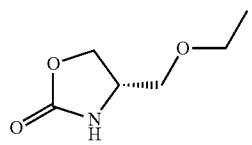

To a stirred solution of Intermediate 111 (1.20 g, 4.49 mmol) in tetrahydrofuran (50 mL), 1M solution of potassium t-butoxide in tetrahydrofuran (9.0 mL, 8.98 mmol) was added at 0° C. and the mixture was stirred at room temperature for 30 minutes. The reaction mixture was quenched with water (25 mL) at 0° C. and extracted with ethyl acetate (3×25 mL). The combined organic layers were washed with water (20 mL), brine solution (20 mL) and dried over sodium sulfate and the solvents were removed under vacuum. The crude product obtained was purified by silica gel flash column chromatography using a gradient of ethyl acetate in pet. ether. Yield: 0.31 g (48%). $^1$H NMR (400 MHz, DMSO-d$_6$) δ: 1.09 (t, 3H), 3.45 (q, 2H), 3.86 (quin, 1H), 3.99 (dd, 1H), 4.31 (t, 1H), 7.72 (br s, 1H). Note: two of the ring CH$_2$ protons merged with the DMSO-d$_6$ water peak.

Intermediate 113

(4S)-3-{6-[(2R,6R)-2,6-Dimethylmorpholin-4-yl]-5-(1,3-dioxolan-2-yl)-7-fluoro-1,2-benzoxazol-3-yl}-4-(ethoxymethyl)-1,3-oxazolidin-2-one

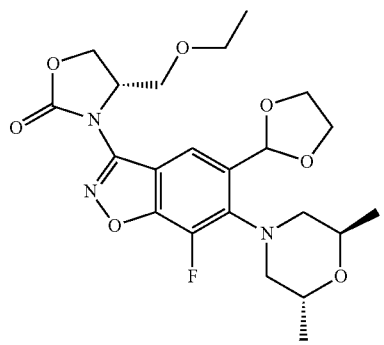 [SMILES: CCOC[C@H]1COC(=O)N1c1noc2c(F)c(N3C[C@@H](C)O[C@H](C)C3)c(C3OCCO3)cc12]

To a stirred solution of sodium hydride (0.06 g, 2.19 mmol) in dimethyl formamide (15 mL), a solution of Intermediate 112 (0.32 g, 2.19 mmol) in dimethyl formamide (15 mL) was added slowly at 0° C. over a period of 10 minutes and the mixture was stirred at the room temperature for 1 hour. A solution of Intermediate 11 (0.60 g, 1.68 mmol) in dimethyl formamide (15 mL) was added at the same temperature and the mixture was heated at 90° C. for 3 hours. The reaction was quenched with saturated ammonium chloride solution (10 mL) and extracted with ethyl acetate (3×10 mL). The combined organic layers were dried over anhydrous sodium sulfate and the solvents were removed under vacuum. The crude product was purified by silica gel column chromatography using a gradient of ethyl acetate in pet. ether and the product obtained as colorless solid. Yield: 0.20 g (25%). $^1$H NMR (400 MHz, DMSO-d6) δ: 1.00 (t, 3H), 1.12 (br s, 6H), 2.89-2.91 (m, 2H), 3.19-3.26 (m, 2H), 3.37-3.46 (m, 2H), 3.58-3.61 (m, 1H), 3.83-3.88 (m, 1H), 3.93-4.09 (m, 6H), 4.43 (dd, 1H), 4.67-4.70 (m, 2H), 6.16 (s, 1H), 8.27 (s, 1H). MS (ES) MH$^+$: 466.5 for C$_{22}$H$_{28}$FN$_3$O$_7$.

Intermediate 114

Methyl N-[(benzyloxy)carbonyl]-O-(2-methoxyethyl)-L-serinate

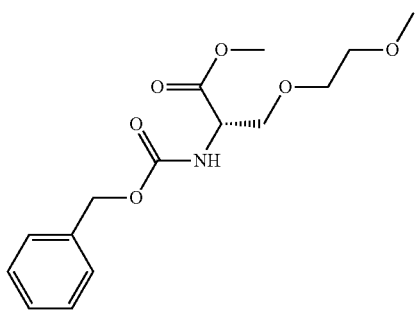 [SMILES: COCCOC[C@H](NC(=O)OCc1ccccc1)C(=O)OC]

Intermediate 114 was synthesized following the procedure described for the preparation of Intermediate 110 using (S)-1-benzyl 2-methyl aziridine-1,2-dicarboxylate (2.0 g, 8.03 mmol) and 2-methoxy ethanol (4.2 mL, 53.15 mmol). Yield: 2.0 g (80%). $^1$H NMR (300 MHz, DMSO-d$_6$) δ: 3.16 (s, 3H), 3.38-3.41 (m, 2H), 3.42-3.52 (m, 2H), 3.55-3.65 (m, 4H), 4.26-4.29 (m, 1H), 4.47-4.48 (m, 1H), 5.03 (s, 2H), 7.21-7.34 (m, 5H), 7.71 (d, 1H).

Intermediate 115

Benzyl [(2R)-1-hydroxy-3-(2-methoxyethoxy)propan-2-yl]carbamate

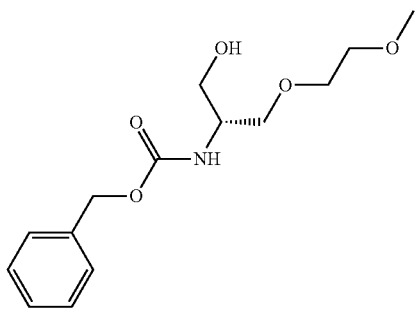 [SMILES: COCCOC[C@@H](CO)NC(=O)OCc1ccccc1]

Intermediate 115 was synthesized following the procedure described for the preparation of Intermediate 111 using Intermediate 114 (2.0 g, 6.43 mmol). Yield: 1.0 g (54%). $^1$H NMR (300 MHz, DMSO-d$_6$) δ: 3.23 (s, 3H), 3.40-3.41 (m, 2H), 3.44-3.47 (m, 2H), 3.51-3.54 (m, 2H), 3.58-3.62 9 m, 1H), 4.47 (d, 1H), 4.66 (t, 1H), 4.99 (s, 2H), 7.03 (d, 1H), 7.19-7.34 (m, 5H).

Intermediate 116

Benzyl [(2R)-1-hydroxy-3-(2-methoxyethoxy)propan-2-yl]carbamate

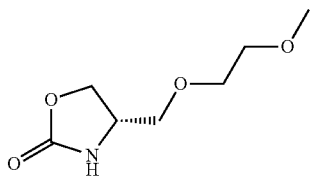

Intermediate 116 was synthesized following the procedure described for the preparation of Intermediate 112 using Intermediate 115 (1.0 g, 3.50 mmol) except the crude product was taken to the next step without purification. Yield: 0.32 g (crude).

Intermediate 117

(4S)-3-{6-[(2R,6R)-2,6-Dimethylmorpholin-4-yl]-5-(1,3-dioxolan-2-yl)-7-fluoro-1,2-benzoxazol-3-yl}-4-[(2-methoxyethoxy)methyl]-1,3-oxazolidin-2-one

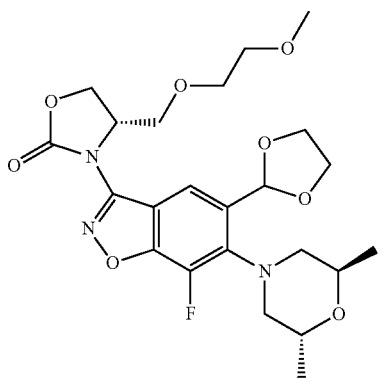 [SMILES: COCCOC[C@H]1COC(=O)N1c1noc2c(F)c(N3C[C@@H](C)O[C@H](C)C3)c(C3OCCO3)cc12]

Intermediate 117 was synthesized following the procedure described for the preparation of Intermediate 113 using Intermediate 116 (0.32 g, 1.82 mmol) and Intermediate 11 (0.50 g, 1.40 mmol). A mixture of the product was eluted from silica gel column with methanol. The UPLC analysis showed that the fraction contained 37% product which was taken to the next step without further purification. Yield: 0.15 g (37% product). MS (ES) MH$^+$: 496.5 for $C_{23}H_{30}FN_3O_8$.

Intermediate 118

5-(1,3-Dioxolan-2-yl)-2,3,4-Trifluoro-N'-hydroxy-N-[(2S)-1-hydroxybut-3-en-2-yl]benzenecarboximidamide

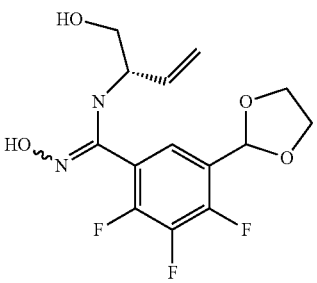 [SMILES: C=C[C@@H](CO)NC(=NO)c1cc(C2OCCO2)c(F)c(F)c1F]

Intermediate 118 was prepared from Intermediate 16 (2.0 g, 7.1 mmol) and (2S)-2-aminobut-3-en-1-ol (0.74 g, 8.54 mmol, prepared according to the literature procedure, *Eur. J. Chem.* 2006, 12, 6607-6620) using a method similar to the one described for the synthesis of Intermediate 71. Yield: 1.4 g (59%). $^1$H NMR (300 MHz, DMSO-d$_6$) δ: 3.36-3.40 (m, 3H), 3.95-4.05 (m, 4H), 4.83-5.00 (m, 3H), 5.87-5.90 (m, 1H), 6.01 (s, 1H), 7.26 (t, 1H), 8.30 (s, 1H), 10.12 (s, 1H). MS (ES) MH$^+$: 333.3 for $C_{14}H_{15}F_3N_2O_4$.

Intermediate 119

(2S)-2-{[5-(1,3-Dioxolan-2-yl)-6,7-difluoro-1,2-benzoxazol-3-yl]amino}but-3-en-1-ol

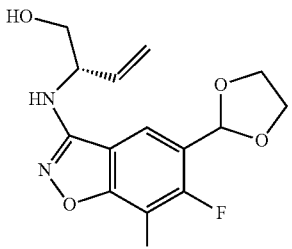

Intermediate 119 was prepared from Intermediate 118 (1.4 g, 4.2 mmol) using a method similar to the one described for the synthesis of Intermediate 72. Yield: 0.75 g (57%). $^1$H NMR (400 MHz, DMSO-d$_6$) δ: 3.56 (t, 2H), 4.01-4.14 (m, 5H), 4.92 (t, 1H), 5.17 (d, 1H), 5.29 (d, 1H), 5.90 (ddd, 1H), 6.09 (s, 1H), 7.34 (d, 1H), 8.07 (d, 1H). MS (ES) MH$^+$: 313.3 for $C_{14}H_{14}F_2N_2O_4$.

Intermediate 120

(4S)-3-[5-(1,3-Dioxolan-2-yl)-6,7-difluoro-1,2-benzoxazol-3-yl]-4-ethenyl-1,3-oxazolidin-2-one

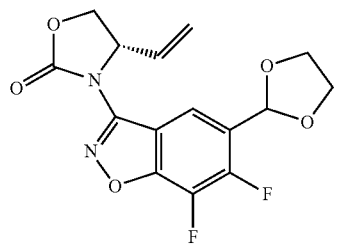 [SMILES: C=C[C@H]1COC(=O)N1c1noc2c(F)c(F)c(C3OCCO3)cc12]

Intermediate 120 was prepared from Intermediate 119 (0.75, 2.4 mmol) using a method similar to the one described for the synthesis of Intermediate 73. Yield: 0.60 g (74%). H NMR (400 MHz, DMSO-d$_6$) δ: 4.00-4.08 (m, 4H), 4.33 (dd, 1H), 4.79 (t, 1H), 5.17 (q, 1H), 5.32 (d, 1H), 5.40 (d, 1H), 5.93 (ddd, 1H), 6.10 (s, 1H), 8.23-8.25 (m, 1H). Yield: 0.60 g (74%). MS (ES) MH$^+$: 339.2 for $Cl_5H_{12}F_2N_2O_5$.

Intermediate 121

(R)-3-(5-(1,3-Dioxolan-2-yl)-6,7-difluorobenzo[d]isoxazol-3-yl)-4-(difluoromethyl)oxazolidin-2-one

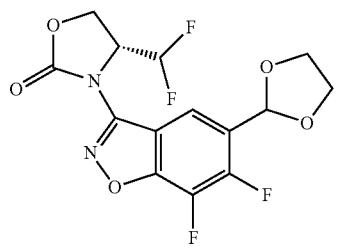 [SMILES: O=C1OC[C@H](C(F)F)N1c1noc2c(F)c(F)c(C3OCCO3)cc12]

To a stirred solution of Intermediate 120 (0.50 g, 0.30 mmol) in a 2:1 mixture of tetrahydrofuran and water (20 mL), osmium (IV) oxide (0.2 mL, 2.5% solution in t-butanol) was added. The resulting mixture was stirred at room temperature for 10 minutes. To this, sodium metaperiodate (3.16 g, 14.75 mmol) was added portion wise over a period of an hour and the reaction mixture was stirred for an additional 16 hours. The reaction mixture was poured into an ice water (15 mL) and extracted with dichloromethane (3×15 ml), washed with water (15 mL), brine and the organic layer was dried over sodium sulfate. Solvents were removed under vacuum at 10° C. and the resulting residue was dissolved in dichloromethane (15 mL). Diethylaminosulfur trifluoride (1 mL) was added at −10° C. and the resulting mixture was stirred at the room temperature for 6 hours before quenching with ice-cooled water (10 mL). The organic layer was washed with saturated sodium bicarbonate solution (5 mL), water (5 mL), brine (5 mL) and the organic layer was dried over sodium sulfate. Removal of solvent under vacuum afforded the title compound which was taken to the next step without further purification. Yield: 0.25 g (47%). $^1$H NMR (400 MHz, DMSO-$d_6$) δ: 3.99-4.08 (m, 4H), 4.69-4.79 (m, 2H), 5.08-5.15 (m, 1H), 6.10 (s, 1H), 6.59 (dt, 1H), 8.28 (dd, 1H). $^{19}$F NMR (376.5 MHz, DMSO-$d_6$) δ: −130.0 (d), 132.4 (d), −139.9 (d), −160.7 (d). MS (ES) MH$^+$: 363.3 for $C_{14}H_{10}F_4N_2O_5$.

Intermediate 122

(R)-3-(4-(Difluoromethyl)-2-oxooxazolidin-3-yl)-6,7-difluorobenzo[d]isoxazole-5-carbaldehyde

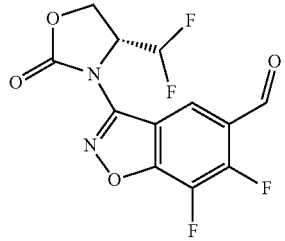 [SMILES: O=Cc1cc2c(N3C(=O)OC[C@@H]3C(F)F)noc2c(F)c1F]

An amount of 6 N hydrochloric acid (2.0 mL) was added to a stirred solution of Intermediate 121 (0.25 g, 0.69 mmol) in 1,4-dioxane (10 mL) at 0° C., and the mixture was stirred at room temperature for 8 hours. The mixture was poured into ice-cooled water (25 mL) and extracted with ethyl acetate (2×50 ml). The combined organic layers were washed with water (15 mL) and brine solution (15 mL before drying over Na$_2$SO$_4$. Removal of solvent afforded the title product. Yield: 0.20 g (91%). $^1$H NMR (300 MHz, DMSO-$d_6$) δ: 4.03-4.04 (m, 1H), 4.71-4.81 (m, 1H), 5.11-5.17 (m, 1H), 6.60 (t, 1H), 8.68 (d, 1H), 10.19 (s, 1H). MS (ES) MH$^+$: 319.2 for $C_{12}H_6F_4N_2O_4$.

Intermediate 123

(3-((R)-4-(Difluoromethyl)-2-oxooxazolidin-3-yl)-6-((2R,6R)-2,6-dimethylmorpholino)-7-fluorobenzo[d]isoxazole-5-carbaldehyde

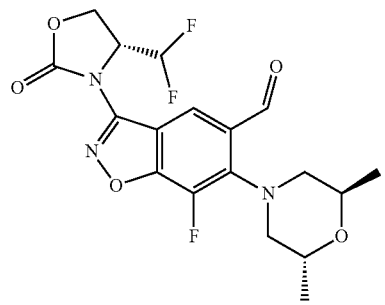 [SMILES: C[C@@H]1CN(c2c(C=O)cc3c(N4C(=O)OC[C@@H]4C(F)F)noc3c2F)C[C@@H](C)O1]

A stirred solution of Intermediate 122 (0.2 g, 0.63 mmol), diisopropyl ethylamine (0.15 g, 1.2 mmol) and (2R,6R)-2,6-dimethylmorpholine (80 mg, 0.67 mmol) in acetonitrile (5 mL) was heated at 80° C. for 16 hours in a sealed tube. After cooling to room temperature, the volatiles were removed under vacuum. The crude product was purified by chromatography over silica gel using a gradient of CHCl$_3$ in ethyl acetate to give the title compound as pale yellow solid. Yield: 0.16 g (62%). $^1$H NMR (300 MHz, DMSO-$d_6$) δ: 1.20 (d, 6H), 3.02-3.05 (m, 2H), 3.38-3.41 (m, 2H), 4.10-4.16 (m, 2H), 4.70-4.77 (m, 2H), 5.11-5.15 (m, 1H), 6.47 (dt, 1H), 8.54 (s, 1H), 10.31 (s, 1H). MS (ES) MH$^+$: 414.4 for $C_{18}H_{18}F_3N_3O_5$.

Intermediate 124

(S)—N-(1-Cyclopropyl-2-hydroxyethyl)-5-(1,3-dioxolan-2-yl)-2,3,4-trifluoro-N'-hydroxybenzimidamide

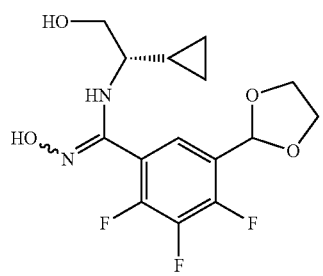 [SMILES: OC[C@@H](NC(=NO)c1cc(C2OCCO2)c(F)c(F)c1F)C1CC1]

Intermediate 124 was synthesized following the procedure described for the preparation of Intermediate 118 using (S)-2-amino-2-cyclopropylethanol (1.38 g, 13.30 mmol) and Intermediate 16 (2.50 g, 8.89 mmol). Yield: 2.2 g (72%). $^1$H NMR (300 MHz, DMSO-$d_6$) δ: −0.79-−0.89 (m, 1H), −0.92-

0.10 (m, 1H), 0.31 (d, 2H), 0.88-0.90 (m, 1H), 2.15-2.30 (m, 1H), 3.39 (t, 2H), 3.94-4.06 (m, 4H), 4.71 (t, 1H), 5.81 (d, 1H), 6.02 (s, 1H), 7.30 (t, 1H), 9.98 (s, 1H).

Intermediate 125

(S)-2-((5-(1,3-Dioxolan-2-yl)-6,7-difluorobenzo[d]isoxazol-3-yl)amino)-2-cyclopropylethanol

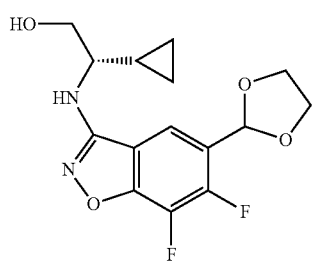 [SMILES: OC[C@@H](Nc1noc2c(F)c(F)c(C3OCCO3)cc12)C1CC1]

Intermediate 125 was synthesized following the procedure described for the preparation of Intermediate 119 using Intermediate 124 (2.20 g, 6.40 mmol). Yield: 1.80 g (87%). $^{1}$H NMR (400 MHz, DMSO-d$_6$) δ: 0.23-0.25 (m, 1H), 0.37-0.45 (m, 3H), 1.01-1.12 (m, 1H), 3.03-3.05 (m, 1H), 3.53-3.56 (m, 1H), 3.64-3.65 (m, 1H), 4.03-4.10 (m, 4H), 4.75 (t, 1H), 6.08 (s, 1H), 7.16 (d, 1H), 8.05 (dd, 1H). MS (ES) MH$^+$: 327.3 for C$_{15}$H$_{16}$F$_2$N$_2$O$_4$.

Intermediate 126

(S)-3-(5-(1,3-Dioxolan-2-yl)-6,7-difluorobenzo[d]isoxazol-3-yl)-4-cyclopropyloxazolidin-2-one

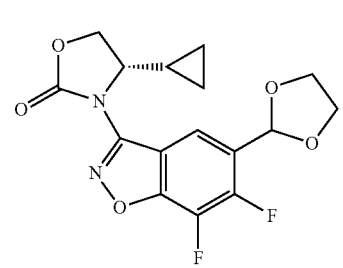 [SMILES: O=C1OC[C@H](C2CC2)N1c1noc2c(F)c(F)c(C3OCCO3)cc12]

Intermediate 126 was synthesized following the procedure described for the preparation of Intermediate 120 using Intermediate 125 (1.20 g, 3.67 mmol). Yield: 1.10 g (85%). $^{1}$H NMR (400 MHz, DMSO-d$_6$) δ: 0.28-0.31 (m, 1H), 0.42-0.44 (m, 1H), 0.53-0.56 (m, 2H), 1.21-1.23 (m, 1H), 4.01-4.08 (m, 4H), 4.21-4.25 (m, 1H), 4.30-4.33 (m, 1H), 4.70 (t, 1H), 6.10 (s, 1H), 8.21 (dd, 1H). MS (ES) MH$^+$: 353.3 for C$_{16}$H$_{14}$F$_2$N$_2$O$_5$.

Intermediate 127

(S)-3-(4-Cyclopropyl-2-oxooxazolidin-3-yl)-6,7-difluorobenzo[d]isoxazole-5-carbaldehyde Intermediate 127 was synthesized following the procedure described for the preparation of Intermediate 122 using Intermediate 126 (1.10 g, 3.12 mmol). Yield: 0.91 g (95%). $^{1}$H NMR (400 MHz, DMSO-d$_6$) δ: 0.30-0.34 (m, 1H), 0.44-0.49 (m, 1H), 0.56-0.62 (m, 2H), 1.21-1.25 (m, 1H), 4.24-4.28 (m, 1H), 4.32-4.36 (m, 1H), 4.72 (t, 1H), 8.64 (dd, 1H), 10.20 (s, 1H). MS (ES) MH$^+$: 309.3 for C$_{14}$H$_{10}$F$_2$N$_2$O$_4$.

Intermediate 128

3-((S)-4-Cyclopropyl-2-oxooxazolidin-3-yl)-6-((2R,6R)-2,6-dimethylmorpholino)-7-fluorobenzo[d]isoxazole-5-carbaldehyde Intermediate 128 was synthesized following the procedure described for the preparation of Intermediate 123 using Intermediate 127. Yield: 1.0 g (86%). $^{1}$H NMR (300 MHz, DMSO-d$_6$) δ: 0.30-0.34 (m, 1H), 0.44-0.49 (m, 1H), 0.57-0.60 (m, 2H), 1.20 (d, 6H), 2.99-3.03 (m, 2H), 3.31-3.39 (m, 2H), 4.10-4.15 (m, 2H), 4.19-4.33 (m, 2H), 4.69 (t, 1H), 8.30 (s, 1H), 8.47 (s, 1H), 10.31 (s, 1H). MS (ES) MH$^+$: 404.4 for C$_{20}$H$_{22}$FN$_3$O$_5$.

Intermediate 129

5-(1,3-Dioxolan-2-yl)-2,3,4-trifluoro-N'-hydroxy-N-(2-hydroxy-2-(pyridin-2-yl)ethyl)benzimidamide

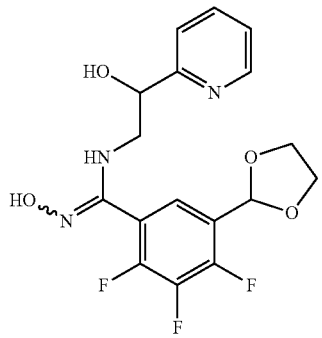 [SMILES: ON=C(NCC(O)c1ccccn1)c1cc(C2OCCO2)c(F)c(F)c1F]

Intermediate 129 was synthesized following the procedure described for the preparation of Intermediate 118 using 2-amino-1-(pyridin-2-yl)ethanol (1.35 g, 6.40 mmol) and Intermediate 16 (1.50 g, 5.33 mmol). Yield: 1.70 g (83%). $^1$H NMR (300 MHz, DMSO-$d_6$) δ: 3.02-3.09 (m, 1H), 3.19-3.39 (m, 1H), 3.96-4.05 (m, 4H), 4.55 (d, 1H), 5.72 (d, 1H), 6.02 (m, 2H), 7.10 (t, 1H), 7.22 (t, 1H), 7.41 (t, 1H), 7.74 (t, 1H), 8.37 (d, 1H), 9.96 (s, 1H). $^{19}$F NMR (376.5 MHz, DMSO-$d_6$) δ: −134.3 (dd), −138.3 (dd), −159.91 (d). MS (ES) MH$^+$: 384.3 for $C_{17}H_{16}F_3N_3O_4$.

Intermediate 130

2-((5-(1,3-Dioxolan-2-yl)-6,7-difluorobenzo[d]isoxazol-3-yl)amino)-1-(pyridin-2-yl)ethanol

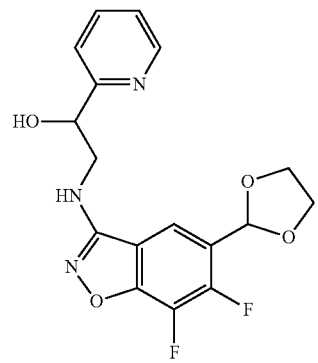 [SMILES: OC(CNc1noc2c(F)c(F)c(C3OCCO3)cc12)c1ccccn1]

Intermediate 130 was synthesized following the procedure described for the preparation of Intermediate 119 using Intermediate 129 (1.60 g, 4.17 mmol). Yield: 1.30 g (86%). $^1$H NMR (400 MHz, DMSO-$d_6$) δ: 3.66 (dd, 1H), 4.00-4.09 (m, 4H), 4.92 (t, 1H), 5.75 (d, 1H), 6.08 (s, 1H), 7.28 (dd, 1H), 7.50 (t, 1H), 7.55 (d, 1H), 7.80 (t, 1H), 8.04 (d, 1H), 8.52 (d, 1H). Note: one more CH proton merged with the DMSO-$d_6$ peak. MS (ES) MH$^+$: 364.3 for $C_{17}H_{15}F_2N_3O_4$.

Intermediate 131

3-(5-(1,3-Dioxolan-2-yl)-6,7-difluorobenzo[d]isoxazol-3-yl)-5-(pyridin-2-yl)oxazolidin-2-one

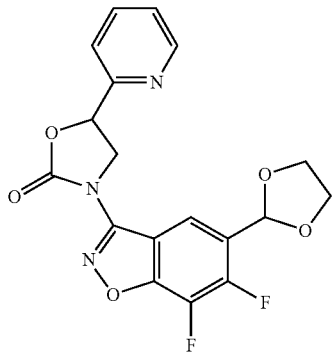 [SMILES: O=C1OC(c2ccccn2)CN1c1noc2c(F)c(F)c(C3OCCO3)cc12]

Intermediate 131 was synthesized following the procedure described for the preparation of Intermediate 120 using Intermediate 130 (1.20 g, 3.30 mmol). Yield: 1.20 g (93%). H NMR (300 MHz, DMSO-$d_6$) δ: 3.98-4.09 (m, 4H), 4.22-4.35 (m, 1H), 4.58 (t, 1H), 6.01 (dd, 1H), 6.10 (s, 1H), 7.46 (dd, 1H), 7.65 (d, 1H), 7.91 (t, 1H), 8.47 (d, 1H), 8.65 (d, 1H). $^{19}$F NMR (376.5 MHz, DMSO-$d_6$) δ: −140.4 (d), −161.10 (d). MS (ES) MH$^+$: 390.3 for $C_{18}H_{13}F_2N_3O_5$

Intermediate 132

6,7-Difluoro-3-(2-oxo-5-(pyridin-2-yl)oxazolidin-3-yl)benzo[d]isoxazole-5-carbaldehyde

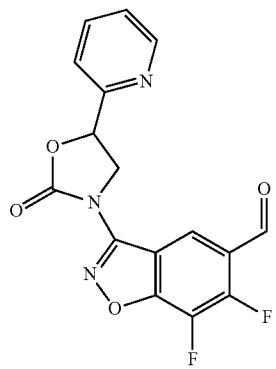 [SMILES: O=Cc1cc2c(N3CC(c4ccccn4)OC3=O)noc2c(F)c1F]

Intermediate 132 was synthesized following the procedure described for the preparation of Intermediate 122 using Intermediate 131 (1.20 g, 3.09 mmol). Yield: 1.0 g (94%). $^1$H NMR (400 MHz, DMSO-$d_6$) δ: 4.35 (dd, 1H), 4.60 (t, 1H), 6.04 (dd, 1H), 7.45-7.49 (m, 1H), 7.70 (d, 1H), 7.93 (t, 1H), 8.65 (d, 1H), 8.86 (d, 1H), 10.20 (s, 1H). $^{19}$F NMR (376.5 MHz, DMSO-$d_6$) δ: −143.1 (d), −160.4 (d). MS (ES) MH$^+$: 346.3 for $C_{16}H_9F_2N_3O_4$.

Intermediate 133

6-((2R,6R)-2,6-Dimethylmorpholino)-7-fluoro-3-(2-oxo-5-(pyridin-2-yl)oxazolidin-3-yl)benzo[d]isoxazole-5-carbaldehyde

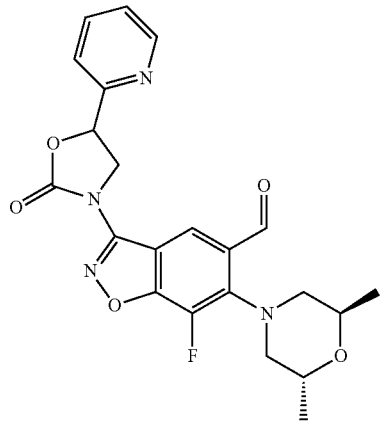 [SMILES: C[C@@H]1CN(c2c(C=O)cc3c(N4CC(c5ccccn5)OC4=O)noc3c2F)C[C@@H](C)O1]

Intermediate 133 was synthesized following the procedure described for the preparation of Intermediate 123 using Intermediate 132 (1.0 g, 2.89 mmol). Yield: 1.0 g (78%). $^1$H NMR (400 MHz, DMSO-d$_6$) δ: 1.21 (d, 6H), 3.00-3.04 (m, 2H), 3.37-3.40 (m, 2H), 4.12-4.15 (m, 2H), 4.33 (dd, 1H), 4.57 (t, 1H), 6.02 (dd, 1H), 7.46-7.48 (m, 1H), 7.66 (d, 1H), 7.91 (t, 1H), 8.65 (d, 1H), 8.71 (s, 1H), 10.30 (s, 1H). MS (ES) MH$^+$: 441.4 for C$_{22}$H$_{21}$FN$_4$O$_5$.

Intermediate 134

5-(1,3-Dioxolan-2-yl)-2,3,4-trifluoro-N'-hydroxy-N-(2-hydroxy-1-(pyridin-2-yl)ethyl)benzimidamide

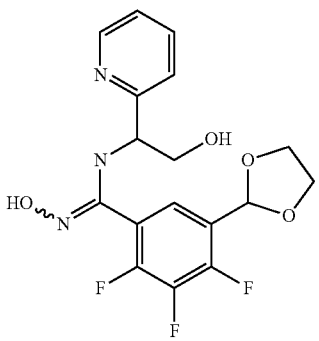 [SMILES: OCC(NC(=NO)c1cc(C2OCCO2)c(F)c(F)c1F)c1ccccn1]

Intermediate 134 was synthesized following the procedure described for the preparation of Intermediate 118 using Intermediate 16 (1.0 g, 3.55 mmol). Yield: 1.05 g (78%). $^1$H NMR (300 MHz, DMSO-d$_6$) δ: 3.59 (t, 2H), 3.93-4.08 (s, 5H), 4.94 (t, 1H), 5.96 (s, 1H), 6.41 (d, 1H), 7.09 (t, 1H), 7.20-7.25 (m, 2H), 7.72 (t, 1H), 8.43 (d, 1H), 10.20 (s, 1H). MS (ES) MH$^+$: 384.3 for C$_{17}$H$_{16}$F$_3$N$_3$O$_4$.

Intermediate 135

2-((5-(1,3-Dioxolan-2-yl)-6,7-difluorobenzo[d]isoxazol-3-yl)amino)-2-(pyridin-2-yl)ethanol

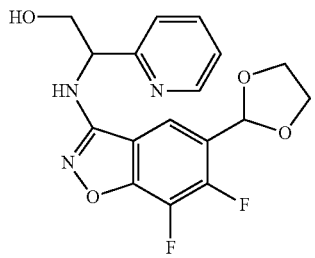

Intermediate 135 was synthesized following the procedure described for the preparation of Intermediate 119 using Intermediate 134 (1.60 g, 2.60 mmol). Yield: 0.78 g (73%). $^1$H NMR (400 MHz, DMSO-d$_6$) δ: 3.79-3.85 (m, 2H), 4.03-4.14 (m, 4H), 4.74 (q, 1H), 5.02 (t, 1H), 6.10 (s, 1H), 7.26 (dd, 1H), 7.41 (d, 1H), 7.72 (t, 1H), 7.74 (dd, 1H), 8.17 (d, 1H), 8.54 (d, 1H). MS (ES) MH$^+$: 364.3 for C$_{17}$H$_{15}$F$_2$N$_3$O$_4$.

Intermediate 136

3-(5-(1,3-Dioxolan-2-yl)-6,7-difluorobenzo[d]isoxazol-3-yl)-4-(pyridin-2-yl)oxazolidin-2-one

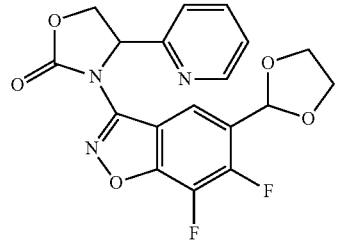 [SMILES: O=C1OCC(c2ccccn2)N1c1noc2c(F)c(F)c(C3OCCO3)cc12]

Intermediate 136 was synthesized following the procedure described for the preparation of Intermediate 120 using Intermediate 135 (1.0 g, 2.75 mmol). Yield: 0.90 g (84%). $^1$H NMR (300 MHz, DMSO-d$_6$) δ: 3.99-4.10 (m, 4H), 4.44 (dd, 1H), 4.97 (t, 1H), 5.75 (dd, 1H), 6.09 (s, 1H), 7.34 (dd, 1H), 7.55 (d, 1H), 7.82 (t, 1H), 8.41 (d, 1H), 8.51 (d, 1H). MS (ES) MH$^+$: 390.3 for C$_{18}$H$_{13}$F$_2$N$_3$O$_5$.

Intermediate 137

6,7-Difluoro-3-(2-oxo-4-(pyridin-2-yl)oxazolidin-3-)benzo[d]isoxazole-5-carbaldehyde

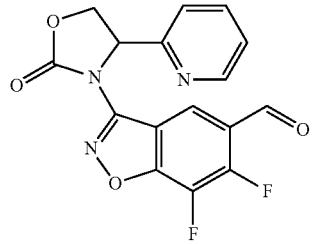 [SMILES: O=Cc1cc2c(N3C(=O)OCC3c3ccccn3)noc2c(F)c1F]

Intermediate 137 was synthesized following the procedure described for the preparation of Intermediate 122 using Intermediate 136 (0.90 g, 2.31 mmol). Yield: 0.75 g (94%). ¹H NMR (400 MHz, DMSO-d₆) δ: 4.49 (dd, 1H), 5.01 (t, 1H), 5.79 (dd, 1H), 7.35-7.38 (m, 1H), 7.59 (d, 1H), 7.85 (dt, 1H), 8.54 (d, 1H), 8.83 (d, 1H), 10.20 (s, 1H). MS (ES) MH⁺: 346.3 for $C_{16}H_9F_2N_3O_4$.

Intermediate 138

6-((2R,6R)-2,6-Dimethylmorpholino)-7-fluoro-3-(2-oxo-4-(pyridin-2-yl)oxazolidin-3-yl)benzo[d]isoxazole-5-carbaldehyde

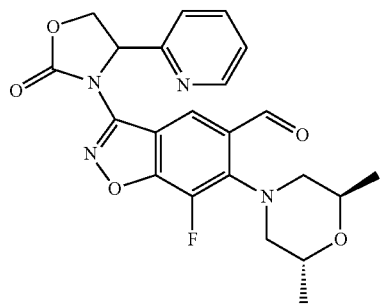 [SMILES: C[C@@H]1CN(c2c(C=O)cc3c(N4C(=O)OCC4c4ccccn4)noc3c2F)C[C@@H](C)O1]

Intermediate 138 was synthesized following the procedure described for the preparation of Intermediate 123 using Intermediate 137 (0.75 g, 2.17 mmol). Yield: 0.85 g (89%). H NMR (300 MHz, DMSO-d₆) δ: 1.20 (d, 6H), 2.96-3.00 (m, 2H), 3.31-3.36 (m, 2H), 4.00-4.13 (m, 2H), 4.45 (dd, 1H), 4.98 (t, 1H), 5.75 (dd, 1H), 7.33 (t, 1H), 7.54 (d, 1H), 7.82 (t, 1H), 8.51 (d, 1H), 8.65 (d, 1H), 10.30 (s, 1H). MS (ES) MH⁺: 441.4 for $C_{22}H_{21}FN_4O_5$.

Intermediate 139

5-(1,3-Dioxolan-2-yl)-2,3,4-trifluoro-N'-hydroxy-N-(2-hydroxy-1-(pyridin-4-yl)ethyl)benzimidamide

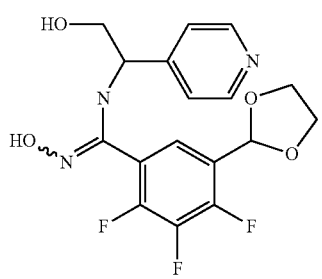 [SMILES: OCC(NC(=NO)c1cc(C2OCCO2)c(F)c(F)c1F)c1ccncc1]

Intermediate 139 was synthesized following the procedure described for the preparation of Intermediate 118 using Intermediate 16 (1.08 g, 3.84 mmol). Yield: 0.91 g (62%). ¹H NMR (300 MHz, DMSO-d₆) δ: 3.55-3.68 (m, 2H), 3.82-3.92 (m, 4H), 3.98-4.08 (m, 1H), 5.05 (t, 1H), 5.93 (s, 1H), 6.51 (d, 1H), 6.92-6.96 (m, 1H), 7.11 (d, 2H), 8.41 (d, 2H), 10.30 (s, 1H). MS (ES) MH⁺: 384.3 for $C_{17}H_{16}F_3N_3O_4$.

Intermediate 140

2-((5-(1,3-Dioxolan-2-yl)-6,7-difluorobenzo[d]isoxazol-3-yl)amino)-2-(pyridin-4-yl)ethanol

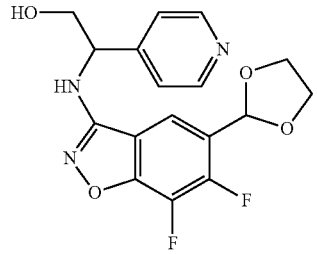 [SMILES: OCC(Nc1noc2c(F)c(F)c(C3OCCO3)cc12)c1ccncc1]

Intermediate 140 was synthesized following the procedure described for the preparation of Intermediate 119 using Intermediate 139 (0.90 g, 2.34 mmol). Yield: 0.60 g (71%). ¹H NMR (300 MHz, DMSO-d₆) δ: 3.73 (t, 2H), 4.00-4.12 (m, 4H), 4.66 (q, 1H), 5.12 (t, 1H), 6.08 (s, 1H), 7.39 (d, 2H), 7.89 (d, 1H), 8.11 (t, 1H), 8.49 (d, 2H). MS (ES) MH⁺: 364.3 for $C_{17}H_{15}F_2N_3O_4$.

Intermediate 141

3-(5-(1,3-Dioxolan-2-yl)-6,7-difluorobenzo[d]isoxazol-3-yl)-4-(pyridin-4-yl)oxazolidin-2-one

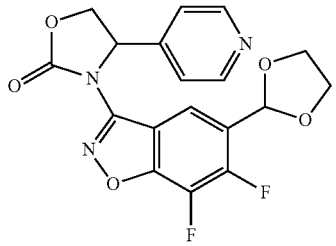 [SMILES: O=C1OCC(c2ccncc2)N1c1noc2c(F)c(F)c(C3OCCO3)cc12]

Intermediate 141 was synthesized following the procedure described for the preparation of Intermediate 120 using Intermediate 140 (0.60 g, 1.65 mmol). Yield: 0.61 g (95%). ¹H NMR (400 MHz, DMSO-d₆) δ: 4.01-4.10 (m, 4H), 4.36 (dd, 1H), 5.02 (t, 1H), 5.75 (dd, 1H), 6.10 (s, 1H), 7.49 (dd, 2H), 8.38 (dd, 1H), 8.55 (dd, 2H). MS (ES) MH⁺: 390.3 for $C_{18}H_{13}F_2N_3O_5$.

Intermediate 142

6,7-Difluoro-3-(2-oxo-4-(pyridin-4-yl)oxazolidin-3-yl)benzo[d]isoxazole-5-carbaldehyde

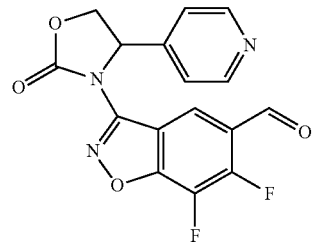 [SMILES: O=Cc1cc2c(N3C(=O)OCC3c3ccncc3)noc2c(F)c1F]

Intermediate 142 was synthesized following the procedure described for the preparation of Intermediate 122 TQ-100-14-V using Intermediate 141 (0.60 g, 1.54 mmol). Yield: 0.47 g (88%). $^1$H NMR (400 MHz, DMSO-d$_6$) δ: 4.40 (dd, 1H), 5.05 (t, 1H), 5.77 (dd, 1H), 7.51 (d, 2H), 8.57 (d, 2H), 8.78 (d, 1H), 10.22 (s, 1H). MS (ES) MH$^+$: 346.3 for C$_{16}$H$_9$F$_2$N$_3$O$_4$.

Intermediate 143

6-((2R,6R)-2,6-Dimethylmorpholino)-7-fluoro-3-(2-oxo-4-(pyridin-4-yl)oxazolidin-3-yl)benzo[d]isoxazole-5-carbaldehyde

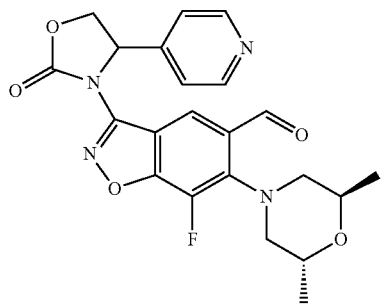 [SMILES: C[C@@H]1CN(c2c(C=O)cc3c(N4C(=O)OCC4c4ccncc4)noc3c2F)C[C@@H](C)O1]

Intermediate 143 was synthesized following the procedure described for the preparation of Intermediate 123 using Intermediate 142 (0.46 g, 1.33 mmol). Yield: 0.52 g (89%). H NMR (300 MHz, DMSO-d$_6$) δ: 1.36 (d, 6H), 2.87-2.99 (m, 2H), 3.31-3.37 (m, 2H), 4.08-4.12 (m, 2H), 4.36 (t, 1H), 5.01 (t, 1H), 5.74 (t, 1H), 7.46 (d, 2H), 8.54 (d, 2H), 8.62 (d, 1H), 10.31 (s, 1H). MS (ES) MH$^+$: 441.4 for C$_{22}$H$_{21}$FN$_4$O$_5$.

Intermediate 144

(2R,3R)-2-Amino-3-methoxybutan-1-ol

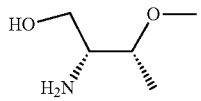

To a stirred solution of (2S,3R)-methyl 2-amino-3-methoxybutanoate (10.0 g, 75.19 mmol) in tetrahydrofuran (150 mL), sodium borohydride (10.28 g, 270.7 mmol) and iodine (24.7 g, 97.77 mmol) was added and the mixture was refluxed over a period of 16 hours. The mixture was filtered and the volatiles were removed under vacuum and the crude product was taken to the next step without further purification. Yield: 7.0 g (78%).

Intermediate 145

5-(1,3-Dioxolan-2-yl)-2,3,4-trifluoro-N'-hydroxy-N-((2R,3R)-1-hydroxy-3-methoxybutan-2-yl)benzimidamide

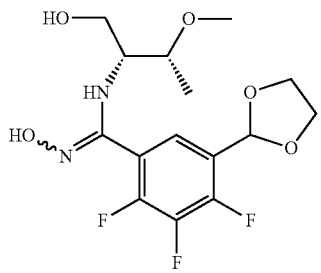 [SMILES: CO[C@H](C)[C@@H](CO)NC(=NO)c1cc(C2OCCO2)c(F)c(F)c1F]

To a stirred solution of Intermediate 144 (7.0 g, 58.82 mmol) in dimethyl formamide (25 mL), triethylamine (11.91 g, 117.64 mmol) was added and the mixture was stirred at the room temperature for 20 minutes. To this solution, Intermediate 16 (3.50 g, 12.43 mmol) was added and the mixture was stirred at the room temperature for another 2 hours. The mixture was poured into ice cold water (50 mL) and extracted with ethyl acetate (3×50 mL). The organic layers were washed with water (2×25 mL), brine solution (25 mL) and dried over sodium sulfate. Removal of solvent afforded crude product which was purified by silica gel flash column chromatography using a gradient of ethyl acetate in pet. ether. Yield: 1.8 g (40%). $^1$H NMR (400 MHz, DMSO-d$_6$) δ: 1.02 (d, 3H), 2.72-2.74 (m, 1H), 3.22 (s, 3H), 3.41-3.43 (m, 1H), 3.98-4.05 (m, 4H), 4.69 (t, 1H), 5.51 (d, 1H), 6.04 (s, 1H), 7.34 (t, 1H), 10.08 (s, 1H). Note: NH and OH protons did not appear. $^{19}$F NMR (376.5 MHz, DMSO-d$_6$) δ: −134.33 (m), −138.45 (m), −159.75 (m). MS (ES) MH$^+$: 365.2 for C$_{15}$H$_{19}$F$_3$N$_2$O$_5$.

Intermediate 146

(2R,3R)-2-((5-(1,3-Dioxolan-2-yl)-6,7-difluorobenzo[d]isoxazol-3-yl)amino)-3-methoxybutan-1-ol

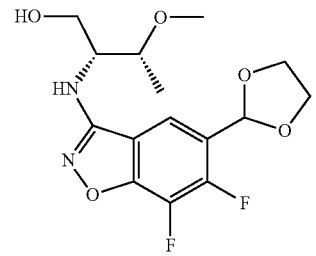 [SMILES: CO[C@H](C)[C@@H](CO)Nc1noc2c(F)c(F)c(C3OCCO3)cc12]

To a stirred solution of Intermediate 145 (1.8 g, 4.96 mmol) in dimethyl formamide (20 mL), cesium carbonate (3.55 g, 10.90 mmol) was added and the mixture was stirred at the room temperature for 16 hours. Water (10 mL) was added to the mixture and extracted with ethyl acetate (3×25 mL). The organic layers were washed with water (2×15 mL), brine solution (15 mL) and dried over sodium sulfate. Removal of the solvent afforded crude product which was further purified by silica gel flash column chromatography using 75% ethyl acetate in pet.ether. Yield: 1.30 g (76%). $^1$H NMR (400 MHz, DMSO-d$_6$) δ: 1.12 (d, 3H), 3.30 (s, 3H), 3.51-3.52 (m, 1H), 3.59-3.66 (m, 3H), 4.01-4.10 (m, 4H), 4.74 (t, 1H), 6.07 (s, 1H), 7.12 (d, 1H), 8.16 (d, 1H). $^{19}$F NMR (376.5 MHz, DMSO-d$_6$) δ: −143.58 (d), −162.18 (d). MS (ES) MH$^+$: 345.2 for C$_{15}$H$_{18}$F$_2$N$_2$O$_5$.

Intermediate 147

(R)-3-(5-(1,3-Dioxolan-2-yl)-6,7-difluorobenzo[d]isoxazol-3-yl)-4-((R)-1-methoxyethyl)oxazolidin-2-one

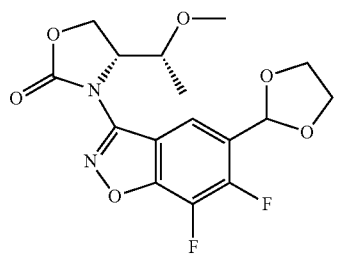 [SMILES: CO[C@H](C)[C@H]1COC(=O)N1c1noc2c(F)c(F)c(C3OCCO3)cc12]

To a stirred solution of Intermediate 146 (1.30 g, 3.78 mmol) in acetonitrile (20 mL), triethylamine (0.76 g, 7.56 mmol) was added at 0° C. and the mixture was stirred for 15 minutes. To this solution, bis(2,5-dioxopyrrolidin-1-yl) carbonate (or) disuccinimidyl carbonate (1.06 g, 4.16 mmol) was added at 0° C. and the mixture was stirred at the room temperature for 16 hours. The volatiles were removed under vacuum and the residue was dissolved in ethyl acetate (25 mL), washed with water (10 mL), brine solution (10 mL) and dried over sodium sulfate. Removal of solvent under vacuum afforded pale yellow solid which was purified in a Combi-Flash instrument using a gradient of ethyl acetate in pet. ether. Yield: 0.40 g (29%). $^1$H NMR (300 MHz, DMSO-d$_6$) δ: 1.03 (d, 3H), 3.32 (s, 3H), 3.96-4.08 (m, 4H), 4.49-4.53 (m, 1H), 4.63 (t, 1H), 4.78-4.83 (m, 1H), 6.08 (s, 1H), 8.27 (d, 1H). $^{19}$F NMR (376.5 MHz, DMSO-d$_6$) δ: −140.41 (d), −161.03 (d). MS (ES) MH$^+$: 371.3 for C$_{16}$H$_{16}$F$_2$N$_2$O$_6$.

Intermediate 148

6,7-Difluoro-3-((R)-4-((R)-1-methoxyethyl)-2-oxooxazolidin-3-yl)benzo[d]isoxazole-5-carbaldehyde

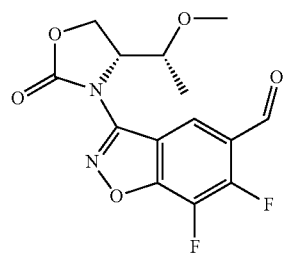 [SMILES: CO[C@H](C)[C@H]1COC(=O)N1c1noc2c(F)c(F)c(C=O)cc12]

To a stirred solution of Intermediate 147 (0.40 g, 1.08 mmol) in 1,4-dioxane (4 mL), 6N hydrochloric acid (2 mL) was added at 0° C. and the mixture was stirred at the room temperature for 1 hour. The mixture was poured into ice-cooled water (25 mL) and extracted with ethyl acetate (3×25 mL). The organic layers were washed with water (15 mL), brine solution (15 mL) and dried over sodium sulfate. Removal of the solvent afforded the title product. Yield: 0.35 g (99%). $^1$H NMR (300 MHz, DMSO-d$_6$) δ: 1.03 (d, 3H), 3.32 (s, 3H), 3.96-4.08 (m, 4H), 4.49-4.53 (m, 1H), 4.63 (t, 1H), 4.78-4.83 (m, 1H), 6.08 (s, 1H), 8.27 (d, 1H). $^{19}$F NMR (376.5 MHz, DMSO-d$_6$) δ: −140.41 (d), −161.03 (d). MS (ES) MH$^+$: 327.2 for C$_{14}$H$_{12}$F$_2$N$_2$O$_5$.

Intermediate 149

6-((2R,6R)-2,6-Dimethylmorpholino)-7-fluoro-3-((R)-4-((R)-1-methoxyethyl)-2-oxooxazolidin-3-yl)benzo[d]isoxazole-5-carbaldehyde

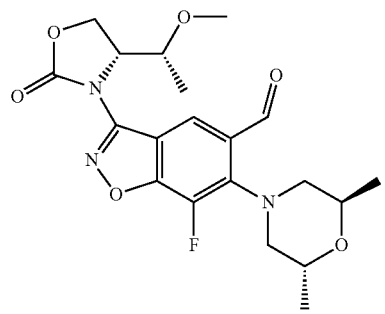 [SMILES: CO[C@H](C)[C@H]1COC(=O)N1c1noc2c(F)c(N3C[C@@H](C)O[C@H](C)C3)c(C=O)cc12]

To a stirred solution of Intermediate 148 (0.35 g, 1.07 mmol) in acetonitrile (4 mL), was added diisopropyl ethylamine (0.21 g, 1.61 mmol) followed by (2R,6R)-2,6-dimethylmorpholine (0.13 g, 1.07 mmol) and the mixture was heated at 80° C. for 16 hours in a sealed tube. It was cooled to room temperature and the volatiles were removed under vacuum to obtain the crude product was purified in a Combi-Flash instrument using a gradient of ethyl acetate in pet. ether to obtain the title compound as pale yellow solid. Yield: 0.25 g (56%). $^1$H NMR (300 MHz, DMSO-d$_6$) δ: 1.02 (d, 3H), 1.20 (d, 6H), 2.97-3.03 (m, 2H), 3.28 (s, 3H), 3.35-3.39 (m, 2H), 3.97-4.01 (m, 1H), 4.10-4.15 (m, 2H), 4.51-4.54 (m, 1H), 4.63 (t, 1H), 4.81-4.84 (m, 1H), 8.54 (s, 1H), 10.29 (s, 1H). $^{19}$F NMR (376.5 MHz, DMSO-d$_6$) δ: −146.80 (s). MS (ES) MH$^+$: 422.5 for C$_{20}$H$_{24}$FN$_3$O$_6$.

Intermediate 150

Benzyl ((2R,3S)-1-hydroxy-3-methoxybutan-2-yl)carbamate

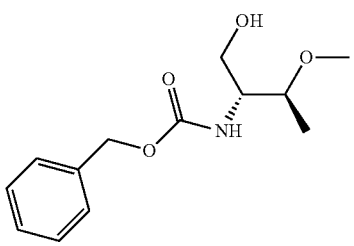 [SMILES: CO[C@@H](C)[C@@H](CO)NC(=O)OCc1ccccc1]

To a stirred solution of (2S,3S)-methyl 2-(((benzyloxy) carbonyl)amino)-3-methoxybutanoate (prepared according to the literature procedure: *Bioorg. Med. Chem. Lett.* 15 (2005) 1447-1449, 1.60 g, 5.68 mmol) in a 3:1 mixture of tetrahydrofuran and methanol (12 mL), sodium borohydride (0.43 g, 11.38 mmol) was added and the mixture was stirred at room temperature for 2 hours. The volatiles were removed and the residue was dissolved in ethyl acetate (25 mL) and washed with brine (10 mL). Removal of the solvent afforded crude product which was purified by silica gel column chromatography using a gradient of ethyl acetate in pet. ether. Yield: 1.32 g (92%). $^1$H NMR (400 MHz, DMSO-$d_6$) δ: 1.01 (d, 3H), 3.22 (s, 3H), 3.36-3.42 (m, 3H), 3.57-3.60 (m, 1H), 4.57 (t, 1H), 5.02 (s, 2H), 6.98-7.01 (m, 1H), 7.31-7.37 (m, 5H). MS (ES) MH$^+$: 254.4 for $C_{13}H_{19}F_3NO_4$.

Intermediate 151

(2R,3S)-2-Amino-3-methoxybutan-1-ol

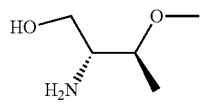

To a stirred solution of Intermediate 150 (1.32 g, 5.20 mmol) in ethyl acetate (50 mL), and 10% palladium on charcoal (0.13 g, 10 wt %) was added and the mixture was stirred at the room temperature under 20 mm pressure of hydrogen for 6 hours. The mixture was filtered and the volatiles were removed under vacuum and the crude product was taken to the next step without further purification. Yield: 0.47 g (47%)

Intermediate 152

5-(1,3-Dioxolan-2-yl)-2,3,4-trifluoro-N'-hydroxy-N-((2R,3S)-1-hydroxy-3-methoxybutan-2-yl)benzimid-amide

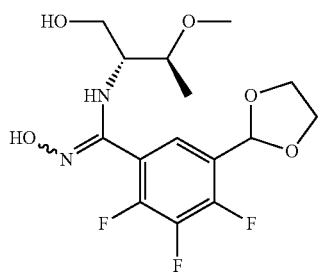 [SMILES: CO[C@@H](C)[C@@H](CO)NC(=NO)c1cc(C2OCCO2)c(F)c(F)c1F]

Intermediate 152 was synthesized following the procedure described for the preparation of Intermediate 145 using Intermediate 151 (0.47 g, 4.02 mmol). Yield: 0.50 g (35%). $^1$H NMR (400 MHz, DMSO-$d_6$) δ: 1.00 (d, 3H), 3.02 (s, 3H), 3.27-3.32 (m, 2H), 3.41 (d, 2H), 3.96-4.06 (m, 4H), 4.68 (t, 1H), 5.67 (d, 1H), 6.03 (s, 1H), 7.33-7.34 (m, 1H), 10.03 (s, 1H). $^{19}$F NMR (376.5 MHz, DMSO-$d_6$) δ: -134.26 (m), -138.79 (m), -160.03 (m). MS (ES) MH$^+$: 365.5 for $C_{15}H_{19}F_3N_2O_5$.

Intermediate 153

(2R,3S)-2-((5-(1,3-dioxolan-2-yl)-6,7-difluorobenzo [d]isoxazol-3-yl)amino)-3-methoxybutan-1-ol

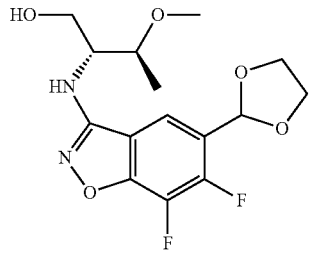 [SMILES: CO[C@@H](C)[C@@H](CO)Nc1noc2c(F)c(F)c(C3OCCO3)cc12]

Intermediate 153 was synthesized following the procedure described for the preparation of Intermediate 146 using Intermediate 152 (0.50 g, 1.37 mmol). Yield: 0.32 g (67%). $^1$H NMR (300 MHz, DMSO-$d_6$) δ: 1.15 (d, 3H), 3.25 (s, 3H), 3.52-3.60 (m, 4H), 3.98-4.10 (m, 4H), 4.70 (t, 1H), 6.06 (s, 1H), 7.09 (d, 1H), 8.09 (d, 1H). $^{19}$F NMR (376.5 MHz, DMSO-$d_6$) δ: -143.51 (d), -162.06 (d). MS (ES) MH$^+$: 345.5 for $C_{15}H_{18}F_2N_2O_5$.

Intermediate 154

(R)-3-(5-(1,3-Dioxolan-2-yl)-6,7-difluorobenzo[d] isoxazol-3-yl)-4-((S)-1-methoxyethyl)oxazolidin-2-one

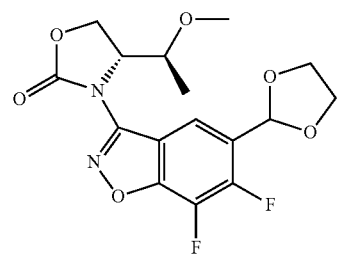 [SMILES: CO[C@@H](C)[C@H]1COC(=O)N1c1noc2c(F)c(F)c(C3OCCO3)cc12]

Intermediate 154 was synthesized following the procedure described for the preparation of Intermediate 147 using Intermediate 153 (0.25 g, 0.72 mmol). Yield: 0.08 g (30%). $^1$H NMR (400 MHz, DMSO-$d_6$) δ: 1.11 (d, 3H), 3.15 (s, 3H), 3.98-4.08 (m, 5H), 4.55-4.61 (m, 3H), 6.09 (s, 1H), 8.30 (d, 1H). $^{19}$F NMR (376.5 MHz, DMSO-$d_6$) δ: -140.43 (d), -161.01 (d). MS (ES) MH$^+$: 371.4 for $C_{16}H_{16}F_2N_2O_6$ Intermediate 155

6,7-Difluoro-3-((R)-4-((S)-1-methoxyethyl)-2-oxooxazolidin-3-yl)benzo[d]isoxazole-5-carbaldehyde

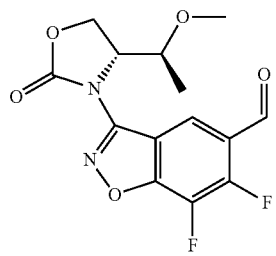 [SMILES: CO[C@@H](C)[C@H]1COC(=O)N1c1noc2c(F)c(F)c(C=O)cc12]

Intermediate 155 was synthesized following the procedure described for the preparation of Intermediate 148 using Intermediate 154 (0.08 g, 0.22 mmol). The crude product was taken to the next step without purification. Yield: 0.06 g (85%).

Intermediate 156

6-((2R,6R)-2,6-Dimethylmorpholino)-7-fluoro-3-((R)-4-((S)-1-methoxyethyl)-2-oxooxazolidin-3-yl)benzo[d]isoxazole-5-carbaldehyde

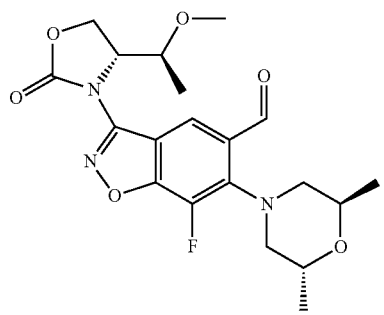 [SMILES: CO[C@@H](C)[C@H]1COC(=O)N1c1noc2c(F)c(N3C[C@@H](C)O[C@H](C)C3)c(C=O)cc12]

Intermediate 156 was synthesized following the procedure described for the preparation of Intermediate 149 using Intermediate 155 (0.06 g, 0.18 mmol). The crude product was taken to the next step without purification. Yield: 0.04 g (52%). MS (ES) MH+: 422.5 for $C_{20}H_{24}FN_3O_6$ Intermediate 157

Ethyl 2-((diphenylmethylene)amino)-2-(pyrazin-2-yl)acetate

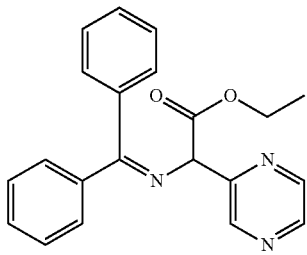 [SMILES: CCOC(=O)C(N=C(c1ccccc1)c1ccccc1)c1cnccn1]

A mixture of ethyl 2-((diphenylmethylene)amino)acetate (6.0 g, 22.47 mmol), 2-bromopyrazine (7.1 g, 44.90 mmol), potassium carbonate (9.30 g, 67.40 mmol) and tetrabutyl ammonium iodide (8.10 g, 22.40 mmol) in N-methyl-2-pyrrolidone (25 mL) was heated in a sealed tube at 110° C. for 16 hours. The mixture was poured into water (100 mL) and extracted with ethyl acetate (3×50 mL). The organic layers were washed with brine (25 mL) and dried over sodium sulfate. Removal of solvent under vacuum afforded crude product which was purified in Combi-Flash instrument using a gradient of methanol in chloroform. Yield: 4.90 g (63%). $^1$H NMR (300 MHz, DMSO-$d_6$) δ: 1.16 (t, 3H), 4.07 (q, 2H), 5.26 (s, 1H), 7.18 (dd, 2H), 7.38-7.61 (m, 8H), 8.56 (d, 1H), 8.57 (d, 1H), 8.60 (s, 1H). MS (ES) MH+: 346.3 for $C_{21}H_{19}N_3O_2$.

Intermediate 158

Ethyl 2-amino-2-(pyrazin-2-yl)acetate

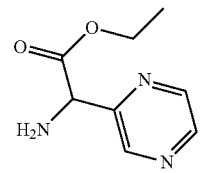

To a stirred solution of Intermediate 157 (4.9 g, 14.20 mmol) in dioxane (20 mL), 3N hydrochloric acid (20 mL) was added and the mixture was stirred at room temperature for 3 hours. The volatiles were removed completely under vacuum and the product obtained as its hydrochloride salt has been taken to the next step without purification. Yield: 2.4 g (92%). $^1$H NMR (300 MHz, DMSO-$d_6$) δ: 1.13 (t, 3H), 4.19 (q, 2H), 5.66 (s, 1H), 8.73-8.77 (m, 2H), 8.95 (d, 1H), 9.19 (br s, 3H). MS (ES) MH+: 182.3 for $C_8H_{11}N_3O_2$.

Intermediate 159

Ethyl 2-((tert-butoxycarbonyl)amino)-2-(pyrazin-2-yl)acetate

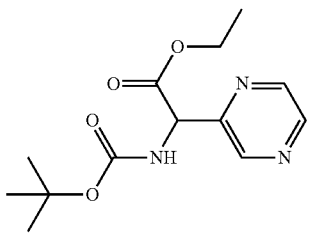 [SMILES: CCOC(=O)C(NC(=O)OC(C)(C)C)c1cnccn1]

To a stirred solution of Intermediate 158 (2.4 g, 11.60 mmol) in dichloromethane (25 mL), di-t-butyl dicarbonate (2.88 g, 12.76 mmol) and triethylamine (5 mL) were added and the mixture was refluxed for 2 hours. The volatiles were removed completely under vacuum and the crude product was taken to the next step without purification. Yield: 2.80 g (90%).

Intermediate 160 tert-Butyl (2-hydroxy-1-(pyrazin-2-yl)ethyl)carbamate

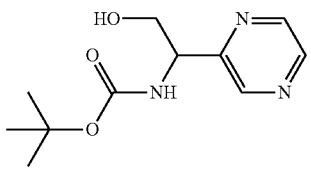 [SMILES: CC(C)(C)OC(=O)NC(CO)c1cnccn1]

To a stirred solution of Intermediate 163 (2.80 g, 9.96 mmol) in a 1:1 mixture of tetrahydrofuran and methanol (50 mL), sodium borohydride (0.37 g, 9.96 mmol) was added and the mixture was stirred at room temperature for 16 hours. The volatiles were removed under vacuum and the residue was dissolved in ethyl acetate (25 mL) and washed with brine (10 mL). Removal of the solvent afforded crude product which was taken to the next step without purification. Yield: 1.8 g (76%)

Intermediate 161

2-Amino-2-(pyrazin-2-yl)ethanol

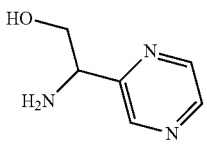

To a stirred solution of Intermediate 160 (1.80 g, 7.50 mmol) 3N hydrochloric acid in diethyl ether (20 mL) was added and the mixture was stirred at the room temperature for 3 hours. The volatiles were removed completely under vacuum and the product was taken to the next step without purification. Yield: 1.1 g (83%). MS (ES) MH$^+$: 140.2 for $C_6H_9N_3O$.

Intermediate 162

5-(1,3-Dioxolan-2-yl)-2,3,4-trifluoro-N'-hydroxy-N-(2-hydroxy-1-(pyrazin-2-yl)ethyl)benzimidamide

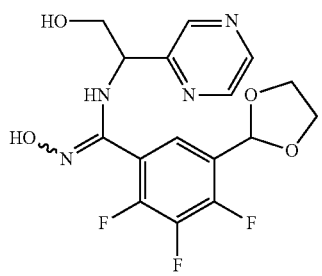 [SMILES: OCC(NC(=NO)c1cc(C2OCCO2)c(F)c(F)c1F)c1cnccn1]

Intermediate 162 was synthesized following the procedure described for the preparation of Intermediate 118 using Intermediate 161 (1.10 g, 6.32 mmol) and Intermediate 16 (1.78 g, 6.32 mmol). Yield: 0.96 g (40%). MS (ES) MH$^+$: 385.4 for $C_{16}H_{15}F_3N_4O_4$ Intermediate 163

2-((5-(1,3-Dioxolan-2-yl)-6,7-difluorobenzo[d]isoxazol-3-yl)amino)-2-(pyrazin-2-yl)ethanol

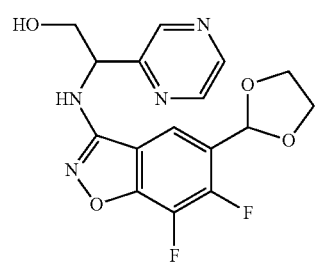 [SMILES: OCC(Nc1noc2c(F)c(F)c(C3OCCO3)cc12)c1cnccn1]

Intermediate 163 was synthesized following the procedure described for the preparation of Intermediate 119 using Intermediate 162 (0.96 g, 2.50 mmol). Yield: 0.52 g (55%). $^1$H NMR (400 MHz, DMSO-d$_6$) δ: 3.87 (t, 2H), 4.00-4.09 (m, 4H), 4.80 (q, 1H), 5.09 (t, 1H), 6.08 (s, 1H), 7.96 (d, 1H), 8.13 (d, 1H), 8.54 (d, 1H), 8.61 (d, 1H), 8.68 (s, 1H). MS (ES) MH$^+$: 365.4 for $C_{16}H_{14}F_2N_4O_4$.

Intermediate 164

3-(5-(1,3-Dioxolan-2-yl)-6,7-difluorobenzo[d]isoxazol-3-yl)-4-(pyrazin-2-yl)oxazolidin-2-one

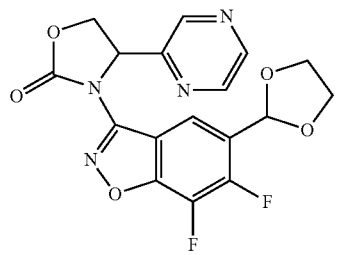 [SMILES: O=C1OCC(c2cnccn2)N1c1noc2c(F)c(F)c(C3OCCO3)cc12]

Intermediate 164 was synthesized following the procedure described for the preparation of Intermediate 120 using Intermediate 163 (0.25 g, 0.69 mmol). Yield: 0.16 g (59%). $^1$H NMR (300 MHz, DMSO-d$_6$) δ: 3.98-4.09 (m, 4H), 4.54 (dd, 1H), 4.99 (t, 1H), 5.87 (dd, 1H), 6.09 (s, 1H), 8.39 (dd, 1H), 8.61-8.63 (m, 2H), 8.86 (d, 1H). $^{19}$F NMR (376.5 MHz, DMSO-d$_6$) δ: −140.24 (d), −160.93 (d). MS (ES) MH$^+$: 391.4 for $C_{17}H_{12}F_2N_4O_6$.

Intermediate 165

6,7-Difluoro-3-(2-oxo-4-(pyrazin-2-yl)oxazolidin-3-yl)benzo[d]isoxazole-5-carbaldehyde

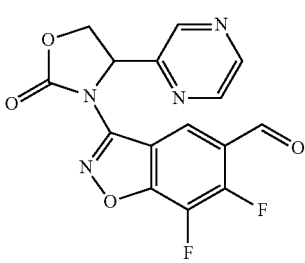 [SMILES: O=Cc1cc2c(N3C(=O)OCC3c3cnccn3)noc2c(F)c1F]

Intermediate 165 was synthesized following the procedure described for the preparation of Intermediate 122 using Intermediate 164 (0.16 g, 2.41 mmol). Yield: 0.12 g (86%). $^1$H NMR (300 MHz, DMSO-d$_6$) δ: 4.56 (dd, 1H), 5.01 (t, 1H), 5.88 (dd, 1H), 8.61-8.64 (m, 2H), 8.80 (d, 1H), 8.88 (d, 1H), 10.18 (s, 1H). $^{19}$F NMR (376.5 MHz, DMSO-d$_6$) δ: −142.93 (d), −160.18 (d). MS (ES) MH$^+$: 347.4 for $C_{16}H_8F_2N_4O_4$.

Intermediate 166

6-((2R,6R)-2,6-Dimethylmorpholino)-7-fluoro-3-(2-oxo-4-(pyrazin-2-yl)oxazolidin-3-yl)benzo[d]isoxazole-5-carbaldehyde

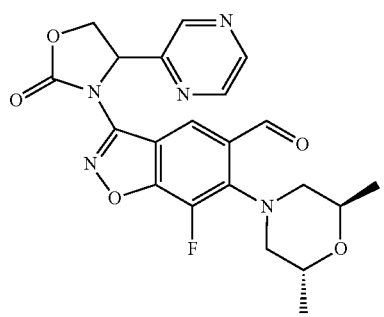 [SMILES: C[C@@H]1CN(c2c(C=O)cc3c(N4C(=O)OCC4c4cnccn4)noc3c2F)C[C@@H](C)O1]

Intermediate 166 was synthesized following the procedure described for the preparation of Intermediate 123 using Intermediate 165 (0.12 g, 0.35 mmol). Yield: 0.12 g (80%). $^1$H NMR (300 MHz, DMSO-d$_6$) δ: 1.21 (d, 6H), 2.98-3.00 (m, 2H), 3.31-3.33 (m, 2H, merged in DMSO peak), 4.11-4.13 (m, 2H), 4.56 (dd, 1H), 5.01 (t, 1H), 5.88 (dd, 1H), 8.63-8.67 (m, 3H), 8.88 (s, 1H), 10.31 (s, 1H). $^{19}$F NMR (376.5 MHz, DMSO-d$_6$) δ: −142.93 (d), −160.18 (d). MS (ES) MH$^+$: 442.5 for $C_{21}H_{20}FN_5O_5$.

Intermediate 167

5-(1,3-Dioxolan-2-yl)-2,3,4-trifluoro-N'-hydroxy-N-(2-hydroxy-1-(pyrimidin-2-yl)ethyl)benzimidamide

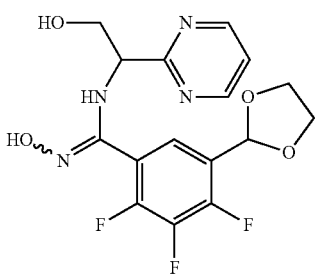 [SMILES: OCC(NC(=NO)c1cc(C2OCCO2)c(F)c(F)c1F)c1ncccn1]

Intermediate 167 was synthesized synthesized following the procedure described for the preparation of Intermediate 118 using 2-amino-2-(pyrimidin-2-yl)ethanol Intermediate 161 (1.0 g, 5.7 mmol) and Intermediate 16 (1.60 g, 5.71 mmol). Yield: 1.0 g (42%). MS (ES) MH$^+$: 385.5 for $C_{16}H_{15}F_3N_4O_4$

Intermediate 168

2-((5-(1,3-Dioxolan-2-yl)-6,7-difluorobenzo[d]isoxazol-3-yl)amino)-2-(pyrimidin-2-yl)ethanol

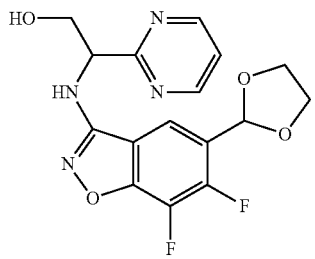 [SMILES: OCC(Nc1noc2c(F)c(F)c(C3OCCO3)cc12)c1ncccn1]

Intermediate 168 was synthesized following the procedure described for the preparation of Intermediate 119 using Intermediate 167 (1.0 g, 2.51 mmol). Yield: 0.42 g (45%). $^1$H NMR (400 MHz, DMSO-d$_6$) δ: 3.86-3.94 (m, 2H), 4.01-4.11 (m, 4H), 4.84-4.87 (m, 1H), 5.02 (t, 1H), 6.10 (s, 1H), 7.39 (t, 1H), 7.85 (d, 1H), 8.18 (d, 1H), 8.76 (d, 2H). $^{19}$F NMR (376.5 MHz, DMSO-d$_6$) δ: −143.35 (d), 161.90 (d). MS (ES) MH$^+$: 365.4 for $C_{16}H_{14}F_2N_4O_4$.

Intermediate 169

3-(5-(1,3-Dioxolan-2-yl)-6,7-difluorobenzo[d]isoxazol-3-yl)-4-(pyrimidin-2-yl)oxazolidin-2-one

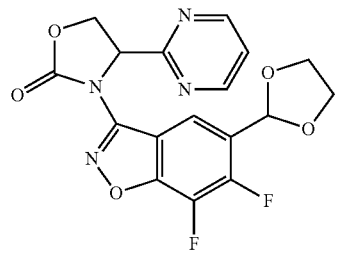 [SMILES: O=C1OCC(c2ncccn2)N1c1noc2c(F)c(F)c(C3OCCO3)cc12]

Intermediate 169 was synthesized following the procedure described for the preparation of Intermediate 120 using Intermediate 168 (0.34 g, 0.93 mmol). Yield: 0.25 g (70%). MS (ES) MH$^+$: 391.4 for $C_{17}H_{12}F_2N_4O_5$.

Intermediate 170

6,7-Difluoro-3-(2-oxo-4-(pyrimidin-2-yl)oxazolidin-3-yl)benzo[d]isoxazole-5-carbaldehyde

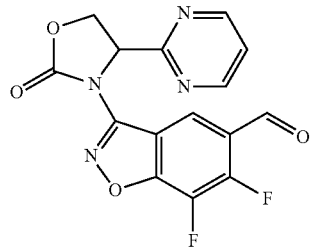 [SMILES: O=Cc1cc2c(N3C(=O)OCC3c3ncccn3)noc2c(F)c1F]

Intermediate 170 was synthesized following the procedure described for the preparation of Intermediate 122 using Intermediate 169 (0.25 g, 2.41 mmol). The crude product was taken to the next step without purification. Yield: 0.14 g (64%). MS (ES) MH+: 347.4 for $C_{15}H_8F_2N_4O_4$.

Intermediate 171

6-((2R,6R)-2,6-Dimethylmorpholino)-7-fluoro-3-(2-oxo-4-(pyrimidin-2-yl)oxazolidin-3-yl)benzo[d]isoxazole-5-carbaldehyde

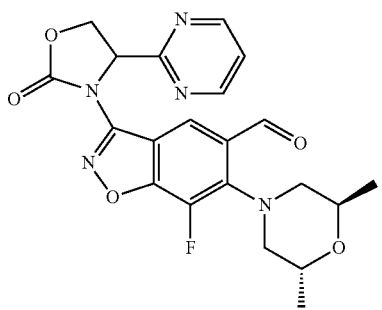

Intermediate 171 was synthesized following the procedure described for the preparation of Intermediate 123 using Intermediate 170 (0.14 g, 0.26 mmol). Yield: 0.12 g (63%). $^1$H NMR (400 MHz, DMSO-$d_6$) δ: 1.22 (d, 6H), 2.98-3.02 (m, 2H), 3.36-3.39 (m, 2H), 4.11-4.14 (m, 2H), 4.54 (dd, 1H), 5.05 (t, 1H), 5.75 (s, 1H), 7.49-7.52 (m, 1H), 8.69 (d, 1H), 8.81-8.83 (m, 2H), 10.31 (s, 1H). $^{19}$F NMR (376.5 MHz, DMSO-$d_6$) δ: −146.69 (d). MS (ES) MH+: 442.5 for $C_{21}H_{20}FN_5O_5$.

Intermediate 172

(S)-5-(1,3-Dioxolan-2-yl)-2,3,4-trifluoro-N'-hydroxy-N-(1-hydroxybut-3-yn-2-yl)benzimidamide

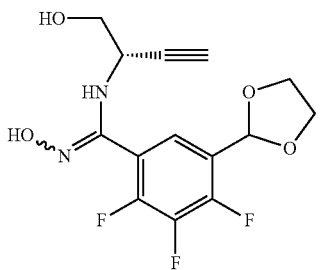 [SMILES: C#C[C@@H](CO)NC(=NO)c1cc(C2OCCO2)c(F)c(F)c1F]

Intermediate 172 was synthesized following the procedure described for the preparation of Intermediate 118 using (S)-2-aminobut-3-yn-1-ol (prepared according to the literature procedure from Garner aldehyde; *Eur. J. Org. Chem.* 2009, 3619-3627, 0.30 g, 2.44 mmol) and Intermediate 16 (0.65 g, 2.32 mmol). Yield: 0.53 g (65%). $^1$H NMR (300 MHz, DMSO-$d_6$) δ: 3.16 (d, 1H), 3.50 (t, 2H), 3.60-3.70 (m, 1H), 3.98-4.05 (m, 4H), 5.12 (t, 1H), 6.04-6.10 (m, 2H), 7.34 (t, 1H), 10.23 (s, 1H). $^{19}$F NMR (376.5 MHz, DMSO-$d_6$) δ: −133.64 (m), −138.05 (m), −159.54 (m). MS (ES) MH+: 331.4 for $C_{14}H_{13}F_3N_2O_4$.

Intermediate 173

(S)-2-((5-(1,3-Dioxolan-2-yl)-6,7-difluorobenzo[d]isoxazol-3-yl)amino)but-3-yn-1-ol

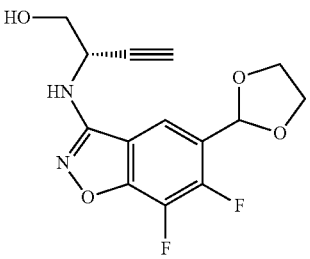 [SMILES: C#C[C@@H](CO)Nc1noc2c(F)c(F)c(C3OCCO3)cc12]

Intermediate 173 was synthesized following the procedure described for the preparation of Intermediate 119 using Intermediate 172 (0.51 g, 1.55 mmol). Yield: 0.27 g (55%). $^1$H NMR (300 MHz, DMSO-$d_6$) δ: 3.24 (d, 1H), 3.65 (t, 2H), 3.98-4.05 (m, 4H), 4.32-4.34 (m, 1H), 5.20 (t, 1H), 6.08 (s, 1H), 7.70 (d, 1H), 8.01 (d, 1H). $^{19}$F NMR (376.5 MHz, DMSO-$d_6$) δ: −142.96 (d), −161.66 (d). MS (ES) MH+: 311.4 for $C_{14}H_{12}F_2N_2O_4$.

Intermediate 174

(S)-3-(5-(1,3-Dioxolan-2-yl)-6,7-difluorobenzo[d]isoxazol-3-yl)-4-ethynyloxazolidin-2-one

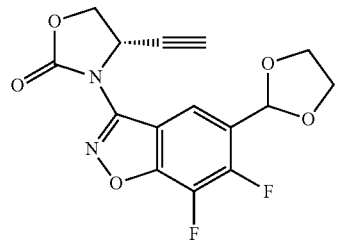 [SMILES: C#C[C@H]1COC(=O)N1c1noc2c(F)c(F)c(C3OCCO3)cc12]

Intermediate 174 was synthesized following the procedure described for the preparation of Intermediate 120 using Intermediate 173 (0.25 g, 0.81 mmol). Yield: 0.25 g (92%). $^1$H NMR (400 MHz, DMSO-$d_6$) δ: 3.69 (d, 1H), 3.99-4.08 (m, 4H), 4.56 (dd, 1H), 4.85 (t, 1H), 5.41-5.45 (m, 1H), 6.11 (s, 1H), 8.27 (dd, 1H). $^{19}$F NMR (376.5 MHz, DMSO-$d_6$) δ: −140.16 (d), −160.70 (d). MS (ES) MH+: 337.4 for $Cl_5H_{10}F_2N_2O_5$.

Intermediate 175

(S)-3-(4-Ethynyl-2-oxooxazolidin-3-yl)-6,7-difluorobenzo[d]isoxazole-5-carbaldehyde

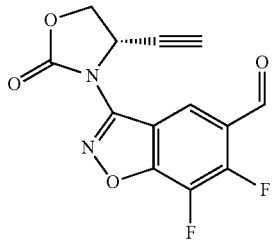 [SMILES: C#C[C@H]1COC(=O)N1c1noc2c(F)c(F)c(C=O)cc12]

Intermediate 175 was synthesized following the procedure described for the preparation of Intermediate 122 using Intermediate 174 (0.25 g, 0.74 mmol). Yield: 0.14 g (65%).

¹H NMR (300 MHz, DMSO-d₆) δ: 3.70 (d, 1H), 4.58 (dd, 1H), 4.86 (t, 1H), 5.41-5.46 (m, 1H), 8.67 (dd, 1H), 10.18 (s, 1H). ¹⁹F NMR (376.5 MHz, DMSO-d₆) δ: −142.87 (d), −159.98 (d). MS (ES) MH⁺: 293.3 for $C_{13}H_6F_2N_2O_4$.

Intermediate 176

6-((2R,6R)-2,6-dimethylmorpholino)-3-((S)-4-ethynyl-2-oxooxazolidin-3-yl)-7-fluorobenzo[d]isoxazole-5-carbaldehyde

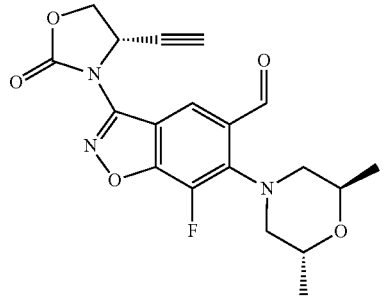 [SMILES: C#C[C@H]1COC(=O)N1c1noc2c(F)c(N3C[C@@H](C)O[C@H](C)C3)c(C=O)cc12]

Intermediate 176 was synthesized following the procedure described for the preparation of Intermediate 123 using Intermediate 175 (0.14 g, 0.48 mmol). Yield: 0.08 g (43%). ¹H NMR (300 MHz, DMSO-d₆) δ: 1.21 (d, 6H), 2.98-3.04 (m, 2H), 3.36-3.40 (m, 2H), 3.67 (d, 1H), 4.12-4.13 (m, 2H), 4.56 (dd, 1H), 4.81 (t, 1H), 5.39-5.43 (m, 1H), 8.51 (s, 1H), 10.30 (s, 1H). ¹⁹F NMR (376.5 MHz, DMSO-d₆) δ: −146.52 (s). MS (ES) MH⁺: 388.5 for $C_{19}H_{18}FN_3O_5$.

Intermediate 177

(S)-3-(7-chloro-6-((2R,6R)-2,6-dimethylmorpholino)-5-(1,3-dioxolan-2-yl)benzo[d]isoxazol-3-yl)-4-methyloxazolidin-2-one

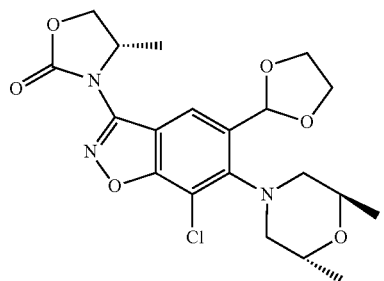 [SMILES: C[C@@H]1CN(c2c(C3OCCO3)cc3c(N4C(=O)OC[C@@H]4C)noc3c2Cl)C[C@@H](C)O1]

Intermediate 177 was synthesized following the procedure described for the preparation of Intermediate 42 using (S)-4-methyloxazolidin-2-one (synthesized according to the procedure described in Nishiyama, T.; Matsui, Shigeki; Yamada, F. J. Het. Chem. (1986), 23(5), 1427-9) and Intermediate 52. ¹H NMR (300 MHz, DMSO-d6) δ: 1.1 (br. s., 3H) 1.3 (br. s., 3H) 1.4 (d, 3H) 2.7-2.8 (m, 1H) 2.95-3.2 (m, 2H) 3.5-3.7 (m, 1H) 3.9-4.1 (m, 7H) 4.6-4.8 (m, 2H) 6.2 (s, 1H) 8.4 (s, 1H). MS (ES) MH⁺: 438 for $C_{20}H_{24}ClN_3O_6$.

Intermediate 178

S(S)—N-[(1S)-2-[tert-Butyl(dimethyl)silyl]oxy-1-(2-methyl-1,2,4-triazol-3-yl)ethyl]-2-methyl-propane-2-sulfinamide

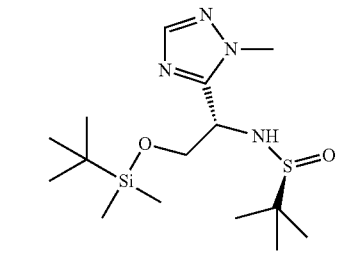 [SMILES: Cn1ncnc1[C@@H](CO[Si](C)(C)C(C)(C)C)N[S@@](=O)C(C)(C)C]

n-Butyl lithium (185 ml, 462 mmol) was added dropwise at −78° C. under nitrogen to a solution of 1-methyl-1H-[1,2,4]triazole (8 g, 96.43 mmol) in tetrahydrofuran (1000 mL), and the solution was stirred at this temperature for 30 minutes. A solution of [S(S)]—N-[2-[[(1,1-dimethylethyl)dimethylsilyl]oxy]ethylidene]-2-methyl-2-propanesulfinamide (107 g, 385 mmol) Rech, J. C. et al. JACS (2007), 129(3), 490-491) in 1200 mL tetrahydrofuran was added dropwise at −78° C. and stirred for 3 hours. The mixture was quenched with saturated aqueous NH₄Cl (200 mL) and extracted with ethyl acetate (1000 ml×3). The combined organic layers were washed with saturated aqueous NaCl and dried over Na₂SO₄. Solids were filtered off, and the filtrate was concentrated to give crude material that was purified by silica gel column chromatography (gradient elution with petroleum ether/ethyl acetate from 20/1 to 3/1) to give the title compound (100 g, 72%) as a yellow oil. ¹H NMR (400 MHz, CDCl₃) δ 0.00 (s, 3H), 0.04 (s, 3H), 0.85 (s, 3H), 1.3 (s, 9H), 4.0 (s, 3H), 4.2-4.6 (m, 2H), 4.7 (m, 1H), 7.9 (s, 1H).

Intermediate 179

(2S)-2-Amino-2-(2-methyl-1,2,4-triazol-3-yl)ethanol

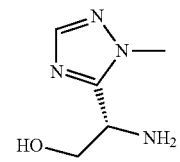

An amount of 2 M of HCl in tert-butyl methyl ether (320 mL) was added slowly to a solution of Intermediate 178 (70 g, 194 mmol) in MeOH (330 mL) at 0° C. The mixture was stirred in cooling bath overnight. Tert-butyl methyl ether (200 mL) was added and the mixture was stirred for 1 hour. Solids from the mixture was filtered to give the title compound as a white solid of the bis-HCl salt (23 g, 87%). ¹H NMR (400 MHz, D₂O) δ 3.75 (s, 3H), 3.8 (d, 2H) 4.7 (t, 1H), 7.8 (s, 1H). MS (ES) MH⁺: 143 for $C_5H_{10}F_2N_4O$.

Intermediate 180

(S)-2-(5-(1,3-dioxolan-2-yl)-6,7-difluorobenzo[d]isoxazol-3-ylamino)-2-(1-methyl-1H-1,2,4-triazol-5-yl)ethanol

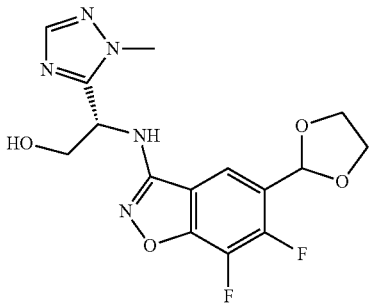 [SMILES: Cn1ncnc1[C@@H](CO)Nc1noc2c(F)c(F)c(C3OCCO3)cc12]

Intermediate 180 was synthesized following the procedure described for the preparation of Intermediate 17 using Intermediate 179 and Intermediate 16. MS (ES) MH$^+$: 368 for C$_{15}$H$_{15}$F$_2$N$_5$O$_4$.

Intermediate 181

(S)-3-(5-(1,3-Dioxolan-2-yl)-6,7-difluorobenzo[d]isoxazol-3-yl)-4-(1-methyl-1H-1,2,4-triazol-5-yl)oxazolidin-2-one

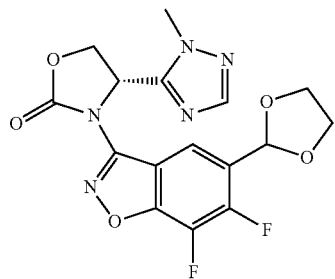 [SMILES: Cn1ncnc1[C@H]1COC(=O)N1c1noc2c(F)c(F)c(C3OCCO3)cc12]

Intermediate 181 was synthesized following the procedure described for the preparation of Intermediate 18 using Intermediate 180. $^1$H NMR (300 MHz, CDCl$_3$) δ 1.6 (br.s., 4H), 4.0-4.1 (m, 2H), 4.15 (s, 3H), 4.8-5.0 (m, 1H), 5.8 (dd, 1H), 7.9 (s, 1H), 8.4 (dd, 1H). MS (ES) MH$^+$: 394 for C$_{16}$H$_{13}$F$_2$N$_5$O$_5$.

Intermediate 182

(S)-6,7-Difluoro-3-(4-(1-methyl-1H-1,2,4-triazol-5-yl)-2-oxooxazolidin-3-yl)benzo[d]isoxazole-5-carbaldehyde

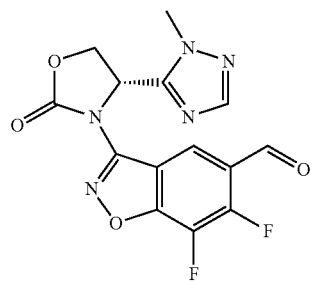 [SMILES: Cn1ncnc1[C@H]1COC(=O)N1c1noc2c(F)c(F)c(C=O)cc12]

Intermediate 182 was synthesized following the procedure described for the preparation of Intermediate 19 using Intermediate 181. MS (ES) MH$^+$: 350 for C$_{14}$H$_9$F$_2$N$_2$O$_4$

Intermediate 183

6-((2R,6R)-2,6-Dimethylmorpholino)-7-fluoro-3-((S)-4-(1-methyl-1H-1,2,4-triazol-5-yl)-2-oxooxazolidin-3-yl)benzo[d]isoxazole-5-carbaldehyde

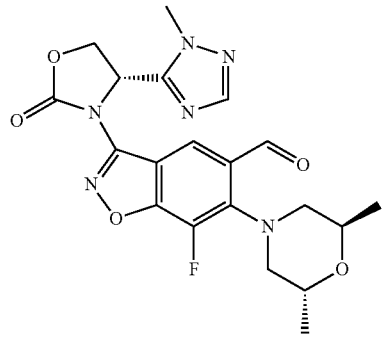 [SMILES: C[C@@H]1CN(c2c(C=O)cc3c(N4C(=O)OC[C@@H]4c4ncnn4C)noc3c2F)C[C@@H](C)O1]

Intermediate 183 was synthesized following the procedure described for the preparation of Intermediate 20 using Intermediate 182. MS (ES) MH$^+$: 445 for C$_{20}$H$_{21}$FN$_6$O$_5$.

Intermediate 184

S(R)—N-[(1R)-2-[tert-Butyl(dimethyl)silyl]oxy-1-(2-methyl-1,2,4-triazol-3-yl)ethyl]-2-methyl-propane-2-sulfinamide

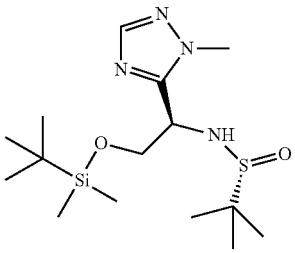 [SMILES: Cn1ncnc1[C@H](CO[Si](C)(C)C(C)(C)C)N[S@](=O)C(C)(C)C]

An amount of n-butyl lithium (38.57 mL, 96.43 mmol) was added dropwise at −78° C. under nitrogen to a solution of 1-methyl-1H-[1,2,4]triazole (8 g, 96.43 mmol) in tetrahydrofuran (250 ml), and the solution was stirred at this temperature for 30 minutes. A solution of [S(R)]—N-[2-[[(1,1-dimethylethyl)dimethylsilyl]oxy]ethylidene]-2-methyl-2-propanesulfinamide (22.3 g (80.36 mmol) (Seguin, C. et al. *J. Org. Chem.* (2009), 74(18), 6986-6992) in 20 mL tetrahydrofuran was added dropwise at −78° C. and stirred for 3 hours. The mixture was quenched with saturated aqueous NH$_4$Cl (40 ml). The above reaction was carried out again in a second batch. The two batches after the aqueous NH$_4$Cl were combined and extracted with ethyl acetate (100 ml×3). The combined organic layers were washed with saturated aqueous NaCl and dried over Na$_2$SO$_4$. Solids were filtered off, and the filtrate was concentrated to give crude material that was purified by silica gel column chromatography (gradient elution with petroleum ether/ethyl acetate from 20/1 to 3/1) to give the title compound (31.8 g, 55%) as a yellow oil. $^1$H NMR (400 MHz, CDCl$_3$) δ 0.00 (s, 3H), 0.04 (s, 3H), 0.85 (s, 3H), 1.3 (s, 9H), 4.0 (s, 3H), 4.2-4.6 (m, 2H), 4.7 (m, 1H), 7.9 (s, 1H).

Intermediate 185

(2R)-2-Amino-2-(2-methyl-1,2,4-triazol-3-yl)ethanol

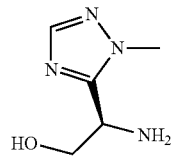

An amount of 2 M of HCl in tert-butyl methyl ether (210 mL) was added slowly to a solution of Intermediate 184 (45 g, 135 mmol) in MeOH (210 mL) at 0° C. The mixture was stirred in cooling bath overnight. Tert-butyl methyl ether (200 mL) was added and the mixture was stirred for 1 hour. Solids from the mixture were filtered to give the title compound as a white solid of the bis-HCl salt (23 g, 87%). $^1$H NMR (400 MHz, d4-MeOH) δ 3.9 (d, 2H) 4.0 (s, 3H), 4.8 (t, 1H), 8.0 (s, 1H). MS (ES) MH$^+$: 143 for C$_5$H$_{10}$F$_2$N$_4$O.

Intermediate 186

(R)-2-(5-(1,3-Dioxolan-2-yl)-6,7-difluorobenzo[d]isoxazol-3-ylamino)-2-(1-methyl-1H-1,2,4-triazol-5-yl)ethanol

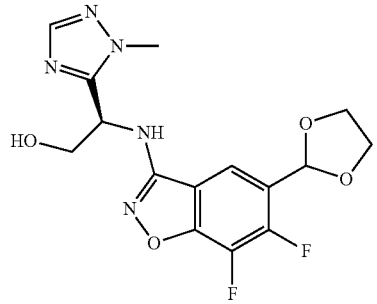 [SMILES: Cn1ncnc1[C@H](CO)Nc1noc2c(F)c(F)c(C3OCCO3)cc12]

Intermediate 186 was synthesized following the procedure for the preparation of Intermediate 17 using Intermediate 185 and Intermediate 16. MS (ES) MH$^+$: 368 for C$_{13}$H$_{15}$F$_2$N$_3$O$_4$.

Intermediate 187

(R)-3-(5-(1,3-Dioxolan-2-yl)-6,7-difluorobenzo[d]isoxazol-3-yl)-4-(1-methyl-1H-1,2,4-triazol-5-yl)oxazolidin-2-one

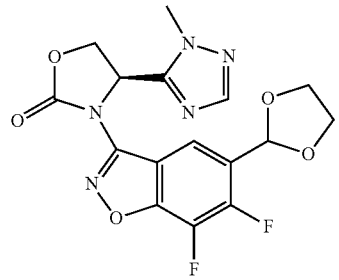 [SMILES: Cn1ncnc1[C@@H]1COC(=O)N1c1noc2c(F)c(F)c(C3OCCO3)cc12]

Intermediate 187 was synthesized following the procedure for the preparation of Intermediate 18 using Intermediate 186. $^1$H NMR (300 MHz, CDCl$_3$) δ 1.6 (br.s., 4H), 4.0-4.1 (m, 2H), 4.15 (s, 3H), 4.75-5.0 (m, 1H), 5.8 (dd, 1H), 7.9 (s, 1H), 8.4 (dd, 1H). MS (ES) MH$^+$: 394 for C$_{16}$H$_{13}$F$_2$N$_3$O$_3$.

Intermediate 188

(R)-6,7-Difluoro-3-(4-(1-methyl-1H-1,2,4-triazol-5-yl)-2-oxooxazolidin-3-yl)benzo[d]isoxazole-5-carbaldehyde

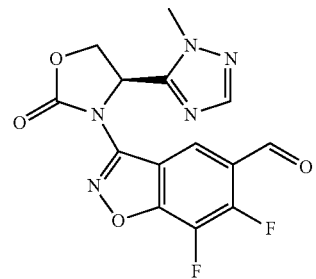 [SMILES: Cn1ncnc1[C@@H]1COC(=O)N1c1noc2c(F)c(F)c(C=O)cc12]

Intermediate 188 was synthesized following the procedure for the preparation of Intermediate 19 using Intermediate 187. MS (ES) MH$^+$: 350 for C$_{14}$H$_9$F$_2$N$_2$O$_4$.

Intermediate 189

6-((2R,6R)-2,6-Dimethylmorpholino)-7-fluoro-3-((R)-4-(1-methyl-1H-1,2,4-triazol-5-yl)-2-oxooxazolidin-3-yl)benzo[d]isoxazole-5-carbaldehyde

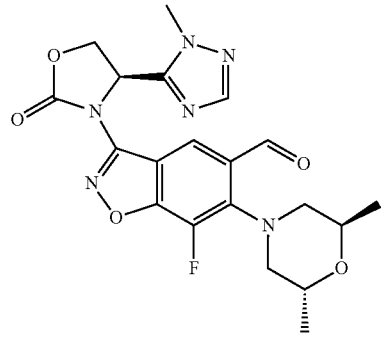 [SMILES: C[C@@H]1CN(c2c(C=O)cc3c(N4C(=O)OC[C@H]4c4ncnn4C)noc3c2F)C[C@@H](C)O1]

Intermediate 189 was synthesized following the procedure for the preparation of Intermediate 20 using Intermediate 188. MS (ES) MH$^+$: 445 for $C_{20}H_{21}FN_6O_5$.

Intermediate 190

(2S,3S)-Methyl 2-(((benzyloxy)carbonyl)amino)-3-hydroxybutanoate

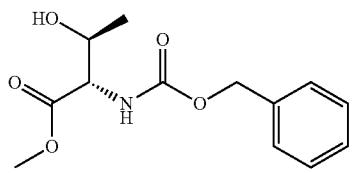 [SMILES: COC(=O)[C@@H](NC(=O)OCc1ccccc1)[C@H](C)O]

To a stirred solution of (2S,3S)-methyl 2-amino-3-hydroxybutanoate (2.5 g, 14.73 mmol) in a 1:1 mixture of tetrahydrofuran and water (50 mL), sodium bicarbonate (1.9 g, 22.10 mmol) was added and the mixture was cooled to 0° C. and to this benzyl chloroformate (2.76 g, 16.21 mmol) was added drop wise over a period of 30 minutes. The mixture was then stirred at the room temperature for 16 hours. The reaction mixture was diluted with ethyl acetate (25 mL), organic layers were separated, washed with brine (25 mL) and dried over sodium sulfate. Removal of solvents under vacuum afforded the crude product which has been purified by silica gel column chromatography (230-400 mesh) using a gradient of ethyl acetate in pet.ether. Yield: 3.4 g (86%) $^1$H NMR (400 MHz, DMSO-d$_6$) δ: 1.09 (d, 3H), 3.89 (s, 3H), 3.99 (t, 1H), 4.01-4.06 (m, 1H), 5.00 (d, 1H), 5.04 (s, 2H), 7.30-7.40 (m, 5H), 7.63 (d, 1H). MS (ES) MH$^+$: 268.1 for $C_{13}H_{17}NO_5$.

Intermediate 191

(2S,3S)-Methyl 2-(((benzyloxy)carbonyl)amino)-3-((tetrahydro-2H-pyran-2-yl)oxy)butanoate

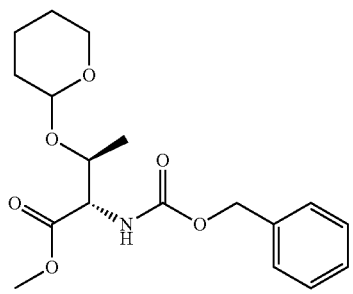 [SMILES: COC(=O)[C@@H](NC(=O)OCc1ccccc1)[C@H](C)OC1CCCCO1]

To a stirred solution of Intermediate 190 (2.0 g, 7.89 mmol) in dichloromethane (20 mL), pyridinium p-toluene sulfonate (0.79 g, 3.16 mmol) and 2,3-dihydropyran (1.02 g, 11.85 mmol) were added at once and the solution was stirred at the room temperature for 16 hours. Saturated sodium bicarbonate solution (50 mL) was added to the reaction mixture, the organic layer was separated and the aqueous layer was extracted with dichloromethane (2×50 mL). Combined organic layers were washed with water (50 mL) and brine solution (50 mL) and dried over sodium sulfate. Removal of solvent afforded the crude product which was purified by flash column chromatography (silica gel: 60-120 mesh) using a gradient of ethyl acetate in pet.ether. Yield: 2.4 g (87%). $^1$H NMR (300 MHz, DMSO-d$_6$) δ: 1.10 & 1.15 (d, 3H), 1.41-1.58 (m, 6H), 3.36-3.43 (m, 1H), 3.63 (s, 3H), 3.69-3.73 (m, 1H), 3.99 (q, 1H), 4.15 & 4.27 (t, 1H), 4.57 & 4.72 (s, 1H), 5.03 (s, 2H), 7.28-7.34 (m, 5H), 7.71 & 7.79 (d, 1H).

Intermediate 192

Benzyl ((2R,3S)-1-hydroxy-3-((tetrahydro-2H-pyran-2-yl)oxy)butan-2-yl)carbamate

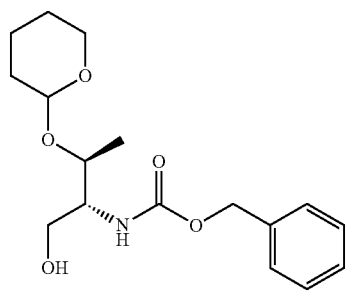 [SMILES: C[C@H](OC1CCCCO1)[C@@H](CO)NC(=O)OCc1ccccc1]

To a stirred solution of Intermediate 191 (2.4 g, 7.12 mmol) in a 7:3 mixture of tetrahydrofuran and methanol (20 mL), sodium borohydride (0.32 g, 8.55 mmol) was added portion wise at 5° C. and the solution was stirred at the room temperature for 3 hours. The volatiles were removed under vacuum and the residue was dissolved in ethyl acetate (50 mL) and washed with water (25 mL). The aqueous layer was extracted with ethyl acetate (2×25 mL). The combined organic layers were washed with brine solution (25 mL) and dried over sodium sulfate. Removal of solvents afforded the crude product which was taken to the next step without further purification. Yield: 1.6 g (70%).

Intermediate 193

(2R,3S)-2-amino-3-((tetrahydro-2H-pyran-2-yl)oxy)butan-1-ol

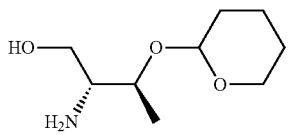

To a stirred solution Intermediate 192 (1.6 g, 4.95 mmol) in ethyl acetate (20 mL), triethylamine (1 mL) and 10% palladium on charcoal (0.16 g, 10 wt %) was added and the mixture was stirred at the room temperature under 20 mm pressure of hydrogen for 6 hours. The mixture was filtered and the volatiles were removed under vacuum and the crude product was taken to the next step without purification. Yield: 0.93 g (99%).

Intermediate 194

5-(1,3-dioxolan-2-yl)-2,3,4-Trifluoro-N'-hydroxy-N-((2R,3S)-1-hydroxy-3-((tetrahydro-2H-pyran-2-yl)oxy)butan-2-yl)benzimidamide

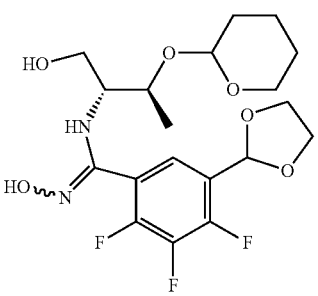 [SMILES: C[C@H](OC1CCCCO1)[C@@H](CO)NC(=NO)c1cc(C2OCCO2)c(F)c(F)c1F]

To a stirred solution of Intermediate 194 (0.95 g, 5.02 mmol) in dimethyl formamide (10 mL), triethylamine (0.76 g, 7.53 mmol) was added and the mixture was stirred at the room temperature for 20 minutes. Intermediate 16 (1.41 g, 5.02 mmol) was added and the mixture was stirred at the room temperature for another 2 hours. The mixture was poured into ice cold water (50 mL) and extracted with ethyl acetate (3×50 mL). The organic layers were washed with water (2×25 mL), brine solution (25 mL) and dried over sodium sulfate. Removal of solvent afforded the crude product which was purified by silica gel flash column chromatography using a gradient of ethyl acetate in pet. ether. This compound obtained as a mixture of diastereomers. Yield: 1.0 g (46%) $^1$H NMR (400 MHz, DMSO-$d_6$) δ: 1.01 & 1.09 (d, 3H), 1.16-1.56 (m, 6H), 2.77-2.79 & 2.88-2.90 (m, 1H), 3.38-3.78 (m, 5H), 3.99-4.05 (m, 4H), 4.43 & 4.56 (s, 1H), 4.66 & 4.74 (t, 1H), 5.69 & 5.80 (d, 1H), 6.03 (s, 1H), 7.36-7.38 (m, 1H), 10.00 & 10.09 (s, 1H). $^{19}$F NMR (376.5 MHz, DMSO-$d_6$) δ: −133.89 (m), −138.56 (m), −159.90 (m). MS (ES) MH$^+$: 435.3 for $C_{19}H_{25}F_3N_2O_6$.

Intermediate 195

(2R,3S)-2-((5-(1,3-Dioxolan-2-yl)-6,7-difluorobenzo[d]isoxazol-3-yl)amino)-3-((tetrahydro-2H-pyran-2-yl)oxy)butan-1-ol

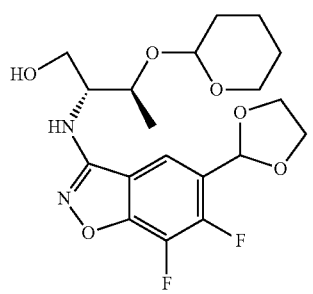 [SMILES: C[C@H](OC1CCCCO1)[C@@H](CO)Nc1noc2c(F)c(F)c(C3OCCO3)cc12]

To a stirred solution of Intermediate 194 (1.0 g, 2.30 mmol) in dimethyl formamide (10 mL), cesium carbonate (1.13 g, 3.45 mmol) was added and the mixture was stirred at the room temperature for 16 hours. Water (10 mL) was added to the mixture and the solution was extracted with ethyl acetate (3×25 mL). The organic layers were washed with water (25 mL), brine solution (25 mL) and dried over sodium sulfate. Removal of solvent afforded the crude product which was further purified by silica gel flash column chromatography using 75% ethyl acetate in pet.ether. This compound was obtained as a mixture of diastereomers. Yield: 0.60 g (63%). MS (ES) MH$^+$: 415.3 for $C_{19}H_{24}F_2N_2O_6$.

Intermediate 196

(4R)-3-(5-(1,3-dioxolan-2-yl)-6,7-difluorobenzo[d]isoxazol-3-yl)-4-((1S)-1-((tetrahydro-2H-pyran-2-yl)oxy)ethyl)oxazolidin-2-one

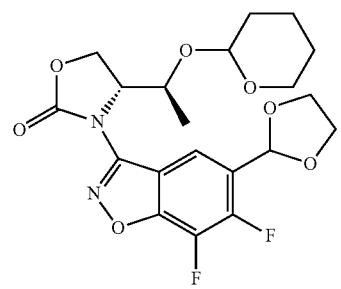 [SMILES: C[C@H](OC1CCCCO1)[C@H]1COC(=O)N1c1noc2c(F)c(F)c(C3OCCO3)cc12]

To a stirred solution of Intermediate 195 (0.60 g, 1.45 mmol) in acetonitrile (10 mL), triethylamine (0.5 mL, 3.62 mmol) was added at 0° C. and the mixture was stirred for 15 minutes. To this, bis(2,5-dioxopyrrolidin-1-yl) carbonate (or) disuccinimidyl carbonate (0.93 g, 3.62 mmol) was added at 0° C. and the mixture was stirred at the room temperature for 16 hours. The volatiles were removed under vacuum and the residue was dissolved in ethyl acetate (10 mL), washed with water (5 mL), brine solution (5 mL) and dried over sodium sulfate. Removal of solvent under vacuum afforded pale yellow solid which was purified in a Combi-Flash instrument using a gradient of ethyl acetate in pet.ether. This compound obtained as a mixture of diastereomers. Yield: 0.23 g (36%). $^1$H NMR (400 MHz, DMSO-$d_6$) δ: 1.10 & 1.19 (d, 3H), 1.22-1.72 (m, 6H), 2.85-2.92 & 3.01-3.12 (m, 1H), 3.65-3.67 (m, 1H), 4.00-4.05 (m, 4H), 4.32-4.35 (m, 1H), 4.57-4.65 (m, 4H), 6.09 (s, 1H), 8.26 & 8.36 (d, 1H). $^{19}$F NMR (376.5 MHz, DMSO-$d_6$) δ: −140.34 & −140.59 (d), −160.87 & 161.19 (d).

Intermediate 197

6,7-Difluoro-3-((R)-4-((S)-1-hydroxyethyl)-2-oxooxazolidin-3-yl)benzo[d]isoxazole-5-carbaldehyde

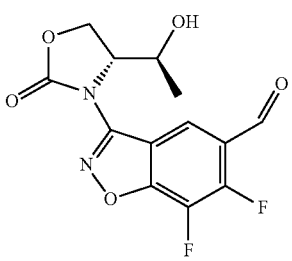 [SMILES: C[C@H](O)[C@H]1COC(=O)N1c1noc2c(F)c(F)c(C=O)cc12]

To a stirred solution of Intermediate 196 (0.23 g, 0.68 mmol) in 1,4-dioxane (3 mL), 6N hydrochloric acid (3 mL) was added at 0° C. and the mixture was stirred at room temperature for 1 hour. The mixture was poured into ice-cooled water (25 mL) and extracted with ethyl acetate (3×25 mL). The organic layers were washed with water (15 mL), brine solution (15 mL) and dried over sodium sulfate. Removal of solvent afforded the crude product which was taken to the next step without purification. Yield: 0.15 g (92%). MS (ES) MH$^+$: 313.1 for $C_{13}H_{10}F_2N_2O_5$.

Intermediate 198

6-((2R,6R)-2,6-Dimethylmorpholino)-7-fluoro-3-((R)-4-((S)-1-hydroxyethyl)-2-oxooxazolidin-3-yl)benzo[d]isoxazole-5-carbaldehyde

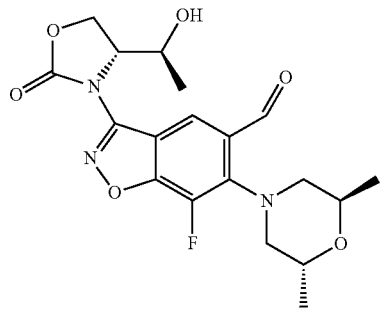 [SMILES: C[C@@H]1CN(c2c(C=O)cc3c(N4C(=O)OC[C@@H]4[C@H](C)O)noc3c2F)C[C@@H](C)O1]

To a stirred solution of Intermediate 197 (0.15 g, 0.48 mmol) in acetonitrile (2 mL), was added diisopropyl ethylamine (0.09 g, 0.72 mmol) followed by (2R,6R)-2,6-dimethylmorpholine (0.06 g, 0.53 mmol) and the mixture was heated at 80° C. for 6 hours in a sealed tube. The solution was cooled to room temperature and the volatiles were removed under vacuum to obtain the crude product which was purified in a Combi-Flash instrument using a gradient of ethyl acetate in pet.ether to obtain the title compound as pale yellow solid. Yield: 0.12 g (77%). $^1$H NMR (400 MHz, DMSO-d$_6$) δ: 1.05 (d, 3H), 1.22 (d, 6H), 2.99-3.04 (m, 2H), 3.36-3.39 (m, 2H), 4.12-4.15 (m, 2H), 4.31-4.33 (m, 1H), 4.52-4.60 (m, 3H), 5.22 (d, 1H), 8.63 (s, 1H), 10.32 (s, 1H). $^{19}$F NMR (376.5 MHz, DMSO-d$_6$) δ: −146.94 (d). MS (ES) MH$^+$: 408.3 for $C_{19}H_{22}FN_3O_6$.

Intermediate 199

[(4R)-3-{6-[(2R,6R)-2,6-dimethylmorpholin-4-yl]-5-(1,3-dioxolan-2-yl)-7-fluoro-1,2-benzoxazol-3-yl}-2-oxo-1,3-oxazolidin-4-yl]methyl methanesulfonate

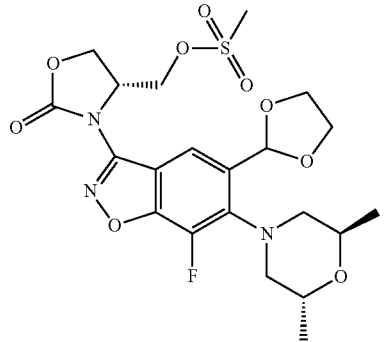 [SMILES: C[C@@H]1CN(c2c(C3OCCO3)cc3c(N4C(=O)OC[C@@H]4COS(C)(=O)=O)noc3c2F)C[C@@H](C)O1]

To a stirred solution of Intermediate 107 (0.3 g, 0.68 mmol) in dichloromethane (5 mL), triethylamine (0.14 mL, 1.02 mmol) and methanesulfonyl chloride (0.12 g, 1.02 mmol) were added at 0° C. followed by methanesulfonyl chloride (1.63 g, 8.55 mmol). The resulting solution was stirred at room temperature for a period of an hour. Water (2 mL) was added to the reaction mixture and it was extracted with ethyl acetate (2×10 mL). The organic layers were washed with brine solution (5 mL), dried over sodium sulfate and solvents were removed under vacuum to obtained crude product which was purified by silica gel flash column chromatography using a gradient of ethyl acetate in hexane. Yield: 0.25 g (71%). $^1$H NMR (400 MHz, DMSO-d$_6$) δ: 1.18 (d, 6H), 2.88-2.92 (m, 2H), 3.18 (s, 3H), 3.21-3.24 (m, 2H), 3.95-4.01 (m, 2H), 4.04-4.10 (m, 4H), 4.46-4.52 (m, 2H), 4.74-4.78 (m, 2H), 4.94-4.95 (m, 1H), 6.17 (s, 1H), 8.23 (s, 1H). MS (ES) MH$^+$: 516.4 for $C_{21}H_{26}FN_3O_9S$.

Intermediate 200

[(4S)-3-{6-[(2R,6R)-2,6-Dimethylmorpholin-4-yl]-7-fluoro-5-formyl-1,2-benzoxazol-3-yl}-2-oxo-1,3-oxazolidin-4-yl]acetonitrile

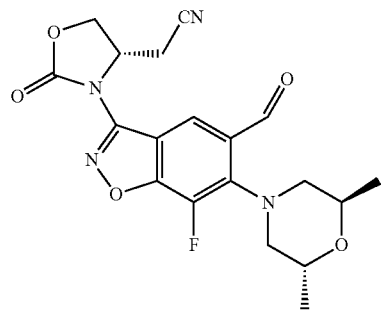 [SMILES: C[C@@H]1CN(c2c(C=O)cc3c(N4C(=O)OC[C@@H]4CC#N)noc3c2F)C[C@@H](C)O1]

To a stirred solution of Intermediate 199 (0.28 g, 0.54 mmol) in acetonitrile (5 mL), 1M solution of tetrabutyl ammonium fluoride in tetrahydrofuran (0.2 mL, 0.65 mmol) and trimethylsilyl cyanide (0.08 mL, 0.65 mmol) were added and the mixture was stirred at the room temperature for 2 days. Water (2 mL) was added to the reaction mixture and it was extracted with ethyl acetate (2×10 mL). The organic layers were washed with brine solution (5 mL), dried over sodium sulfate and solvents were removed under vacuum to obtained crude product which was purified by silica gel flash column chromatography using a gradient of ethyl acetate in hexane. Yield: 0.11 g (50%). $^1$H NMR (400 MHz, DMSO-d$_6$) δ: 1.20 (d, 6H), 2.98-3.04 (m, 2H), 3.14-3.20 (m, 2H), 3.32-3.40 (m, 2H), 4.08-4.12 (m, 2H), 4.47-4.51 (m, 1H), 4.81 (t, 1H), 4.90-4.92 (m, 1H), 8.56 (s, 1H), 10.30 (s, 1H). MS (ES) MH$^+$: 403.4 for $C_{19}H_{19}FN_4O_5$.

Intermediate 201

(R)-4-((R)-1,2-Dihydroxyethyl)-3-(6-((2R,6R)-2,6-dimethylmorpholino)-5-(1,3-dioxolan-2-yl)-7-fluorobenzo[d]isoxazol-3-yl)oxazolidin-2-one

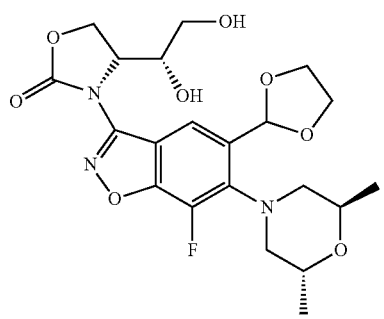

To a solution of Intermediate 120 (0.50 g, 1.15 mmol) in a mixture of t-butanol and water (10 mL; 1:1), AD-mix-β (5.0 g) was added and the mixture was stirred at the room temperature for 16 hours. Solid sodium sulfite (5.0 g) was added to this mixture at 0° C. and it was stirred at room temperature for an hour. The mixture was extracted with ethyl acetate (3×15 mL) and the combined organic layers were washed with water (10 mL), brine (10 mL) and dried over sodium sulfate. Removal of solvent under vacuum afforded solid which was taken to the next step without further purification. Yield: 0.50 g (93%). $^1$HNMR (400 MHz, DMSO-d$_6$) δ: 1.22 (br s, 6H), 2.88-2.92 (m, 2H), 3.20-3.22 (m, 2H), 3.32-3.36 (m, 1H), 3.43-3.44 (m, 1H), 3.96-4.01 (m, 2H), 4.03-4.10 (m, 4H), 4.16-4.18 (m, 1H), 4.56-4.62 (m, 2H), 4.75-4.76 (m, 1H), 4.86 (t, 1H), 5.36 (d, 1H), 6.18 (s, 1H), 8.33 (s, 1H). MS (ES) MH$^+$: 468.3 for $C_{21}H_{26}FN_3O_8$.

Intermediate 202

(R)-4-((S)-1,2-Dihydroxyethyl)-3-(6-((2R,6R)-2,6-dimethylmorpholino)-5-(1,3-dioxolan-2-yl)-7-fluorobenzo[d]isoxazol-3-yl)oxazolidin-2-one

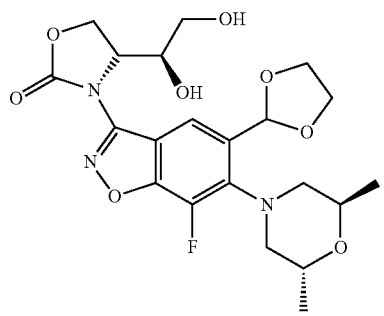

Intermediate 202 was synthesized following the procedure described for the preparation of Intermediate 201 using Intermediate 120 (0.50 g, 1.15 mmol) and AD-mix-α (5.0 g). $^1$H NMR (400 MHz, DMSO-d$_6$) δ: 1.23 (br s, 6H), 2.87-2.91 (m, 2H), 3.20-3.22 (m, 2H), 3.33-3.36 (m, 1H), 3.43-3.44 (m, 1H), 3.96-4.02 (m, 2H), 4.03-4.10 (m, 4H), 4.16-4.17 (m, 1H), 4.56-4.64 (m, 2H), 4.75-4.76 (m, 1H), 4.86 (t, 1H), 5.36 (d, 1H), 6.18 (s, 1H), 8.33 (s, 1H). MS (ES) MH$^+$: 468.3 for $C_{21}H_{26}FN_3O_8$.

Intermediate 203

(5R)-3-{6-[(2R,6R)-2,6-Dimethylmorpholin-4-yl]-5-(1,3-dioxolan-2-yl)-7-fluoro-1,2-benzoxazol-3-yl}-2-oxo-1,3-oxazolidine-5-carbonitrile

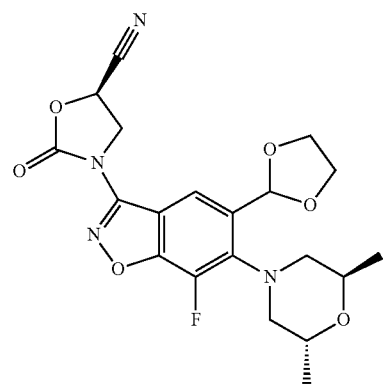 [SMILES: C[C@@H]1CN(c2c(C3OCCO3)cc3c(N4C[C@H](C#N)OC4=O)noc3c2F)C[C@@H](C)O1]

A solution of Intermediate 89 (0.38 g, 0.84 mmol) in trichloroacetonitrile (5 mL) was heated at 95° C. for 2 hours. The volatiles were evaporated and the crude product was purified by silica gel flash column chromatography using a gradient of 25-30% ethyl acetate in hexane. Yield: 0.13 g (36%). $^1$H NMR (400 MHz, DMSO-d$_6$) δ: 1.25 (br s, 6H), 2.88-2.92 (m, 2H), 3.22 (d, 2H), 3.96-4.01 (m, 2H), 4.04-4.10 (m, 4H), 4.34-4.37 (m, 1H), 4.48 (t, 1H), 5.93 (dd, 1H), 6.17 (s, 1H), 8.35 (s, 1H). MS (ES) MH$^+$: 433.3 for $C_{20}H_{21}FN_4O_6$.

Intermediate 204

(2S,3R)-Methyl 2-(((benzyloxy)carbonyl)amino)-3-((tetrahydro-2H-pyran-2-yl)oxy)butanoate

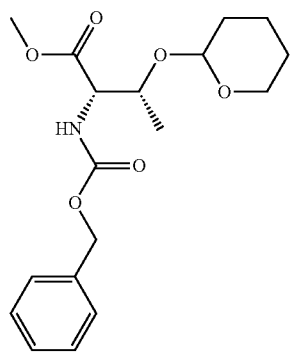 [SMILES: COC(=O)[C@@H](NC(=O)OCc1ccccc1)[C@@H](C)OC1CCCCO1]

To a stirred solution of (2S,3R)-methyl 2-(((benzyloxy)carbonyl)amino)-3-hydroxybutanoate (5.0 g, 18.72 mmol) in dichloromethane (100 mL), pyridinium p-toluene sulfonate (0.47 g, 1.87 mmol) and 2,3-dihydropyran (2.6 mL, 28.08 mmol) were added at once and the solution was stirred at room temperature for 16 hours. Saturated sodium bicarbonate solution (50 mL) was added to the reaction mixture, the organic layer was separated and the aqueous layer was extracted with dichloromethane (2×50 mL). The combined organic layers were washed with water (50 mL) and brine solution (50 mL) and dried over sodium sulfate. Removal of solvent afforded the crude product which was purified by flash column chromatography (silica gel: 60-120 mesh) using a gradient of ethyl acetate in pet.ether. The product was obtained as mixture of diastereomers. Yield: 5.9 g (90%). $^1$H NMR (400 MHz, DMSO-$d_6$) δ: 1.10 & 1.15 (d, 3H), 1.38-1.72 (m, 6H), 3.39-3.41 (m, 1H), 3.60-3.64 (m, 1H), 3.65 (s, 3H), 4.17-4.25 (m, 2H), 4.57 & 4.67 (t, 1H), 5.05 & 5.06 (s, 2H), 7.31-7.37 (m, 5H), 7.26 & 7.58 (d, 1H).

Intermediate 205

Benzyl ((2R,3R)-1-hydroxy-3-((tetrahydro-2H-pyran-2-yl)oxy)butan-2-yl)carbamate

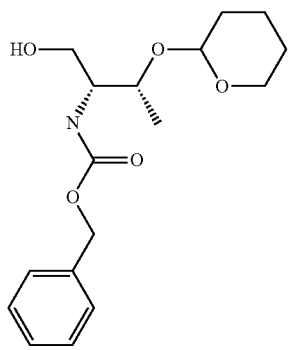 [SMILES: C[C@@H](OC1CCCCO1)[C@@H](CO)NC(=O)OCc1ccccc1]

To a stirred solution of Intermediate 204 (5.90 g, 16.80 mmol) in a 7:3 mixture of tetrahydrofuran and methanol (200 mL), sodium borohydride (1.60 g, 42.02 mmol) was added portion wise at 5° C. and the solution was stirred at room temperature for 3 hours. Volatiles were removed under vacuum and the residue was dissolved in ethyl acetate (50 mL), washed with water (25 mL) and the aqueous layer was extracted with ethyl acetate (2×25 mL). The combined organic layers were washed with brine solution (25 mL) and dried over sodium sulfate. Removal of solvents afforded the crude product which has been taken to the next step without further purification. Yield: 4.9 g (90%). MS (ES) MH$^+$: 324.3 for $C_{17}H_{25}NO_5$ Intermediate 206

(2R,3R)-2-Amino-3-((tetrahydro-2H-pyran-2-yl)oxy)butan-1-ol

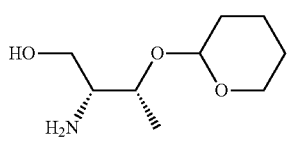

To a stirred solution of Intermediate 205 (4.9 g, 15.17 mmol) in ethyl acetate (50 mL), triethylamine (1 mL) and 10% palladium on charcoal (1.0 g, 10 wt %) was added and the mixture was stirred at room temperature under 20 mm pressure of hydrogen for 6 hours. The mixture was filtered and the volatiles were removed under vacuum and the crude product has been taken to the next step without purification. Yield: 2.5 g (87%)

Intermediate 207

5-(1,3-Dioxolan-2-yl)-2,3,4-trifluoro-N'-hydroxy-N-((2R,3R)-1-hydroxy-3-((tetrahydro-2H-pyran-2-yl)oxy)butan-2-yl)benzimidamide

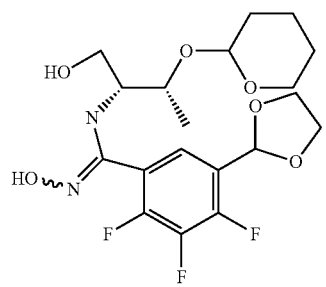 [SMILES: C[C@@H](OC1CCCCO1)[C@@H](CO)NC(=NO)c1cc(C2OCCO2)c(F)c(F)c1F]

To a stirred solution of Intermediate 206 (2.5 g, 13.22 mmol) in dimethyl formamide (20 mL), triethylamine (2.0 g, 19.84 mmol) was added and the mixture was stirred at the room temperature for 20 minutes. To this, Intermediate 16 (3.1 g, 11.24 mmol) was added and the mixture was stirred at the room temperature for another 2 hours. The mixture was poured into ice cold water (50 mL), extracted with ethyl acetate (3×50 mL), organic layers were washed with water (2×25 mL), brine solution (25 mL) and dried over sodium sulfate. Removal of solvent afforded the crude product which was purified by silica gel flash column chromatography using a gradient of ethyl acetate in pet. ether. Yield: 2.2 g (38%). $^1$H NMR (400 MHz, DMSO-$d_6$) δ: 1.08 & 1.12 (d, 3H), 1.44-1.72 (m, 6H), 3.65-3.85 (m, 1H), 3.36-3.42 (m, 2H), 3.76-3.78 (m, 2H), 3.96-4.05 (m, 5H), 4.57-4.75 (m, 2H), 5.61 (d, 1H), 6.04 (s, 1H), 7.36-7.38 (m, 1H), 10.04 & 10.08 (s, 1H). $^{19}$F NMR (376.5 MHz, DMSO-$d_6$) δ: −134.33 (m), −138.45 (m), −159.79 (m). MS (ES) MH$^+$: 435.3 for $C_{19}H_{25}F_3N_2O_6$.

Intermediate 208

(2R,3R)-2-((5-(1,3-Dioxolan-2-yl)-6,7-difluorobenzo[d]isoxazol-3-yl)amino)-3-((tetrahydro-2H-pyran-2-yl)oxy)butan-1-ol

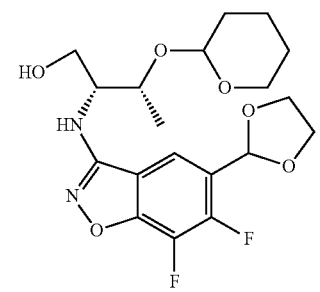 [SMILES: C[C@@H](OC1CCCCO1)[C@@H](CO)Nc1noc2c(F)c(F)c(C3OCCO3)cc12]

To a stirred solution of Intermediate 207 (2.2 g, 5.07 mmol) in dimethyl formamide (25 mL), cesium carbonate (3.65 g, 11.19 mmol) was added and the mixture was stirred at room temperature for 16 hours. Water (10 mL) was added to the mixture, extracted with ethyl acetate (3×25 mL), the organic layers were washed with water (25 mL), brine solution (25 mL) and dried over sodium sulfate. Removal of solvent afforded the crude product which was further purified by silica gel flash column chromatography using 75% ethyl acetate in pet.ether. Yield: 1.3 g (62%). $^1$H NMR (400 MHz, DMSO-$d_6$) δ: 1.10 & 1.18 (d, 3H), 1.41-1.80 (m, 6H), 3.42-3.44 (m, 1H), 3.57-3.60 (m, 2H), 3.61-3.63 (m, 1H), 3.70-3.72 (m, 1H), 4.00-4.08 (m, 5H), 4.65-4.77 (m, 2H), 6.07 (s, 1H), 7.09 & 7.11 (d, 1H), 8.13 (t, 1H). $^{19}$F NMR (376.5 MHz, DMSO-$d_6$) δ: −143.47 (m), −162.10 (m). MS (ES) MH$^+$: 415.3 for $C_{19}H_{24}F_2N_2O_6$.

Intermediate 209

(4R)-3-(5-(1,3-Dioxolan-2-yl)-6,7-difluorobenzo[d] isoxazol-3-yl)-4-((1R)-1-((tetrahydro-2H-pyran-2-yl) oxy)ethyl)oxazolidin-2-one

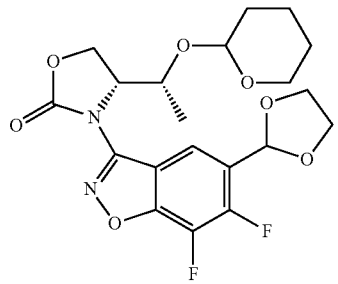 [SMILES: C[C@@H](OC1CCCCO1)[C@H]1COC(=O)N1c1noc2c(F)c(F)c(C3OCCO3)cc12]

To a stirred solution of Intermediate 208 (0.35 g, 0.84 mmol) in acetonitrile (10 mL), triethylamine (0.17 g, 1.69 mmol) was added at 0° C. and the mixture was stirred for 15 minutes. To this, bis(2,5-dioxopyrrolidin-1-yl) carbonate or disuccinimidyl carbonate (0.23 g, 0.89 mmol) was added at 0° C. and the mixture was stirred at the room temperature for 16 hours. Volatiles were removed under vacuum and the residue was dissolved in ethyl acetate (10 mL), washed with water (5 mL), brine solution (5 mL) and dried over sodium sulfate. Removal of solvent under vacuum afforded pale yellow solid which was purified in a Combi-Flash instrument using a gradient of ethyl acetate in pet.ether. Yield: 0.12 g (32%). $^1$H NMR (300 MHz, DMSO-$d_6$) δ: 1.03 & 1.09 (d, 3H), 1.22-1.72 (m, 6H), 3.42-3.44 (m, 1H), 3.70-3.85 (m, 1H), 4.00-4.04 (m, 4H), 4.35 (t, 1H), 4.55 (t, 1H), 4.62-4.68 (m, 2H), 4.79 (t, 1H), 6.09 (s, 1H), 8.25 (d, 1H). $^{19}$F NMR (376.5 MHz, DMSO-$d_6$) δ: −140.46 (d), −161.07 (m).

Intermediate 210

6,7-Difluoro-3-((R)-4-((R)-1-hydroxyethyl)-2-oxooxazolidin-3-yl)benzo[d]isoxazole-5-carbaldehyde

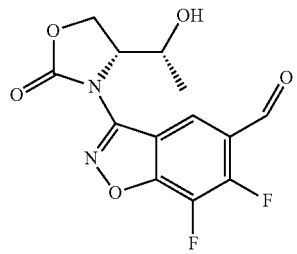 [SMILES: C[C@@H](O)[C@H]1COC(=O)N1c1noc2c(F)c(F)c(C=O)cc12]

To a stirred solution of Intermediate 209 (0.12 g, 0.27 mmol) in 1,4-dioxane (2 mL), 6N hydrochloric acid (2 mL) was added at 0° C. and the mixture was stirred at the room temperature for 1 hour. The mixture was poured into ice-cooled water (25 mL) and extracted with ethyl acetate (3×25 mL). Organic layers were washed with water (15 mL), brine solution (15 mL) and dried over sodium sulfate. Removal of solvent afforded the title product. Yield: 0.07 g (82%). $^1$H NMR (300 MHz, DMSO-$d_6$) δ: 0.99 (d, 3H), 4.27-4.28 (m, 1H), 4.57-4.66 (m, 3H), 5.28 (d, 1H), 8.70 (d, 1H), 10.18 (s, 1H). $^{19}$F NMR (376.5 MHz, DMSO-$d_6$) δ: −140.41 (d), −161.03 (d). MS (ES) MH$^+$: 313.1 for $C_{13}H_{10}F_2N_2O_5$.

Intermediate 211

6-((2R,6R)-2,6-Dimethylmorpholino)-7-fluoro-3-((R)-4-((R)-1-hydroxyethyl)-2-oxooxazolidin-3-yl) benzo[d]isoxazole-5-carbaldehyde

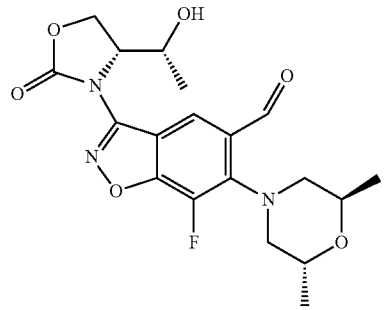 [SMILES: C[C@@H]1CN(c2c(C=O)cc3c(N4C(=O)OC[C@@H]4[C@@H](C)O)noc3c2F)C[C@@H](C)O1]

To a stirred solution of Intermediate 210 (0.07 g, 0.22 mmol) in acetonitrile (2 mL), was added diisopropyl ethylamine (0.04 g, 0.34 mmol) followed by (2R,6R)-2,6-dimethylmorpholine (0.03 g, 0.25 mmol) and the mixture was heated at 80° C. for 6 hours in a sealed tube. The solution was cooled to room temperature and the volatiles were removed under vacuum to obtain the crude product which was purified in a Combi-Flash instrument using a gradient of ethyl acetate in pet.ether to obtain the title compound as pale yellow solid. Yield: 0.07 g (77%). $^1$H NMR (300 MHz, DMSO-$d_6$) δ: 0.98 (d, 3H), 1.20 (d, 6H), 2.99-3.03 (m, 2H), 3.35-3.39 (m, 2H), 4.11-4.13 (m, 1H), 4.25-4.35 (m, 1H), 4.57-4.63 (m, 4H), 5.25 (d, 1H), 8.55 (s, 1H), 10.30 (s, 1H). $^{19}$F NMR (376.5 MHz, DMSO-$d_6$) δ: −161.03 (d). MS (ES) MH$^+$: 408.3 for $C_{19}H_{22}FN_3O_6$.

Intermediate 212

5-(1,3-Dioxolan-2-yl)-2,3,4-trifluoro-N-((2R,3R)-11-fluoro-3-hydroxybutan-2-yl)-N'-hydroxybenzimidamide

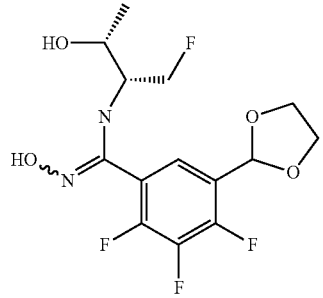 [SMILES: C[C@@H](O)[C@H](CF)NC(=NO)c1cc(C2OCCO2)c(F)c(F)c1F]

Intermediate 212 was synthesized following the procedure for the preparation of Intermediate 207 using (2R,3S)-3-amino-4-fluorobutan-2-ol (0.35 g, 2.48 mmol) (prepared according to the literature procedure; *Tet. Lett.* 1985, 26, 4687 & WO2005/66119 A2, 2005, column 27-28 and Intermediate 16 (0.84 g, 2.98 mmol). Yield: 0.55 g (83%). $^1$H NMR (300 MHz, DMSO-d$_6$) δ: 1.02 (d, 3H), 3.69 (br s, 2H), 3.97-4.00 (m, 4H), 4.17-4.44 (m, 3H), 5.76 (d, 1H), 6.03 (s, 1H), 7.29 (t, 1H), 10.18 (s, 1H). MS (ES) MH$^+$: 353.4 for C$_{14}$H$_{16}$F$_4$N$_2$O$_4$.

Intermediate 213

(2R,3R)-3-((5-(1,3-Dioxolan-2-yl)-6,7-difluorobenzo[d]isoxazol-3-yl)amino)-4-fluorobutan-2-ol

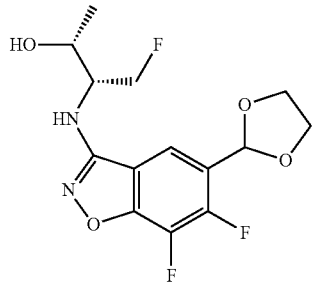 [SMILES: C[C@@H](O)[C@H](CF)Nc1noc2c(F)c(F)c(C3OCCO3)cc12]

Intermediate 213 was synthesized following the procedure for the preparation of Intermediate 208 using Intermediate 204 (0.39 g, 1.08 mmol). Yield: 0.26 g (73%). MS (ES) MH$^+$: 333.4 for C$_{14}$H$_{15}$F$_3$N$_2$O$_4$.

Intermediate 214

(4R,5R)-3-(5-(1,3-Dioxolan-2-yl)-6,7-difluorobenzo[d]isoxazol-3-yl)-4-(fluoromethyl)-5-methyloxazolidin-2-one

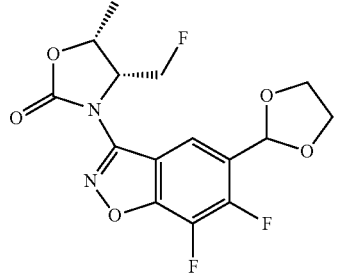 [SMILES: C[C@H]1OC(=O)N(c2noc3c(F)c(F)c(C4OCCO4)cc23)[C@H]1CF]

Intermediate 214 was synthesized following the procedure for the preparation of Intermediate 209 using Intermediate 205 0.26 g, 0.78 mmol). Yield: 0.07 g (25%). H NMR (300 MHz, DMSO-d$_6$) δ: 1.52 (d, 3H), 4.00-4.05 (m, 4H), 4.49 (d, 1H), 4.73 (dd, 1H), 4.86-5.06 (m, 2H), 6.09 (s, 1H), 8.30 (d, 1H). $^{19}$F NMR (376.5 MHz, DMSO-d$_6$) δ: −140.27 (d), −161.04 (d), −236.04 (s). MS (ES) MH$^+$: 359.3 for C$_{15}$H$_{13}$F$_3$N$_2$O$_5$.

Intermediate 215

6,7-Difluoro-3-((4R,5R)-4-(fluoromethyl)-5-methyl-2-oxooxazolidin-3-yl)benzo[d]isoxazole-5-carbaldehyde

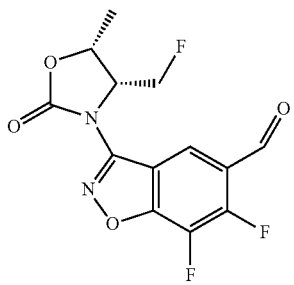 [SMILES: C[C@H]1OC(=O)N(c2noc3c(F)c(F)c(C=O)cc23)[C@H]1CF]

Intermediate 215 was synthesized following the procedure for the preparation of Intermediate 210 using Intermediate 206 (0.07 g, 0.20 mmol). Yield: 0.06 g (85%). MS (ES) MH$^+$: 315.3 for C$_{13}$H$_9$F$_3$N$_2$O$_4$.

Intermediate 216

6-((2R,6R)-2,6-Dimethylmorpholino)-7-fluoro-3-((4R,5R)-4-(fluoromethyl)-5-methyl-2-oxooxazolidin-3-yl)benzo[d]isoxazole-5-carbaldehyde

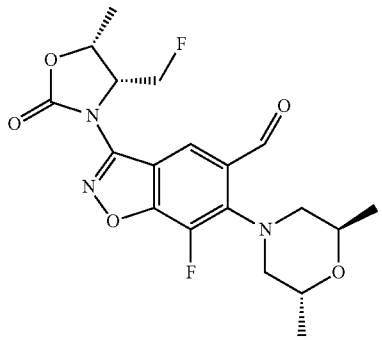 [SMILES: C[C@@H]1CN(c2c(C=O)cc3c(N4C(=O)O[C@H](C)[C@@H]4CF)noc3c2F)C[C@@H](C)O1]

Intermediate 216 was synthesized following the procedure for the preparation of Intermediate 211 using Intermediate 207 (0.06 g, 0.18 mmol). Yield: 0.03 g (33%). $^1$H NMR (300 MHz, DMSO-d$_6$) δ: 1.20 (d, 6H), 1.52 (d, 3H), 2.99-3.03 (m, 2H), 4.10-4.12 (m, 3H), 4.49 (d, 2H), 4.73 (dd, 1H), 4.87-4.94 (m, 1H), 5.05 (d, 1H), 8.55 (s, 1H), 10.30 (s, 1H). 5 $^{19}$F NMR (376.5 MHz, DMSO-d$_6$) δ: −146.81 (s), −236.15 (s).

Intermediate 217

5-(1,3-Dioxolan-2-yl)-2,3,4-trifluoro-N'-hydroxy-N-((2S,3R)-3-hydroxy-1-methoxybutan-2-yl)benzimidamide

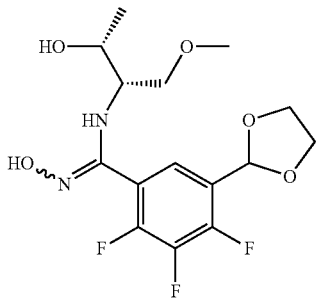

Intermediate 217 was synthesized following the procedure for the preparation of Intermediate 207 using (2R,3S)-3-amino-4-methoxybutan-2-ol (0.73 g, 4.70 mmol), prepared according to the literature procedure; *Tet. Lett.* 1985, 26, 4687. (The amino alcohol was prepared as a mixture of diastereomers in the ratio of 1:3) and Intermediate 16 (1.45 g, 5.15 mmol). The product has been taken to the next step without further purification. Yield: 1.25 g (73%). MS (ES) MH$^+$: 365.4 for $C_{15}H_{19}F_3N_2O_5$.

Intermediate 218

(2R,3S)-3-((5-(1,3-dioxolan-2-yl)-6,7-difluorobenzo[d]isoxazol-3-yl)amino)-4-methoxybutan-2-ol

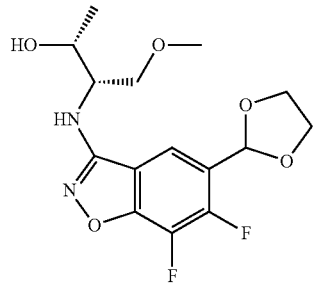 [SMILES: COC[C@H](Nc1noc2c(F)c(F)c(C3OCCO3)cc12)[C@@H](C)O]

Intermediate 218 was synthesized following the procedure described for the preparation of Intermediate 208 using Intermediate 217 (1.25 g, 3.43 mmol). The product was taken to the next step without further purification. Yield: 0.60 g (51%). MS (ES) MH$^+$: 345.4 for $C_{15}H_{18}F_2N_2O_5$.

Intermediate 219

(4S,5R)-3-(5-(1,3-Dioxolan-2-yl)-6,7-difluorobenzo[d]isoxazol-3-yl)-4-(methoxymethyl)-5-methyloxazolidin-2-one

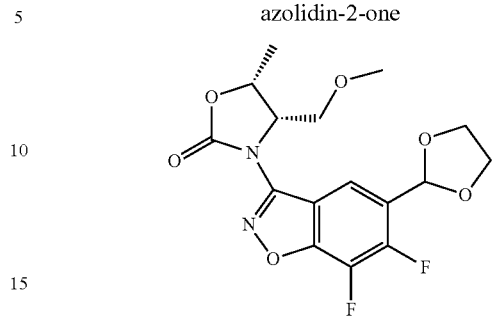

Intermediate 219 was synthesized following the procedure described for the preparation of Intermediate 209 using Intermediate 218 (0.50 g, 1.45 mmol). The product has been taken to the next step without further purification. Yield: 0.33 g (61%). MS (ES) MH$^+$: 371.4 for $C_{16}H_{16}F_2N_2O_6$.

Intermediate 220

6,7-Difluoro-3-((4S,5R)-4-(methoxymethyl)-5-methyl-2-oxooxazolidin-3-yl)benzo[d]isoxazole-5-carbaldehyde

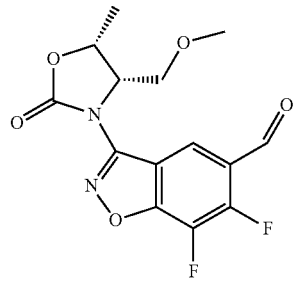 [SMILES: COC[C@H]1[C@@H](C)OC(=O)N1c1noc2c(F)c(F)c(C=O)cc12]

Intermediate 220 was synthesized following the procedure described for the preparation of Intermediate 210 using Intermediate 219 (0.33 g, 0.89 mmol) and the product has been taken to the next step without further purification. Yield: 0.28 g (96%). MS (ES) MH$^+$: 327.4 for $C_{14}H_{12}F_2N_2O_5$.

Intermediate 221

6-((2R,6R)-2,6-Dimethylmorpholino)-7-fluoro-3-((4S,5R)-4-(methoxymethyl)-5-methyl-2-oxooxazolidin-3-yl)benzo[d]isoxazole-5-carbaldehyde

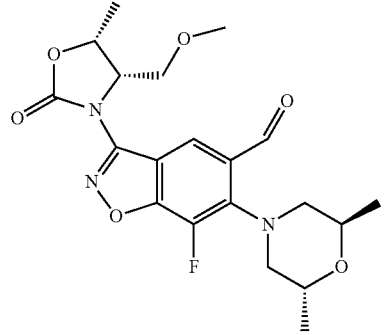 [SMILES: COC[C@H]1[C@@H](C)OC(=O)N1c1noc2c(F)c(N3C[C@@H](C)O[C@H](C)C3)c(C=O)cc12]

Intermediate 221 was synthesized following the procedure described for the preparation of Intermediate 211 using Intermediate 220 (0.38 g, 0.86 mmol). The product has been taken to the next step without further purification. Yield: 0.28 g (77%). MS (ES) MH+: 422.5 for $C_{20}H_{24}FN_3O_6$.

EXAMPLES

Example 1

(2R,4S,4aS)-11-Fluoro-2,4-dimethyl-8-(2-oxo-1,3-oxazolidin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

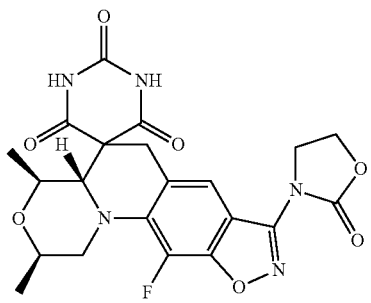 [SMILES: C[C@@H]1CN2c3c(cc4c(N5CCOC5=O)noc4c3F)CC3(C(=O)NC(=O)NC3=O)[C@H]2[C@H](C)O1]

A mixture of Intermediate 17 (0.04 g, 0.1 mmol) and barbituric acid (0.01 g, 0.1 mmol) in acetic acid (3 ml) was heated at 110° C. for 2 hours. The solvents were evaporated and the residue was dissolved in methanol (1 mL). Water (3 mL) was added to precipitate solids that were filtered and purified by reverse phase HPLC (10 mM ammonium acetate in water, —CH₃CN) to afford the title compound as part of a racemic mixture in the form of a solid. Yield: 15 mg (35%). ¹H NMR (400 MHz, DMSO-d₆) δ: 0.9 (d, 3H), 1.1 (d, 3H), 2.9 (d, 1H), 3.1 (t, 1H), 3.7 (t, 2H), 3.8 (m, 1H), 3.9 (d, 1H), 4.1 (m, 3H), 4.6 (t, 2H), 7.75 (s, 1H), 11.5 (s, 1H), 11.8 (s, 1H). MS (ES) MH+: 474.4 for $C_{21}H_{20}FN_5O_7$.

Alternative Synthesis of Example 1

Intermediate 6 (800 mg, 1.95 mmol) and pyrimidine-2,4,6(1H,3H,5H)-trione (250 mg, 1.95 mmol) in a mixture of acetic acid (8 mL) and water (2 mL) was heated at 110° C. for 3.5 hours. The solvent was removed and the reaction mixture was purified using Super Critical Fluid Chromatography (Chiralpak IA column with 40% isopropanol and 60% CO₂ mobile phase) to give the title compound (571 mg, 61.7% yield) as a solid as the first eluting compound. ¹H NMR (300 MHz, DMSO-d₆) δ 0.9 (d, 3H) 1.1 (d, 3H) 2.8-3.2 (m, 2H) 7.7 (s, 1H) 11.4 (s, 1H) 11.8 (s, 1H). MS (ES) MH+: 474 for $C_{21}H_{20}FN_5O_7$.

Also isolated from the synthesis of Alternative Synthesis of Example 1 as the second component eluting from the HPLC purification was (2R,4R,4aR)-11-fluoro-2,4-dimethyl-8-(2-oxo-1,3-oxazolidin-3-yl)-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione (40 mg):

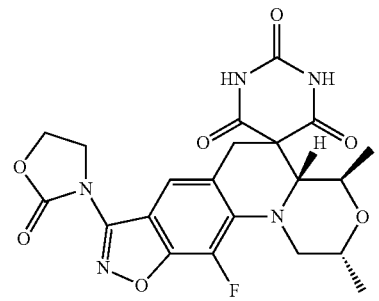 [SMILES: C[C@@H]1CN2c3c(cc4c(N5CCOC5=O)noc4c3F)CC3(C(=O)NC(=O)NC3=O)[C@@H]2[C@@H](C)O1]

¹H NMR (300 MHz, DMSO-d₆) δ 0.95 (d, 3H), 1.3 (d, 3H), 3.1 (d, 1H), 3.45-4.3 (m, 8H), 4.5-4.7 (m, 2H), 7.75 (s, 1H), 11.45 (br. s., 1H), 11.7 (br. s., 1H). MS (ES) MH+: 474 for $C_{21}H_{20}FN_5O_7$.

Example 2

(2R,4S,4aS)-11-Fluoro-2,4-dimethyl-8-[(4R)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

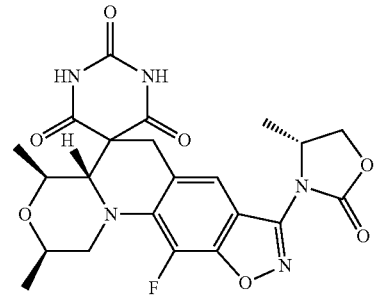 [SMILES: C[C@@H]1CN2c3c(cc4c(N5C(=O)OC[C@H]5C)noc4c3F)CC3(C(=O)NC(=O)NC3=O)[C@H]2[C@H](C)O1]

A stirred mixture of Intermediate 8 (0.15 g, 0.36 mmol) and barbituric acid (0.04 g, 0.3 mmol) in acetic acid (1 ml) was heated at 85° C. for 16 hours. The solvents were evaporated, the residue was dissolved in methanol (2 ml) and water (5 ml) was added. The precipitated solids were filtered and purified by reverse phase HPLC (10 mM ammonium acetate in water, CH₃CN), eluting two components. The second eluting component was isolated as a solid and identified as the title compound. Yield: 35 mg (21%). ¹H NMR (400 MHz, DMSO-d₆) δ: 0.9 (d, 3H), 1.3 (d, 3H), 1.4 (d, 3H), 2.9 (d, 1H), 3.1 (t, 1H), 3.6-3.65 (m, 2H), 3.8 (m, 1H), 3.9 (d, 1H), 4.1 (d, 1H), 4.2 (q, 1H), 4.6-4.7 (m, 2H), 7.6 (s, 1H), 11.5 (s, 1H), 11.8 (s, 1H). MS (ES) MH+: 488.4 for $C_{22}H_{22}FN_5O_7$: $[\alpha]_D^{20}=-239$ (c=1; MeOH).

Also isolated from the synthesis of Example 2 as the first component eluting from the HPLC purification was (2S,4R,4aR)-11-fluoro-2,4-dimethyl-8-[(4R)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

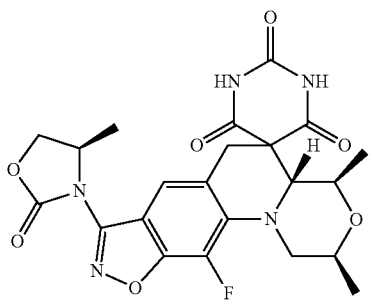 [SMILES: C[C@@H]1COC(=O)N1c1noc2c(F)c3c(cc12)CC1(C(=O)NC(=O)NC1=O)[C@@H]1[C@@H](C)O[C@@H](C)CN31]

Yield: 20 mg (12%). ¹H NMR (400 MHz, DMSO-d₆) δ: 0.9 (d, 3H), 1.3 (d, 3H), 1.4 (d, 3H), 2.9 (d, 1H), 3.1 (t, 1H), 3.6 (m, 2H), 3.75 (m, 1H), 3.9 (d, 1H), 4.1 (d, 1H), 4.2 (q, 1H), 4.6-4.7 (m, 2H), 7.6 (s, 1H), 11.45 (s, 1H), 11.8 (s, 1H). MS (ES) MH⁺: 488.4 for $C_{22}H_{22}FN_5O_7$ $[\alpha]_D^{20}$=+73 (c=1; MeOH).

Examples 3 to 34 were prepared from barbituric acid and the indicated starting material using the method described (with any variation noted) for the synthesis of Example 2, unless otherwise noted.

Example 3

(2R,4S,4aS)-11-Fluoro-2,4-dimethyl-8-[(5S)-5-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

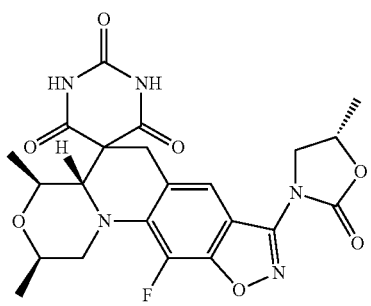 [SMILES: C[C@@H]1CN2c3c(cc4c(N5C[C@H](C)OC5=O)noc4c3F)CC3(C(=O)NC(=O)NC3=O)[C@H]2[C@H](C)O1]

Example 3 was prepared from Intermediate 9. The title compound was obtained as the second eluting component from the HPLC purification. ¹H NMR (400 MHz, DMSO-d₆) δ: 0.9 (d, 3H), 1.1 (d, 3H), 1.45 (d, 3H), 2.9 (d, 1H), 3.1 (t, 1H), 3.65-3.7 (m, 2H), 3.75 (m, 2H), 3.9 (d, 1H), 4.1 (d, 1H), 4.2 (t, 1H), 4.95 (h, 1H), 7.7 (s, 1H), 11.4 (s, 1H), 11.8 (s, 1H). MS (ES) MH⁺: 488.4 for $C_{22}H_{22}FN_5O_7$; $[\alpha]_D$20=−130 (c=1; MeOH).

Also isolated from the synthesis of Example 3 as the first component eluting from the HPLC purification was (2S,4R,4aR)-11-fluoro-2,4-dimethyl-8-[(5S)-5-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

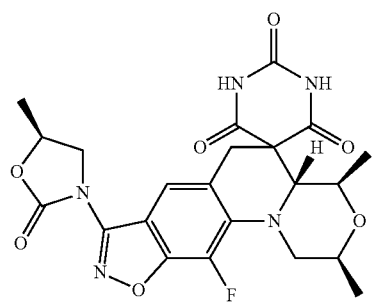 [SMILES: C[C@H]1CN(c2noc3c(F)c4c(cc23)CC2(C(=O)NC(=O)NC2=O)[C@@H]2[C@@H](C)O[C@@H](C)CN42)C(=O)O1]

¹H NMR (400 MHz, DMSO-d₆) δ: 0.9 (d, 3H), 1.1 (d, 3H), 1.45 (d, 3H), 2.9 (d, 1H), 3.10 (t, 1H), 3.65 (m, 2H), 3.7 (m, 2H), 3.9 (d, 1H), 4.1 (d, 1H), 4.2 (t, 1H), 4.95 (h, 1H), 7.75 (s, 1H), 11.4 (s, 1H), 11.8 (s, 1H). MS (ES) MH⁺: 488.4 for $C_{22}H_{22}FN_5O_7$; $[\alpha]_D^{20}$=+101 (c=1; MeOH).

Example 4

(2R,4S,4aS)-11-Fluoro-2,4-dimethyl-8-[(5R)-5-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

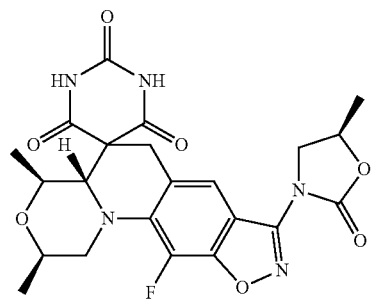 [SMILES: C[C@@H]1CN(c2noc3c(F)c4c(cc23)CC2(C(=O)NC(=O)NC2=O)[C@H]2[C@H](C)O[C@H](C)CN42)C(=O)O1]

Example 4 was prepared from Intermediate 10. The title compound was obtained as the first eluting component from the HPLC purification. ¹H NMR (400 MHz, DMSO-d₆) δ: 0.9 (d, 3H), 1.1 (d, 3H), 1.45 (d, 3H), 2.9 (d, 1H), 3.1 (t, 1H), 3.65 (m, 2H), 3.7-3.8 (m, 2H), 3.9 (d, 1H), 4.1 (d, 1H), 4.2 (t, 1H), 4.95 (h, 1H), 7.75 (s, 1H), 11.45 (s, 1H), 11.8 (s, 1H). MS (ES) MH⁺: 488.4 for $C_{22}H_{22}FN_5O_7$; $[\alpha]_D^{20}$=−188 (c=1; MeOH).

Also isolated from the synthesis of Example 4 as the second component eluting from the HPLC purification was (2S,4R,4aR)-11-fluoro-2,4-dimethyl-8-[(5R)-5-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

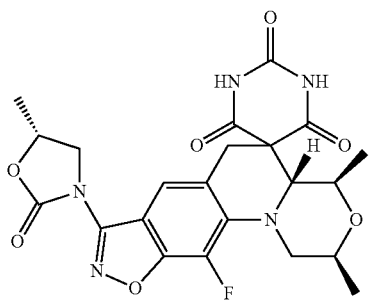 [SMILES: C[C@@H]1CN(c2noc3c(F)c4c(cc23)CC2(C(=O)NC(=O)NC2=O)[C@@H]2[C@@H](C)O[C@@H](C)CN42)C(=O)O1]

¹H NMR (400 MHz, DMSO-d₆) δ: 0.9 (d, 3H), 1.1 (d, 3H), 1.45 (d, 3H), 2.9 (d, 1H), 3.1 (t, 1H), 3.65 (m, 2H), 3.7-3.8 (m, 2H), 3.9 (d, 1H), 4.1 (d, 1H), 4.2 (t, 1H), 4.95 (h, 1H), 7.7 (s, 1H), 11.4 (s, 1H), 11.8 (s, 1H). MS (ES) MH⁺: 488.4 for C₂₂H₂₂FN₅O₇. [α]_D^{20}=+179 (c=1; MeOH).

Alternative Syntheses for Example 4

First Alternative Synthesis

Intermediate 12 (1.67 g, 3.96 mmol) and pyrimidine-2,4,6(1H,3H,5H)-trione (0.508 g, 3.96 mmol) in a mixture of acetic acid (8 mL) and water (2 mL) was heated at 110° C. for 2 hours. The solvent was removed and the reaction mixture was purified by Super Critical Fluid Chromatography (Chiralpak IA column with 30% isopropanol and 70% CO₂ mobile phase) to give the title compound (1.560 g, 81%) as a solid as the first eluting component. ¹H NMR (300 MHz, DMSO-d₆) δ: 0.9 (d, 3H), 1.1 (d, 3H), 1.45 (d, 3H), 2.8-3.2 (m, 2H), 3.6-4.3 (m, 7H), 4.9-5.1 (m, 1H), 7.75 (s, 1H), 11.4 (s, 1H), 11.8 (s, 1H). MS (ES) MH⁺: 488 for C₂₂H₂₂FN₅O₇.

Also isolated from the synthesis of Example 4 (First Alternative Synthesis) as the second component eluting from the HPLC purification was (2R,4R,4aR)-11-fluoro-2,4-dimethyl-8-[(5R)-5-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

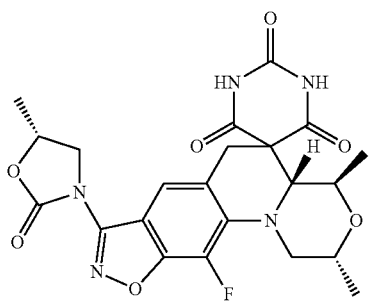 [SMILES: C[C@@H]1CN(c2noc3c(F)c4c(cc23)CC2(C(=O)NC(=O)NC2=O)[C@@H]2[C@@H](C)O[C@H](C)CN42)C(=O)O1]

¹H NMR (300 MHz, DMSO-d₆) δ: 0.95 (d, 3H), 1.3 (d, 3H), 1.5 (d, 3H), 3.1 (d, 1H), 3.5-4.3 (m, 8H), 4.8-5.1 (m, 1H), 7.75 (s, 1H), 11.5 (br. s., 2H). MS (ES) MH⁺: 488 for C₂₂H₂₂FN₅O₇.

Example 4

Second Alternative Synthesis

Intermediate 20 (64 mg, 0.17 mmol) and pyrimidine-2,4,6(1H,3H,5H)-trione (25 mg, 0.20 mmol) in 3 mL of ethanol was heated at 120° C. for 2 hours. Solvent was removed and the reaction mixture was purified by Super Critical Fluid Chromatography (Chiralpak IA column with 30% isopropanol and 70% CO₂ mobile phase) to give the title compound as a solid as the first eluting component. ¹H NMR (300 MHz, DMSO-d₆) δ 0.9 (d, 3H), 1.1 (d, 3H), 1.45 (d, 3H), 2.8-3.2 (m, 2H), 3.6-4.3 (m, 7H), 4.9-5.1 (m, 1H), 7.75 (s, 1H), 11.4 (s, 1H), 11.8 (s, 1H). MS (ES) MH⁺: 488 for C₂₂H₂₂FN₅O₇.

Example 5

(2R,4S,4aS)-11-Fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

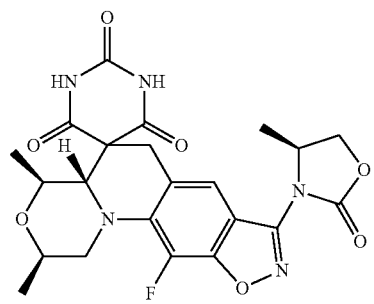 [SMILES: C[C@@H]1CN2c3c(cc4c(N5C(=O)OC[C@@H]5C)noc4c3F)CC3(C(=O)NC(=O)NC3=O)[C@H]2[C@H](C)O1]

Example 5 was prepared from Intermediate 21. The title compound was isolated by reverse phase HPLC (10 mM ammonium acetate in water, CH3CN) as the first eluting of two components. ¹H NMR (400 MHz, DMSO-d₆) δ: 0.9 (d, 3H), 1.15 (d, 3H), 1.4 (d, 3H), 2.9 (d, 1H), 3.1 (t, 1H), 3.5-3.6 (m, 2H), 3.8 (m, 1H), 3.9 (d, 1H), 4.0 (d, 1H), 4.2 (q, 1H), 4.6-4.7 (m, 2H), 7.6 (s, 1H), 11.5 (s, 1H), 11.8 (s, 1H). MS (ES) MH⁺: 488.4 for C₂₂H₂₂FN₅O₇; [α]_D^{20}=−92 (c=1; MeOH).

Also isolated from the synthesis of Example 5 as the second eluting component from HPLC purification was (2S,4R,4aR)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

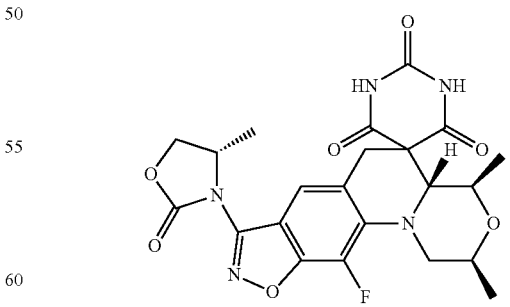

¹H NMR (400 MHz, DMSO-d₆) δ: 0.9 (d, 3H), 1.15 (d, 3H), 1.4 (d, 3H), 2.9 (d, 1H), 3.1 (t, 1H), 3.6-3.7 (m, 2H), 3.8-4.0 (m, 1H), 3.9 (d, 1H), 4.1 (d, 1H), 4.2 (q, 1H), 4.6-4.7 (m, 2H), 7.6 (s, 1H), 11.5 (s, 1H), 11.8 (s, 1H). MS (ES) MH⁺: 488.4 for C₂₂H₂₂FN₅O₇; [α]_D^{20}=+224 (c=1; MeOH).

Alternative Synthesis of Example 5

A solution of Intermediate 22 (1.14 g, 2.71 mmol) and pyrimidine-2,4,6(1H,3H,5H)-trione (0.346 g, 2.71 mmol) in acetic acid (8 mL) and of water (2 mL) was heated at 110° C. for 2 hours. The solvent was removed and the reaction mixture was purified using Super Critical Fluid Chromatography (Chiralpak IC column with 30% methanol and 70% $CO_2$ mobile phase). The first eluting compound was further purified by dissolving in acetonitrile (30 mL) and diluting with water (60 mL) to give the title compound as a solid. (0.910 g, 69.0% yield). $^1$H NMR (300 MHz, DMSO-$d_6$) δ: 60.9 (d, 3H), 1.15 (d, 3H), 1.4 (d, 3H), 2.9 (d, 1H), 3.1 (t, 1H), 3.6-3.7 (m, 2H), 3.8 (m, 1H), 3.9 (d, 1H), 4.1 (d, 1H), 4.2 (q, 1H), 4.6-4.75 (m, 2H), 7.6 (s, 1H), 11.4 (s, 1H), 11.8 (s, 1H). MS (ES) MH$^+$: 488 for $C_{22}H_{22}FN_5O_7$.

Also isolated from the synthesis of Alternative Synthesis of Example 5 as the second component eluting from the HPLC purification was (2R,4R,4aR)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

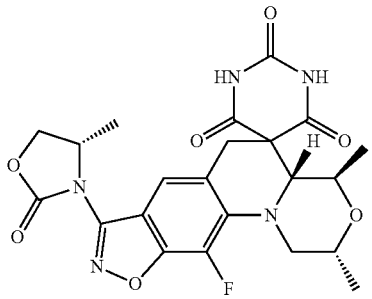 [SMILES: C[C@@H]1CN2c3c(cc4c(N5C(=O)OC[C@@H]5C)noc4c3F)CC3(C(=O)NC(=O)NC3=O)[C@@H]2[C@@H](C)O1]

$^1$H NMR (300 MHz, DMSO-$d_6$) δ: 1.0 (d, 3H), 1.3 (d, 3H), 1.4 (d, 3H), 3.1 (d, 1H), 3.5-4.3 (m, 7H), 4.5-4.8 (m, 2H), 7.6 (s, 1H), 11.5 (br. s., 1H), 11.7 (br. s., 1H). MS (ES) MH$^+$: 488 for $C_{22}H_{22}FN_5O_7$.

Example 6

(2R,4S,4aS)-8-[(4S)-4-Ethyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

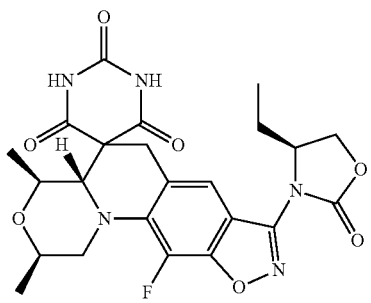 [SMILES: CC[C@H]1COC(=O)N1c1noc2c(F)c3c(cc12)CC1(C(=O)NC(=O)NC1=O)[C@H]1[C@H](C)O[C@H](C)CN31]

Example 6 was prepared from Intermediate 23. The title compound was obtained as the first eluting component from the HPLC purification. $^1$H NMR (400 MHz, DMSO-$d_6$) δ: 0.8 (t, 3H), 0.9 (d, 3H), 1.1 (d, 3H), 1.75-1.9 (m, 2H), 2.90 (d, 1H), 1.8 (t, 1H), 3.5 (m, 1H), 3.65-3.7 (m, 1H), 3.8-4.0 (m, 1H), 3.9 (d, 1H), 419 (d, 1H), 4.3-4.3 (m, 1H), 4.55 (m, 1H), 4.6-4.7 (m, 1H), 7.6 (s, 1H). MS (ES) MH$^+$: 502.4 for $C_{23}H_{24}FN_5O_7$; $[\alpha]_D^{20}$=−24 (c=1; MeOH).

Also isolated from the synthesis of Example 6 as the second component eluting from the HPLC purification was (2S,4R,4aR)-8-[(4S)-4-ethyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

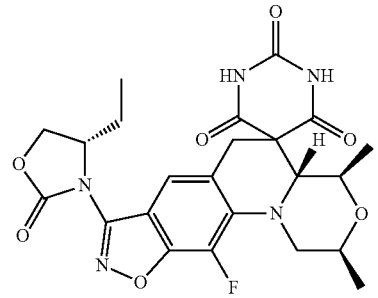 [SMILES: CC[C@H]1COC(=O)N1c1noc2c(F)c3c(cc12)CC1(C(=O)NC(=O)NC1=O)[C@@H]1[C@@H](C)O[C@@H](C)CN31]

$^1$H NMR (400 MHz, DMSO-$d_6$) δ: 0.8 (t, 3H), 0.9 (d, 3H), 1.1 (d, 3H), 1.8 (m, 2H), 2.9 (d, 1H), 3.1 (t, 1H), 3.5-3.6 (m, 1H), 3.6-3.7 (m, 1H), 3.7 (m, 1H), 3.8 (m, 1H), 3.9 (d, 1H), 4.1 (d, 1H), 4.3-4.35 (m, 1H), 4.5-4.6 (m, 1H), 7.6 (s, 1H). MS (ES) MH$^+$: 502.4 for $C_{23}H_{24}FN_5O_7$; $[\alpha]_D^{20}$=+101 (c=1; MeOH).

Example 7

(2R,4S,4aS)-8-[(4R)-4-Ethyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione)

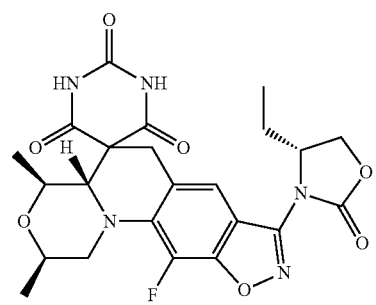 [SMILES: CC[C@@H]1COC(=O)N1c1noc2c(F)c3c(cc12)CC1(C(=O)NC(=O)NC1=O)[C@H]1[C@H](C)O[C@H](C)CN31]

Example 7 was prepared from Intermediate 24. The title compound was obtained as the second eluting component from the HPLC purification. $^1$H NMR (400 MHz, DMSO-$d_6$) δ: 0.8 (t, 3H), 0.9 (d, 3H), 1.15 (d, 3H), 1.8-1.85 (m, 2H), 2.9 (d, 1H), 3.1 (t, 1H), 3.65 (m, 2H), 3.8 (m, 1H), 3.9 (d, 1H), 4.1 (d, 1H), 4.3-4.4 (m, 1H), 4.5-4.6 (m, 1H), 4.6-4.7

(m, 1H), 7.6 (s, 1H), 11.5 (s, 1H), 11.8 (s, 1H). MS (ES) MH⁺: 502.4 for $C_{23}H_{24}FN_5O_7$; $[\alpha]_D^{20}$=+101 (c=1; MeOH).

Also isolated from the synthesis of Example 7 as the first component eluting from the HPLC purification was (2S,4R,4aR)-8-[(4R)-4-ethyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

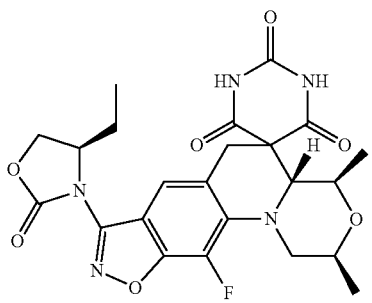 [SMILES: CC[C@@H]1COC(=O)N1c1noc2c(F)c3c(cc12)CC1(C(=O)NC(=O)NC1=O)[C@@H]1[C@@H](C)O[C@@H](C)CN31]

$^1$H NMR (400 MHz, DMSO-d₆) δ: 0.8 (t, 3H), 0.9 (d, 3H), 1.15 (d, 3H), 1.8-1.9 (m, 2H), 2.9 (d, 1H), 3.1 (t, 1H), 3.6-3.7 (m, 2H), 3.8 (m, 1H), 3.9 (d, 1H), 4.1 (d, 1H), 4.3-4.35 (m, 1H), 4.6 (m, 1H), 4.65-4.7 (m, 1H), 7.6 (s, 1H), 11.5 (s, 1H), 11.8 (s, 1H). MS (ES) MH⁺: 502.4 for $C_{23}H_{24}FN_5O_7$; $[\alpha]_D^{20}$=+59 (c=1; MeOH).

Example 8

(2R,4S,4aS)-11-Fluoro-2,4-dimethyl-8-[(4R)-2-oxo-4-phenyl-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

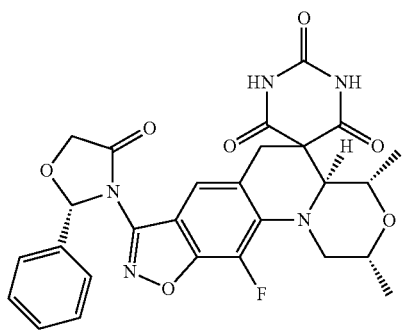 [SMILES: C[C@@H]1CN2c3c(cc4c(N5C(=O)CO[C@H]5c5ccccc5)noc4c3F)CC3(C(=O)NC(=O)NC3=O)[C@H]2[C@H](C)O1]

Example 8 was prepared from Intermediate 25. The title compound was obtained as the second eluting component from the HPLC purification. $^1$H NMR (400 MHz, DMSO-d₆) δ: 0.9 (d, 3H), 1.1 (d, 3H), 2.9 (d, 1H), 3.1 (t, 1H), 3.6-3.7 (m, 2H), 3.8 (m, 1H), 3.9 (d, 1H), 4.1 (d, 1H), 4.3 (q, 1H), 5.0 (t, 1H), 5.7 (q, 1H), 7.2-7.4 (m, 5H), 7.65 (s, 1H), 11.6 (br s, 2H). MS (ES) MH⁺: 550.5 for $C_{27}H_{24}FN_5O_7$; $[\alpha]_D^{20}$=−125 (c=0.1; MeOH).

Also isolated from the synthesis of Example 8 as the first component eluting from the HPLC purification was (2S,4R,4aR)-11-fluoro-2,4-dimethyl-8-[(4R)-2-oxo-4-phenyl-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

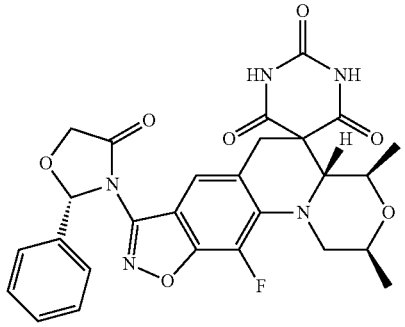 [SMILES: C[C@H]1CN2c3c(cc4c(N5C(=O)CO[C@H]5c5ccccc5)noc4c3F)CC3(C(=O)NC(=O)NC3=O)[C@@H]2[C@@H](C)O1]

$^1$H NMR (400 MHz, DMSO-d₆) δ: 0.9 (d, 3H), 1.1 (d, 3H), 2.9 (d, 1H), 3.1 (t, 1H), 3.6-3.7 (m, 2H), 3.7-3.8 (m, 1H), 3.9 (d, 1H), 4.1 (d, 1H), 4.3 (q, 1H), 5.0 (t, 1H), 5.7 (q, 1H), 7.3-7.4 (m, 5H), 7.65 (s, 1H), 11.5 (br s, 1H), 11.9 (br s, 1H). MS (ES) MH⁺: 550.5 for $C_{27}H_{24}FN_5O_7$; $[\alpha]_D^{20}$=+249 (c=0.1; MeOH).

Example 9

(2R,4S,4aS)-11-Fluoro-2,4-dimethyl-8-[(4S)-2-oxo-4-phenyl-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

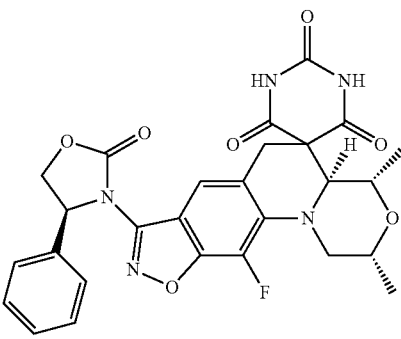 [SMILES: C[C@@H]1CN2c3c(cc4c(N5C(=O)OC[C@@H]5c5ccccc5)noc4c3F)CC3(C(=O)NC(=O)NC3=O)[C@H]2[C@H](C)O1]

Example 9 was prepared from Intermediate 26. The title compound was obtained as the first eluting component from the HPLC purification. $^1$H NMR (400 MHz, DMSO-d₆) δ: 0.9 (d, 3H), 1.1 (d, 3H), 2.95 (d, 1H), 3.1 (t, 1H), 3.6 (m, 2H), 3.65-3.7 (m, 1H), 3.9 (d, 1H), 4.1 (d, 1H), 4.35 (q, 1H), 5.0 (t, 1H), 5.7 (q, 1H), 7.3-7.65 (m, 5H), 7.65 (s, 1H), 11.5 (s, 1H), 11.8 (s, 1H). MS (ES) MH⁺: 550.5 for $C_{27}H_{24}FN_5O_7$; $[\alpha]_D^{20}$=−228 (c=1; MeOH).

Also isolated from the synthesis of Example 9 as the second component eluting from the HPLC purification was (2S,4R,4aR)-11-fluoro-2,4-dimethyl-8-[(4S)-2-oxo-4-phenyl-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

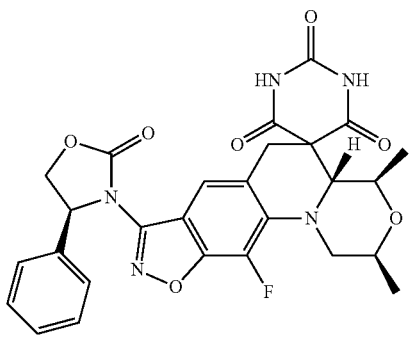 [SMILES: C[C@H]1CN2c3c(cc4c(N5C(=O)OC[C@@H]5c5ccccc5)noc4c3F)CC3(C(=O)NC(=O)NC3=O)[C@@H]2[C@@H](C)O1]

¹H NMR (400 MHz, DMSO-d₆) δ: 0.9 (d, 3H), 1.1 (d, 3H), 2.9 (d, 1H), 3.1 (t, 1H), 3.6-3.7 (m, 2H), 3.75 (m, 1H), 3.9 (d, 1H), 4.05 (d, 1H), 4.3 (q, 1H), 5.0 (t, 1H), 5.7 (q, 1H), 7.3-7.4 (m, 5H), 7.7 (s, 1H), 11.5 (s, 1H), 11.8 (s, 1H). MS (ES) MH⁺: 550.5 for $C_{27}H_{24}FN_5O_7$; $[\alpha]_D^{20}$=+151 (c=1; MeOH).

Example 10

(2R,4S,4aS)-8-[(4R)-4-Benzyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

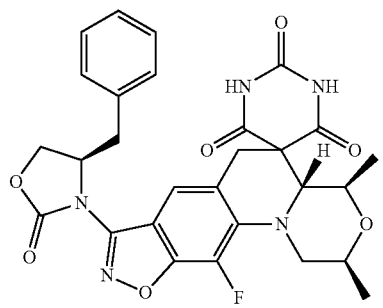

¹H NMR (400 MHz, DMSO-d₆) δ: 0.9 (d, 3H), 1.1 (d, 3H), 2.9 (d, 1H), 3.05-3.1 (m, 2H), 3.1-3.2 (m, 1H), 3.6-3.7 (m, 2H), 3.8 (m, 1H), 3.95 (d, 1H), 4.1 (d, 1H), 4.4 (dd, 1H), 4.5 (t, 1H), 4.8 (m, 1H), 7.2 (m, 2H), 7.2-7.3 (m, 3H), 7.6 (s, 1H), 11.7 (br s, 2H). MS (ES) MH⁻: 562.4 for $C_{28}H_{26}FN_5O_7$; $[\alpha]_D^{20}$=+224 (c=0.1; MeOH).

Example 11

(2R,4S,4aS)-8-[(4S)-4-Benzyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

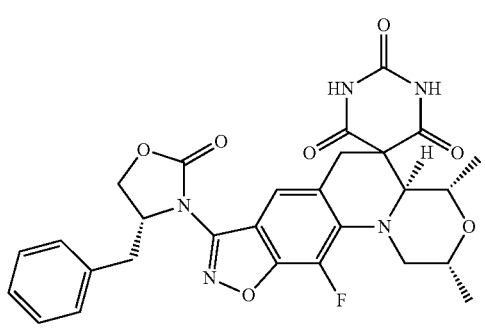 [SMILES: C[C@@H]1CN2c3c(cc4c(N5C(=O)OC[C@H]5Cc5ccccc5)noc4c3F)CC3(C(=O)NC(=O)NC3=O)[C@H]2[C@H](C)O1]

Example 10 was prepared from Intermediate 27. The title compound was obtained as the second eluting component from the HPLC purification. ¹H NMR (400 MHz, DMSO-d₆) δ: 0.9 (d, 3H), 1.1 (d, 3H), 2.9 (d, 1H), 3.1-3.2 (m, 3H), 3.6-3.7 (m, 2H), 3.8 (m, 1H), 3.9 (d, 1H), 4.1 (d, 1H), 4.3-4.4 (m, 1H), 4.5 (t, 1H), 4.8 (m, 1H), 7.2 (m, 2H), 7.2-7.3 (m, 3H), 7.6 (s, 1H), 11.65 (br s, 2H). MS (ES) MH⁺: 564.5 for $C_{28}H_{26}FN_5O_7$; $[\alpha]_D^{20}$=−274 (c=0.1; MeOH).

Also isolated from the synthesis of Example 10 as the first component eluting from the HPLC purification was (2S,4R,4aR)-8-[(4R)-4-benzyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

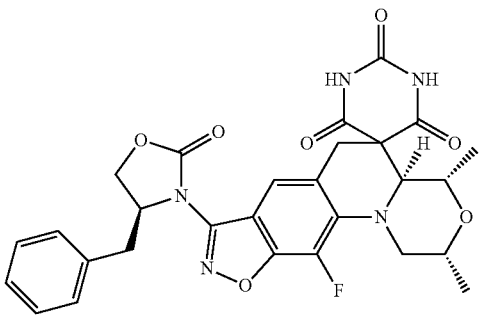 [SMILES: C[C@@H]1CN2c3c(cc4c(N5C(=O)OC[C@@H]5Cc5ccccc5)noc4c3F)CC3(C(=O)NC(=O)NC3=O)[C@H]2[C@H](C)O1]

Example 11 was prepared from Intermediate 28. The title compound was obtained as the first eluting component from the HPLC purification. ¹H NMR (400 MHz, DMSO-d₆) δ: 0.9 (d, 3H), 1.1 (d, 3H), 2.9 (d, 1H), 3.1-3.15 (m, 2H), 3.2 (m, 1H), 3.6-3.7 (m, 2H), 3.8 (m, 1H), 3.9 (d, 1H), 4.1 (d, 1H), 4.4 (dd, 1H), 4.5 (t, 1H), 4.8 (m, 1H), 7.2 (m, 2H), 7.2-7.3 (m, 3H), 7.6 (s, 1H), 11.45 (br s, 1H), 11.85 (br s, 1H). MS (ES) MH⁺: 564.5 for $C_{28}H_{26}FN_5O_7$; $[\alpha]_D^{20}$=−115 (c=0.1; MeOH).

Also isolated from the synthesis of Example 11 as the second component eluting from the HPLC purification was (2S,4R,4aR)-8-[(4S)-4-benzyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

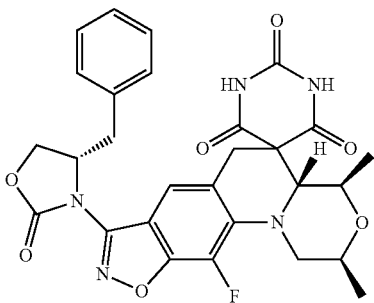 [SMILES: C[C@H]1CN2c3c(cc4c(N5C(=O)OC[C@@H]5Cc5ccccc5)noc4c3F)CC3(C(=O)NC(=O)NC3=O)[C@@H]2[C@@H](C)O1]

¹H NMR (400 MHz, DMSO-d₆) δ: 0.9 (d, 3H), 1.1 (d, 3H), 2.9 (d, 1H), 3.1-3.2 (m, 3H), 3.6-3.7 (m, 2H), 3.8 (m, 1H), 3.9 (d, 1H), 4.1 (d, 1H), 4.4 (dd, 1H), 4.55 (t, 1H), 4.8 (m, 1H), 7.2-7.3 (m, 5H), 7.6 (s, 1H), 11.6 (br s, 2H). MS (ES) MH⁺: 564.5 for $C_{28}H_{26}FN_5O_7$; $[α]_D^{20}$=+163 (c=0.1; MeOH).

Example 12

(2R,4S,4aS)-8-(5,5-Dimethyl-2-oxo-1,3-oxazolidin-3-yl)-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

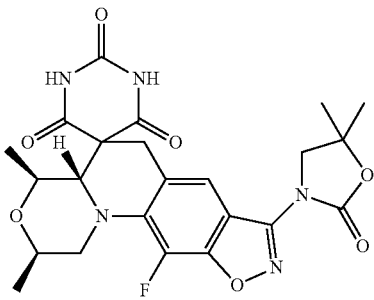 [SMILES: C[C@@H]1CN2c3c(cc4c(N5CC(C)(C)OC5=O)noc4c3F)CC3(C(=O)NC(=O)NC3=O)[C@H]2[C@H](C)O1]

Example 12 was prepared from Intermediate 29. The title compound was obtained as part of a racemic mixture. ¹H NMR (400 MHz, DMSO-d₆) δ: 0.9 (d, 3H), 1.1 (d, 3H), 1.5 (s, 6H), 2.9 (d, 1H), 3.1 (t, 1H), 3.65-3.7 (m, 2H), 3.8 (m, 1H), 3.9-3.95 (m, 3H), 4.1 (d, 1H), 7.8 (s, 1H), 11.5 (s, 1H), 11.8 (s, 1H). MS (ES) MH⁺: 502.4 for $C_{23}H_{24}FN_6O_7$.

Example 13

(2R,4S,4aS)-8-[(5S)-5-Ethyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

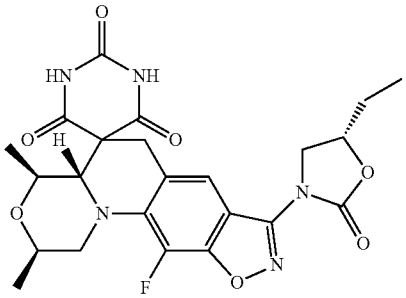 [SMILES: CC[C@H]1CN(c2noc3c(F)c4c(cc23)CC2(C(=O)NC(=O)NC2=O)[C@H]2[C@H](C)O[C@H](C)CN42)C(=O)O1]

Example 13 was prepared from Intermediate 31. For the reaction, 100% acetic acid was used with heating for 3 hours at 90° C. ¹H NMR (400 MHz, DMSO-d₆) δ: 0.9 (d, 3H), 1.0 (t, 3H), 1.1 (d, 3H), 1.8 (q, 2H), 2.9 (d, 1H), 3.1 (t, 1H), 3.6-3.7 (m, 2H), 3.7-3.8 (m, 2H), 3.9 (d, 1H), 4.1 (d, 1H), 4.2 (t, 1H), 4.8 (q, 1H), 7.8 (s, H), 11.5 (s, H), 11.8 (s, H).

Example 14

(2R,4S,4aS)-8-[(5R)-5-Ethyl-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

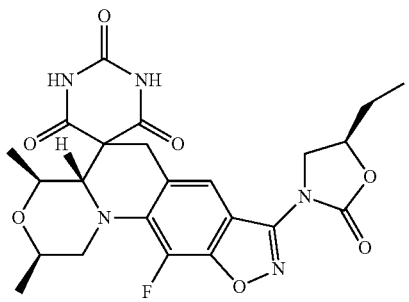 [SMILES: CC[C@@H]1CN(c2noc3c(F)c4c(cc23)CC2(C(=O)NC(=O)NC2=O)[C@H]2[C@H](C)O[C@H](C)CN42)C(=O)O1]

Example 14 was prepared from Intermediate 30. ¹H NMR (400 MHz, DMSO-d₆) δ: 0.9 (d, 3H), 1.0 (t, 3H), 1.1 (d, 3H), 1.8 (q, 2H), 2.9 (d, 1H), 3.1 (t, 1H), 3.6-3.7 (m, 2H), 3.8 (m, 2H), 3.9 (d, 1H), 4.1 (d, 1H), 4.2 (t, 1H), 4.8 (q, 1H), 7.7 (s, 1H), 11.45 (s, 1H), 11.8 (s, 1H). MS (ES) MH⁺: 502.4 for $C_{23}H_{24}FN_6O_7$; $[α]_D^{20}$=−177 (c=1; MeOH).

Example 15

(2R,4S,4aS)-11-Fluoro-8-[(4R)-4-(fluoromethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

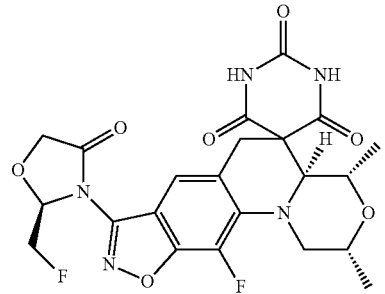 [SMILES: C[C@@H]1CN2c3c(cc4c(N5C(=O)CO[C@@H]5CF)noc4c3F)CC3(C(=O)NC(=O)NC3=O)[C@H]2[C@H](C)O1]

Example 15 was prepared from Intermediate 35. The title compound was obtained as the first eluting component from the HPLC purification. ¹H NMR (400 MHz, DMSO-d₆) δ: 0.9 (d, 3H), 1.1 (d, 3H), 2.9 (d, 1H), 3.1 (t, 1H), 3.9 (d, 1H), 3.65-3.7 (m, 1H), 3.75-3.8 (m, 1H), 3.9 (d, 1H), 4.1 (d, 1H), 4.5 (dd, 1H), 4.6 (d, 1H), 4.7 (d, 1H), 4.9 (m, 2H), 7.6 (s, 1H), 11.0 (br s, 2H). MS (ES) MH⁺: 506.5 for $C_{22}H_{21}F_2N_5O_7$, $[α]_D^{20}$=−74.4 (c=1.12; MeOH), $R_T$=14.08 min.

Also isolated from the synthesis of Example 15 as the second component eluting from the HPLC purification was (2S,4R,4aR)-11-fluoro-8-[(4R)-4-(fluoromethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

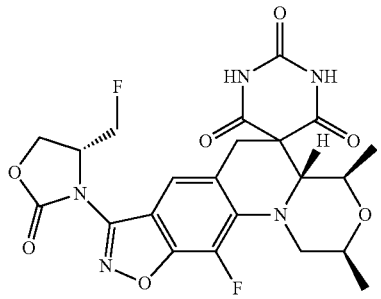 [SMILES: C[C@H]1CN2c3c(cc4c(N5C(=O)OC[C@@H]5CF)noc4c3F)CC3(C(=O)NC(=O)NC3=O)[C@@H]2[C@@H](C)O1]

$^1$H NMR (400 MHz, DMSO-$d_6$) δ: 0.9 (d, 3H), 1.1 (d, 3H), 2.9 (d, 1H), 3.1 (t, 1H), 3.6 (d, 1H), 3.65-3.7 m, 1H), 3.75-3.8 (m, 1H), 3.9 (d, 1H), 4.1 (d, 1H), 4.5 (dd, 1H), 4.59 (d, 1H), 4.70 (m, 1H), 4.9 (m, 2H), 7.6 (s, 1H), 11.0 (br s, 2H). MS (ES) MH$^+$: 506.5 for $C_{22}H_{21}F_2N_5O_7$; $[\alpha]_D^{20}$=+210 (c=1.08; MeOH); $R_T$=14.78 min.

Example 16

(2R,4S,4aS)-11-Fluoro-8-[(4S)-4-(fluoromethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

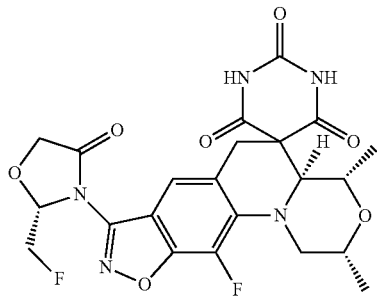 [SMILES: C[C@@H]1CN2c3c(cc4c(N5C(=O)CO[C@H]5CF)noc4c3F)CC3(C(=O)NC(=O)NC3=O)[C@H]2[C@H](C)O1]

Example 16 was prepared from Intermediate 36. The title compound was obtained as the second eluting component from the HPLC purification. $^1$H NMR (400 MHz, DMSO-$d_6$) δ: 0.9 (d, 3H), 1.1 (d, 3H), 2.9 (d, 1H), 3.1 (t, 1H), 3.6 (d, 1H), 3.65-3.7 (m, 1H), 3.75-3.8 (m, 1H), 3.9 (d, 1H), 4.1 (d, 1H), 4.5 (dd, 1H), 4.6 (d, 1H), 4.70 (m, 1H), 4.9 (m, 2H), 7.6 (s, 1H), 11.5 (s, 1H), 11.8 (s, 1H). MS (ES) MH$^+$: 506.5 for $C_{22}H_{21}F_2N_5O_7$; $[\alpha]_D^{20}$=−38.6 (c=1.08; MeOH), $R_T$=21.50 min.

Also isolated from the synthesis of Example 16 as the first component eluting from the HPLC purification was (2S,4R,4aR)-11-fluoro-8-[(4S)-4-(fluoromethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

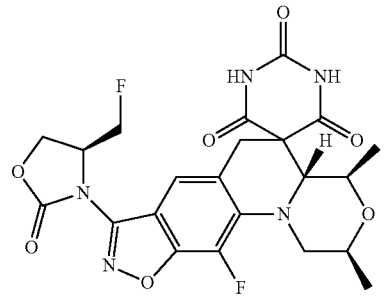 [SMILES: C[C@H]1CN2c3c(cc4c(N5C(=O)OC[C@H]5CF)noc4c3F)CC3(C(=O)NC(=O)NC3=O)[C@@H]2[C@@H](C)O1]

$^1$H NMR (400 MHz, DMSO-$d_6$) δ: 0.9 (d, 3H), 1.1 (d, 3H), 2.9 (d, 1H), 3.1 (t, 1H), 3.6 (d, 1H), 3.65-3.7 (m, 1H), 3.75-38 (m, 1H), 3.9 (d, 1H), 4.1 (d, 1H), 4.5 (dd, 1H), 4.6 (d, 1H), 4.70 (m, 1H), 4.9 (m, 2H), 7.6 (s, 1H), 11.5 (s, 1H), 11.8 (s, 1H). MS (ES) MH$^+$: 506.5 for $C_{22}H_{21}F_2N_5O_7$, $[\alpha]_D^{20}$=+64.9 (c=1.07; MeOH): $R_T$=17.62 min.

Examples 17 and 18

(2R,4S,4aS)-11-Fluoro-8-[(4S)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione and (2R,4S,4aS)-11-fluoro-8-[(4R)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

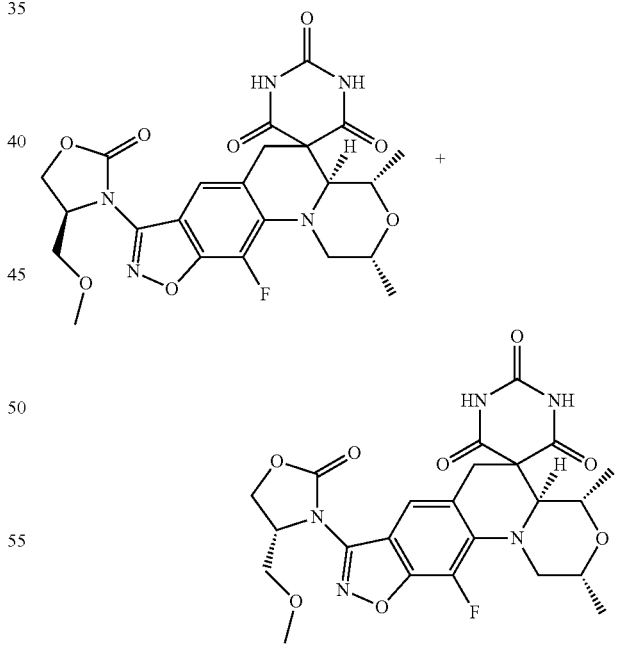

The starting material was a mixture of Intermediate 37 and Intermediate 38. The reaction of the starting material according to the indicated procedure produced the two diastereomers depicted above, along with each diastereomer's corresponding enantiomer. The two diastereomers were separated via HPLC. Each diastereomer was obtained along with its corresponding enantiomer. $^1$H NMR (400

MHz, DMSO-d$_6$) δ: 0.9 (d, 3H), 1.15 (d, 3H), 2.9 (d, 1H), 3.1 (t, 1H), 3.2 (s, 3H), 3.5-3.55 (m, 1H), 3.65-3.7 (m, 2H), 3.8-3.9 (m, 2H), 3.9 (d, 1H), 4.1 (d, 1H), 4.45-4.5 (m, 1H), 4.6-4.65 (m, 2H), 7.7 (s, 1H), 11.5 (br s, 1H), 11.8 (br s, 1H). MS (ES) MH$^+$: 518.4 for C$_{23}$H$_{24}$FN$_6$O$_8$.

The diastereomers from the mixture of Examples 17 and 18 were separated using Super Critical Fluid Chromatography (Chiralpak IA column with 20% methanol and 80% CO$_2$ mobile phase). Four components were separated.

Example 17

(2R,4S,4aS)-11-Fluoro-8-[(4S)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

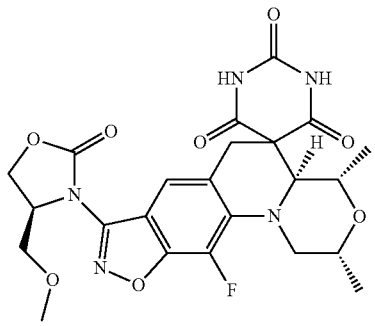

The title compound was obtained as the first eluting component from the HPLC purification. $^1$HNMR (300 MHz, DMSO-d$^6$) δ: 0.9 (s, 3H), 1.1 (s, 3H), 2.9 (d, 1H), 3.1 (t, 1H), 3.25 (s, 3H), 3.5 (d, 1H), 3.6-3.7 (m, 2H), 3.7-3.9 (m, 2H), 3.9 (d, 1H), 4.1 (d, 1H), 4.4 (m, 1H), 4.6-4.7 (m, 2H), 7.65 (s, 1H), 11.5 (br s, 2H). Optical Rotation: [α]$_D^{20}$=−128; MS (ES) MH$^+$: 518 for C$_{23}$H$_{24}$FN$_5$O$_8$.

Example 18

(2R,4S,4aS)-11-Fluoro-8-[(4R)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

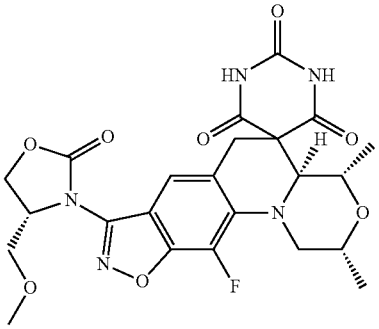 [SMILES: COC[C@@H]1COC(=O)N1c1noc2c(F)c3c(cc12)CC1(C(=O)NC(=O)NC1=O)[C@H]1[C@H](C)O[C@H](C)CN31]

The title compound was obtained as the fourth eluting component from the HPLC purification. $^1$H NMR (300 MHz, DMSO-d$^6$) δ: 0.9 (s, 3H), 1.1 (s, 3H), 2.9 (d, 1H), 3.1 (t, 1H), 3.2 (s, 3H), 3.5-3.7 (m, 3H), 3.7-3.9 (m, 2H), 3.9 (d, 1H), 4.1 (d, 1H), 4.4 (m, 1H), 4.6-4.7 (m, 2H), 7.1 (s, 1H), 11.5 (br s, 2H). Optical Rotation: [α]$_D^{20}$=−189; MS (ES) MH$^+$: 518 for C$_{23}$H$_{24}$FN$_5$O$_8$.

Also isolated from the synthesis of Examples 17 and 18 as the second component eluting from the HPLC purification was (2S,4R,4aR)-11-fluoro-8-[(4R)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

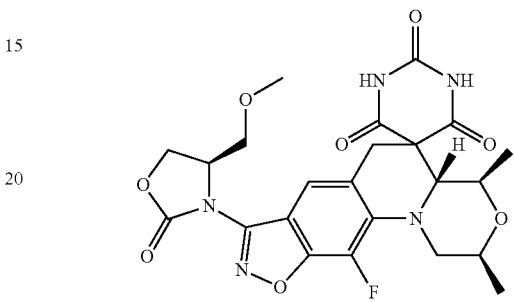

$^1$HNMR (300 MHz, DMSO-d$^6$) δ: 0.88 (s, 3H), 1.1 (s, 3H), 2.9 (d, 1H), 3.1 (t, 1H), 3.25 (s, 3H), 3.5-3.7 (m, 3H), 3.7-3.9 (m, 2H), 3.9 (d, 1H), 4.1 (d, 1H), 4.4 (m, 1H), 4.6-4.7 (m, 2H), 7.6 (s, 1H), 11.55 (br s, 2H). Optical Rotation: [α]$_D^{20}$=+135; MS (ES) MH$^+$: 518 for C$_{23}$H$_{24}$FN$_5$O$_8$.

Also isolated from the synthesis of Examples 17 and 18 as the third component eluting from the HPLC purification was (2S,4R,4aR)-11-fluoro-8-[(4S)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

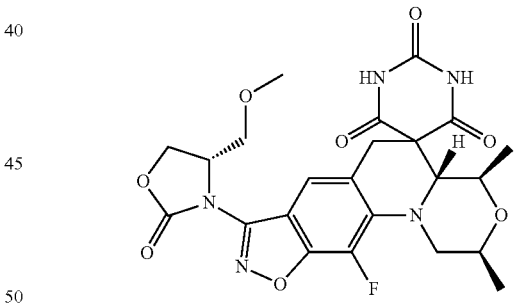

$^1$HNMR (300 MHz, DMSO-d$^6$) δ: 0.9 (s, 3H), 1.1 (s, 3H), 2.1 (d, 1H), 3.1 (t, 1H), 3.2 (s, 3H), 3.5-3.7 (m, 3H), 3.7-3.9 (m, 2H), 3.9 (d, 1H), 4.1 (d, 1H), 4.4 (m, 1H), 4.6-4.7 (m, 2H), 7.1 (s, 1H), 11.6 (br s, 2H). Optical Rotation: [α]$_D^{20}$=+208; MS (ES) MH$^+$: 518 for C$_{23}$H$_{24}$FN$_5$O$_8$.

Alternative Synthesis of Example 17

A stirred solution of Intermediate 40 (0.67 g, 1.5 mmol) and barbituric acid (0.21 g, 1.6 mmol) in acetic acid (10 mL) was heated to 95° C. for 4 hours. The solvents were evaporated and the residue was dissolved in methanol (2 mL). Water (5 mL) was added to precipitate solids that were collected and chromatographed by chiral HPLC [Chiralpak IC (250×4.6) mm; hexane:ethanol (80:20); 1.0 ml/min] to separate the title compound as the second eluting component. ¹H NMR (400 MHz, DMSO-d₆) δ: 0.9 (d, 3H), 1.1 (d, 3H), 2.9 (d, 1H), 3.1 (t, 1H), 3.25 (s, 3H), 3.5 (d, 1H), 3.6-3.7 (m, 2H), 3.85 (m, 1H), 3.85-3.9 (d, 1H), 3.9 (d, 1H), 4.1 (d, 1H), 4.45-4.5 (m, 1H), 4.6-4.7 (m, 2H), 7.65 (s, 1H), 11.5 (s, 1H), 11.8 (s, 1H). MS (ES) MH⁺: 518.4 for $C_{23}H_{24}FN_5O_8$; $[\alpha]_D^{20}$=−93.8 (c=1.14; MeOH), $R_T$=20.7 min.

Also isolated from the synthesis of Example 17 (Alternative Synthesis) as the first component eluting from the HPLC purification was (2S,4R,4aR)-11-fluoro-8-[(4S)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione:

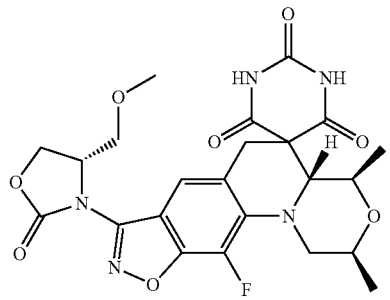 [SMILES: COC[C@H]1COC(=O)N1c1noc2c(F)c3c(cc12)CC1(C(=O)NC(=O)NC1=O)[C@@H]1[C@@H](C)O[C@@H](C)CN31]

¹H NMR (400 MHz, DMSO-d₆) δ: 0.9 (d, 3H), 1.1 (d, 3H), 2.9 (d, 1H), 3.1 (t, 1H), 3.2 (s, 3H), 3.5 (d, 1H), 3.6-3.7 (m, 2H), 3.85 (m, 1H), 3.85-3.9 (d, 1H), 3.9 (d, 1H), 4.1 (d, 1H), 4.45-4.5 (m, 1H), 4.6-4.65 (m, 2H), 7.7 (s, 1H), 11.5 (s, 1H), 11.8 (s, 1H). MS (ES) MH⁺: 518.4 for $C_{23}H_{24}FN_5O_8$; $[\alpha]_D^{20}$=+159.4 (c=1.04; MeOH), $R_T$=17.8 min.

Example 19

(2R,4S,4aS)-11-Fluoro-8-((S)-5-(fluoromethyl)-2-oxooxazolidin-3-yl)-2,4-dimethyl-2,4,4a,6-tetrahydro-1H,1'H-spiro[isoxazolo[4,5-g][1,4]oxazino[4,3-g]quinoline-5,5'-pyrimidine]-2',4',6'(3'H)-trione

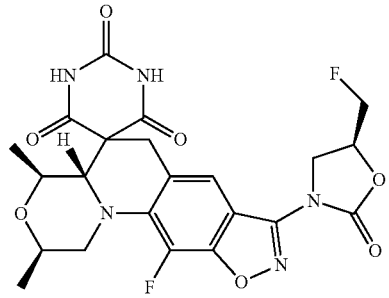 [SMILES: C[C@@H]1CN2c3c(cc4c(N5C[C@@H](CF)OC5=O)noc4c3F)CC3(C(=O)NC(=O)NC3=O)[C@H]2[C@H](C)O1]

Example 19 was prepared from Intermediate 44. The title compound was obtained as the major eluting component from Super Critical Fluid Chromatography (Chiralpak IA column, 80% CO₂, 20% isopropanol) to isolate the major eluting component. ¹H NMR (300 MHz, DMSO-d6) δ: 0.9 (d, 3H) 1.1 (d, 3H) 2.8-3.2 (m, 2H) 3.6-4.0 (m, 5H) 4.0-4.3 (m, 2H) 4.6-5.2 (m, 3H) 7.75 (s, 1H) 11.4 (s, 1H) 11.8 (s, 1H). MS (ES) MH⁺: 506 for $C_{22}H_{21}F_2N_5O_7$.

Example 20

(2R,4S,4aS)-11-Chloro-8-[(5S)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

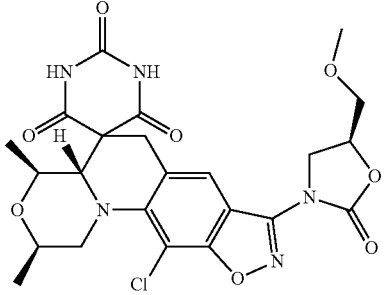 [SMILES: COC[C@@H]1CN(c2noc3c(Cl)c4c(cc23)CC2(C(=O)NC(=O)NC2=O)[C@H]2[C@H](C)O[C@H](C)CN42)C(=O)O1]

Example 20 was prepared from Intermediate 53. The title compound was obtained as the major eluting component from reverse phase HPLC (20-50% acetonitrile/water gradient with 0.1% TFA) purification. ¹H NMR (300 MHz, DMSO-d6) δ: 0.9 (d, 3H), 1.2 (d, 3H), 2.8-3.2 (m, 2H), 3.3 (d, 6H), 3.5-3.75 (m, 3H), 3.75-4.1 (m, 3H), 4.2 (t, 1H), 4.5 (d, 1H) 4.8-5.3 (m, 1H), 7.85 (s, 1H), 11.4 (br. s, 1H), 11.8 (br s., 1H). MS (ES) MH⁺: 534 for $C_{23}H_{24}ClN_5O_8$.

Example 21

(2R,4S,4aS)-11-Chloro-8-[(5R)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

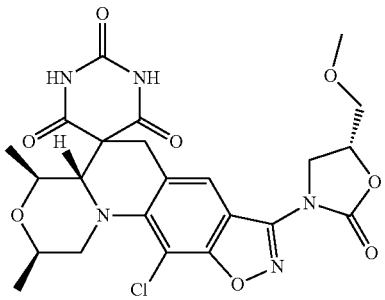 [SMILES: COC[C@H]1CN(c2noc3c(Cl)c4c(cc23)CC2(C(=O)NC(=O)NC2=O)[C@H]2[C@H](C)O[C@H](C)CN42)C(=O)O1]

The starting material was Intermediate 54. The title compound was obtained as the major eluting component from reverse phase HPLC (20-50% acetonitrile/water gradient with 0.1% TFA) purification. ¹H NMR (300 MHz, DMSO-d6) δ: 0.9 (d, 3H), 1.2 (d, 3H), 2.9-3.2 (m, 2H), 3.2-3.45 (m, 6H), 3.5-3.75 (m, 3H), 3.8-4.1 (m, 3H), 4.15 (t, 1H), 4.35-4.6 (m, 1H), 4.85-5.1 (m, 1H), 7.85 (s, 1H). MS (ES) MH⁺: 534 for $C_{23}H_{24}ClN_5O_8$.

Example 22

((2R,4S,4aS)-11-Chloro-2,4-dimethyl-8-((R)-5-methyl-2-oxooxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

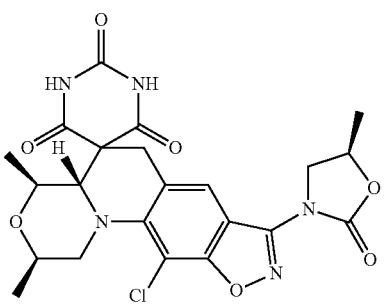 [SMILES: C[C@@H]1CN(c2noc3c(Cl)c4c(cc23)CC2(C(=O)NC(=O)NC2=O)[C@H]2[C@H](C)O[C@H](C)CN42)C(=O)O1]

Example 22 was prepared from Intermediate 55. The title compound was obtained as the major eluting component from Super Critical Fluid Chromatography (Chiralpak IA column, 60% CO$_2$, 40% MeOH). $^1$H NMR (300 MHz, DMSO-d6) δ: 0.9 (d, 3H) 1.2 (d, 3H) 1.45 (d, 3H) 2.9-3.1 (m, 2H) 3.6-3.8 (m, 3H) 3.9-4.05 (m, 2H) 4.2 (dd, 1H) 4.5 (d, 1H) 7.85 (s, 1H) 11.4 (s, 1H) 11.8 (s, 1H). MS (ES) MH$^+$: 504 for C$_{22}$H$_{22}$ClN$_5$O$_7$.

Example 23

(2R,4S,4aS)-8-((4S,5R)-4,5-Dimethyl-2-oxooxazolidin-3-yl)-11-fluoro-2,4,4a,6-tetrahydro-1H,1'H-spiro[isoxazolo[4,5-g][1,4]oxazino[4,3-a]quinoline-5,5'-pyrimidine]-2',4',6'(3'H)-trione

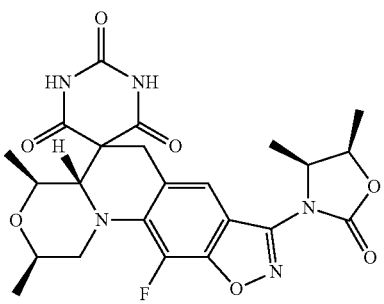 [SMILES: C[C@@H]1CN2c3c(cc4c(N5C(=O)O[C@H](C)[C@@H]5C)noc4c3F)CC3(C(=O)NC(=O)NC3=O)[C@H]2[C@H](C)O1]

Example 23 was prepared from Intermediate 56. The title compound was obtained as the major eluting component from reverse phase HPLC (20-50% acetonitrile/water gradient with 0.1% TFA) purification. $^1$H NMR (300 MHz, DMSO-d6) δ: 0.9 (d, 3H) 1.15 (d, 3H) 1.3 (d, 3H) 1.4 (d, 3H), 2.9 (d, 1H), 3.1 (t, 1H), 3.6-3.7 (m, 2H), 3.7-3.8 (m, 1H), 3.9 (d, 1H), 4.1 (d, 1H), 4.5-4.6 (m, 1H), 4.8-5.1 (m, 1H), 7.6 (s, 1H), 11.4 (s, 1H), 11.8 (s, 1H). MS (ES) MH$^+$: 502 for C$_{23}$H$_{24}$FN$_5$O$_7$; [α]$_D^{20}$=-221 (c=0.1; MeOH).

Example 24

(2R,4S,4aS)-8-((4R,5S)-4,5-Dimethyl-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

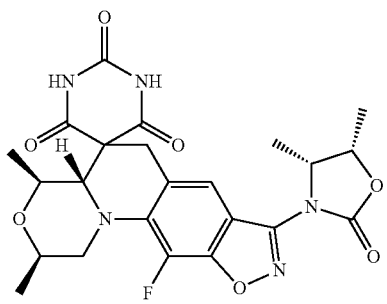 [SMILES: C[C@@H]1CN2c3c(cc4c(N5C(=O)O[C@@H](C)[C@H]5C)noc4c3F)CC3(C(=O)NC(=O)NC3=O)[C@H]2[C@H](C)O1]

Example 24 was prepared from Intermediate 57. The title compound was obtained as the major eluting component from reverse phase HPLC (20-50% acetonitrile/water gradient with 0.1% TFA) purification. $^1$H NMR (300 MHz, DMSO-d6) δ: 0.9 (d, 3H), 1.15 (d, 3H), 1.35 (d, 3H), 1.33 (d, 3H), 2.8-3.0 (m, 1H), 3.1 (t, 1H), 3.5-3.7 (m, 2H), 3.7-3.9 (m, 1H), 3.9 (d, 1H), 4.1 (d, 1H), 4.6 (m, 1H), 5.0 (m, 1H), 7.6 (s, 1H), 11.5 (s, 1H), 11.8 (s, 1H). MS (ES) MH$^+$: 502 for C$_{23}$H$_{24}$FN$_5$O$_7$; [α]$_D^{20}$=-117 (c=0.1; MeOH).

Example 25

(2R,4S,4aS)-8-((S)-4-Allyl-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

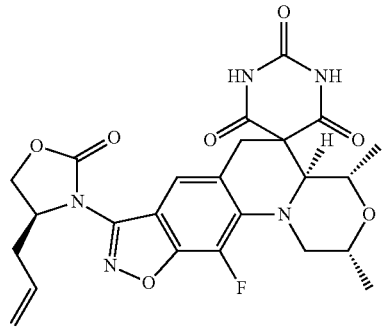 [SMILES: C=CC[C@H]1COC(=O)N1c1noc2c(F)c3c(cc12)CC1(C(=O)NC(=O)NC1=O)[C@H]1[C@H](C)O[C@H](C)CN31]

Example 25 was prepared from Intermediate 61. The title compound was obtained as the major eluting component from reverse phase HPLC (20-50% acetonitrile/water gradient with 0.1% TFA) purification. $^1$H NMR (400 MHz, DMSO-d6) δ: 0.7-1.0 (m, 3H), 1.1 (d, 3H), 2.55-2.65 (m, 2H), 2.7 (d, 1H), 2.8-3.0 (m, 2H), 3.1 (t, 1H), 3.5-3.7 (m, 2H), 3.7-3.9 (m, 1H), 4.1 (d, 1H), 4.6-4.7 (m, 2H), 5.0-5.3 (m, 2H), 5.7-5.85 (m, 1H), 7.6 (s, 1H), 11.4 (s, 1H), 11.8 (s, 1H). MS (ES) MH$^+$: 514 for C$_{24}$H$_{24}$FN$_5$O$_7$.

Example 26

(2R,4S,4aS)-11-Fluoro-8-((S)-5-(hydroxymethyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

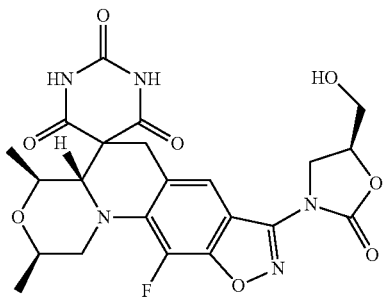 [SMILES: C[C@@H]1CN2c3c(cc4c(N5C[C@@H](CO)OC5=O)noc4c3F)CC3(C(=O)NC(=O)NC3=O)[C@H]2[C@H](C)O1]

Example 26 was prepared from Intermediate 43. The title compound was obtained as the major eluting component from Super Critical Fluid Chromatography (Chiralpak IA column, 70% $CO_2$, 30% MeOH) to isolate the major eluting component. $^1$H NMR (300 MHz, DMSO-d6) δ: 0.9 (d, 3H) 1.1 (d, 3H) 2.9 (d, 1H) 3.0-3.2 (m, 1H) 3.5-3.8 (m, 5H) 3.85-4.0 (m, 2H) 4.0-4.2 (m, 2H) 4.75-4.9 (m, 1H) 5.2 (t, 1H) 7.8 (s, 1H) 11.4 (s, 1H) 11.75 (s, 1H). MS (ES) MH$^+$: 504 for $C_{22}H_{22}FN_5O_8$.

Examples 27 and 28

((2R,4S,4aS)-11-Fluoro-2,4-dimethyl-8-[(4R-(tetrahydro-2H-pyran-4-yl)-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione and (2R,4S,4aS)-11-fluoro-2,4-dimethyl-8-[(4S-(tetrahydro-2H-pyran-4-yl)-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

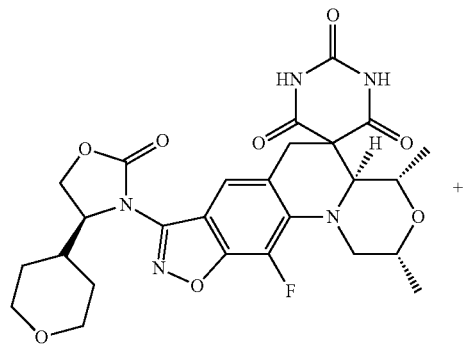

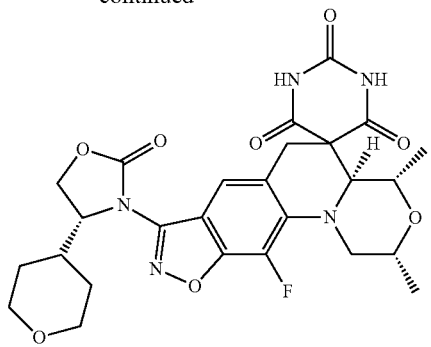

Example 27 and Example 28 were prepared from Intermediate 65. The title compounds were separated by reverse phase HPLC (20-50% acetonitrile/water gradient with 0.1% TFA) purification. Two diastereomers corresponding to the title compounds were isolated, but the configurations for each the oxazolidinone rings were not determined.

Example 27 was the first eluting diastereomer. $^1$H NMR (400 MHz, DMSO-d6) δ: 0.9 (d, 3H), 1.15 (d, 3H), 1.2-1.5 (m, 4H), 2.9 (d, 1H), 3.0-3.3 (m, 4H), 3.6-3.7 (m, 4H), 3.7-4.0 (m, 3H), 4.1 (d, 1H), 4.4-4.7 (m, 2H), 7.6 (s, 1H), 11.5 (s, 1H), 11.8 (s, 1H). MS (ES) MH$^+$: 558 for $C_{26}H_{28}FN_5O_8$.

Example 28 was the second eluting diastereomer. $^1$H NMR (400 MHz, DMSO-d6) δ: 0.9 (d, 3H) 1.15 (d, 3H) 1.2-1.5 (m, 4H) 2.2-2.4 (m, 2H) 2.9 (d, 1H) 3.0-3.3 (m, 3H) 3.5-3.7 (m, 2H) 3.7-4.0 (m, 4H) 4.1 (d, 1H) 4.4-4.7 (m, 3H) 7.6 (s, 1H) 11.45 (s, 1H) 11.8 (s, 1H). MS (ES) MH$^+$: 558 for $C_{26}H_{28}FN_5O_8$.

Example 29

(2R,4S,4aS)-11-Fluoro-8-((S)-4-(3-hydroxypropyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

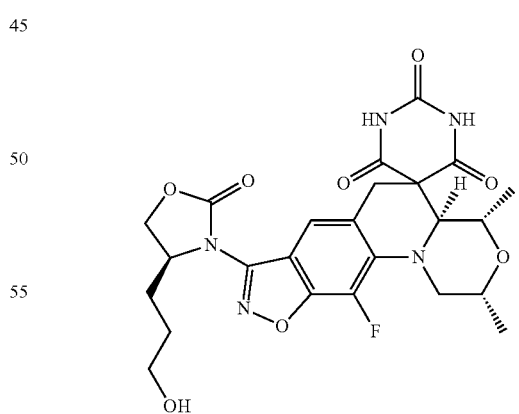

Example 29 was prepared from Intermediate 69. The title compound was obtained as the major eluting component from Super Critical Fluid Chromatography (Chiralpak IA column) to isolate the major eluting component. $^1$H NMR (300 MHz, DMSO-d6) δ: 0.9 (d, 3H) 1.1 (d, 3H) 1.3-1.5 (m, 2H) 1.7-2.0 (m, 2H) 2.9 (d, 1H) 3.0-3.2 (m, 1H) 3.3-3.45 (m, 2H) 3.6-3.85 (m, 3H) 3.9-4.15 (m, 2H) 4.3-4.7 (m, 4H) 7.6 (s, 1H) 11.45 (s, 1H) 11.8 (s, 1H). MS (ES) MH+: 532 for $C_{24}H_{26}FN_5O_8$.

Example 30

(2R,4S,4aS)-11-Fluoro-8-((S)-4-(3-fluoropropyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

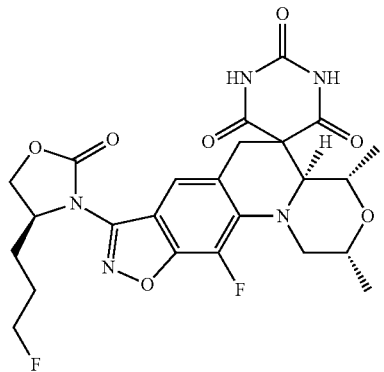 [SMILES: C[C@@H]1CN2c3c(cc4c(N5C(=O)OC[C@@H]5CCCF)noc4c3F)CC3(C(=O)NC(=O)NC3=O)[C@H]2[C@H](C)O1]

The starting material was Intermediate 70. The title compound was obtained as the major eluting component from Super Critical Fluid Chromatography (Chiralpak IA column) to isolate the major eluting component. $^1$H NMR (300 MHz, DMSO-d6) δ: 0.9 (d, 3H) 1.15 (d, 3H) 1.5-2.05 (m, 4H) 2.9 (d, 1H) 3.05-3.2 (m, 1H) 3.6-4.2 (m, 5H) 4.3-4.7 (m, 5H) 7.6 (s, 1H) 11.5 (s, 1H) 11.7 (s, 1H). MS (ES) MH+: 534 for $C_{24}H_{25}F_2N_5O_7$.

Example 31

(2R,4S,4aS)-11-Fluoro-8-((S)-4-(2-hydroxyethyl)-2-oxooxazolidin-3-yl)-2,4-dimethyl-2,4,4a,6-tetrahydro-1H,1'H-spiro[isoxazolo[4,5-g][1,4]oxazino[4,3-g]quinoline-5,5'-pyrimidine]-2',4',6'(3'H)-trione

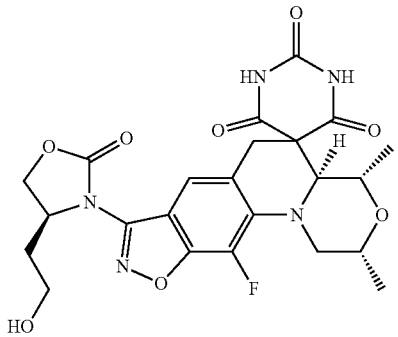 [SMILES: C[C@@H]1CN2c3c(cc4c(N5C(=O)OC[C@@H]5CCO)noc4c3F)CC3(C(=O)NC(=O)NC3=O)[C@H]2[C@H](C)O1]

Example 31 was prepared from Intermediate 74. The title compound was obtained as the major eluting component from Super Critical Fluid Chromatography (Chiralpak IA column). $^1$H NMR (300 MHz, DMSO-d6) δ: 0.9 (d, 3H), 1.2 (d, 3H), 1.8-1.9 (m, 1H), 2.1-2.3 (m, 1H), 3.0 (d, 1H), 3.1-3.2 (m, 1H), 3.5-3.6 (m, 2H), 3.6-3.7 (m, 2H), 3.8-3.9 (m, 1H), 4.0 (d, 1H), 4.1 (d, 1H), 4.5 (q, 1H), 4.6-4.8 (m, 3H), 7.7 (s, 1H), 11.5, (br. s, 2H). MS (ES) MH+: 518.5 for $C_{23}H_{24}FN_5O_8$.

Example 32

(2R,4S,4aS)-11-Chloro-8-((S)-5-(fluoromethyl)-2-oxooxazolidin-3-yl)-2,4-dimethyl-2,4,4a,6-tetrahydro-1H,1'H-spiro[isoxazolo[4,5-g][1,4]oxazino[4,3-g]quinoline-5,5'-pyrimidine]-2',4',6'(3'H)-trione

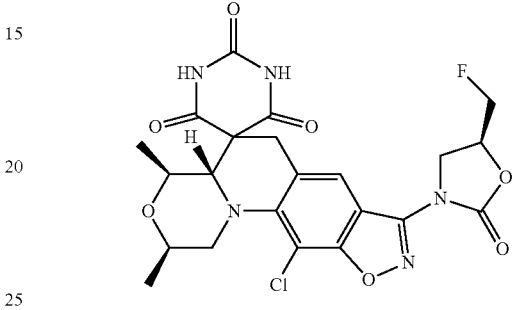

Example 32 was prepared from Intermediate 77. The title compound was obtained as the major eluting component from Super Critical Fluid Chromatography (Chiralpak IA column, 70% $CO_2$, 30% EtOH) to isolate the major eluting component. $^1$H NMR (300 MHz, DMSO-d6) δ: 0.9 (d, 3H) 1.3 (d, 3H) 2.9-3.1 (m, 2H) 3.6-3.7 (m, 2H) 3.8-4.0 (m, 3H) 4.25 (t, 1H) 4.45-4.9 (m, 3H) 5.0-5.2 (m, 1H) 7.85 (s, 1H) 11.5 (s, 1H) 11.7 (s, 1H). MS (ES) MH+: 522 for $C_{22}H_{22}ClFN_5O_7$.

Example 33

(2R,4S,4aS)-11-Chloro-8-((S)-4-(3-hydroxypropyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

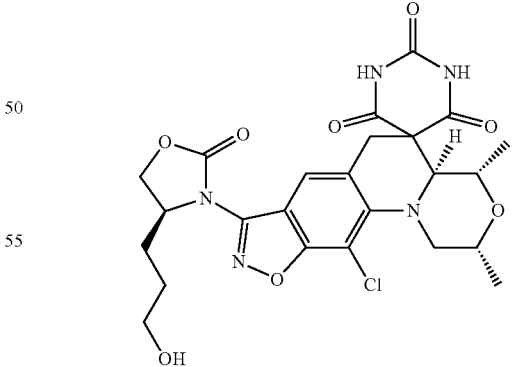

Example 33 was prepared from Intermediate 79. The title compound was obtained as the major eluting component from Super Critical Fluid Chromatography (Chiralpak IA column, 70% $CO_2$, 30% MeOH) to isolate the major eluting component. $^1$H NMR (300 MHz, DMSO-d6) δ: 0.9 (d, 3H) 1.15 (d, 3H) 1.5-2.05 (m, 4H) 2.9 (d, 1H) 3.05-3.2 (m, 1H)

3.6-4.2 (m, 5H) 4.3-4.7 (m, 5H) 7.6 (s, 1H) 11.5 (s, 1H) 11.7 (s, 1H). MS (ES) MH+: 534 for C$_{24}$H$_{25}$F$_2$N$_5$O$_7$.

Example 34

(2R,4S,4aS)-11-Chloro-8-((S)-4-(3-fluoropropyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

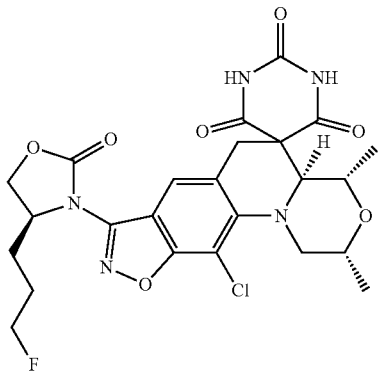 [SMILES: C[C@@H]1CN2c3c(cc4c(N5C(=O)OC[C@@H]5CCCF)noc4c3Cl)CC3(C(=O)NC(=O)NC3=O)[C@H]2[C@H](C)O1]

Example 34 was prepared from Intermediate 80. The title compound was obtained as the major eluting component from Super Critical Fluid Chromatography (Chiralpak IA column, 60% CO$_2$, 40% MeOH) to isolate the major eluting component. $^1$H NMR (300 MHz, DMSO-d6) δ: 0.9 (d, 3H) 1.2 (d, 3H) 1.5-2.0 (m, 4H) 2.9-3.1 (m, 2H) 3.5-3.7 (m, 2H) 3.9-4.05 (m, 2H) 4.3-4.75 (m, 6H) 7.7 (s, 1H) 11.4 (s., 1H) 11.75 (s, 1H). MS (ES) MH+: 550 for C$_{24}$H$_{25}$ClFN$_5$O$_7$.

Example 35

(2R,4S,4aS)-11-Fluoro-8-[(5S)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

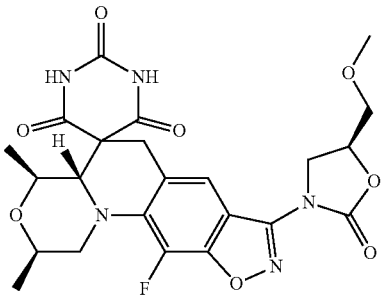 [SMILES: COC[C@@H]1CN(c2noc3c(F)c4c(cc23)CC2(C(=O)NC(=O)NC2=O)[C@H]2[C@H](C)O[C@H](C)CN42)C(=O)O1]

Intermediate 81 (445 mg, 0.99 mmol) and pyrimidine-2,4,6(1H,3H,5H)-trione (126 mg, 0.99 mmol) in a mixture of acetic acid (8 mL) and water (2 mL) was heated at 110° C. for 2 hrs. The solvent was removed and the reaction mixture was purified using Super Critical Fluid Chromatography ((S,S) Whelk-O1 column with 25% of 85:15 acetonitrile methanol and 75% CO$_2$ mobile phase) to give (2R,4S,4aS)-11-fluoro-8-((S)-5-(methoxymethyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione (368 mg, 72.1%) as a solid as the first eluting compound. $^1$H NMR (300 MHz, DMSO-d$_6$) δ: 1.0 (d, 3H), 1.3 (d, 3H), 1.4 (d, 3H), 3.1 (d, 1H), 3.-4.3 (m, 7H), 4.5-4.8 (m, 2H), 7.6 (s, 1H), 11.5 (br. s., 1H), 11.7 (br. s., 1H). MS (ES) MH+: 518 for C$_{23}$H$_{24}$FN$_5$O$_8$.

Also isolated from the synthesis of Example 35 as the second component eluting from the HPLC purification was ((2R,4R,4aR)-11-fluoro-8-[(5S)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione (27 mg)

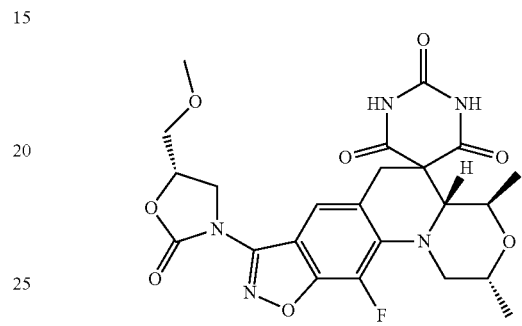

$^1$H NMR (300 MHz, DMSO-d$_6$) δ: 0.9 (d, 3H), 1.3 (d, 3H), 3.1 (d, 1H), 3.3 (s, 3H), 3.5-4.3 (m, 10H), 4.8-5.1 (m, 1H), 7.8 (s, 1H), 11.4 (s, 1H), 11.7 (s, 1H). MS (ES) MH+: 518 for C$_{23}$H$_{24}$FN$_5$O$_8$.

Example 36

(2R,4S,4aS)-11-Fluoro-8-[(5R)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

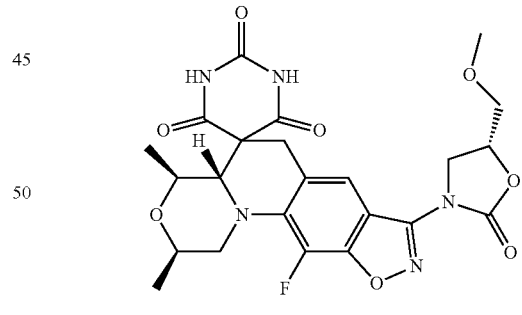

A mixture of Intermediate 82 (487 mg, 1.08 mmol) and pyrimidine-2,4,6(1H,3H,5H)-trione (138 mg, 1.08 mmol) in acetic acid (8 mL) and water (2 mL) was heated at 110° C. for 2 hours. The solvent was removed and the reaction mixture was purified using Super Critical Fluid Chromatography (Chiralpak IA column with 40% isopropanol and 60% CO$_2$ mobile phase) to give the title compound (408 mg, 73.1%) as a solid as the first eluting component. $^1$H NMR (300 MHz, DMSO-d$_6$) δ: 0.9 (d, 3H), 1.1 (d, 3H), 2.9-3.2 (m, 2H), 3.3 (s, 3H), 3.6-4.2 (m, 9H), 4.9-5.1 (m, 1H), 7.75 (s, 1H), 11.4 (s, 1H), 11.8 (s, 1H). MS (ES) MH+: 518 for C$_{23}$H$_{24}$FN$_5$O$_8$

Example 37

(2R,4S,4aS)-11-Fluoro-8-[(5R)-5-(hydroxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

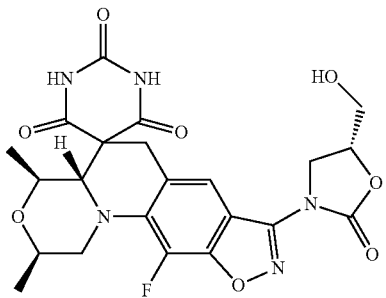 [SMILES: C[C@@H]1CN2c3c(cc4c(N5C[C@H](CO)OC5=O)noc4c3F)CC3(C(=O)NC(=O)NC3=O)[C@H]2[C@H](C)O1]

To a solution of Intermediate 87 (0.10 g, 0.22 mmol) in acetic acid (5 mL), barbituric acid (0.04 g, 0.3 mmol) was added and the mixture was heated at 95° C. for 3 hours. Volatiles were removed completely under vacuum, water (2 mL) was added to the residue and filtered. The residue was subjected to preparative HPLC using ammonium acetate method to obtain the pure title compound. Yield: 0.03 g (26%) $^1$H NMR (400 MHz, DMSO-$d_6$) δ: 0.88 (d, 3H), 1.13 (d, 3H), 2.90 (d, 1H), 3.13 (t, 1H), 3.58-3.78 (m, 5H), 3.89-3.94 (m, 2H), 4.08-4.14 (m, 2H), 4.86-4.87 (m, 1H), 5.26 (t, 1H), 7.77 (s, 1H), 11.44 (s, 1H), 11.81 (s, 1H). MS (ES) MH$^+$: 504.3 for $C_{22}H_{22}FN_5O_8$.

Example 38

(2R,4S,4aS)-11-Fluoro-8-[(5R)-5-(fluoromethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

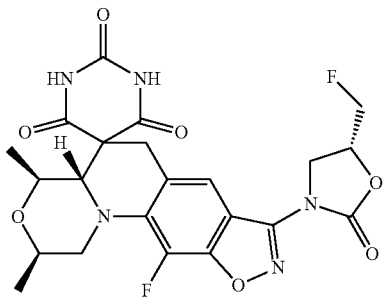 [SMILES: C[C@@H]1CN2c3c(cc4c(N5C[C@H](CF)OC5=O)noc4c3F)CC3(C(=O)NC(=O)NC3=O)[C@H]2[C@H](C)O1]

To a solution of Intermediate 84 (0.05 g, 0.11 mmol) in acetic acid (2 mL), barbituric acid (0.02 g, 0.11 mmol) was added and the mixture was heated at 95° C. for 3 hours. Volatiles were removed completely under vacuum, water (2 mL) was added to the residue and filtered. The title compound obtained after purification by preparative HPLC using ammonium acetate and acetonitrile method. Yield: 0.02 g (34%). $^1$H NMR (400 MHz, DMSO-$d_6$) δ: 0.89 (d, 3H), 1.14 (d, 3H), 2.90 (d, 1H), 3.11 (t, 1H), 3.62-3.71 (m, 2H), 3.71-3.78 (m, 1H), 3.88-3.95 (m, 2H), 4.10 (d, 1H), 4.22 (t, 1H), 4.67-4.71 (m, 1H), 4.77-4.84 (m, 1H), 5.09-5.12 (m, 1H), 7.76 (s, 1H), 11.46 (s, 1H), 11.83 (s, 1H). MS (ES) MH$^+$: 506.5 for $C_{22}H_{21}F_2N_5O_7$

Example 39

(2R,4S,4aS)-11-Fluoro-2,4-dimethyl-8-((S)-2-oxo-4-vinyloxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

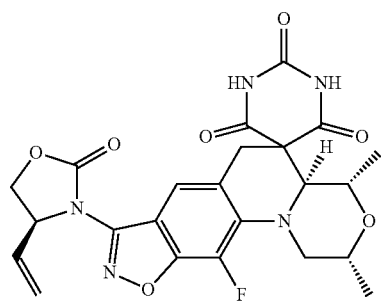 [SMILES: C=C[C@H]1COC(=O)N1c1noc2c(F)c3c(cc12)CC1(C(=O)NC(=O)NC1=O)[C@H]1[C@H](C)O[C@H](C)CN31]

To a stirred solution of Intermediate 88 (0.15 g, 0.34 mmol) in acetic acid (5 mL), barbituric acid (0.05 g, 0.38 mmol) was added and the mixture was heated at 95° C. for 3 hours. Volatiles were removed under vacuum and the resulting residue was dissolved in methanol (0.5 mL), water (3 mL) was added to it and filtered and the residue was washed with water to obtain the title compound. Yield: 0.05 g (30%). $^1$HNMR (400 MHz, DMSO-$d_6$) δ: 0.90 (d, 3H), 1.14 (d, 3H), 2.94 (d, 1H), 3.11 (t, 1H), 3.64-3.68 (m, 2H), 3.76-3.80 (m, 1H), 3.94 (d, 1H), 4.10 (d, 1H), 4.28-4.31 (m, 1H), 4.76 (t, 1H), 5.11 (q, 1H), 5.30 (d, 1H), 5.36 (d, 1H), 5.90 (dd, 1H), 7.57 (m, 1H), 11.48 (s, 1H), 11.84 (s, 1H). MS (ES) MH$^+$: 500.3 for $C_{23}H_{22}FN_5O_7$.

Example 40

(2R,4S,4aS)-11-Fluoro-8-{(5R)-5-[(hydroxyimino)methyl]-2-oxo-1,3-oxazolidin-3-yl}-2,4-dimethyl-1,2,4,4a-tetrahydro-2'H,6H-spiro[1,4-oxazino[4,3a][1,2]oxazolo[4,5-g]quinoline-5,5'-pyrimidine]-2',4',6'(1'H,3'H)-trione

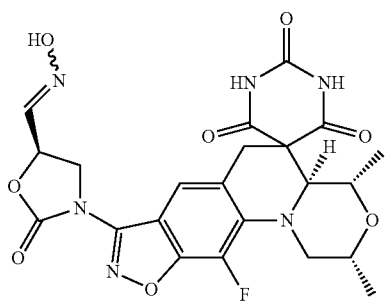 [SMILES: C[C@@H]1CN2c3c(cc4c(N5C[C@H](C=NO)OC5=O)noc4c3F)CC3(C(=O)NC(=O)NC3=O)[C@H]2[C@H](C)O1]

To a solution of Intermediate 89 (0.15 g, 0.3 mmol) in acetic acid (10 mL), barbituric acid (0.05 g, 0.4 mmol) was added and the mixture was heated at 95° C. for 3 hours. Volatiles were removed completely under vacuum, water (4 mL) was added to the residue and filtered. The solid thus obtained was further purified by silica gel column chromatography using a gradient of chloroform in methanol. We have obtained this compound as an undefined mixture of E & Z isomers (1:2 is the ratio). Yield: 0.06 g (34%). ¹HNMR (400 MHz, DMSO-$d_6$) δ: 0.89 (d, 3H), 1.14 (d, 3H), 2.93 (d, 1H), 3.11 (t, 1H), 3.65-3.80 (m, 3H), 3.94 (d, 1H), 4.10 (d, 1H), 4.30-4.32 & 4.47-4.51 (m, 1H), 4.76 & 4.88 (t, 1H), 5.24-5.30 & 5.48-5.55 (m, 1H), 7.10-7.14 & 7.51-7.75 (m, 2H), 11.28 & 11.48 (s, 1H), 11.45 (s, 1H), 11.85 (s, 1H). MS (ES) MH⁺: 517.3 for $C_{22}H_{21}FN_6O_8$.

Example 41

(4S)-3-[(2R,4S,4aS)-11-Fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-2-oxo-1,3-oxazolidine-4-carbonitrile

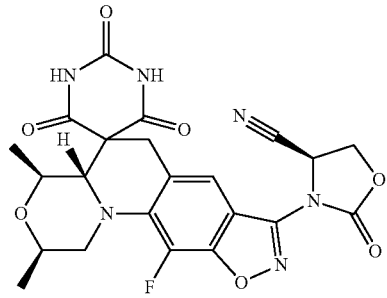 [SMILES: C[C@@H]1CN2c3c(cc4c(N5C(=O)OC[C@@H]5C#N)noc4c3F)CC3(C(=O)NC(=O)NC3=O)[C@H]2[C@H](C)O1]

To a solution Intermediate 92 (0.08 g, 0.17 mmol) in acetic acid (5 mL), barbituric acid (0.03 g, 0.2 mmol) was added and the mixture was heated at 95° C. for 3 hours. Volatiles were removed completely under vacuum, water (2 mL) was added to the residue and filtered. The obtained solid was further purified by preparative TLC using 9:1 mixture of chloroform and methanol. Yield: 0.03 g (34%). ¹HNMR (400 MHz, DMSO-$d_6$) δ: 0.89 (d, 3H), 1.15 (d, 3H), 2.92 (d, 1H), 3.13 (t, 1H), 3.65-3.82 (m, 2H), 3.95 (d, 1H), 4.82-4.86 (m, 2H), 5.58-5.61 (m, 1H), 7.68 (s, 1H), 11.49 (s, 1H), 11.84 (s, 1H). MS (ES) MH⁺: 499.3 for $C_{22}H_{19}FN_6O_7$.

Example 42

(2R,4S,4aS)-11-Fluoro-8-{(4S)-4-[(methoxyimino)methyl]-2-oxo-1,3-oxazolidin-3-yl}-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

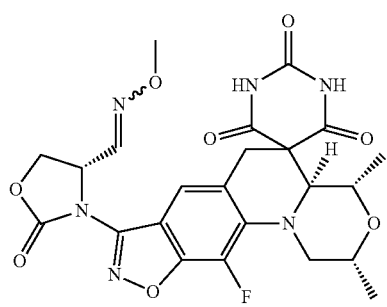 [SMILES: CON=C[C@H]1COC(=O)N1c1noc2c(F)c3c(cc12)CC1(C(=O)NC(=O)NC1=O)[C@H]1[C@H](C)O[C@H](C)CN31]

To a solution of Intermediate 93 (0.07 g, 0.15 mmol) in acetic acid (5 mL), barbituric acid (0.03 g, 0.2 mmol) was added and the mixture was heated at 95° C. for 3 hours. The volatiles were removed completely under vacuum, water (2 mL) was added to the residue and filtered. The obtained solid was further purified by preparative TLC using 9:1 mixture of chloroform and methanol. We have obtained this compound as an undefined mixture of E & Z isomers (1:0.65 is the ratio). Yield: 0.03 g (30%). ¹HNMR (400 MHz, DMSO-$d_6$) δ: 0.89 (d, 3H), 1.13 (d, 3H), 2.93 (d, 1H), 3.11 (t, 1H), 3.65-3.80 (m, 3H), 3.74 & 3.85 (s, 3H), 3.94 (d, 1H), 4.10 (d, 1H), 4.30-4.32 & 4.47-4.51 (m, 1H), 4.76 & 4.88 (t, 1H), 5.24-5.30 & 5.48-5.55 (m, 1H), 7.27 & 7.68 (d, 1H), 7.63 & 7.74 (s, 1H), 11.45 (s, 1H), 11.82 (s, 1H). MS (ES) MH⁺: 531.2 for $C_{23}H_{23}FN_6O_8$.

Example 43

(2R,4S,4aS)-11-Fluoro-8-{(5R)-5-(methoxyimino)methyl]-2-oxo-1,3-oxazolidin-3-yl}-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

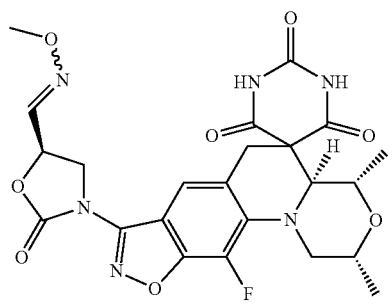

To a solution of Intermediate 94 (0.13 g, 0.28 mmol) in acetic acid (5 mL), barbituric acid (0.04 g, 0.28 mmol) was added and the mixture was heated at 95° C. for 3 hours. The volatiles were removed completely under vacuum, water (2 mL) was added to the residue and filtered. The solid thus obtained was further purified by preparative TLC using 9:1 mixture of chloroform and methanol. We have obtained this compound as an undefined mixture of E & Z isomers (3:1 is the ratio). Yield: 0.03 g (20%). ¹HNMR (400 MHz, DMSO-$d_6$) δ: 0.94 (d, 3H), 1.14 (d, 3H), 2.91 (d, 1H), 3.11 (t, 1H), 3.62-3.67 (m, 2H), 3.71-3.81 (m, 1H), 3.84-3.95 (m, 4H), 4.10-4.16 (m, 2H), 4.29-4.39 (m, 1H), 5.37-5.42 & 5.73-5.75 (m, 1H), 7.30 & 7.73 (d, 1H), 7.76 (s, 1H), 11.46 (s, 1H), 11.83 (s, 1H). MS (ES) MH⁺: 531.2 for $C_{23}H_{23}FN_6O_8$.

Example 44

(2R,4S,4aS)-8-[(5R)-5-(Azidomethyl)-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

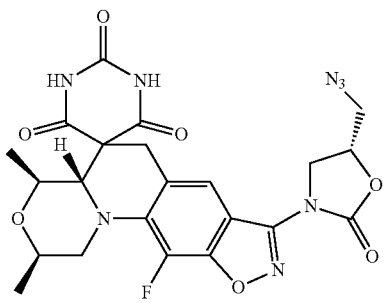 [SMILES: C[C@@H]1CN2c3c(cc4c(N5C[C@H](CN=[N+]=[N-])OC5=O)noc4c3F)CC3(C(=O)NC(=O)NC3=O)[C@H]2[C@H](C)O1]

To a solution of Intermediate 96 (0.12 g, 0.25 mmol) in acetic acid (3 mL), barbituric acid (0.03 g, 0.25 mmol) was added and the mixture was heated at 95° C. for 3 hours. Volatiles were removed completely under vacuum, water (2 mL) was added to the residue and filtered. The residue was subjected to preparative HPLC using formic acid/acetonitrile method to obtain the pure title compound. Yield: 0.03 g (22%). $^1$HNMR (400 MHz, DMSO-d$_6$) δ: 0.88 (d, 3H), 1.13 (d, 3H), 2.90 (d, 1H), 3.14 (t, 1H), 3.63-3.70 (m, 2H), 3.74-3.86 (m, 4H), 3.93 (d, 1H), 4.10 (d, 1H), 4.18 (t, 1H), 5.00-5.06 (m, 1H), 7.75 (s, 1H), 11.44 (s, 1H), 11.81 (s, 1H). MS (ES) MH$^+$: 529.3 for $C_{22}H_{21}FN_8O_7$.

Example 45

(2R,4S,4aS)-11-Fluoro-2,4-dimethyl-8-((R)-4-((methylthio)methyl)-2-oxooxazolidin-3-yl)-2,4,4a,6-tetrahydro-1H,1'H-spiro[isoxazolo[4,5-g][1,4]oxazino[4,3-g]quinoline-5,5'-pyrimidine]-2',4',6'(3'H)-trione

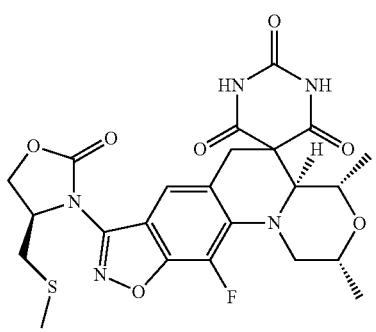 [SMILES: CSC[C@H]1COC(=O)N1c1noc2c(F)c3c(cc12)CC1(C(=O)NC(=O)NC1=O)[C@H]1[C@H](C)O[C@H](C)CN31]

To a solution of Intermediate 101 (0.20 g, 0.43 mmol) in acetic acid (10 mL), barbituric acid (0.066 g, 0.51 mmol) was added and the mixture was heated at 95° C. for 3 hours. The volatiles were removed completely under vacuum, water (2 mL) was added to the residue and filtered. The solid thus obtained was further purified by preparative HPLC using ammonium acetate/acetonitrile method. Yield: 0.05 g (22%). $^1$H NMR (400 MHz, DMSO-d$_6$) δ: 0.87 (d, 3H), 1.13 (d, 3H), 2.04 (s, 3H), 2.9 (d, 1H), 3.01-3.07 (m, 2H), 3.10 (t, 1H), 3.62-3.68 (m, 2H), 3.75-3.79 (m, 1H), 3.92 (d, 1H), 4.09 (d, 1H), 4.37 (dd, 1H), 4.67-4.72 (m, 1H), 4.78-4.83 (m, 1H), 7.64 (s, 1H), 11.47 (s, 1H), 11.82 (s, 1H). MS (ES) MH$^+$: 534.4 for $C_{23}H_{24}FN_5O_7S$.

Example 46

(2R,4S,4aS)-11-Fluoro-2,4-dimethyl-8-((R)-4-((methylsulfonyl)methyl)-2-oxooxazolidin-3-yl)-2,4,4a,6-tetrahydro-1H,1'H-spiro[isoxazolo[4,5-g][1,4]oxazino[4,3-g]quinoline-5,5'-pyrimidine]-2',4',6'(3'H)-trione

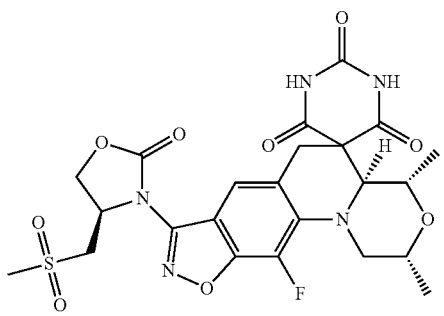

Example 46 was synthesized following the procedure described for the preparation of Example 45 using Intermediate 102 (0.20 g, 0.40 mmol). Yield: 0.06 (26%). $^1$H NMR (400 MHz, DMSO-d$_6$) δ: 0.88 (d, 3H), 1.14 (d, 3H), 2.92 (d, 1H), 3.09-3.14 (m, 4H), 3.63-3.69 (m, 2H), 3.77-3.82 (m, 2H), 3.91-3.95 (m, 2H), 4.09 (d, 1H), 4.64 (dd, 1H), 4.78 (t, 1H), 5.07-5.08 (m, 1H), 7.63 (s, 1H), 11.44 (s, 1H), 11.83 (s, 1H). MS (ES) MH$^+$: 566.2 for $C_{23}H_{24}FN_5O_9S$; $[α]_D^{20}$=−105.76 (c=1.00; MeOH).

Example 47 and Example 48

(2R,4S,4aS)-8-((R)-4-(Azidomethyl)-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione and (2R,4S,4aS)-8-((S)-4-(azidomethyl)-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

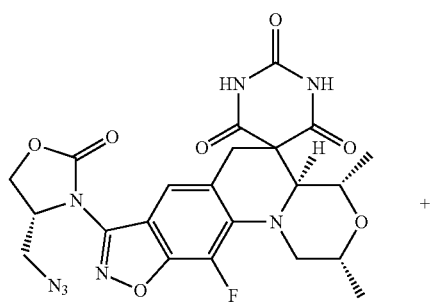

+

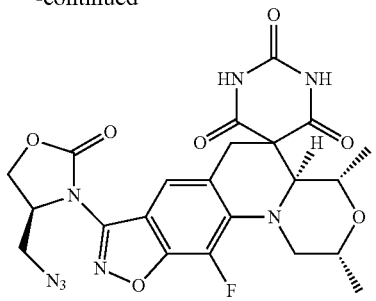

To a solution of Intermediate 109 (0.25 g, 0.54 mmol) in acetic acid (10 mL), barbituric acid (0.07 g, 0.54 mmol) was added and the mixture was heated at 90° C. for 16 hours. The volatiles were removed completely under vacuum, water (2 mL) was added to the residue and filtered. The solid thus obtained was further purified by silica gel column chromatography using a gradient of methanol in chloroform. Yield: 0.25 g (86%).

Chiral HPLC analysis [chiralcel OD-H (250×4.6) mm, 5 µm; Mobile Phase 'A' hexane; Mobile Phase 'B': Ethanol (50:50)] showed the presence of 1:1 ratio of two isomers that were separated by Chiral HPLC [Column: chiralcel OD-H; Mobile Phase: Hexane:Ethanol (50:50)].

Example 47 was the first eluting diastereomer. $^1$H NMR (400 MHz, DMSO-d$_6$) δ: 0.89 (d, 3H), 1.15 (d, 3H), 2.92 (d, 1H), 3.12 (t, 1H), 3.64-3.81 (m, 4H), 3.94 (d, 1H), 4.09-4.15 (m, 2H), 4.37-4.43 (m, 1H), 4.67 (t, 1H), 4.76-4.79 (m, 1H), 7.67 (s, 1H), 11.48 (s, 1H), 11.84 (s, 1H). R$_T$=8.21 min: Yield: 0.04 g. MS (ES) MH$^+$: 529.3 for C$_{22}$H$_{21}$FN$_8$O$_7$ Example 48 was the second eluting diastereomer. $^1$H NMR (400 MHz, DMSO-d$_6$) δ: 0.89 (d, 3H), 1.15 (d, 3H), 2.92 (d, 1H), 3.11 (t, 1H), 3.63-3.79 (m, 4H), 3.94 (d, 1H), 4.09-4.16 (m, 2H), 4.39-4.41 (m, 1H), 4.67 (t, 1H), 4.74-4.76 (m, 1H), 7.64 (s, 1H), 11.48 (s, 1H), 11.84 (s, 1H). R$_T$=11.40 min: Yield: 0.03 g. MS (ES) MH$^+$: 529.3 for C$_{22}$H$_{21}$FN$_8$O$_7$ Example 49

(2R,4S,4aS)-8-[(4S)-4-(Ethoxymethyl)-2-oxo-1,3-oxazolidin-3-yl]-11-fluoro-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

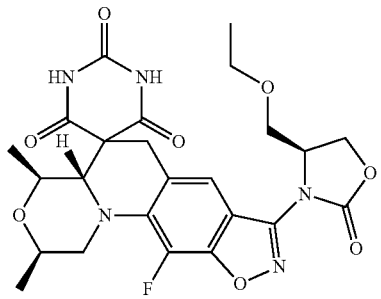 [SMILES: CCOC[C@H]1COC(=O)N1c1noc2c(F)c3c(cc12)CC1(C(=O)NC(=O)NC1=O)[C@H]1[C@H](C)O[C@H](C)CN31]

To a solution of Intermediate 113 (0.20 g, 0.43 mmol) in acetic acid (4 mL), barbituric acid (0.06 g, 0.43 mmol) was added and the mixture was heated at 95° C. for 2 hours. Volatiles were removed completely under vacuum, and the residue was purified by reverse phase prep. HPLC using ammonium acetate/acetonitrile method. The off white solid thus obtained was stirred in water (1 mL) for 10 minutes, filtered and dried. Yield: 0.08 g (35%). $^1$H NMR (400 MHz, DMSO-d6) δ: 0.88 (d, 3H), 1.03 (t, 3H), 1.14 (d, 3H), 2.91 (d, 1H), 3.11 (t, 1H), 3.40-3.44 (m, 2H), 3.56-3.68 (m, 3H), 3.74-3.80 (m, 1H), 3.85 (dd, 1H), 3.93 (d, 1H), 4.09 (d, 1H), 4.41 (dd, 1H), 4.62-4.70 (m, 2H), 7.64 (s, 1H), 11.45 (s, 1H), 11.81 (s, 1H). MS (ES) MH$^+$: 532.4 for C$_{24}$H$_{26}$FN$_5$O$_8$.

Example 50

(2R,4S,4aS)-11-Fluoro-8-{(4S)-4-[(2-methoxyethoxy)methyl]-2-oxo-1,3-oxazolidin-3-yl}-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

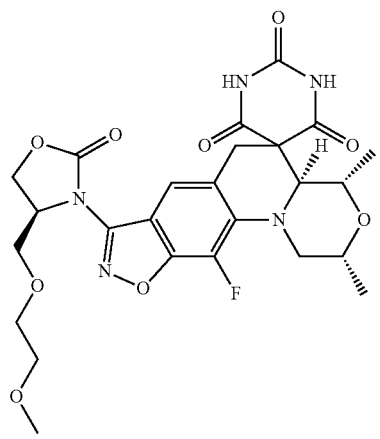 [SMILES: COCCOC[C@H]1COC(=O)N1c1noc2c(F)c3c(cc12)CC1(C(=O)NC(=O)NC1=O)[C@H]1[C@H](C)O[C@H](C)CN31]

Example 50 was synthesized following the procedure described for the preparation of Example 49 using Intermediate 117 (0.15 g, with 37% product). Purification was performed by reverse phase prep. HPLC using ammonium acetate/methanol method. Yield: 0.01 g. $^1$H NMR (400 MHz, DMSO-d$_6$) δ: 0.88 (d, 3H), 1.14 (d, 3H), 2.91 (d, 1H), 3.08-3.14 (m, 1H), 3.15 (s, 3H), 3.34-3.38 (m, 2H), 3.50-3.52 (m, 2H), 3.60-3.68 (m, 3H), 3.74-3.80 (m, 1H), 3.88-3.94 (m, 2H), 4.09 (d, 1H), 4.40-4.43 (m, 1H), 4.64-4.68 (m, 2H), 7.64 (s, 1H), 11.60 (br s, 2H). MS (ES) MH$^+$: 562.4 for C$_{22}$H$_{28}$FN$_5$O$_9$.

Example 51

(2R,4S,4aS)-8-((R)-4-(Difluoromethyl)-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

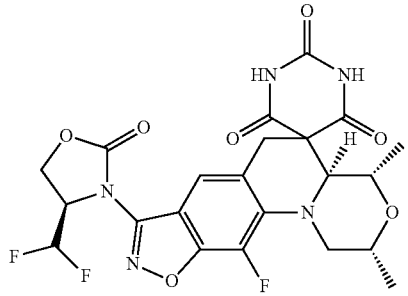 [SMILES: C[C@@H]1CN2c3c(cc4c(N5C(=O)OC[C@@H]5C(F)F)noc4c3F)CC3(C(=O)NC(=O)NC3=O)[C@H]2[C@H](C)O1]

A mixture of Intermediate 123 (90 mg, 0.13 mmol) and 17 mg barbituric acid (17 mg, 0.13 mmol) in 2-propanol (5 mL) was heated at 90° C. for 16 hours. The volatiles were removed under vacuum, and the residue was stirred in water (5 mL) for 10 minutes and filtered. Analysis of the collected solid residue showed the presence of mixture of two diastereomers. The solids were suspended in methanol (5 mL) and heated in a microwave reactor at 150° C. for 2 hours. Water (10 mL) was added and the solids were collected by filtration and dried in vacuo. The solid thus obtained was further purified by preparative HPLC using an aqueous ammonium acetate/acetonitrile gradient. Yield: 70 mg (60%). $^1$H NMR (400 MHz, DMSO-$d_6$) δ: 0.89 (d, 3H), 1.15 (d, 3H), 2.92 (d, 1H), 3.12 (t, 1H), 3.65-3.72 (m, 2H), 3.78-3.82 (m, 1H), 3.95 (d, 1H), 4.11 (d, 1H), 4.66 (dd, 1H), 4.73 (t, 1H), 5.04-5.10 (m, 1H), 6.59 (t, 1H), 7.64 (s, 1H), 11.65 (s, 1H), 11.83 (s, 1H). $^{19}$F NMR (376.5 MHz, DMSO-d6) δ: −130.45 (d), −133.57 (d), −158.12 (s). MS (ES) MH$^+$: 524.4 for $C_{22}H_{20}F_3N_5O_7$.

Example 52

(2R,4S,4aS)-8-((S)-4-Cyclopropyl-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

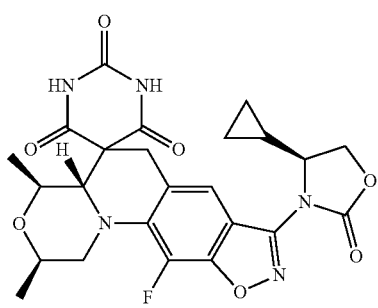 [SMILES: C[C@@H]1CN2c3c(cc4c(N5C(=O)OC[C@@H]5C5CC5)noc4c3F)CC3(C(=O)NC(=O)NC3=O)[C@H]2[C@H](C)O1]

A mixture of Intermediate 128 (1.0 g, 2.48 mmol), barbituric acid (0.04 g, 0.29 mmol) in 2-propanol (2 mL) was heated at 130° C. in a microwave oven over a period of 2 hours.

Volatiles were removed under vacuum and the residue was stirred in water (5 mL) for 10 min and filtered. This was suspended in methanol (2 mL) and water (5 mL) was added to that and filtered. Yield: 1.0 g (79%). $^1$H NMR (400 MHz, DMSO-$d_6$) δ: 0.28-0.30 (m, 1H), 0.42-0.44 (m, 1H), 0.52-0.57 (m, 2H), 0.89 (d, 3H), 1.15 (d, 3H), 2.94 (d, 1H), 3.12 (t, 1H), 3.62-3.69 (m, 2H), 3.73-3.82 (m, 1H), 3.95 (d, 1H), 4.11 (d, 1H), 4.19-4.21 (m, 1H), 4.23-4.28 (m, 1H), 4.66 (t, 2H), 7.53 (s, 1H), 11.48 (s, 1H), 11.84 (s, 1H). MS (ES) MH$^+$: 514.4 for $C_{24}H_{24}FN_5O_7$.

Examples 53 and 54

(2R,4S,4aS)-11-Fluoro-2,4-dimethyl-8-((R)-2-oxo-5-(pyridin-2-yl)oxazolidin-3-yl)-2,4,4a, 6-tetrahydro-1H,1'H-spiro[isoxazolo[4,5-g][1,4]oxazino[4,3-a] quinoline-5,5'-pyrimidine]-2',4',6'(3'H)-trione and (2R,4S,4aS)-11-fluoro-2,4-dimethyl-8-((S)-2-oxo-5-(pyridin-2-yl)oxazolidin-3-yl)-2,4,4a,6-tetrahydro-1H,1'H-spiro[isoxazolo[4,5-g][1,4]oxazino[4,3-a] quinoline-5,5'-pyrimidine]-2',4',6'(3'H)-trione

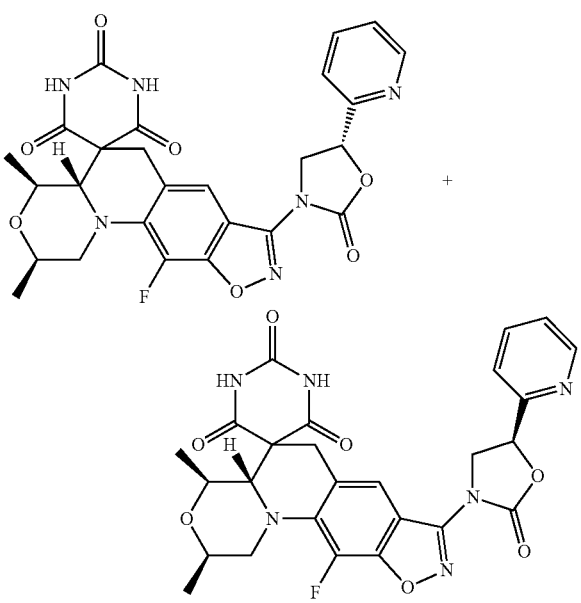

A mixture of Intermediate 133 (1.0 g, 2.27 mmol), barbituric acid (0.32 g, 2.50 mmol) in 2-propanol (10 mL) was heated at 130° C. in a microwave oven over a period of 2 hours. The volatiles were removed under vacuum and the residue was stirred in water (5 mL) for 10 minutes and filtered. The residue was purified in a Combi-Flash instrument using a gradient of methanol in chloroform. Yield: 1.0 g (80%). Chiral HPLC analysis showed that [Column: Chiralpak IC (250×4.6) mm Mobile Phase: Hexane:Ethanol (25:75)] presence of 45%+6%+5%+42% of the isomers. The two major isomers were separated by Chiral HPLC [Column: Chiralpak IC; Mobile Phase: Hexane:Ethanol (25:75)].

Example 53 was the first eluting diastereomer. $R_T$=8.98 min: $[\alpha]_D^{25}$=−197.07 (c=0.123; dimethylformamide). $^1$H NMR (400 MHz, DMSO-$d_6$) δ: 0.88 (d, 3H), 1.13 (d, 3H), 2.92 (d, 1H), 3.11 (t, 1H), 3.63-3.70 (m, 2H), 3.76-3.81 (m, 1H), 3.93 (d, 1H), 4.10 (d, 1H), 4.26 (dd, 1H), 4.54 (t, 1H), 5.95 (dd, 1H), 7.45 (ddd, 1H), 7.62 (d, 1H), 7.78 (s, 1H), 7.91 (dt, 1H), 8.65 (d, 1H), 11.40 (s, 1H), 11.80 (s, 1H). $^{19}$F NMR (376.5 MHz, DMSO-$d_6$) δ: −158.1 (s). Yield: 0.25 g. MS (ES) MH$^+$: 551.4 for $C_{26}H_{23}FN_6O_7$.

Example 54 was the second eluting diastereomer. $R_T$=17.50 min: $[\alpha]_D^{25}$=−109.13 (c=0.103; dimethylformamide). $^1$H NMR (400 MHz, DMSO-$d_6$) δ: 0.88 (d, 3H), 1.14 (d, 3H), 2.92 (d, 1H), 3.12 (t, 1H), 3.62-3.69 (m, 2H), 3.77-3.81 (m, 1H), 3.93 (d, 1H), 4.10 (d, 1H), 4.28 (dd, 1H), 4.52 (t, 1H), 5.95 (dd, 1H), 7.45 (ddd, 1H), 7.63 (d, 1H), 7.78 (s, 1H), 7.91 (dt, 1H), 8.64 (d, 1H), 11.40 (s, 1H), 11.80 (s, 1H). $^{19}$F NMR (376.5 MHz, DMSO-$d_6$) δ: −158.1 (s). Yield: 0.22 g. MS (ES) MH$^+$: 551.4 for $C_{26}H_{23}FN_6O_7$

Examples 55 and 56

(2R,4S,4aS)-11-Fluoro-2,4-dimethyl-8-((R)-2-oxo-4-(pyridin-2-yl)oxazolidin-3-yl)-2,4,4a, 6-tetrahydro-1H,1'H-spiro[isoxazolo[4,5-g][1,4]oxazino[4,3-g]quinoline-5,5'-pyrimidine]-2',4',6'(3'H)-trione and (2R,4S,4aS)-11-fluoro-2,4-dimethyl-8-((S)-2-oxo-4-(pyridin-2-yl)oxazolidin-3-yl)-2,4,4a, 6-tetrahydro-1H,1'H-spiro[isoxazolo[4,5-g][1,4]oxazino[4,3-a]quinoline-5,5'-pyrimidine]-2',4',6'(3'H)-trione

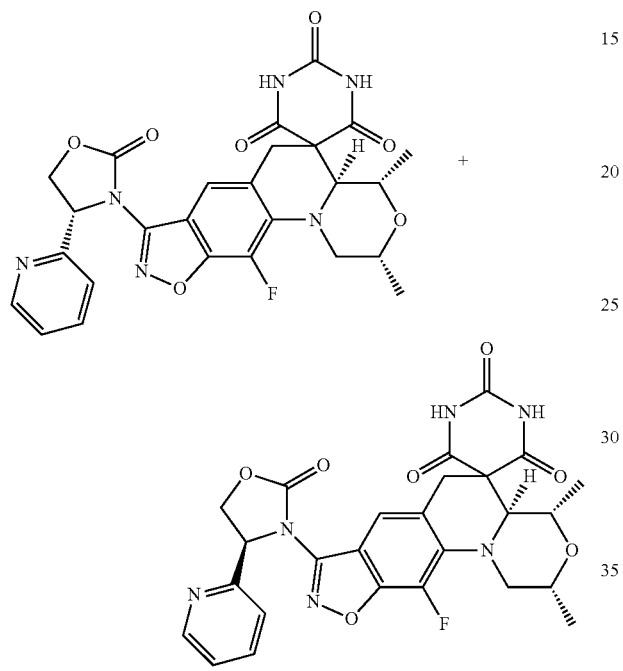

A mixture of Intermediate 138 (1.0 g, 2.27 mmol), barbituric acid (0.32 g, 2.50 mmol) in 2-propanol (10 mL) was heated at 130° C. in a microwave oven for 2 hours. The volatiles were removed under vacuum and the residue was stirred in water (5 mL) for 10 min and filtered. The residue was purified in a Combi-Flash instrument using a gradient of methanol in chloroform. Yield: 0.95 g (90%). Chiral HPLC analysis showed that [Column: Chiralpak IC (250×4.6) mm Mobile Phase: hexane:ethanol (25:75)] presence of 45%+6%+5%+42% of the isomers. The two major isomers were separated by Chiral HPLC [Column: Chiralpak IC; Mobile Phase: Hexane:Ethanol (25:75)].

Example 55 was the first eluting diastereomer. $R_T$=10.22 min: $[\alpha]_D^{25}$=−339.4 (c=0.10; dimethylformamide). $^1$H NMR (400 MHz, DMSO-d$_6$) δ: 0.88 (d, 3H), 1.12 (d, 3H), 2.91 (d, 1H), 3.09 (t, 1H), 3.60-3.67 (m, 2H), 3.71-3.76 (m, 1H), 3.93 (d, 1H), 4.09 (d, 1H), 4.35-4.43 (m, 1H), 4.94 (t, 1H), 5.72 (dd, 1H), 7.33-7.37 (m, 1H), 7.51 (d, 1H), 7.75 (s, 1H), 7.82 (dt, 1H), 8.54 (d, 1H), 11.48 (s, 1H), 11.83 (s, 1H). $^{19}$F NMR (376.5 MHz, DMSO-d$_6$) δ: −158.3 (s). Yield: 0.20 g. MS (ES) MH$^+$: 551.4 for $C_{26}H_{23}FN_6O_7$.

Example 56 was the second eluting diastereomer. $R_T$=6.67 min: $[\alpha]_D^{25}$=−109.13 (c=0.112; dimethylformamide). $^1$H NMR (400 MHz, DMSO-d$_6$) δ: 0.89 (d, 3H), 1.12 (d, 3H), 2.92 (d, 1H), 3.08 (t, 1H), 3.64-3.67 (m, 2H), 3.69-3.71 (m, 1H), 3.92 (d, 1H), 4.07 (d, 1H), 4.39-4.42 (m, 1H), 4.94 (t, 1H), 5.70 (dd, 1H), 7.33-7.36 (m, 1H), 7.49 (d, 1H), 7.72 (s, 1H), 7.82 (dt, 1H), 8.52 (d, 1H), 11.48 (s, 1H), 11.83 (s, 1H). $^{19}$F NMR (376.5 MHz, DMSO-d$_6$) δ: −158.2 (s). Yield: 0.22 g. MS (ES) MH$^+$: 551.4 for $C_{26}H_{23}FN_6O_7$.

Examples 57 and 58

(2R,4S,4aS)-11-Fluoro-2,4-dimethyl-8-((R)-2-oxo-4-(pyridin-4-yl)oxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione and (2R,4S,4aS)-11-fluoro-2,4-dimethyl-8-((S)-2-oxo-4-(pyridin-4-yl)oxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

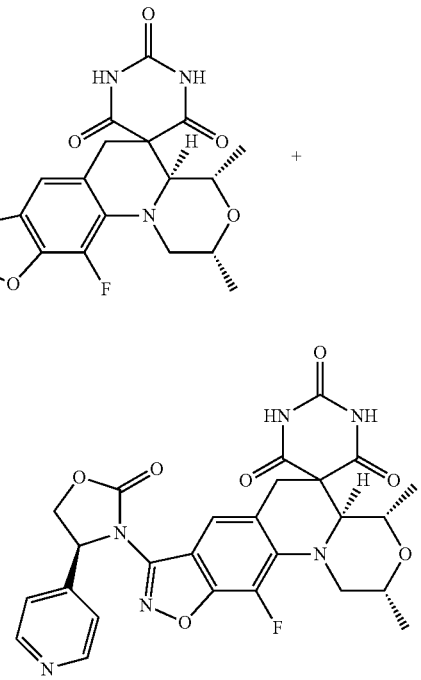

A mixture of Intermediate 143 (0.52 g, 1.18 mmol), barbituric acid (0.17 g, 1.3 mmol) in 2-propanol (5 mL) was heated at 130° C. in a microwave oven for 2 hours. The volatiles were removed under vacuum and the residue was stirred in water (5 mL) for 10 minutes and filtered. The residue was purified in a Combi-Flash instrument using a gradient of methanol in chloroform. Yield: 0.63 g (97%). Chiral HPLC analysis showed that [Column: Chiralpak IC (250×4.6) mm Mobile Phase: Hexane:Ethanol (50:50)] presence of 41%+5%+5%+44% of the isomers. The two major isomers were separated by Chiral HPLC [Column: Chiralpak IC; Mobile Phase: Hexane:Ethanol (25:75) with 0.1% diethylamine]: $^1$H NMR of the final compounds suggest that the samples contain a diethylamine impurity.

Example 57 was the first eluting diastereomer. $t_R$=7.61 min: $[\alpha]_D^{25}$=−130.1 (c=0.10; dimethylformamide). $^1$H NMR (400 MHz, DMSO-d$_6$) δ: 0.88 (d, 3H), 1.14 (d, 3H), 2.94 (d, 1H), 3.09 (t, 1H), 3.58-3.67 (m, 2H), 3.74-3.76 (m, 1H), 3.94 (d, 1H), 4.08 (d, 1H), 4.33 (dd, 1H), 4.98 (t, 1H), 5.69 (dd, 1H), 7.41 (d, 2H), 7.71 (s, 1H), 8.57 (dd, 2H). Note: Peaks corresponding to the NH protons did not appear. Yield: 0.81 g. MS (ES) MH$^+$: 551.4 for $C_{26}H_{23}FN_6O_7$.

Example 58 was the second eluting diastereomer. $t_R$=15.38 min: $[\alpha]_D^{25}$=−73.39 (c=0.112; dimethylformamide). $^1$H NMR (400 MHz, DMSO-d$_6$) δ: 0.89 (d, 3H), 1.13 (d, 3H), 2.92 (d, 1H), 3.08 (t, 1H), 3.62-3.66 (m, 2H), 3.67-3.69 (m, 1H), 3.93 (d, 1H), 4.06 (d, 1H), 4.32 (dd, 1H), 4.99 (t, 1H), 5.70 (dd, 1H), 7.39 (d, 2H), 7.70 (s, 1H), 8.55 (dd, 2H). Note: Peaks corresponding to the NH protons did not appear. Yield: 0.11 g. MS (ES) MH$^+$: 551.4 for $C_{26}H_{23}FN_6O_7$.

Example 59

(2R,4S,4aS)-11-Fluoro-8-((R)-4-((R)-1-methoxyethyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

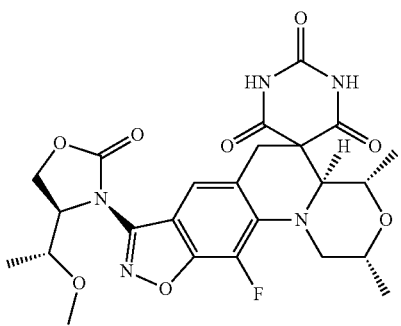

A mixture of Intermediate 149 (0.25 g, 0.59 mmol), barbituric acid (0.08 g, 0.59 mmol) in 2-propanol (9 mL) was heated in a microwave reactor at 130° C. over a period of 2 h. The volatiles were removed under vacuum and the residue was stirred in water (2 mL) for 10 min and filtered. Yield: 0.26 g (81%). UPLC showed the presence of 9:1 mixture of diastereomers and the major isomer has been separated by chiral HPLC using chiralpak IC [hexane:ethanol (70:30); $t_R$=8.67 min] and characterized. $^1$H NMR (400 MHz, DMSO-d$_6$) δ: 0.88 (d, 3H), 1.01 (d, 3H), 1.13 (d, 3H), 2.91 (d, 1H), 3.10 (t, 1H), 3.28 (s, 3H), 3.63-3.69 (m, 2H), 3.76-3.78 (m, 1H), 3.93 (d, 1H), 3.96-3.99 (m, 1H), 4.10 (d, 1H), 4.46-4.49 (m, 1H), 4.59 (t, 1H), 4.76-4.79 (m, 1H), 7.62 (s, 1H), 11.48 (s, 1H), 11.82 (s, 1H). $^{19}$F NMR (376.5 MHz, DMSO-d$_6$) δ: −158.11 (s). MS (ES) MH$^+$: 532.4 for $C_{24}H_{26}FN_5O_8$.

Example 60

(2R,4S,4aS)-11-Fluoro-8-((R)-4-((S)-1-methoxyethyl)-2-oxooxazolidin-3-yl)-2,4-dimethyl-2,4,4a,6-tetrahydro-1H,1'H-spiro[isoxazolo[4,5-g][1,4]oxazino[4,3-g]quinoline-5,5'-pyrimidine]-2',4',6'(3'H)-trione

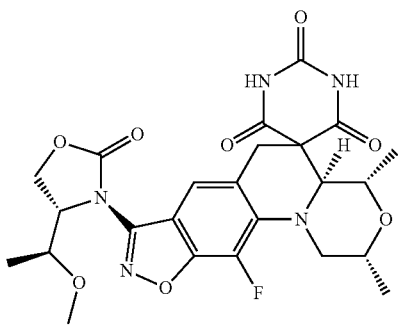

A mixture of Intermediate 156 (0.04 g, 0.1 mmol), barbituric acid (0.01 g, 0.1 mmol) in 2-propanol (1 mL) was heated in a microwave reactor at 130° C. over a period of 2 hours. Volatiles were removed under vacuum and the residue was stirred in water (0.5 mL) for 10 minutes and filtered. Yield: 0.05 g (98%). UPLC showed the presence of 61%+5%+18%+3% mixture of diastereomers and the major isomer (61%) has been separated by chiral HPLC using chiralpak IC column [hexane:ethanol (70:30); $t_R$=8.42 min] and characterized. $^1$H NMR (400 MHz, DMSO-d$_6$) δ: 0.89 (d, 3H), 1.10 (d, 3H), 1.15 (d, 3H), 2.91 (d, 1H), 3.12 (t, 1H), 3.15 (s, 3H), 3.63-3.70 (m, 2H), 3.76-3.80 (m, 1H), 3.93-3.99 (m, 2H), 4.11 (d, 1H), 4.51-4.26 (m, 3H), 7.65 (s, 1H), 11.44 (s, 1H), 11.78 (s, 1H). $^{19}$F NMR (376.5 MHz, DMSO-d$_6$) δ: −158.17 (s). MS (ES) MH$^+$: 532.5 for $C_{24}H_{26}FN_5O_8$ Examples 61 and 62

(2R,4S,4aS)-11-Fluoro-2,4-dimethyl-8-((R)-2-oxo-4-(pyrazin-2-yl)oxazolidin-3-yl)-2,4,4a,6-tetrahydro-1H,1'H-spiro[isoxazolo[4,5-g][1,4]oxazino[4,3-g]quinoline-5,5'-pyrimidine]-2',4',6'(3'H)-trione and (2R,4S,4aS)-11-fluoro-2,4-dimethyl-8-((S)-2-oxo-4-(pyrazin-2-yl)oxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

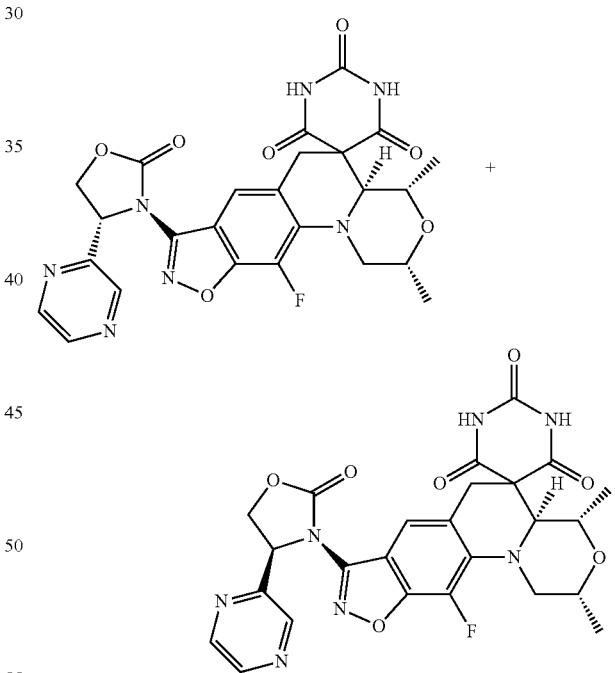

A mixture of Intermediate 166 (0.12 g, 0.27 mmol), barbituric acid (0.04 g, 0.27 mmol) in 2-propanol (1.5 mL) was heated at 130° C. in a microwave oven over a period of 2 hours. The volatiles were removed under vacuum and the residue was stirred in water (5 mL) for 10 min and filtered. Yield: 0.13 g (87%). Chiral HPLC analysis showed that [Column: Chiralpak IA (250×4.6) mm Mobile Phase: Hexane:Ethanol (40:60)] presence of 45%+6%+5%+42% of the isomers. The two major isomers were separated by Chiral HPLC [Column: Chiralpak IA; Mobile Phase: Hexane:Ethanol (40:60)].

Example 61 was the first eluting diastereomer. $t_R$=9.43 min: $[\alpha]_D^{25}$=−310.4 (c=0.2; MeOH). $^1$H NMR (400 MHz, DMSO-$d_6$) δ: 0.87 (d, 3H), 1.11 (d, 3H), 2.90 (d, 1H), 3.09 (t, 1H), 3.62-3.69 (m, 2H), 3.73-3.77 (m, 1H), 3.91 (d, 1H), 4.05 (d, 1H), 4.48 (dd, 1H), 4.94 (t, 1H), 5.80 (dd, 1H), 7.71 (s, 1H), 8.61-8.62 (m, 2H), 8.81 (s, 1H), 11.46 (s, 1H), 11.83 (s, 1H). $^{19}$F NMR (376.5 MHz, DMSO-$d_6$) δ: −158.25 (s). Yield: 0.04 g. MS (ES) MH$^+$: 552.5 for $C_{25}H_{22}FN_7O_7$.

Example 62 was the second eluting diastereomer. $t_R$=18.04 min: $[\alpha]_D^{25}$=−176.0 (c=0.2; MeOH). $^1$H NMR (400 MHz, DMSO-$d_6$) δ: 0.87 (d, 3H), 1.11 (d, 3H), 2.90 (d, 1H), 3.08 (t, 1H), 3.60-3.75 (m, 3H), 3.91 (d, 1H), 4.06 (d, 1H), 4.48 (dd, 1H), 4.95 (t, 1H), 5.81 (dd, 1H), 7.74 (s, 1H), 8.62 (s, 2H), 8.82 (s, 1H), 11.47 (br s, 1H), 11.81 (br s, 1H). $^{19}$F NMR (376.5 MHz, DMSO-$d_6$) δ: −158.15 (s). Yield: 0.05 g. MS (ES) MH$^+$: 552.5 for $C_{25}H_{22}FN_7O_7$ Examples 63 and 64

(2R,4S,4aS)-11-Fluoro-2,4-dimethyl-8-((R)-2-oxo-4-(pyrimidin-2-yl)oxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione and (2R,4S,4aS)-11-fluoro-2,4-dimethyl-8-((S)-2-oxo-4-(pyrimidin-2-yl)oxazolidin-3-yl)-2,4,4a,6-tetrahydro-1H,1'H-spiro[isoxazolo[4,5-g][1,4]oxazino[4,3-g]quinoline-5,5'-pyrimidine]-2',4',6'(3'H)-trione

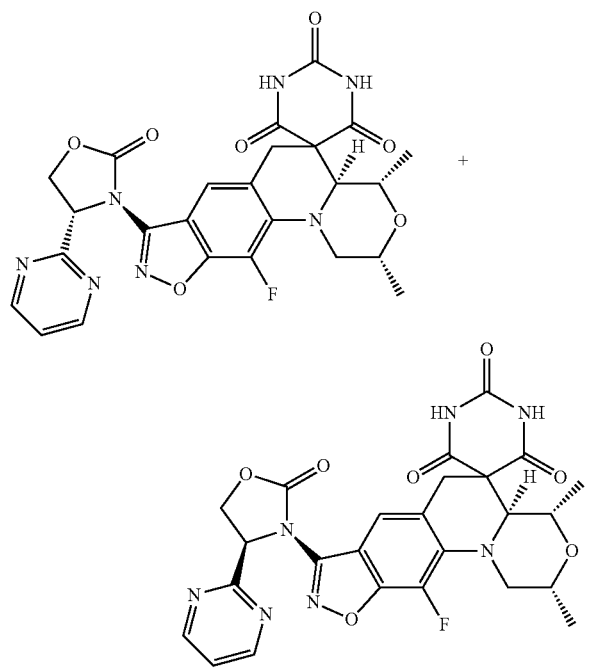

A mixture of Intermediate 171 (0.12 g, 0.27 mmol), barbituric acid (0.04 g, 0.27 mmol) in 2-propanol (1.5 mL) was heated at 130° C. in a microwave oven over a period of 2 hours. The volatiles were removed under vacuum and the residue was stirred in water (5 mL) for 10 minutes and filtered. Yield: 0.13 g (87%). Chiral HPLC analysis showed that [Column: Chiralpak IC (250×4.6) mm Mobile Phase: Hexane:Ethanol (70:30)] presence of 45%+6%+5%+42% of the isomers. The two major isomers were separated by Chiral HPLC [Column: Chiralpak IC; Mobile Phase: Hexane:Ethanol (70:30)].

Example 63 was the first eluting diastereomer. $t_R$=13.09 min: $[\alpha]_D^{25}$=−183.23 (c=0.31; MeOH). $^1$H NMR (400 MHz, DMSO-$d_6$) δ: 0.89 (d, 3H), 1.13 (d, 3H), 2.92 (d, 1H), 3.10 (t, 1H), 3.63-3.77 (m, 3H), 3.94 (d, 1H), 4.08 (d, 1H), 4.47 (dd, 1H), 5.01 (t, 1H), 5.71 (dd, 1H), 7.50 (t, 1H), 7.82 (s, 1H), 8.84 (d, 2H), 11.51 (s, 1H), 11.83 (s, 1H). $^{19}$F NMR (376.5 MHz, DMSO-$d_6$) δ: −158.30 (s). MS (ES) MH$^+$: 552.5 for $C_{25}H_{22}FN_7O_7$.

Example 64 was the second eluting diastereomer. $t_R$=30.80 min: $[\alpha]_D^{25}$=−112.25 (c=0.38; MeOH). $^1$H NMR (400 MHz, DMSO-$d_6$) δ: 0.89 (d, 3H), 1.13 (d, 3H), 2.94 (d, 1H), 3.10 (t, 1H), 3.64-3.79 (m, 3H), 3.94 (d, 1H), 4.07 (d, 1H), 4.31 (dd, 1H), 5.01 (t, 1H), 5.68 (dd, 1H), 7.49 (t, 1H), 7.75 (s, 1H), 8.82 (d, 2H), 11.46 (br s, 1H), 11.81 (br s, 1H). $^{19}$F NMR (376.5 MHz, DMSO-$d_6$) δ: −158.15 (s). MS (ES) MH$^+$: 552.5 for $C_{25}H_{22}FN_7O_7$.

Example 65

(2R,4S,4aS)-8-((S)-4-Ethynyl-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

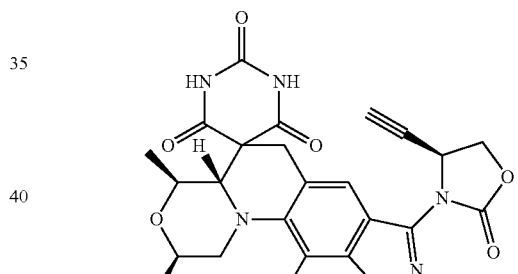

A mixture of Intermediate 176 (0.08 g, 0.21 mmol), barbituric acid (0.03 g, 0.21 mmol) in 2-propanol (2 mL) was heated at 130° C. in a microwave oven over a period of 2 hours. The volatiles were removed under vacuum and the residue was stirred in water (5 mL) for 10 minutes and filtered. This was suspended in methanol (0.5 mL) and water (5 mL) was added to that and filtered. Yield: 0.09 g (92%). Reverse phase HPLC analysis in Phenomenex Gemini C18 (250×4.6) mm, 5 μm [Mobile Phase 'A': 10 mM Ammonium acetate in water; Mobile Phase 'B': Acetonitrile; $t_R$=9.72 min] showed the presence of 7%+87% mixture of diastereomers and the major isomer has been separated by reverse phase HPLC [Phenomenex Gemini C18 (Mobile Phase 'A': 10 mM Ammonium acetate in water; Mobile Phase 'B': Acetonitrile)]. $^1$H NMR (400 MHz, DMSO-$d_6$) δ: 0.88 (d, 3H), 1.14 (d, 3H), 2.92 (d, 1H), 3.11 (t, 1H), 3.62 (d, 1H), 3.64-3.68 (m, 2H), 3.77-3.79 (m, 1H), 3.94 (d, 1H), 4.10 (d, 1H), 4.51 (dd, 1H), 4.80 (t, 1H), 5.35-5.39 (m, 1H), 7.59 (s, 1H), 11.45 (s, 1H), 11.82 (s, 1H). MS (ES) MH$^+$: 498.4 for $C_{23}H_{20}FN_5O_7$.

Example 66

(2R,4S,4aS)-11-Chloro-2,4-dimethyl-8-((S)-4-methyl-2-oxooxazolidin-3-yl)-2,4,4a,6-tetrahydro-1H,1'H-spiro[isoxazolo[4,5-g][1,4]oxazino[4,3-g]quinoline-5,5'-pyrimidine]-2',4',6'(3'H)-trione

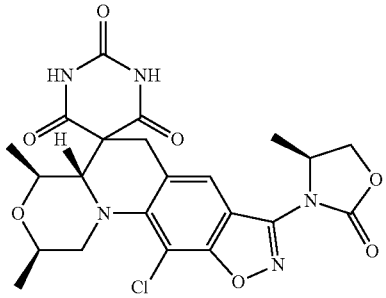 [SMILES: C[C@@H]1CN2c3c(cc4c(N5C(=O)OC[C@@H]5C)noc4c3Cl)CC3(C(=O)NC(=O)NC3=O)[C@H]2[C@H](C)O1]

Example 66 was synthesized following the procedure described for the preparation of Example 2 using Intermediate 177. The title compound was obtained by chromatography on silica gel (50% Ethyl acetate in hexanes) to isolate the major eluting component, which was further purified by Super Critical Fluid Chromatography (Chiralpak IA column) to isolate the major eluting component. $^1$H NMR (300 MHz, DMSO-$d_6$) δ: 0.9 (d, 3H) 1.2 (d, 3H) 1.4 (d, 3H) 2.9-3.15 (m, 2H) 3.5-3.7 (m, 2H) 3.9-4.1 (m, 2H) 4.1-4.25 (m, 1H) 4.4-4.8 (m, 3H) 7.7 (s, 1H) 11.4 (s, 1H) 11.8 (s, 1H). MS (ES) MH$^+$: 504 for $C_{22}H_{22}ClN_6O_7$.

Example 67

(2R,4S,4aS)-11-Fluoro-8-[(4S)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

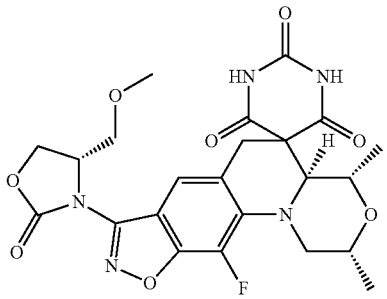 [SMILES: COC[C@H]1COC(=O)N1c1noc2c(F)c3c(cc12)CC1(C(=O)NC(=O)NC1=O)[C@H]1[C@H](C)O[C@H](C)CN31]

A stirred solution of Intermediate 40 (0.67 g, 1.5 mmol) and barbituric acid (0.21 g, 1.6 mmol) in acetic acid (10 mL) was heated to 95° C. for 4 hours. The solvents were evaporated and the residue was dissolved in methanol (2 mL). Water (5 mL) was added to precipitate solids that were collected and chromatographed by chiral HPLC [Chiralpak IC (250×4.6) mm; hexane:ethanol (80:20); 1.0 ml\min] to separate the title compound as the second eluting component. $^1$H NMR (400 MHz, DMSO-$d_6$) δ: 0.9 (d, 3H), 1.1 (d, 3H), 2.9 (d, 1H), 3.1 (t, 1H), 3.25 (s, 3H), 3.5 (d, 1H), 3.6-3.7 (m, 2H), 3.85 (m, 1H), 3.85-3.9 (d, 1H), 3.9 (d, 1H), 4.1 (d, 1H), 4.45-4.5 (m, 1H), 4.6-4.7 (m, 2H), 7.65 (s, 1H), 11.5 (s, 1H), 11.8 (s, 1H). MS (ES) MH$^+$: 518.4 for $C_{23}H_{24}FN_5O_8$; $[\alpha]_D^{20}$=−93.8 (c=1.14; MeOH), $R_T$=20.7 min.

Also isolated in the synthesis of Example 67 was (2S,4R,4aR)-11-fluoro-8-[(4S)-4-(methoxymethyl)-2-oxo-1,3-oxazolidin-3-yl]-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione (first eluting component from chiral HPLC purification):

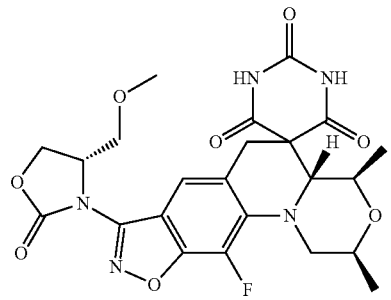 [SMILES: COC[C@H]1COC(=O)N1c1noc2c(F)c3c(cc12)CC1(C(=O)NC(=O)NC1=O)[C@@H]1[C@@H](C)O[C@@H](C)CN31]

$^1$H NMR (400 MHz, DMSO-$d_6$) δ: 0.9 (d, 3H), 1.1 (d, 3H), 2.9 (d, 1H), 3.1 (t, 1H), 3.2 (s, 3H), 3.5 (d, 1H), 3.6-3.7 (m, 2H), 3.85 (m, 1H), 3.85-3.9 (d, 1H), 3.9 (d, 1H), 4.1 (d, 1H), 4.45-4.5 (m, 1H), 4.6-4.65 (m, 2H), 7.7 (s, 1H), 11.5 (s, 1H), 11.8 (s, 1H). MS (ES) MH$^+$: 518.4 for $C_{23}H_{24}FN_5O_8$; $[\alpha]_D^{20}$=+159.4 (c=1.04; MeOH), $R_T$=17.8 min.

Example 68

(2R,4S,4aS)-11-Fluoro-2,4-dimethyl-8-((S)-4-(1-methyl-1H-1,2,4-triazol-5-yl)-2-oxooxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

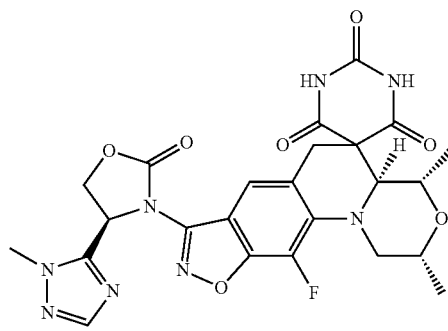

Example 68 was synthesized following the procedure described for the preparation of Example 2 using Intermediate 183. The title compound was obtained by SFC purification using a Chiralpak OJ (250×4.6 mm) column (Carbon dioxide:Ethanol (75:25); 1.0 mL/min). $^1$H NMR (400 MHz, DMSO-$d_6$) δ 0.9 (d, 3H), 1.1 (d, 3H), 2.9 (d, 1H), 3.15 (m, 1H) 3.5-3.8 (m, 3H), 3.8-4.2 (m, 5H), 4.55 (dd, 1H), 4.8-5.1 (m, 1H), 5.0 (dd, 1H), 7.7 (s, 1H), 7.9 (s, 1H) 11.4 (s, 1H), 11.8 (s, 1H). MS (ES) MH$^+$: 558 for $C_{24}H_{23}FN_8O_7$.

Example 69

(2R,4S,4aS)-11-Fluoro-2,4-dimethyl-8-((R)-4-(1-methyl-1H-1,2,4-triazol-5-yl)-2-oxooxazolidin-3-yl)-2,4,4a,6-tetrahydro-1H,1'H-spiro[isoxazolo[4,5-g][1,4]oxazino[4,3-a]quinoline-5,5'-pyrimidine]-2',4',6'(3'H)-trione

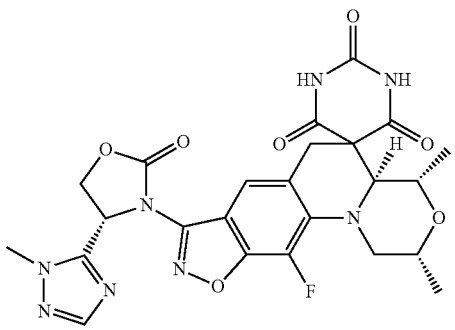

Example 69 was synthesized following the procedure described for the preparation of Example 2 using Intermediate 189. The title compound was obtained by SFC purification using Chiralpak OJ (250×4.6 mm) column (Carbon dioxide:Ethanol (75:25); 1.0 ml\min). $^1$H NMR (400 MHz, DMSO-$d_6$) δ 0.9 (d, 3H), 1.1 (d, 3H), 2.9 (d, 1H), 3.15 (m, 1H) 3.5-3.8 (m, 3H), 3.8-4.2 (m, 5H), 4.55 (dd, 1H), 4.8-5.1 (m, 1H), 6.0 (dd, 1H), 7.7 (s, 1H), 7.9 (s, 1H) 11.4 (s, 1H), 11.8 (s, 1H). MS (ES) MH$^+$: 558 for $C_{24}H_{23}FN_8O_7$.

Example 70

(2R,4S,4aS)-11-Fluoro-8-((R)-4-((S)-1-hydroxyethyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

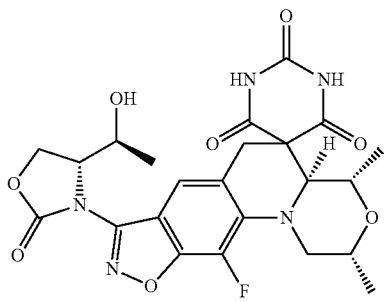 [SMILES: C[C@@H]1CN2c3c(cc4c(N5C(=O)OC[C@@H]5[C@H](C)O)noc4c3F)CC3(C(=O)NC(=O)NC3=O)[C@H]2[C@H](C)O1]

A mixture of Intermediate 198 (0.12 g, 0.30 mmol) and barbituric acid (0.04 g, 0.30 mmol) in 2-propanol (2 mL) was heated in a microwave reactor at 130° C. over a period of 2 hours. The volatiles were removed under vacuum and the residue was stirred in water (0.5 mL) for 10 min and filtered. Yield: 0.05 g (61%) $^1$H NMR (400 MHz, DMSO-$d_6$) δ: 0.89 (d, 3H), 1.04 (d, 3H), 1.14 (d, 3H), 2.92 (d, 1H), 3.10 (t, 1H), 3.59-3.69 (m, 2H), 3.77-3.78 (m, 1H), 3.94 (d, 1H), 4.10 (d, 1H), 4.32 (quin, 1H), 4.45-4.49 (m, 1H), 4.53-4.55 (m, 2H), 5.29 (d, 1H), 7.73 (s, 1H), 11.83 (br s, 2H). $^{19}$F NMR (376.5 MHz, DMSO-$d_6$) δ: −158.38 (s). MS (ES) MH$^+$: 518.3 for $C_{23}H_{24}FN_6O_8$.

Example 71

{(4S)-3-[(2R,4S,4aS)-11-Fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-2-oxo-1,3-oxazolidin-4-yl}acetonitrile

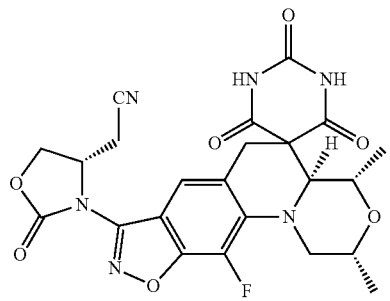 [SMILES: C[C@@H]1CN2c3c(cc4c(N5C(=O)OC[C@@H]5CC#N)noc4c3F)CC3(C(=O)NC(=O)NC3=O)[C@H]2[C@H](C)O1]

To a stirred solution of Intermediate 200 (0.1 g, 0.23 mmol) in isopropyl alcohol (5 mL), barbituric acid (0.03 g, 0.25 mmol) was added and the mixture was stirred at 95° C. for 16 hours. The volatiles were removed completely under vacuum and water (5 mL) was added to the residue and filtered. Yield: 0.10 g (77%). Chiral HPLC analysis [column: chiralcel OD-H, eluant: hexane:ethanol (50:50)] showed that it is a mixture of four isomer in the ratio of 33:45:17:5. The isomer with the ration of 33% has been separated by chiral HPLC [Column: chiralcel OD-H, eluant: hexane:ethanol (50:50)] and identified as Example 71. $^1$H NMR (400 MHz, DMSO-$d_6$) δ: 0.89 (d, 3H), 1.15 (d, 3H), 2.92 (d, 1H), 3.12-3.19 (m, 2H), 3.39-3.40 (m, 1H), 3.65-3.70 (m, 2H), 3.74-3.78 (m, 1H), 3.94 (d, 1H), 4.10 (d, 1H), 4.44 (dd, 1H), 4.78 (t, 1H), 4.87-4.89 (m, 1H), 7.69 (s, 1H), 11.47 (s, 1H), 11.83 (s, 1H). MS (ES) MH$^+$: 513.2 for $C_{23}H_{21}FN_6O_7$.

Example 72

(2R,4S,4aS)-8-((R)-4-((R)-1,2-Dihydroxyethyl)-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

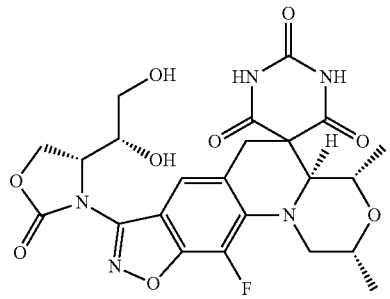 [SMILES: C[C@@H]1CN2c3c(cc4c(N5C(=O)OC[C@@H]5[C@@H](O)CO)noc4c3F)CC3(C(=O)NC(=O)NC3=O)[C@H]2[C@H](C)O1]

To a stirred solution of Intermediate 201 (0.35 g, 0.75 mmol) in ethanol (4 mL), barbituric acid (0.19 g, 14.9 mmol)

and 2 N hydrochloric acid (4 mL) were added and the mixture was heated in a microwave reactor at 120° C. for 2 hours. The volatiles were removed completely under vacuum, water (3 mL) was added and solid was filtered to afford the title compound. Yield: 0.35 g (88%) Note: Chiral HPLC analysis [Column: Chiralpak AD-H (250×4.6) mm; Mobile Phase: Hexane:Ethanol (70:30)] showed that the reaction mixture was 89% de. The major isomer (Example 72) was separated by chiral HPLC [Column: Chiralpak AD-H; Mobile Phase: Hexane:Ethanol (70:30)]. $^1$HNMR (400 MHz, DMSO-$d_6$) δ: 0.88 (d, 3H), 1.13 (d, 3H), 2.92 (d, 1H), 3.10 (t, 1H), 3.34-3.40 (m, 2H), 3.62-3.68 (m, 2H), 3.75-3.79 (m, 1H), 3.92 (d, 1H), 4.09 (d, 1H), 4.18 (q, 1H), 4.48-4.53 (m, 1H), 4.56-4.59 (m, 1H), 4.69-4.73 (m, 1H), 4.84 (t, 1H), 5.40 (q, 1H), 7.72 (s, 1H), 11.44 (s, 1H), 11.82 (s, 1H). MS (ES) MH$^+$: 534.2 for $C_{23}H_{24}FN_5O_9$.

Example 73

(2R,4S,4aS)-8-((R)-4-((S)-1,2-Dihydroxyethyl)-2-oxooxazolidin-3-yl)-11-fluoro-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

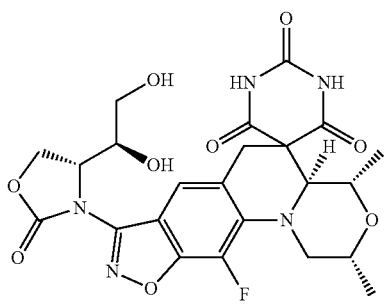

Example 73 was synthesized following the procedure described for the preparation of Example 72 using Intermediate 202 (0.40 g, 0.85 mmol). The product was obtained after subjected to reverse phase HPLC purification by ammonium acetate method. Yield: 0.25 g (54%). Note: Chiral HPLC analysis [Column: Chiralpak AD-H (250×4.6) mm; Mobile Phase: hexane:ethanol (70:30)] showed that the reaction produced a mixture of the compound in 58% de. Both the major (Example 73) and minor isomers were separated by chiral HPLC.

The major isomer (Example 73) was the second eluting diastereomer: RT=9.99 min. $^1$HNMR (400 MHz, DMSO-$d_6$) δ: 0.88 (d, 3H), 1.13 (d, 3H), 2.92 (d, 1H), 3.10 (t, 1H), 3.32-3.44 (m, 2H), 3.64-3.68 (m, 2H), 3.76-3.80 (m, 1H), 3.93 (d, 1H), 4.10 (d, 1H), 4.19 (q, 1H), 4.49-4.53 (m, 1H), 4.56-4.60 (m, 1H), 4.70-4.73 (m, 1H), 4.84 (t, 1H), 5.40 (q, 1H), 7.72 (s, 1H), 11.43 (s, 1H), 11.81 (s, 1H). MS (ES) MH$^+$: 534.2 for $C_{23}H_{24}FN_5O_9$.

Example 74

(2R,4S,4aS)-11-fluoro-8-{(4S)-4-[(hydroxyimino)methyl]-2-oxo-1,3-oxazolidin-3-yl}-2,4-dimethyl-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

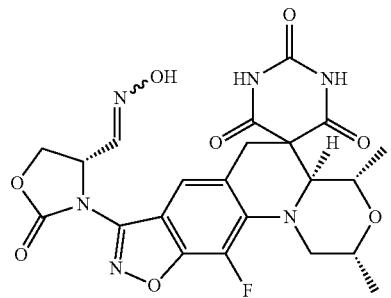 [SMILES: C[C@@H]1CN2c3c(cc4c(N5C(=O)OC[C@@H]5C=NO)noc4c3F)CC3(C(=O)NC(=O)NC3=O)[C@H]2[C@H](C)O1]

To a solution of Intermediate 91 (0.15 g, 0.3 mmol) in acetic acid (10 mL), barbituric acid (0.05 g, 0.4 mmol) was added and the mixture was heated at 95° C. for 3 hours. The volatiles were removed completely under vacuum, water (4 mL) was added to the residue and the solution was filtered. The solid thus obtained was further purified by silica gel column chromatography using a gradient of chloroform in methanol. The compound was obtained as an undefined mixture of E & Z isomers (1:0.65 is the ratio). Yield: 0.06 g (34%). $^1$HNMR (400 MHz, DMSO-$d_6$) δ: 0.89 (d, 3H), 1.14 (d, 3H), 2.93 (d, 1H), 3.11 (t, 1H), 3.65-3.80 (m, 3H), 3.94 (d, 1H), 4.10 (d, 1H), 4.30-4.32 & 4.47-4.51 (m, 1H), 4.76 & 4.88 (t, 1H), 5.24-5.30 & 5.48-5.55 (m, 1H), 7.10-7.14 & 7.51-7.75 (m, 2H), 11.28 & 11.48 (s, 1H), 11.45 (s, 1H), 11.85 (s, 1H). MS (ES) MH$^+$: 517.3 for $C_{22}H_{21}FN_6O_8$.

Examples 75 and 76

(5R)-3-[(2R,4S,4aS)-11-Fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-2-oxo-1,3-oxazolidine-5-carbonitrile and (5S)-3-[(2R,4S,4aS)-11-fluoro-2,4-dimethyl-2',4',6'-trioxo-1,1',2,3',4,4',4a,6'-octahydro-2'H,6H-spiro[1,4-oxazino[4,3-a][1,2]oxazolo[4,5-g]quinoline-5,5'-pyrimidin]-8-yl]-2-oxo-1,3-oxazolidine-5-carbonitrile

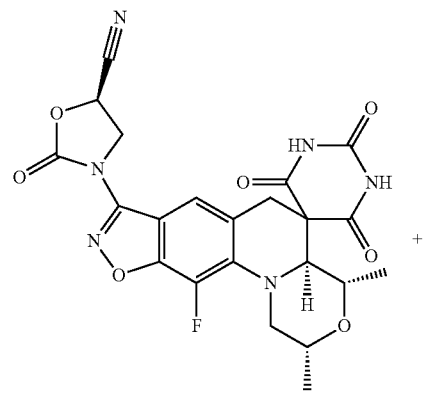

+

-continued

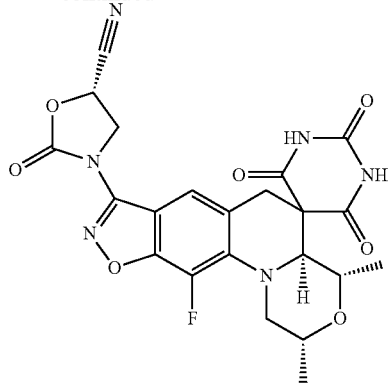

To a solution of Intermediate 203 (0.13 g, 0.3 mmol) in acetic acid (5 mL), barbituric acid (0.04 g, 0.3 mmol) was added and the mixture was heated at 95° C. for 3 hours. The volatiles were removed completely under vacuum and water (2 mL) was added to the residue and the solution was filtered. HPLC analysis [Column Xbridge C18 (150 mm×4.6 mm) 3.5µ, mobile phase: 10 mM ammonium acetate in water and methanol] showed that the reaction produced a 1:1 mixture of isomers, which were separated by reverse phase HPLC (Xbridge C18; mobile phase: 10 mM ammonium acetate in water and methanol). Yield: 0.03 g (34%).

Example 75 (Less polar isomer): $^1$HNMR (400 MHz, DMSO-$d_6$) δ: 0.88 (d, 3H), 1.13 (d, 3H), 2.88 (d, 1H), 3.10 (t, 1H), 3.58-3.68 (m, 2H), 3.76-3.82 (m, 1H), 3.94 (d, 1H), 4.10 (d, 1H), 4.31-4.35 (m, 1H), 4.45 (t, 1H), 5.88 (dd, 1H), 7.67 (s, 1H), 11.60 (br s, 2H). MS (ES) MH$^+$: 499.3 for $C_{22}H_{19}FN_6O_7$.

Example 76 (More polar isomer): $^1$HNMR (400 MHz, DMSO-$d_6$) δ: 0.88 (d, 3H), 1.13 (d, 3H), 2.90 (d, 1H), 3.11 (t, 1H), 3.64-3.70 (m, 2H), 3.74-3.80 (m, 1H), 3.93 (d, 1H), 4.09 (d, 1H), 4.30-4.34 (m, 1H), 4.47 (t, 1H), 5.89 (dd, 1H), 7.67 (s, 1H), 11.44 (s, 1H), 11.81 (s, 1H). MS (ES) MH$^+$: 499.3 for $C_{22}H_{19}FN_6O_7$.

Example 77

(2R,4S,4aS)-11-fluoro-8-((R)-4-((R)-1-hydroxyethyl)-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

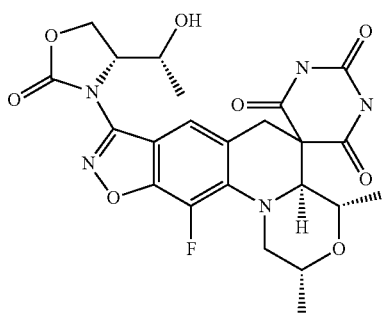

A mixture of Intermediate 211 (0.07 g, 0.17 mmol) and barbituric acid (0.02 g, 0.17 mmol) in 2-propanol (1 mL) was heated in a microwave reactor at 130° C. over a period of 2 hours. The volatiles were removed under vacuum and the residue was stirred in water (0.5 mL) for 10 min and filtered. Yield: 0.08 g (90%). $^1$H NMR (400 MHz, DMSO-$d_6$) δ: 0.89 (d, 3H), 0.98 (d, 3H), 1.15 (d, 3H), 2.92 (d, 1H), 3.12 (t, 1H), 3.64-3.69 (m, 2H), 3.75-3.78 (m, 1H), 3.93 (d, 1H), 4.10 (d, 1H), 4.29 (br s, 1H), 4.52-4.60 (m, 3H), 5.27 (d, 1H), 7.64 (s, 1H), 11.49 (s, 1H), 11.83 (s, 1H). $^{19}$F NMR (376.5 MHz, DMSO-$d_6$) δ: −158.15 (s). MS (ES) MH$^+$: 518.4 for $C_{23}H_{24}FN_5O_8$.

Example 78

(2R,4S,4aS)-11-Fluoro-8-((4R,5R)-4-(fluoromethyl)-5-methyl-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

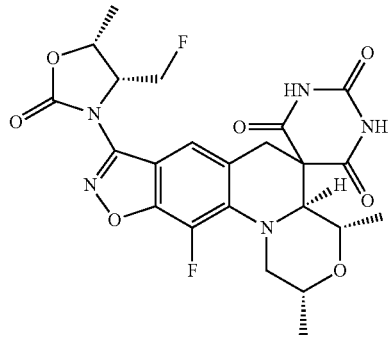 [SMILES: C[C@@H]1CN2c3c(cc4c(N5C(=O)O[C@H](C)[C@@H]5CF)noc4c3F)CC3(C(=O)NC(=O)NC3=O)[C@H]2[C@H](C)O1]

A mixture of Intermediate 216 (0.03 g, 0.06 mmol) and barbituric acid (0.008 g, 0.06 mmol) in 2-propanol (0.5 mL) was heated at 130° C. in a microwave reactor over a period of 2 hours. Volatiles were removed under vacuum and the residue was stirred in water (1 mL) for 10 minutes and filtered. This was suspended in methanol (0.5 mL), water (1 mL) was added to that and filtered. Yield: 0.03 g (81%). $^1$H NMR (400 MHz, DMSO-$d_6$) δ: 0.89 (d, 3H), 1.15 (d, 3H), 1.51 (d, 3H), 2.93 (d, 1H), 3.12 (t, 1H), 3.65-3.70 (m, 2H), 3.77-3.78 (m, 1H), 3.95 (d, 1H), 4.11 (d, 1H), 4.35-4.58 (m, 1H), 4.71 (dd, 1H), 4.86-4.89 (m, 1H), 4.99-5.01 (m, 1H), 7.63 (5, 1H), 11.46 (5, 1H), 11.82 (5, 1H). MS (ES) MH$^+$: 520.5 for $C_{23}H_{23}F_2N_6O_7$.

Examples 79 and 80

(2R,4S,4aS)-11-fluoro-8-((4S,5R)-4-(methoxymethyl)-5-methyl-2-oxooxazolidin-3-yl)-2,4-dimethyl-2,4,4a,6-tetrahydro-1H,1'H-spiro[isoxazolo[4,5-g][1,4]oxazino[4,3-g]quinoline-5,5'-pyrimidine]-2',4',6'(3'H)-trione and (2R,4S,4aS)-11-fluoro-8-((4R,5R)-4-(methoxymethyl)-5-methyl-2-oxooxazolidin-3-yl)-2,4-dimethyl-2,4,4a,6-tetrahydro-1H,1'H-spiro[isoxazolo[4,5-g][1,4]oxazino[4,3-a]quinoline-5,5'-pyrimidine]-2',4',6'(3'H)-trione

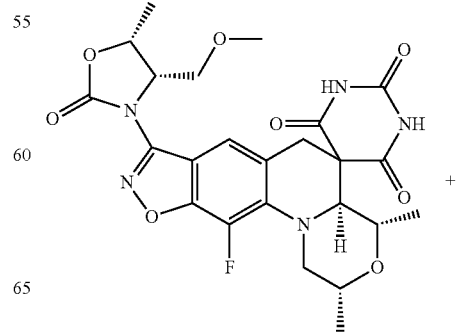

-continued

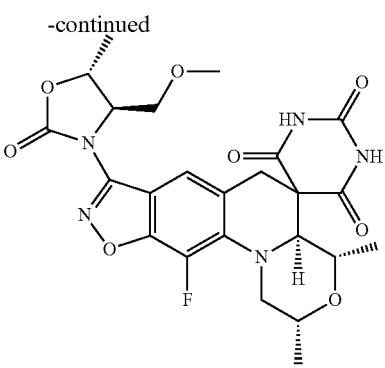

A mixture of Intermediate 221 (0.28 g, 0.67 mmol), barbituric acid (0.09 g, 0.67 mmol) in 2-propanol (5 mL) was heated at 130° C. in a microwave oven over a period of 2 hours. The volatiles were removed under vacuum and the residue was stirred in water (5 mL) for 10 minutes and filtered. The product was suspended in methanol (0.5 mL) and water (5 mL) was added to that and filtered. Yield: 0.34 g (96%). Chiral HPLC [Column: Chiralpak IA (250×4.6) mm, Mobile Phase: 0.1% diethylamine in Hexane:Ethanol (50:50] showed the presence of 17%+51% of diastereomers. These peaks have been separated by reverse phase HPLC [Chiralpak IA; Mobile Phase: 0.1% diethylamine in Hexane: Ethanol (50:50)].

Example 79 (first eluting diastereomer): $t_R$=6.53 min; $[\alpha]_D^{25}$=−121.46 (c=0.22; MeOH $^1$H NMR (400 MHz, DMSO-$d_6$) δ: 0.88 (d, 3H), 1.13 (d, 3H), 1.46 (d, 3H), 2.88 (d, 1H), 3.09 (t, 1H), 3.19 (s, 3H), 3.56-3.59 (m, 2H), 3.67 (t, 1H), 3.74-3.77 (m, 1H), 3.85-3.88 (m, 1H), 3.93-3.95 (m, 1H), 4.09 (d, 1H), 4.55 (s, 1H), 5.02 (t, 1H), 7.66 (s, 1H), 11.40 (br s, 2H). $^{19}$F NMR (376.5 MHz, DMSO-$d_6$) δ: −158.49 (s). MS (ES) MH$^+$: 532.5 for $C_{24}H_{26}FN_5O_8$.

Example 80 (second eluting diastereomer): $t_R$=8.22 min; $[\alpha]_D^{25}$=−129.17 (c=0.30; MeOH). $^1$H NMR (400 MHz, DMSO-$d_6$) δ: 0.89 (d, 3H), 1.14 (d, 3H), 1.45 (d, 3H), 2.90 (d, 1H), 3.12 (t, 1H), 3.22 (s, 3H), 3.55-3.62 (m, 2H), 3.66 (t, 1H), 3.77-3.78 (m, 1H), 3.82-3.86 (m, 1H), 3.92-3.94 (m, 1H), 4.10 (d, 1H), 4.23 (s, 1H), 4.76 (t, 1H), 7.61 (s, 1H), 11.18 (br s, 2H). $^{19}$F NMR (376.5 MHz, DMSO-$d_6$) δ: −158.21 (s). MS (ES) MH$^+$: 532.5 for $C_{24}H_{26}FN_5O_8$.

Biological Activity

Compounds of Formula (I) inhibit bacterial DNA gyrase and are therefore of interest for their antibacterial effects. The compounds are active against Gram-positive, Gram-negative and atypical bacteria. These properties may be assessed using, for example, the assays described below.

Susceptibility Testing (MIC)—Assay 1 Minimum Inhibitory Concentrations (MICs) were determined by the broth microdilution method in accordance with the Clinical and Laboratory Standards Institute (CLSI) guidelines. In brief, organism suspensions were adjusted to a 0.5 McFarland standard to yield a final inoculum between $3 \times 10^5$ and $7 \times 10^5$ colony-forming units (CFU)/mL. Bacterial inocula were prepared for most organisms in sterile, cation adjusted Mueller-Hinton Broth (Beckton Dickinson). The streptococci were prepared as above in cation adjusted Mueller-Hinton Broth to which 2.5% lysed horse blood (Hema Resource & Supply Inc.) was added. An inoculum volume of 100 μL was added to wells (using a Tecan EVO robot) containing 2 μL of DMSO containing 2-fold serial dilutions of drug. All inoculated microdilution trays were incubated in ambient air at 35° C. for 18-24 hours. Following incubation, the lowest concentration of the drug that prevented visible growth as read at OD600 nm and confirmed by a visual read using a test reading mirror was recorded as the MIC. Performance of the assay was monitored by the use of laboratory quality-control strains and commercially available control compounds with defined MIC spectrums, in accordance with CLSI guidelines. Table 1 provides the MIC results (μM) of Examples 1-77 tested in Assay 1. Table 2 provides the MIC (μg/mL) results of Examples 78-80 tested in Assay 1.

TABLE 1

| Example | Spy$^a$ MIC (μM) | Spn$^b$ MIC (μM) | Spn$^c$ MIC (μM) | Sau$^d$ MIC (μM) | Sau$^e$ MIC (μM) | Sau$^f$ MIC (μM) |
|---|---|---|---|---|---|---|
| 1 | 0.39 | 0.78 | 0.78 | 0.39 | 3.1 | 0.78 |
| 2 | 3.1 | 12 | 3.1 | 3.1 | 12 | 6.2 |
| 3 | 0.78 | 1.6 | 1.6 | 0.39 | 1.6 | 1.6 |
| 4 | 0.36 | 0.42 | 0.46 | 0.25 | 0.67 | 0.47 |
| 5 | 0.36 | 0.39 | 0.46 | 0.36 | 0.78 | 0.71 |
| 6 | 3.1 | 6.2 | 3.1 | 1.6 | 6.2 | 12 |
| 7 | 6.2 | 25 | 12 | 6.2 | 12 | 25 |
| 8 | 12 | 50 | 50 | 6.2 | 12 | 200 |
| 9 | 0.78 | 1.6 | 1.6 | 0.78 | 0.78 | 12 |
| 10 | 25 | 50 | 50 | 6.2 | 12 | 200 |
| 11 | 3.1 | 3.1 | 3.1 | 1.6 | 1.6 | 25 |
| 12 | 3.1 | 6.2 | 6.2 | 1.6 | 3.1 | 25 |
| 13 | 0.39 | 0.78 | 0.78 | 0.39 | 0.78 | 0.78 |
| 14 | 0.78 | 0.78 | 0.78 | 0.39 | 0.78 | 1.6 |
| 15 | <0.20 | 0.28 | 0.39 | 0.28 | 0.78 | 0.39 |
| 16 | 0.39 | 0.39 | 0.39 | 0.39 | 1.6 | 1.6 |
| 17 | 0.55 | 0.55 | 0.55 | 0.28 | 0.78 | 0.39 |
| 18 | 12 | 3.1 | 6.2 | 3.1 | 6.2 | 12 |
| 19 | <0.20 | <0.20 | 0.24 | 0.14 | 0.78 | 0.28 |
| 20 | 0.28 | 0.28 | 0.28 | 0.28 | 1.1 | 0.39 |
| 21 | 0.78 | 1.6 | 1.6 | 0.78 | 3.1 | 3.1 |
| 22 | 0.39 | 0.39 | 0.39 | <0.20 | 0.78 | 0.78 |
| 23 | 0.39 | 0.78 | 0.78 | 0.39 | 0.78 | 0.78 |
| 24 | 0.78 | 1.6 | 1.6 | 0.39 | 1.6 | 1.6 |
| 25 | 0.78 | 0.78 | 0.78 | 0.39 | 0.39 | 1.6 |
| 26 | <0.20 | 0.28 | 0.55 | 2.2 | 12 | 1.6 |
| 27 | 0.78 | 0.78 | 0.78 | 0.78 | 3.1 | 1.6 |
| 28 | 25 | 25 | 25 | 25 | 50 | 50 |
| 29 | 0.39 | 0.39 | 0.78 | 3.1 | 12 | 3.1 |
| 30 | 0.39 | 0.39 | 0.39 | <0.20 | 0.78 | 0.78 |
| 31 | 0.39 | 0.78 | 0.78 | 3.1 | 12 | 3.1 |
| 32 | <0.20 | 0.39 | 0.39 | <0.20 | 0.78 | 0.39 |
| 33 | 0.39 | 0.39 | 0.39 | 3.1 | 12 | 6.2 |
| 34 | 0.39 | 0.39 | 0.39 | <0.20 | 0.78 | 1.6 |
| 35 | 0.2 | 0.39 | 0.39 | <0.20 | 1.6 | 0.39 |
| 36 | 0.78 | 1.6 | 1.6 | 0.78 | 3.1 | 1.6 |
| 37 | 0.39 | 0.39 | 0.78 | 3.1 | 25 | 6.2 |
| 38 | <0.20 | 0.39 | 0.39 | <0.20 | 1.65 | 0.78 |
| 39 | 0.39 | 0.78 | 0.78 | 0.39 | 1.6 | 1.6 |
| 40 | 0.28 | 0.39 | 0.78 | 0.78 | 3.1 | 1.6 |
| 41 | 0.78 | 0.39 | 0.78 | 0.78 | 1.6 | 1.6 |
| 42 | 0.39 | 0.39 | 0.39 | <0.20 | 0.39 | 1.6 |
| 43 | 0.78 | 0.78 | 1.6 | 0.39 | 0.78 | 1.6 |
| 44 | 0.78 | 0.78 | 1.6 | 0.78 | 3.1 | 3.1 |
| 45 | 0.39 | 0.39 | 0.55 | <0.20 | 0.39 | 0.78 |
| 46 | 0.39 | 0.78 | 1.6 | 1.6 | 6.2 | 1.6 |
| 47 | 0.279 | 0.39 | 0.55 | <0.20 | 0.78 | 0.78 |
| 48 | 6.2 | 12 | 12 | 6.2 | 12 | 50 |
| 49 | 0.78 | 0.78 | 1.6 | 0.39 | 0.78 | 0.78 |
| 50 | 1.6 | 1.6 | 1.6 | 1.6 | 3.1 | 1.6 |
| 51 | 0.55 | 0.78 | 0.78 | 0.28 | 0.55 | 0.78 |
| 52 | 0.78 | 1.6 | 1.6 | 0.78 | 1.6 | 3.1 |
| 53 | 0.464 | 0.39 | 0.55 | 0.098 | 0.39 | 0.55 |
| 54 | 0.78 | 0.78 | 0.78 | 0.39 | 0.78 | 1.6 |
| 55 | 0.78 | 0.78 | 0.78 | 0.78 | 1.6 | 1.6 |
| 56 | 3.1 | 6.2 | 6.2 | 3.1 | 6.2 | 25 |
| 57 | 0.78 | 0.78 | 1.6 | 1.6 | 6.2 | 3.1 |
| 58 | 12 | 50 | 25 | 12 | 50 | 50 |
| 59 | 1.6 | 1.6 | 1.6 | 0.78 | 1.6 | 3.1 |
| 60 | 1.6 | 1.6 | 1.6 | 0.78 | 1.6 | 1.6 |
| 61 | 0.78 | 0.78 | 0.78 | 0.78 | 3.1 | 1.6 |
| 62 | 3.1 | 6.2 | 3.1 | 3.1 | 6.2 | 6.2 |

TABLE 1-continued

| Example | Spy[a] MIC (μM) | Spn[b] MIC (μM) | Spn[c] MIC (μM) | Sau[d] MIC (μM) | Sau[e] MIC (μM) | Sau[f] MIC (μM) |
|---|---|---|---|---|---|---|
| 63 | 0.39 | 0.39 | 0.39 | 0.78 | 3.1 | >200 |
| 64 | 6.2 | 12 | 6.2 | 6.2 | 25 | 25 |
| 65 | 0.78 | 0.78 | 1.6 | 0.39 | 1.6 | 1.6 |
| 66 | 0.39 | 0.39 | 0.78 | 0.39 | 0.78 | 0.78 |
| 67 | 0.28 | 0.4 | 0.55 | 0.28 | 0.55 | 0.55 |
| 68 | 3.1 | 3.1 | 6.2 | 12 | 25 | 12 |
| 69 | 3.1 | 12 | 12 | 12 | 25 | 12 |
| 70 | 1.6 | 1.6 | 3.1 | 12 | 50 | 25 |
| 71 | 1.6 | 1.6 | 1.6 | 3.1 | 6.2 | 3.1 |
| 72 | 0.39 | 0.78 | 3.1 | 25 | 50 | 25 |
| 73 | 0.78 | 0.78 | 3.1 | 25 | 100 | 25 |
| 74 | 1.6 | 1.6 | 1.6 | 6.2 | 12 | 12 |
| 75 | 0.55 | 0.78 | 1.62 | 0.28 | 2.2 | 0.39 |
| 76 | 0.39 | 0.39 | 0.78 | 0.39 | 1.6 | 0.78 |
| 77 | 0.78 | 0.78 | 0.78 | 3.1 | 12 | 6.2 |

[a]*Streptococcus pyrgenes*, in vivo strain.
[b]*Streptococcus pneumoniae*, in vivo strain.
[c]*Streptococcus pneumoniae*, in vivo strain.
[d]*Staphylococcus aureus* in vivo strain, MSQS.
[e]*Staphylococcus aureus*, in vivo strain, MRQR.
[f]*Staphylococcus aureus*, serum.

TABLE 2

| Example | Spy[a] MIC (μg/ml) | Spn[b] MIC (μg/ml) | Spn[c] MIC (μg/ml) | Sau[d] MIC (μg/ml) | Sau[e] MIC (μg/ml) | Sau[f] MIC (μg/ml) |
|---|---|---|---|---|---|---|
| 78 | 1 | 2 | 2 | 1 | 2 | 1 |
| 79 | 1 | 2 | 1 | 1 | 2 | 1 |
| 80 | 16 | 64 | 32 | 16 | 32 | 16 |

[a]*Streptococcus pyrogenes*, in vivo strain.
[b]*Streptococcus pneumoniae*, in vivo strain.
[c]*Streptococcus pneumoniae*, ATCC 49619.
[d]*Staphylococcus aureus*, in vivo strain, ATCC 29213.
[e]*Staphylococcus aureus*, in vivo strain, MRQR.
[f]*Staphylococcus aureus*, in vivo strain, MRSA.

Susceptibility Testing (MIC)—Assay 2

Minimum Inhibitory Concentrations (MICs) were determined by the broth microdilution method in accordance with the Clinical and Laboratory Standards Institute (CLSI) guidelines. In brief, organism suspensions were adjusted to a 0.5 McFarland standard to yield a final inoculum between $3\times10^5$ and $7\times10^5$ colony-forming units (CFU)/mL. Bacterial inocula were generally prepared in sterile, cation adjusted Mueller-Hinton Broth (Becton Dickinson) which included *Escherichia coli, Klebsiella pneumoniae,* and *Pseudomonas aeruginosa. Haemophilus influenzae* bacterial inocula were prepared in sterile, cation adjusted Mueller-Hinton Broth (Becton Dickinson) containing 0.5% yeast extract (Becton Dickinson) plus 30 mL of 15 μg/mL Bovine Hematin stock (Sigma), and 3 mL of 15 μg/mL β-nicotinamide adenine dinucleotide (Sigma). Strains of *Neisseria* were tested for MICs using agar dilution methodology in accordance with CLSI guidelines. For broth microdilution testing, an inoculum volume of 100 μL was added to wells (using a Tecan EVO robot) containing 2 μL of DMSO containing 2-fold serial dilutions of drug. All inoculated microdilution panels were incubated in ambient air at 35° C. for 18-24 hours. Following incubation, the lowest concentration of the drug that prevented visible growth as read at OD600 nm and confirmed by a visual read using a test reading mirror was recorded as the MIC. Performance of the assay was monitored by the use of laboratory quality-control strains and commercially available control compounds with defined MIC spectrums, in accordance with CLSI guidelines. Table 3 provides the MIC results (μM) of Examples 1-77 tested in Assay 2. Table 4 provides the MIC (μg/mL) results of Examples 78-80 tested in Assay 2.

TABLE 3

| Example | Hin[a] MIC (μM) | Eco[b] MIC (μM) | Kpn[c] MIC(nM) | Pae[d] MIC (μM) |
|---|---|---|---|---|
| 1 | 0.78 | 50 | >200 | >200 |
| 2 | 1.6 | 100 | >200 | >200 |
| 3 | 1.6 | 50 | >200 | >200 |
| 4 | 0.47 | 9.9 | 200 | >200 |
| 5 | 0.33 | 4 | >200 | >200 |
| 6 | 3.1 | 100 | 121 | >200 |
| 7 | 12 | 200 | >200 | >200 |
| 8 | 12 | >200 | >200 | >200 |
| 9 | 0.39 | 50 | >200 | >200 |
| 10 | 25 | >200 | >200 | >200 |
| 11 | 3.1 | 50 | >200 | >200 |
| 12 | 3.1 | 100 | >200 | >200 |
| 13 | 0.78 | 12 | 200 | >200 |
| 14 | 0.78 | 25 | 200 | >200 |
| 15 | <0.20 | 12 | >200 | >200 |
| 16 | 0.78 | 25 | 200 | >200 |
| 17 | 0.39 | 50 | >200 | >200 |
| 18 | 3.1 | >200 | >200 | >200 |
| 19 | 0.28 | 8.8 | 200 | >200 |
| 20 | 0.39 | 25 | >200 | >200 |
| 21 | 1.6 | 50 | 200 | >200 |
| 22 | 0.78 | 12 | 200 | >200 |
| 23 | 0.39 | 6.2 | 100 | >200 |
| 24 | 3.1 | 50 | >200 | >200 |
| 25 | 0.78 | 12 | 200 | >200 |
| 26 | <0.20 | 25 | >200 | >200 |
| 27 | 0.39 | 100 | >200 | >200 |
| 28 | 25 | >200 | >200 | >200 |
| 29 | 0.78 | 100 | >200 | >200 |
| 30 | 0.39 | 25 | 200 | >200 |
| 31 | 0.39 | 100 | >200 | >200 |
| 32 | 0.27 | 1.5 | 200 | 200 |
| 33 | 0.78 | 100 | >200 | >200 |
| 34 | 0.39 | 25 | 200 | >200 |
| 35 | 0.78 | 50 | >200 | >200 |
| 36 | 1.6 | 100 | >200 | >200 |
| 37 | 0.39 | 200 | >200 | >200 |
| 38 | 0.39 | 25 | 200 | >200 |
| 39 | 0.39 | 25 | 200 | >200 |
| 40 | 0.39 | 12 | >200 | >200 |
| 41 | 0.78 | 25 | >200 | >200 |
| 42 | 0.39 | 25 | 200 | >200 |
| 43 | 1.6 | 50 | >100 | >100.000 |
| 44 | 0.78 | 50 | >200 | >200 |
| 45 | 0.39 | 25 | 200 | >200 |
| 46 | 0.78 | 100 | >200 | >200 |
| 47 | 0.78 | 25 | 200 | >200 |
| 48 | 6.2 | 200 | >200 | >200 |
| 49 | 1.6 | 50 | >200 | >200 |
| 50 | 3.1 | 200 | >200 | >200 |
| 51 | 0.39 | 12 | 100 | >200 |
| 52 | 0.78 | 25 | 200 | >200 |
| 53 | 1.1 | 35 | >200 | >200 |
| 54 | 3.1 | 100 | >200 | >200 |
| 55 | 0.39 | 50 | >200 | >200 |
| 56 | 3.1 | >200 | >200 | >200 |
| 57 | 0.39 | 100 | >200 | >200 |
| 58 | 6.2 | >200 | >200 | >200 |
| 59 | 1.6 | 100 | >200 | >200 |
| 60 | 1.6 | 100 | >200 | >200 |
| 61 | <0.20 | 100 | >200 | >200 |
| 62 | 3.1 | >200 | >200 | >200 |
| 63 | 0.39 | 100 | >200 | >200 |
| 64 | 3.1 | >200 | >200 | >200 |
| 65 | 0.78 | 3.1 | 200 | >200 |
| 66 | 0.78 | 6.2 | 100 | >200 |
| 67 | 0.55 | 25 | >200 | >200 |
| 68 | 1.6 | 200 | >200 | >200 |
| 69 | 3.1 | >200 | >200 | >200 |
| 70 | 1.6 | 200 | >200 | >200 |
| 71 | 1.6 | 50 | >200 | >200 |
| 72 | 3.1 | >200 | >200 | >200 |

TABLE 3-continued

| Example | Hin[a] MIC (μM) | Eco[b] MIC (μM) | Kpn[c] MIC(nM) | Pae[d] MIC (μM) |
|---|---|---|---|---|
| 73 | 6.2 | >200 | >200 | >200 |
| 74 | 0.78 | 100 | >200 | >200 |
| 75 | 0.78 | 100 | >200 | >200 |
| 76 | 0.78 | 50 | >200 | >200 |
| 77 | 0.78 | 200 | >200 | >200 |

[a]*Haemophilus influenzae*, ATCC 51907, in vivo strain.
[b]*Escherichia coli*, K12.
[c]*Klebsiella pneumoniae*, clinical isolate, mucoid.
[d]*Pseudomonas aeruginosa*, PAO1.

TABLE 4

| Example | Hin[a] MIC (μg/ml) | Eco[b] MIC (μg/ml) | Eco[c] MIC (μg/ml) | Kpn[d] MIC (μg/ml) | Kpn[e] MIC (μg/ml) | Pae[f] MIC (μg/ml) |
|---|---|---|---|---|---|---|
| 78 | 2 | 16 | 32 | >64 | >64 | >64 |
| 79 | 0.5 | 32 | 64 | >64 | >64 | >64 |
| 80 | 1 | >64 | >64 | >64 | >64 | >64 |

[a]*Haemophilus influenzae*, ATCC 49247.
[b]*Escherichia coli*, in vivo strain, ATCC 25922.
[c]*Escherichia coli*, ATCC 35218.
[d]*Klebsiella pneumoniae*, clinical isolate, mucoid.
[e]*Klebsiella pneumoniae*, ATCC 700603.
[f]*Pseudomonoas aeruginosa*, PAO1.

DNA Gyrase Supercoilinq Activity Fluorescence Polarisation Assay

In a black, 384-well polystyrene assay plate, 30 microliters/well of 5 nM *Escherichia coli* DNA gyrase A/B tetramer and 130 micrograms/mL of topologically relaxed plasmid containing the triplex-forming sequence TTCTTCTTCT-TCTTCTTCTTCTTCTTC (SEQ ID NO:1) in an assay buffer consisting of 35 mM Tris-HCl (pH 7.5), 24 mM KCl, 4 mM MgCl2, 2 mM dithiothreitol, 1.8 mM spermidine, 5% (v/v) glycerol, 200 nM bovine serum albumin, 0.8% dimethylsulfoxide, and 0.3 mM ATP were incubated at ambient temperature for (typically 30 minutes) in the absence or presence of 5-10 different concentrations of test compound. The supercoiling reactions were quenched by the addition of 10 microliters/well of 40 nM oligodeoxynucleotide probe in 3× triplex-forming buffer consisting of 150 mM NaCl, and 150 mM sodium acetate at pH 3.5. The oligodeoxynucleotide probe was 5'-BODIPY-FL-labeled TTCTTCTTC (SEQ ID NO:2). After 60 minutes, the fluorescence anisotropy of the BODIPY-FL was measured in a Tecan Ultra plate reader, using 485 nm excitation and 535 nm emission filters equipped with polarizers. The $IC_{50}$ was determined by nonlinear regression using two control reactions. The first contained no test compound but 0.8% DMSO (100% activity) while the second control reaction contained 5 μM Ciprofloxacin and 0.8% DMSO (0% activity).

When tested in an in vitro assay based on the DNA gyrase supercoiling activity fluorescence polarization assay described above, the *E. coli* DNA gyrase supercoiling $IC_{50}$ assay inhibitory activities of Examples 1-77 were determined, as shown in Table 5.

TABLE 5

| Example | Eco Gyr FP Mean IC50 (μM) |
|---|---|
| 1 | 1.3 |
| 2 | 2.7 |
| 3 | 1.44 |
| 4 | 0.39 |
| 5 | 0.169 |
| 6 | 3.3 |
| 7 | 9.7 |
| 8 | 7.3 |
| 9 | 0.71 |
| 10 | 6.7 |
| 11 | 1.2 |
| 12 | 3.2 |
| 13 | 0.51 |
| 14 | 0.57 |
| 15 | 0.13 |
| 16 | 0.19 |
| 17 | 0.14 |
| 18 | 0.81 |
| 19 | 0.16 |
| 20 | 0.42 |
| 21 | 0.54 |
| 22 | 0.21 |
| 23 | 0.52 |
| 24 | >2.1 |
| 25 | 0.26 |
| 26 | 0.17 |
| 27 | 0.53 |
| 28 | >2.1 |
| 29 | 0.27 |
| 30 | 0.5 |
| 31 | 0.42 |
| 32 | 0.63 |
| 33 | 0.26 |
| 34 | 0.23 |
| 35 | 0.31 |
| 36 | 0.59 |
| 37 | 0.12 |
| 38 | 0.067 |
| 39 | 0.097 |
| 40 | 0.38 |
| 41 | 0.46 |
| 42 | 0.29 |
| 43 | 0.44 |
| 44 | 0.53 |
| 45 | 0.26 |
| 46 | 0.17 |
| 47 | 0.15 |
| 48 | >2.1 |
| 49 | 0.38 |
| 50 | 0.2 |
| 51 | 0.43 |
| 52 | 0.9 |
| 53 | 0.38 |
| 54 | 0.94 |
| 55 | 0.15 |
| 56 | 1.9 |
| 57 | 0.76 |
| 58 | 1.5 |
| 59 | 0.86 |
| 60 | 0.95 |
| 61 | 0.34 |
| 62 | 1.4 |
| 63 | 0.38 |
| 64 | >2.1 |
| 65 | 0.12 |
| 66 | 0.17 |
| 67 | 0.33 |
| 68 | 0.22 |
| 69 | 0.6 |
| 70 | 0.61 |
| 71 | 0.16 |
| 72 | 0.29 |
| 73 | 0.34 |
| 74 | 0.47 |
| 75 | 0.71 |
| 76 | 0.55 |
| 77 | 0.53 |
| 78 | 0.44 |
| 79 | >2.1 |
| 80 | 0.17 |

In Vivo Efficacy of Example 5 Against *Staphylococcus aureus* in a Mouse Thigh Model The objective of the study was to determine the efficacy and pharmacokinetic/pharmacodynamic (PK/PD) relationship for Example 5 against *Staphylococcus aureus* (*S. aureus*) in mouse thigh infection models.

The *S. aureus* strains used included a methicillin-resistant isolate obtained from the American Type Culture Collection (ATCC33591) (MRSA). In addition, three *S. aureus* clinical isolates were utilized; (1) a methicillin sensitive isolate (MSSA); (2) a recent methicillin-resistant clinical isolate of the USA300 genotype (USA300) and (3) a recent methicillin-resistant clinical isolate of the USA100 genotype (USA1000).

The MIC against each isolate was determined using the broth microdilution method following CLSI guidelines (Rayner et al. Clinical pharmacodynamics of linezolid in seriously ill patients treated in a compassionate use program. *Clin Pharmacokinet* 2003. 42:1411-23). Ten individual determinations were performed for each strain and the Modal MIC was used for all PK/PD calculations.

All procedures were carried out according to Institutional Animal Care and Use Committee (IACUC) approved protocol 11-03-i. Mice were rendered neutropenic with cyclophosphamide at 150 mg/kg ip on day −4 and 100 mg/kg ip on day −1 (Andes et al. *In vivo pharmacodynamics of a new Oxazolidinone (Linezolid)* AAC 2002, 46(11): 3484-9). Two hours prior to infection, mice received an administration of 50 mg/kg aminobenzotriazole (ABT) orally to inhibit cytochrome P450 (CYP450) activity; mice received a second 50 mg/kg administration 12 h later. Each *S. aureus* isolate was prepared in a similar fashion. A fresh overnight plate was used to inoculate a 25 mL culture of Tryptic Soy broth (TSB). The culture was incubated overnight at 37° C. with 200 rpm shaking. The overnight culture was diluted 1:10 in TSB, the OD600 determined, and entered into a dilution calculator specific for that isolate. The calculated volume of the overnight culture was pipetted into the appropriate volume of saline to obtain the target inoculum level of 5×10⁵ CFU/thigh and a viable count determined in duplicate.

Mice were then assigned to control or treatment groups. At 2 hours after infection, one group of 10 mice was euthanized to determine the viable count in the infected thighs at start of treatment. The remaining groups of mice were administered (1) Example 5, (2) control compounds (levofloxacin or linezolid) or (3) vehicle. Efficacy was determined 24 hours after start of treatment. Mice were euthanized by carbon dioxide asphyxiation and cervical dislocation and the infected thigh removed and dissected. The thighs were weighed and transferred to tubes containing 1 mL of saline for homogenization. Thigh tissue was homogenized (Omni TH homogenizer, Omni International, Warrenton, Va.) and 100 µL of homogenate serially diluted in saline and plated onto tryptic soy agar plates for viable count determination. Plates were incubated at 37° C. overnight.

Initially, single dose time course studies were run for each isolate to determine the optimal dosing regimen. For the *S. aureus* MRSA isolate once daily (uid) dosing was determined to be the optimal regimen, for all other isolates a twice daily (bid, q12) regimen was determined to be optimal. Following the time course study two individual dose response studies were run for each isolate and the results were combined to obtain the AUC/MIC ratios associated with efficacy. The mice were dosed 2.5 to 160 mg/kg/day given qd or bid q12, the volume of administration was 10 mL/kg by bolus intraperidoneal dose and the duration of treatment was 24 hours.

Groups of satellite mice infected with *S. aureus* were used for determining plasma concentrations. Dosing started 2 hours after infection and whole blood samples were taken at time points 0.5, 1, 2, 4, 6, 8, 12 and 24 h by submandibular bleed or by cardiac puncture following carbon dioxide asphyxiation and cervical dislocation. Whole blood was sampled into microcontainer tubes containing ethylenediamine tetraacetic acid (EDTA) (Beckton Dickenson). Three mice per time point were used. Plasma was separated by centrifugation for five minutes at 13200 rpm and stored at −20° C. until bioanalysis.

Biological samples containing Example 5 were extracted using protein precipitation. To one volume of sample, 5 volumes of acetonitrile containing the internal standard (Glyburide) were added. The mixture was then mixed and the plate was centrifuged at 3200 rpm for 5 min. A 200 µL volume of the supernatant was dried down and, reconstituted in mobile phase and the mixture was injected onto liquid chromatography-mass spectrometry (LC-MS). A Sciex API 4000, controlled by Analyst v1.4.2, was used for the acquisition of the data and the quantification of Example 5. LC-MS instrument parameters are provided in Tables 6 and 7, below.

TABLE 6

Liquid Chromatography conditions to detect Example 5 in plasma

| Parameter | Condition | |
|---|---|---|
| Column | ACE C8, 20 × 2.1 mm | |
| Column Temperature | Room Temperature | |
| Flow rate | 0.60 mL/min | |
| Gradient | Time(min) | % B |
| | 0.50 | 10 |
| | 1.50 | 95 |
| | 2.00 | 95 |
| | 2.01 | 10 |
| | 2.30 | Stop |
| Mobile Phase A | 10 mM Ammonium Formate + 0.1% Ammonium Hydroxide | |
| Mobile Phase B | ACN with 0.1% Ammonium Hydroxide | |
| Syringe Wash 1 | 1:1:1:1 MeOH:CAN:IPA:H$_2$O + 0.2% [NH$_4$OH] | |
| Syringe Wash 2 | 10:90 MeOH:H$_2$O + 0.2% Formic Acid | |

TABLE 7

MS/MS parameters for Example 5 and Glyburide detection

| Parameter | Condition | | | | | |
|---|---|---|---|---|---|---|
| Mass Spectrometer | Sciex API 4000 | | | | | |
| Source temperature | 550° C. | | | | | |
| Injection volume | 10 µL | | | | | |
| Ion mode | ESI− | | | | | |
| | Compound ID | Q1 | Q3 | DP | CE | CXP |
| MRM transitions | Example 5 | 486.13 | 42.09 | −85 | −65 | −5 |
| | Glyburide | 492.00 | 170.00 | −55 | −4- | −10 |

Pharmacokinetic Data Analysis:

The plasma profile for each dose group was obtained by calculating the average plasma concentration of compound in each of the three animals per time point. The area under the plasma concentration time curve from zero to infinity (AUC); maximum plasma drug concentration ($C_{max}$); time to reach maximum concentration ($t_{max}$); and plasma half-life ($t_{1/2}$) for each dose group was determined by non-compartmental analysis (WinNonLin 5.2, Pharsight). The non-compartmental Model 200 was used in the analysis.

The AUC for the bid dose regimens were determined by multiplying the AUC value obtained after a single dose by two, assuming no accumulation following a second dose.

Pharmacodynamic Data Analysis:

The number of bacterial colonies grown from the thigh of each animal was adjusted to account for sample dilution and tissue weight to determine the CFU per gram of tissue (CFU/g). The variability in each dose group was determined by calculating the standard error across the animals within the each group.

Pharmacokinetic/Pharmacodynamic Analysis:

The mean log CFU/g obtained for the pre-treatment group was subtracted from the log CFU/g obtained for each individual animal in the treatment groups. The delta in log CFU/g was determined for each animal in the efficacy group and used in the PK/PD analysis. Statistical outliers were determined using the interquartile method and eliminated from the analysis.

The pharmacokinetic parameters of AUC for each dose group were related to the MIC of Example 5 against the each *S. aureus* isolate. The ratio of the AUC to the MIC was determined for each dose group and plotted against the CFU/g of each animal. A murine unbound fraction of 22.1% was used to calculate free plasma concentrations. This value came from the mean of the mouse protein unbound fraction of Example 5 in the range of 1 μM to 50 μM.

The correlation between efficacy and the PK/PD indices total AUC was determined by non linear regression (WinNonlin 5.2, Pharsight). The data was modeled using a sigmoidal $E_{max}$ model shown below, where $E_{max}$ is the maximum growth observed in the absence of drug; $E_0$ is the maximum kill, $EC_{50}$ is the concentration that gives 50% of response, and N is the Hill factor.

$$E = E_{max} - (E_{max} - E_0) \cdot \frac{C^N}{C^N + EC_{50}^N}$$

The PK/PD analysis was performed on the combined dose groups as well as for the individual dose regimens. The goodness of fit was determined by evaluating the variability in the model-calculated parameters, the Aikaike criteria, and the analysis of the weighted residuals.

The PK/PD parameters determined by modeling were used to determine exposures required to reach a static response and as well as 1 log reduction on colony counts compared to the counts at the start of therapy.

The MIC values of the four *S. aureus* isolates determined against Example 5 are presented in Table 8.

The plasma exposures associated with intraperitoneal administration of Example 5 in the presence of ABT were determined in neutropenic mice thigh infected with *S. aureus* MSSA, MRSA and USA300. The combined data was analyzed to build a consensus dose/exposure relationship. The best relationship was associated with a power relationship, $Y=(1,022.7)*(X^{1.2019})$, where Y is the AUC infinity in ηg·h/mL and X is the measured dose in mg/kg.

FIG. 1 illustrates Example 5 dose response against *S. aureus* USA100 in the thigh of neutropenic mice, pre-treated with ABT. Each point represents the mean of 5 animals The error bars represent the standard error. At the start of therapy the bacterial burden was 5.93±0.09 CFU/g. The bacteria grew 3.3 log CFU/g in the vehicle group. Linezolid was administered intraperitoneally in separate experiments for comparison.

Each *S. aureus* isolate grew at least two logarithms in the vehicle control group from the start of treatment; with MSSA, MRSA, USA100 and USA300 growing 1.96±0.08, 3.2±0.12, 2.66±0.16 and 3.1±0.21 CFU/g, respectively. *S. aureus* MRSA was administered once daily (uid) as none of the doses tested re-grew to levels equivalent to the vehicle control group. The other three isolates were tested with an administration regime of two equal doses administered twelve hours apart (bid, q12).

The PK/PD parameters from the simple dose response studies were calculated. It was assumed that the AUC/MIC parameter was the parameter that best correlated with activity as this driver has been shown to correlate best with efficacy both in vitro. For all dose response studies the dosing solutions were analyzed to assess the measured dose and the consensus exposure relationship was used to estimate plasma exposure.

The PK/PD parameters for *S. aureus* MSSA in the neutropenic mouse model were generated from two dose response studies. The AUC values for stasis and a 1-log reduction were determined to be 28 and 69 μg·h/mL, respectively.

The PK/PD parameters for *S. aureus* MRSA in the neutropenic mouse model were generated from the results of two dose response studies. The AUC values for stasis and a 1-log reduction were determined to be 24 and 55 μg·h/mL, respectively.

The PK/PD parameters for *S. aureus* USA300 in the neutropenic mouse model were generated from the results of two dose response studies. The AUC values for stasis and a 1-log reduction were determined to be 91 and 150 μg·h/mL, respectively.

The PK/PD parameters for *S. aureus* USA100 in the neutropenic mouse model were generated from the results of two dose response studies. The AUC values for stasis and a 1-log reduction were determined to be 25 and 47 μg·h/mL, respectively.

Calculated Free AUC/MIC Ratios for Efficacy

The free plasma AUC/MIC magnitudes calculated for the *S. aureus* animal models are presented in Table 9.

TABLE 8

Modal MIC values against *S. aureus* isolates

| Strain | Example 5 MIC (μg/mL) |
|---|---|
| MSSA | 0.0625 |
| MRSA | 0.125 |
| USA100 | 0.125 |
| USA300 | 0.25 |

TABLE 9

Free plasma AUC/MIC magnitudes for Example 5 versus *S. aureus* isolates

| In vivo model | $N^a$ | End point | AUC/MIC (free) |
|---|---|---|---|
| *S. aureus* MSSA neutropenic dose response | 2 | $EC_{50}$ ± SEM (% CV)[b] | 71 ± 28 (44%) |
| | | Stasis ± SEM (% CV)[c] | 98 ± 17 (17%) |
| | | 1-log reduction ± SEM (% CV)[d] | 245 ± 81 (33%) |
| *S. aureus* MRSA | 2 | $EC_{50}$ ± SEM (% CV) | 53 ± 25 (47%) |

TABLE 9-continued

Free plasma AUC/MIC magnitudes for Example 5
versus *S. aureus* isolates

| In vivo model | $N^a$ | End point | AUC/MIC (free) |
|---|---|---|---|
| neutropenic | | Stasis ± SEM (% CV) | 43 ± 5 (11%) |
| dose response | | 1-log reduction ± SEM (% CV) | 96 ± 35 (36%) |

TABLE 9

Free plasma AUC/MIC magnitudes for Example 5
versus *S. aureus* isolates

| In vivo model | $N^a$ | End point | AUC/MIC (free) |
|---|---|---|---|
| *S. aureus* USA300 | 2 | $EC_{50}$ ± SEM (% CV) | 73 ± 38 (52%) |
| neutropenic | | Stasis ± SEM (% CV) | 80 ± 5 (12%) |
| dose response | | 1-log reduction ± SEM (% CV) | 132 ± 16 (12%) |
| *S. aureus* USA100 | 2 | $EC_{50}$ ± SEM (% CV) | 34 ± 14 (40%) |
| neutropenic | | Stasis ± SEM (% CV) | 43 ± 5 (12%) |
| dose response | | 1-log reduction ± SEM (% CV) | 83 ± 23 (28%) |

$^a$Number of studies.
$^b$Effect concentration median ± Standard error of the mean (% coefficient of variance).
$^c$Stasis ± Standard error of the mean (% coefficient of variance).
$^d$1-log reduction ± Standard error of the mean (% coefficient of variance).

Summary

Example 5 showed nonlinear pharmacokinetics over the dosing range. Absorption was good, with maximum concentration attained at 0.5 h post-administration. A dose/exposure relationship was built based upon the plasma PK exposures from a number of efficacy studies and the measured concentration of the dosing solutions. This consensus exposure was utilized, in conjunction with the modal MIC values for the individual isolates and the mouse free plasma levels to determine the free AUC/MIC magnitude associated with a bacteriostatic effect and for a 1-log reduction in the model.

Dose response studies were run in the neutropenic thigh model to determine the relative free AUC/MIC magnitudes required for efficacy. The free AUC/MIC ratio required for a bacteriostatic effect and for a 1-log reduction, relative to the initial bacterial burden for ranged from 43 to 98 and 83 to 245, respectively.

In Vivo Efficacy of Example 5 Against *Streptococcus pyogenes* in a Mouse Thigh Model The objective of the study was to determine the efficacy and pharmacokinetic/pharmacodynamic (PK/PD) relationship for Example 5 against *Streptococcus pyogenes* (*S. pyogenes*) in mouse neutropenic thigh infection model. *S. pyogenes* ATCC12384 obtained from the American Type Culture Collection was used in this study The MIC against *S. pyogenes* ATCC12384 was determined using the broth microdilution method following CLSI guidelines. Three individual determinations were performed for each strain and the Modal MIC was used for all PK/PD calculations. All animal experiments were performed under UK Home Office Licensure with local ethical committee clearance. All experiments were performed by technicians who have completed parts 1, 2 and 3 of the Home Office Personal License course and hold current personal licenses.

All mice were rendered temporarily neutropenic by immunosuppression with cyclophosphamide (Baxter, Norfolk, UK) at 150 mg/kg 4 days before infection and 100 mg/kg one day before infection by intraperitoneal injection (Andes et al, infra). Twenty four hours after the second round of immunosuppression, mice were infected with *S. pyogenes*, ATCC12384 by intramuscular injection into both lateral thigh muscles under temporary inhaled anaesthesia (3% Isoflurane) using $5 \times 10^5$ CFU/mouse thigh. Buprenorphine 0.06 mg/kg was administered subcutaneously (SC) to all mice in the study, in this study pain in the thigh typically causes lameness and loss of use of the effected limb. Buprenorphine was re-administered at 12 hourly intervals starting at the time of infection to ensure on-going pain relief.

In the efficacy studies, 6 mice were used in the 2 h post-infection pre-treatment group; 8 mice were used in the vehicle control and therapeutic treatment groups. Fifteen minutes prior to and twelve hours after infection animals to be treated with test agents and vehicle were administered with 50 mg/kg 1-aminobenzotriazole by oral gavage. Antibacterial treatments were administered 2 h and 14 h post infection, delivered at 10 mL/kg intraperitoneally. The comparator group was treated with 100 mg/kg linezolid at 2 h and 14 h post infection by SC delivery. The control group was treated with vehicle (0.2M meglumine/30% HPβCD) only.

For efficacy studies 24 h post infection (or earlier if the mice reached pre-defined endpoints), the clinical condition of all animals was assessed prior to them being humanely euthanized using pentabarbitone overdose. Both thighs were removed and weighed individually. Individual thigh tissue samples were homogenized using a bead-beater in ice cold sterile phosphate buffered saline. Thigh homogenates were then quantitatively cultured onto blood agar and incubated at 37° C. for 24 h before being counted.

Groups of satellite mice infected with *S. pyogenes*, as described above, were used for determining plasma concentrations. Dosing started 2 hours after infection and whole blood samples were taken at 0.5, 1, 2, 4, 6, 8, 12 and 24 h. Mice from the satellite PK study were euthanized by inhaled 5% isofluorane at specified time points post-treatment, mice were bled immediately by cardiac puncture. Heparinised blood samples were separated by centrifugation for five minutes at 13200 rpm. Plasma samples were stored at minus 80° C. before transfer to the client for analysis.

For the PK arm of the study, 3 mice per time point per unit dose were used. Due to unintended changes in the final work order, the 80 and 160 mg/kg dosing groups initially were administered Example 5 without prior treatment with aminobenzotriazole. Once this was realised, the remaining mice were re-distributed across the dosing groups and group size was reduced to two mice per time point.

Biological samples containing Example 5 were extracted using protein precipitation. To one volume of sample, 5 volumes of acetonitrile containing the internal standard (Glyburide) were added. The mixture was then mixed and the plate was centrifuged at 3200 rpm for 5 min. A 200 μL volume of the supernatant was dried down and, reconstituted in mobile phase and the mixture was injected onto liquid chromatography-mass spectrometry (LC-MS). A Sciex API 4000, controlled by Analyst v1.4.2, was used for the acquisition of the data and the quantification of Example 5. LC-MS instrument parameters are provided in Tables 6 and 7.

The plasma profile for each dose group was obtained by calculating the average plasma concentration of compound in each of the two to three animals per time point. The area under the plasma concentration time curve from zero to infinity (AUC); maximum plasma drug concentration ($C_{max}$); time to reach maximum concentration ($t_{max}$); and plasma half-life ($t_{1/2}$) for each dose group was determined by non-compartmental analysis (WinNonLin 5.2, Pharsight). The non-compartmental Model 200 was used in the analysis. The AUC for the bid dose regimens were determined by multiplying the AUC value obtained after a single dose by two, assuming no accumulation following a second dose. The number of bacterial colonies grown from the thigh of each animal was adjusted to account for sample dilution to determine the CFU per thigh (CFU/thigh). The variability in each dose group was determined by calculating the standard error across the animals within the each group.

The mean log CFU/g obtained for the pre-treatment group was subtracted from the log CFU/g obtained for each individual animal in the treatment groups. The delta in log CFU/g was determined for each animal in the efficacy group and used in the PK/PD analysis. Statistical outliers were determined using the interquartile method and eliminated from the analysis.

The pharmacokinetic parameters of AUC for each dose group were related to the MIC of Example 5 against *S. pyogenes* ATCC12384. The ratio of the AUC to the MIC was determined for each dose group and plotted against the CFU/thigh of each animal. A murine unbound fraction of 22.1% was used to calculate free plasma concentrations. This value came from the mean of the mouse protein unbound fraction of Example 5 in the range of 1 µM to 50 µM.

The correlation between efficacy and the PK/PD indices total AUC was determined by non-linear regression (Win-NonLin 5.2, Pharsight). The data was modelled using a sigmoidal $E_{max}$ model shown below, where $E_{max}$ is the maximum growth observed in the absence of drug; $E_0$ is the maximum kill, $EC_{50}$ is the concentration that gives 50% of response, and N is the Hill factor.

$$E = E_{max} - (E_{max} - E_0) \cdot \frac{C^N}{C^N + EC_{50}^N}$$

The PK/PD analysis was performed on the combined dose groups as well as for the individual dose regimens. The goodness of fit was determined by evaluating the variability in the model-calculated parameters, the Aikaike criteria, and the analysis of the weighted residuals.

The PK/PD parameters determined by modelling were used to determine exposures required to reach a static response and as well as a1-log and a 2-log reduction on colony counts compared to the counts at the start of therapy.

The MIC value for *S. pyogenes* ATCC12384 determined against Example 5 was 0.125 µg/mL.

The plasma exposures associated with intraperitoneal administration of Example 5 in the presence of ABT were determined in neutropenic mice thigh infected with *S. pyogenes* ATCC12384. The calculated pharmacokinetic parameters calculated for each satellite PK are presented in Table 10. This data was compared to a consensus dose/exposure relationship built for plasma exposures in the *S. aureus* neutropenic thigh model. The consensus relationship was defined as $Y=(1,022.7)*(X^{1.2019})$, where Y is the AUC infinity in ηg h/mL and X is the measured dose in mg/kg.

TABLE 10

Plasma pharmacokinetics of Example 5 administered in the presence of ABT in *S. pyogenes* infected mice.

| Dose (mg/kg) Nominal | Measured | AUCinf (ng hr/mL) |
|---|---|---|
| 10 | 4.1 | 32629 |
| 40 | 25.4 | 108851 |
| 60 | 44.2 | 153295 |
| 80 | 66.2 | 251172 |
| 160 | 142.0 | 613542 |

Figure 2:
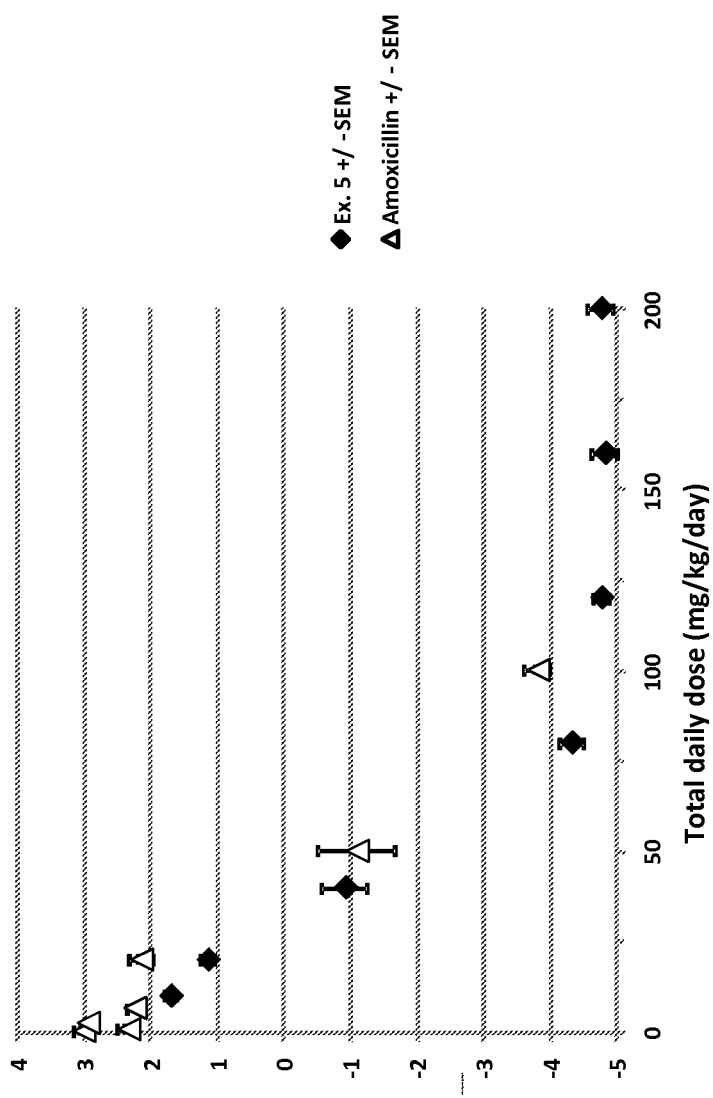
FIG. 2 is a graph illustrating the efficacy of Example 5 in a thigh lesion model induced by *S. pyogenes* ATCC12384 in neutropenic mice.

FIG. 2 illustrates Example 5 dose response against *S. pyogenes* ATCC12384 in the thigh of neutropenic mice, pre-treated with ABT. Each point represents the mean of 16 thighs. At the start of therapy the bacterial burden was 6.38±0.03 CFU/g. The bacteria grew 2.6-log CFU/g in the vehicle group. Amoxicillin was administered intrapertoneally in a separate experiment for comparison.

The PK/PD parameters from the dose response study were calculated. It was assumed that the AUC/MIC parameter is the parameter that best correlates with activity as this driver has been shown to correlate best with efficacy both with previous compounds in the series and was highly associated with efficacy in vitro. The dosing solutions were analyzed to assess the measured dose and the consensus exposure relationship was used to estimate plasma exposure. Calculated AUC values are presented in pg h/mL.

The PK/PD parameters for *S. pyogenes* ATCC12384 in the neutropenic mouse model were generated from a single dose response study. The AUC values for stasis, 1-log and 2-log reduction were determined to be 60, 76 and 95 µg·h/mL, respectively.

The free plasma AUC/MIC magnitudes calculated for the *S. pyogenes* ATCC12384 are presented in Table 11.

TABLE 11

Free plasma AUC/MIC magnitudes for Example 5 versus *S. pyogenes* ATCC12384

| In vivo model | $N^a$ | End point | AUC/MIC (free) |
|---|---|---|---|
| *S. pyogenes* neutropenic dose response | 1 | $EC_{50}$ ± SEM (% CV)$^b$ | 151 ± 7(5%) |
| | | Stasis ± SEM (% CV) | 106 ± 5(5%) |
| | | 1-log reduction ± SEM (% CV) | 135 ± 5(4%) |
| | | 2-log reduction ± SEM (% CV) | 168 ± 6(4%) |

$^a$Number of studies.
$^b$Effect concentration median ± Standard error of the mean (% coefficient of variance).

Summary

Example 5 pharmacokinetics over the dosing range demonstrated exposures consistent with the exposures demonstrated in the *S. aureus* neutropenic thigh model. The consensus exposure was utilized, in conjunction with the *S. pyogenes* ATC12384 MIC value and the mouse free plasma levels to determine the free AUC/MIC magnitude associated with a bacteriostatic effect and for a 1- and 2-log reduction in the model.

Example 5 showed dose-dependent efficacy in vivo against *S. pyogenes* ATC12384 in neutropenic mice. The free AUC/MIC ratio required for a bacteriostatic effect and for 1- and 2-log reductions, relative to the initial bacterial burden were 106, 135 and 168, respectively.

In Vitro Antibacterial Activity of Example 5

The goal of this study was to determine the in vitro antibacterial activity of Example 5 against a collection of Gram-positive, Gram-negative, fastidious, and anaerobic bacterial isolates. Testing performed included minimum inhibitory concentration (MIC), minimum bactericidal concentration (MBCs), and MICs in the presence of serum (mouse and human). The bacterial isolates utilized in these studies consisted primarily of recently obtained geographically diverse clinical isolates, but also included CLSI quality control reference strains, internal screening panel cultures, and isolates with defined resistance mechanisms.

MIC values were determined using either CLSI broth microdilution or agar dilution (N. gonorrhoeae) methodology. For broth microdilution susceptibility testing, stock compound mother plates were prepared and used to spot 2 µL aliquots of serial 2-fold drug dilutions into columns 1-11 of 96-well daughter plates. Column 12 did not contain drug and served as the growth control. An inoculum volume of 100 µL ($5 \times 10E^5$ CFU/mL) was added directly to each well of the 96-well plate using either a Tecan Freedom EVO or a Perkin-Elmer MiniTrak™ MultiPosition liquid handling robot. The MIC Range, $MIC_{50}$ and $MIC_{90}$ were determined for organism groups containing ≥10 isolates. The $MIC_{50}$ and $MIC_{90}$ were defined as the concentration of compound that inhibited the growth of, respectively, 50% and 90% of the combined sets of clinical isolates tested. At least one CLSI quality control reference organism and control compound was used to validate the susceptibility testing to ensure there was no variation between test dates or the control compounds. The MIC and MBC values obtained for each organism/drug combination were determined following Clinical and Laboratory Standards Institute Guidelines (Methods for dilution antimicrobial susceptibility tests for bacteria that grow aerobically; approved standard. Ninth edition. Wayne, Pa. Volume 32. Number 2; Methods for antimicrobial susceptibility testing of anaerobic bacteria; approved standard. Seventh edition. Wayne, Pa. Volume 27 Number 2; and Methods for determining bactericidal activity of antimicrobial agents; approved guideline. Wayne, Pa. Volume 19 Number 18). Susceptibility breakpoint interpretations for reference compounds along with QC ranges for reference bacterial strains are described in CLSI documents Performance standards for antimicrobial susceptibility testing; twenty-first informational supplement. Wayne, Pa. Volume 31. Number 1, and Performance standards for antimicrobial susceptibility testing; twenty-second informational supplement. Wayne, Pa. Volume 32. Number 3. Broth microdilution MIC testing was performed for all species tested with the exceptions of anaerobes and Neisseria gonorrhoeae which utilized agar dilution. Broth microdilution MICs for Legionella pneumophila were performed in Legionella broth. Strains of L. pneumophila were initially grown on buffered charcoal yeast extract (BCYE) agar plates for 48 hours prior to transfer.

MIC values for individual isolates were read visually, MIC determinations (MIC range, $MIC_{50}$, $MIC_{90}$) and cumulative percent inhibition plots were generated using CUMPER (short for Cumulative Percentage); an in-house statistical software program.

The antibacterial spectrum of Example 5 against individual Gram-positive, Gram-negative, and anaerobic bacterial isolates is presented in Tables 12 and 13. Overall, Example 5 was active against the staphylococci, streptococci, Haemophilus influenzae, Moraxella catarrhalis, Clostridium spp., Finegoldia magna, and Prevotella melaninogenica isolates tested. The antibacterial activity of Example 5 and comparators was also evaluated against Staphylococcus aureus, Streptococcus pneumoniae, and S. pyogenes strains with characterized gyrase and topoisomerase mutations. No cross resistance was found for Example 5 against bacterial clinical isolates possessing frequently encountered mutations in either gyrA, gyrB, ParC, or ParE, which are known to cause resistance to quinolones, novobiocin and Coumermycin A1.

Example 5 and comparators were evaluated in $MIC_{90}$ studies against a collection of 676 recently obtained Gram-positive and fastidious Gram-negative bacterial clinical isolates. Against 100 strains of S. aureus, Example 5 ($MIC_{90}$ 0.25 µg/mL) was the most active compound tested and maintained this activity against isolates resistant to levofloxacin, linezolid and vancomycin. This high degree of antibacterial activity and lack of cross resistance was also observed against 99 strains of coagulase negative staphylococci including S. epidermidis ($MIC_{90}$ 0.25 µg/mL, n=37), S. haemolyticus ($MIC_{90}$ 0.25 µg/mL, n=21), S. lugdunensis ($MIC_{90}$ 0.5 µg/mL, n=11), and S. saprophyticus ($MIC_{90}$ 0.5 µg/mL, n=16). Against 100 strains each of S. pneumoniae, S. pyogenes, and S. Agalactiae, Example 5 was very active with $MIC_{50}$ and $MIC_{90}$ values of 0.125 µg/mL and 0.25 µg/mL, respectively. No cross resistance was observed for Example 5 to any of the streptococci resistant to levofloxacin, erythromycin, or amoxicillin.

Compared to the staphylococci and streptococci, reduced activity was observed for Example 5 against enterococci with E. faecalis (n=51) resulting in the lowest MICs (MIC range 0.125-2 µg/mL and $MIC_{90}$ 2 µg/mL) and E. faecium MICs being approximately 8-fold higher ($MIC_{90}$ 16 µg/mL). Activity of Example 5 was measured against 11 strains each of Bacillus subtilis and B. cereus (as a surrogate for B. anthracis. $MIC_{90}$s against both species were 0.5 µg/mL. BSL3 testing of Example 5 against B. anthracis confirmed this activity (MIC range 0.125-1 µg/mL, and $MIC_{90}$ 0.5 µg/mL).

The antibacterial activity of Example 5 also encompassed fastidious Gram-negative organisms including Haemophilus influenzae (n=29), Legionella pneumophila (n=11), and 17 strains of Neisseria gonorrhoeae. MIC ranges versus these organism groups were 0.125-1 µg/mL, 0.008-0.06 µg/mL and 0.03-0.25 µg/mL, respectively. Corresponding $MIC_{90}$s were 1 µg/mL, 0.06 µg/mL and 0.125 µg/mL, respectively. No cross resistance to Example 5 was observed in strains of N. gonorrhoeae resistant to ciprofloxacin.

Serum protein binding effects on MIC values for Example 5 were assessed in varying concentrations of both mouse and human serum (0, 10, 25, and 50%). Against the 9 S. aureus strains tested, a 2- to 8-fold MIC increase was observed for Example 5 in the presence of 50% human serum and greater protein binding effects (8- to 32-fold MIC increases) were observed in 50% mouse serum.

Example 5 and comparators were evaluated for bactericidal activity against 7 S. aureus strains and 1 strain of Streptococcus pyogenes. Example 5, levofloxacin, and vancomycin were bactericidal against all the strains tested with minimum bactericidal concentrations (MBCs) within 2-fold of the MIC. The bactericidal activity of Example 5 was confirmed by in vitro time-kill studies.

TABLE 12

In vitro antibacterial activity of Example 5 against miscellaneous bacterial isolates

| Organism | Example 5 MIC µg/mL |
|---|---|
| Acinetobacter baumannii (in vivo strain) | 4 |
| Acinetobacter baumannii (multi-drug resistant) | 16 |
| Acinetobacter baumannii | 4 |
| Burkholderia cepacia | 64 |
| Candida albicans (ATCC 90028 CLSI QC Strain) | >64 |
| Citrobacter freundii | 16 |
| Citrobacter koseri | 64 |

TABLE 12-continued

In vitro antibacterial activity of Example 5 against miscellaneous bacterial isolates

| Organism | Example 5 MIC µg/mL |
|---|---|
| Enterobacter aerogenes | 64 |
| Enterobacter cloacae | 32 |
| Enterobacter cloacae (Chromosomal AmpC) | 32 |
| Enterococcus faecalis (ATCC 29212 CLSI QC Strain) | 1 |
| Enterococcus faecalis | 2 |
| Enterococcus faecalis (Vancomycin-R, fluoroquinolone-R) | 0.5 |
| Enterococcus faecium | 16 |
| Enterococcus faecium (Vancomycin-R, fluoroquinolone-R) | 8 |
| Escherichia coli (ATCC 25922 CLSI QC Strain) | 2 |
| Escherichia coli (K12(W3110) | 2 |
| Escherichia coli (TolC- of ATCC 25922) | <0.06 |
| Escherichia coli + 2% Human albumin (ATCC 25922) | <0.06 |
| Escherichia coli (ATCC 35218 CLSI QC Strain) | 4 |
| Haemophilus influenzae (ATCC 49619 CLSI QC Strain) | 0.25 |
| Klebsiella oxytoca | 32 |
| Klebsiella pneumoniae (ATCC 700603 CLSI QC Strain) | >64 |
| Klebsiella pneumoniae | 64 |
| Klebsiella pneumoniae (In vivo strain) | 16 |
| Klebsiella pneumoniae | 64 |
| Moraxella catarrhalis (ATCC 43617) | 0.125 |
| Proteus mirabilis | 8 |
| Proteus vulgaris | 32 |
| Pseudomonas aeruginosa (PAO1) | >64 |
| Pseudomonas aeruginosa (PAO1, mexABCDXY-) | 2 |
| Pseudomonas aeruginosa (clinical isolate) | >64 |
| Serratia marcescens | >64 |
| Staphylococcus aureus (ATCC 29213, CLSI QC Strain) | 0.125 |
| Staphylococcus aureus + 2% Human albumin (ATCC 29213, CLSI QC Strain) | 0.25 |
| Staphylococcus aureus (MSSA, in vivo strain) | 0.125 |
| Staphylococcus aureus (MRSA, fluoroquinolone-R) | 0.25 |
| Staphylococcus aureus (MRSA) | 0.5 |
| Staphylococcus aureus (In vivo Strain) | 0.25 |
| Staphylococcus aureus (Mu3, VISA) | 0.25 |
| Staphylococcus aureus (MRSA, USA100) | 0.125 |
| Staphylococcus epidermidis (MRSE) | 0.25 |
| Staphylococcus haemolyticus | 0.25 |
| Staphylococcus lugdunensis | 1 |
| Staphylococcus saprophyticus | 0.5 |
| Streptococcus agalactiae | 0.5 |
| Streptococcus constellatus | 0.03 |
| Streptococcus pyogenes | 0.125 |
| Streptococcus pyogenes | 0.25 |
| Streptococcus pneumonia (ATCC 49619, CLSI QC Strain) | 0.25 |
| Streptococcus pneumonia (In vivo Strain) | 0.25 |
| Streptococcus pneumonia (Penicillin, -erythromycin- and fluoroquinolone-resistant) | 0.25 |
| Stenotrophomonas maltophilia | >64 |

TABLE 13

In vitro antibacterial activity of Example 5 against anaerobic bacterial species

| Organism | Example 5 MIC µg/mL |
|---|---|
| Clostridium difficile (ATCC 70057, CLSI QC Strain) | 0.125 |
| Clostridium difficile | 0.125 |
| Clostridium perfringens | 0.5 |
| Propionibacterium acnes | 2 |
| Finegoldia magna (ATCC 53516) | <0.03 |
| Bacteroides thetaiotaomicron | 8 |
| Bacteroides thetaiotaomicron (ATCC 29741, CLSI QC Strain) | 8 |
| Prevotella melaninogenica | 0.25 |
| Bacteroides fragilis (ATCC 25285, CLSI QC Strain) | 2 |
| Bacteroides fragilis | 4 |
| Bacteroides fragilis | 4 |
| Bacteroides fragilis | 4 |
| Bacteroides fragilis | 8 |

Summary

Example 5 is DNA gyrase/topoisomerase inhibitor with in vitro antibacterial activity against key Gram-positive (S. aureus, S. epidermidis, S. haemolyticus, Streptococcus pneumoniae, S. pyogenes, and S. agalactiae), fastidious Gram-negative (Haemophilus influenzae, Legionella pneumophila, Moraxella catarrhalis, Neisseria gonorrhoeae), and anaerobic (Clostridium difficile) bacterial species including isolates with known resistance to fluoroquinolones. No cross resistance was observed for Example 5 against recent bacterial clinical isolates with resistance to other drug classes, including macrolides, 3-lactams, glycopeptides, and oxazolidinones.

Emergence of Resistance in Staphylococcus aureus and Streptococcus pyogenes with Serial Passage The goal of this study was to determine the emergence of resistance to Example 5 during serial passage in a representative isolate of methicillin-sensitive Staphylococcus aureus, methicillin-resistant S. aureus and Streptococcus pyogenes.

Freshly grown S. aureus 516 and 2398 as well as S. pyogenes 838 were harvested from blood agar plates (Remel, Lenexa Kans.), suspended in 3 mL cation-adjusted Mueller Hinton 2 broth (MHB2)(Sigma-Aldrich, St. Louis Mo.) and a sample frozen as passage zero. These cultures were diluted to a 0.5 McFarland in sterile saline (Remel) which was then diluted 1:200 into fresh broth and used as the inoculum. The media and incubation conditions used throughout the experiment were MHB2 and 36° C. in ambient air for S. aureus and MHB2 with the addition of 2.5% lysed horse blood and 36° C. in 5% $CO_2$ (Hema Resource Inc., Aurora, Oreg.) for S. pyogenes 838.

A series of two-fold increasing concentrations of Example 5 were made in DMSO and 40 µL of each concentration dispensed into wells of a 24-well culture plates (Costar, Corning N.Y.). Plates were sealed and frozen at −80° C. and thawed every day. A total of 2 mL of the inculum was added to each well and the plates were for 20 to 24 hours. Bacterial cells from the well containing the highest concentration of test compound that permitted visible bacterial growth were frozen in 20% glycerol and stored at −70° C. and were also back-diluted to a 0.5 McFarland in sterile saline (Remel) and subsequently diluted into fresh media. This diluted culture, representing cells from 0.5×MIC, was then dispensed into a fresh 24-well culture plate containing the series of increasing concentrations of test compound. This was repeated for twenty days.

The frozen samples were then single colony purified on blood agar plates in the absence of compound and tested for susceptibility using a standard broth microdilution assay, performed in accordance with document M07-A8 of the Clinical Laboratory Standards Institute (Methods for dilution antimicroia susceptibility tests for bacteria that grow aerobically; approved standard. Eighth edition. Wayne, Pa. Volume 29. No. 2. 2009). Isolates from several passages with an elevated MIC value against Example 5 representing a decrease in susceptibility were selected for investigation by sequence analysis. Whole genomic DNA was prepared from selected isolates using a standard Genomic DNA preparation kit (Promega, Madison Wis.). The genes encoding both subunits of DNA gyrase (gyrA and gyrB) and Topoisomerase IV (parC and parE) were amplified using a High Fidelity PCR mix (Roche, Nutley, N.J.). The polymerase chain reaction (PCR) product was purified using a QIAquick PCR Purification kit (Qiagen, Valencia, Calif.) and sequenced in an Applied Biosystems 3100 Genetic Analyzer (ABI, Foster City, Calif.) using the appropriate primers for S. aureus and S. pneumoniae. If changes were observed, a second independent PCR product was amplified and sequenced to confirm the variation was genuine and not as a result of an incorporation error during PCR amplification.

Growth of S. aureus and S. pyogenes over twenty passages in liquid medium containing sub-inhibitory concentrations of Example 5 was done to study the emergence of resistance. After twenty passages in the presence of increasing selective pressure of Example 5, variants of S. aureus and S. pyogenes ARC838 had been isolated that displayed 32-fold, 16-fold, and 8-fold decreases in susceptibility over the starting culture. This loss of susceptibility to Example 5 did not correlate with any changes in susceptibility that was greater than 4-fold to linezolid, vancomycin, and levofloxacin.

In Vitro Activity and Potency of Example 5 Tested Against Neisseria Gonorrheoeae Neisseria gonorrhoeae is a significant cause of worldwide sexually transmitted disease. Penicillin historically was effective in the treatment of gonorrhea but plasmid-mediated penicillinase producing N. gonorrhoeae (PPNG) strains have spread worldwide limiting the empiric use of penicillin to certain geographical regions with a known low-prevalence of PPNG, other penicillin resistance mechanisms. Additionally, resistance development has occurred for several of the alternative antimicrobial class agents used for empiric therapy of gonococcal infections, including fluoroquinolones (ciprofloxacin), tetracyclines and macrolides (azithromycin). A collection of 100 Neisseria gonorrhoeae, including isolates which were non-susceptible to azithromycin, ciprofloxacin, penicillin, and tetracycline, were tested in vitro by the CLSI reference agar dilution method against Example and comparator agents. The results indicated that Example 5 was highly active against all isolates tested (MIC values at ≤0.25 μg/ml) and there appeared to be no cross-resistance with other tested comparator classes.

A total of 100 stock clinical and ATCC quality control N. gonorrhoeae isolates from the collection at JMI Laboratories (North Liberty, Iowa USA) were tested. Collection included strains with the following characteristics:

| Phenotype | No. of Isolates |
|---|---|
| Ciprofloxacin-resistant | 47[a] |
| Penicillin-resistant | 63[b] |
| Ciprofloxacin R & Penicillin R | 24 [c] |
| Total | 100[d] |

[a]Mostly North American and a few European isolates
[b]Approximately equal numbers of North American and Europe isolates
[c] Mostly North American and a few European isolates
[d]Twenty-seven isolates with azithromycin MIC at ≥0.5 μg/mL (non-susceptible)

Methods:
A. MIC values for N. gonorrhoeae were determined using the reference CLSI agar dilution method for gonococci as described in M07-A9 [2012].
B. Agar dilution plates (GC agar base with 1% defined supplement) for N. gonorrhoeae testing were produced by JMI Laboratories.
C. Comparator agents were provided by JMI Laboratories through Sigma-Aldrich or their respective manufacturer.
D. Quality control (QC) ranges and interpretive criteria for the comparator compounds were as published in CLSI M100-S23 [2013] and EUCAST [2013]. The QC strain was N. gonorrhoeae ATCC 49226.

Example 5 was active against all N. gonorrhoeae strains tested exhibiting a MIC range of ≤0.004 to 0.25 μg/mL and a $MIC_{50/90}$ at 0.06/0.125 μg/mL. A total of 99.0% of isolates exhibited MIC values <0.125 μg/mL. There was only one isolate with a MIC value at 0.25 μg/mL.

Example 5 demonstrated similar activity against penicillin-intermediate and -resistant strains with a modal MIC value at 0.06 μg/mL and $MIC_{50/90}$ values of 0.06/0.06 μg/mL and 0.06/0.12 μg/mL [85.7% of isolates at <0.06 μg/mL], respectively.

The ciprofloxacin-intermediate and -resistant strains also showed a modal MIC value to Example 5 at 0.06 μg/mL with $MIC_{50/90}$ values of 0.06/0.12 μg/mL.

Example 5 exhibited similar activity against tetracycline-intermediate and -resistant strains with a modal MIC value at 0.06 μg/mL and $MIC_{50/90}$ values of 0.06/0.06 μg/mL and 0.06/0/0.12 μg/mL [66.7% of isolates at <0.06 μg/mL], respectively.

The modal values for the azithromycin-susceptible and -intermediate isolates were 0.06 μg/mL with $MIC_{50/90}$ values of 0.06/0.06 μg/mL and 0.06/0/0.12 μg/mL [66.7% of isolates at <0.06 μg/mL], respectively.

The $MIC_{50/90}$ values against all 100 isolates for azithromycin were 0.25/0.5 μg/mL; for cefixime, 0.03/0.06 μg/mL; for ceftriaxone 0.015/0.06 μg/mL; for ciprofloxacin, 0.25/≥2 μg/mL; for penicillin 2/>2 μg/mL; and for tetracycline ½ μg/mL.

Example 5 ($MIC_{90}$, 0.12 μg/mL) was four-fold more active than azithromycin ($MIC_{90}$, 0.5 μg/mL), two-fold less active than cefixime and ceftriazone ($MIC_{90}$ 0.06 μg/mL), 16-fold more active than tetracycline ($MIC_{90}$, 2 μg/mL) and >32-fold more active than ciprofloxacin and penicillin ($MIC_{90}$. 2 μg/mL).

Example 5 MIC values when tested against the QC strain (N. gonorrhoeae ATCC 49226) were 0.06, 0.12 and 0.12 μg/mL.

Summary:
Example 5 was highly active against N. gonorrhoeae isolates with 99.0% of isolates exhibiting MIC values <0.125 μg/mL. Example 5 was two-fold less active that cefixime and ceftriaxone and ranged from 4→32-fold more active than azithromycin, ciprofloxacin, penicillin and tetracycline. The modal MIC value for Example 5 remained the same (0.06 μg/mL) for various subsets of isolates including those that were non-susceptible to comparator agents. $MIC_{90}$ values for susceptible phenotypes (ciprofloxacin-susceptible, tetracycline-susceptible and azithromycin-susceptible) were at 0.06 μg/mL. For non-susceptible phenotypes, $MIC_{90}$ values were at 0.06-0.12 μg/mL indicating the high level of activity and the lack of significant cross-resistance of Example 5 with comparator agents.

The invention claimed is:

1. A method for treating a *Neisseria gonorrhoeae* infection in a subject in need thereof comprising administering to the subject an effective amount of a compound according to the structure:

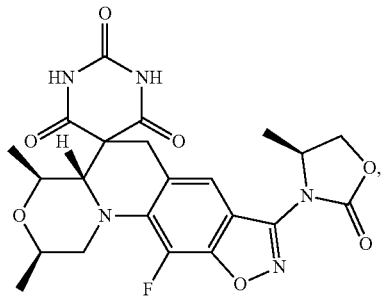 [SMILES: C[C@@H]1CN2c3c(cc4c(N5C(=O)OC[C@@H]5C)noc4c3F)CC3(C(=O)NC(=O)NC3=O)[C@H]2[C@H](C)O1]

or a pharmaceutically acceptable salt thereof.

2. A method for treating pneumonia in a subject in need thereof, comprising administering to the subject an effective amount of a compound according to the structure:

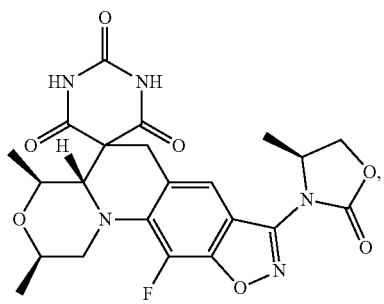 [SMILES: C[C@@H]1CN2c3c(cc4c(N5C(=O)OC[C@@H]5C)noc4c3F)CC3(C(=O)NC(=O)NC3=O)[C@H]2[C@H](C)O1]

or a pharmaceutically acceptable salt thereof.

3. A method for treating a *Burkholderia* spp. infection in a subject in need thereof comprising administering to the subject an effective amount of a compound according to the structure:

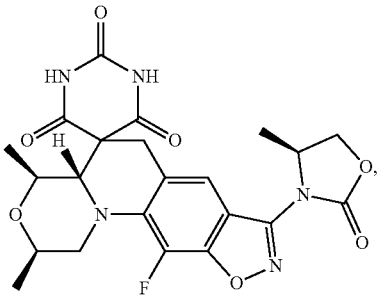 [SMILES: C[C@@H]1CN2c3c(cc4c(N5C(=O)OC[C@@H]5C)noc4c3F)CC3(C(=O)NC(=O)NC3=O)[C@H]2[C@H](C)O1]

or a pharmaceutically acceptable salt thereof.

4. A method for treating a complicated skin and skin structure infection in a subject in need thereof comprising administering to the subject an effective amount of a compound according to the structure:

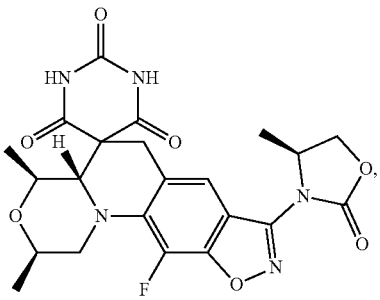 [SMILES: C[C@@H]1CN2c3c(cc4c(N5C(=O)OC[C@@H]5C)noc4c3F)CC3(C(=O)NC(=O)NC3=O)[C@H]2[C@H](C)O1]

or a pharmaceutically acceptable salt thereof.

* * * * *